United States Patent
Singh et al.

(10) Patent No.: US 11,897,970 B2
(45) Date of Patent: Feb. 13, 2024

(54) ANTIBACTERIAL PRODUCTS

(71) Applicant: THE UNIVERSITY OF LIVERPOOL, Liverpool (GB)

(72) Inventors: Ishwar Singh, Lincoln (GB); Edward Taylor, Lincoln (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 520 days.

(21) Appl. No.: 16/491,852

(22) PCT Filed: Mar. 9, 2018

(86) PCT No.: PCT/GB2018/050605
§ 371 (c)(1),
(2) Date: Sep. 6, 2019

(87) PCT Pub. No.: WO2018/162922
PCT Pub. Date: Sep. 13, 2018

(65) Prior Publication Data
US 2021/0139539 A1    May 13, 2021

(30) Foreign Application Priority Data

Mar. 9, 2017   (GB) ..................... 1703753
Sep. 7, 2017   (GB) ..................... 1714389

(51) Int. Cl.
| C07K 7/00 | (2006.01) |
| C07K 7/56 | (2006.01) |
| A61P 31/04 | (2006.01) |
| A61K 38/00 | (2006.01) |

(52) U.S. Cl.
CPC ............. *C07K 7/56* (2013.01); *A61P 31/04* (2018.01); *A61K 38/00* (2013.01)

(58) Field of Classification Search
CPC ........... C07K 7/56; A61P 31/04; A61K 38/00
See application file for complete search history.

(56) References Cited

FOREIGN PATENT DOCUMENTS

| JP | 2004-510830 | 4/2004 |
| JP | 2009-533371 | 9/2009 |
| WO | WO 2014/089053 | 6/2014 |
| WO | WO 2016/034894 | 3/2016 |
| WO | WO 2017/181189 | 4/2017 |
| WO | WO 2018/09042 | 6/2018 |

OTHER PUBLICATIONS

Abdel Monaim S. A. H. et al, "Lysine Scanning of Arg 10-Teixobactin: Deciphering the Role of Hydrophobic and Hydrophilic Residues," *ACS Omega*, 1(6): 1262-1265, 2016.
Abdel Monaim S. A. H. et al., "Re-evaluation of the N-terminal substitution and the D-residues of teixobactin\," *RSC Advances*, 6: 73827-73829, 2016.
Arias, C. et al., "A new antibiotic and the evolution of resistance," *New England Journal of Medicine*, 372(12): 1168-1170, 2015.
Brown, C., "Antibiotic discovery heralds new world of drugs," *CMAJ: Canadian Medical Association journal (Journal de l'Association medicale Canadienne)* 187(4): 241, 2015.
Chen K. H., et al., "Alanine scan reveals modifiable residues in teixobactin," *Chem. Comm.*, 53(82): 11357-11359, 2017.
Craig W. et al., "A Highly Stereoselective and Scalable Synthesis of L-allo-Enduracididine," *Org. Lett*, 4620-4623, 2015.
Hunter, P., "Antibiotic discovery goes underground", *EMBO Reports*, 16: 563-565, 2015.
International Search Report and Written Opinion issued in International Application No. PCT/GB2018/050605, daed Jul. 2, 2018.
Isidro-Llobet et al., "Amino Acid-Protecting Groups," *Chem. Rev.*, 109(6): 2455-2504, 2009.
Jad Y. E. et al., "Synthesis and Biological Evaluation of a Teixobactin Analogue," *Org. Lett.*, 17(24): 6182-6185, 2015.
Juckstock, J. et al., "Multiresistente Keime Gefahr in Klinik und Praxis," *Gynaekologe*, doi:10.1007/s00129-015-3762-4, 2015.
Juckstock, J. et al., "Multiresistente Keime Gefahr in Klinik und Praxis," *Gynaekologe*, doi:10.1007/s00129-015-3762-4, 2015. Machine Translation.

(Continued)

*Primary Examiner* — Jeanette M Lieb
(74) *Attorney, Agent, or Firm* — Parker Highlander PLLC

(57) ABSTRACT

The invention provides novel antibacterial compounds of formulae IA, IB and IC as defined herein. Optionally, the antibacterial compounds can be bonded to a delivery agent that is capable of bonding to one or more structures on a bacterial cell membrane. The invention also provides the use of such compounds in treating or preventing bacterial infections, and processes for their synthesis.

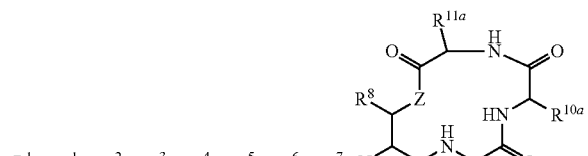

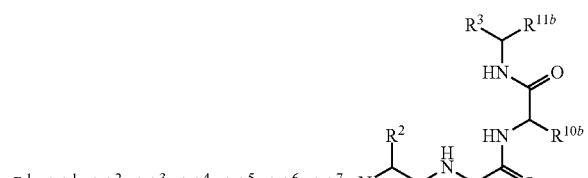

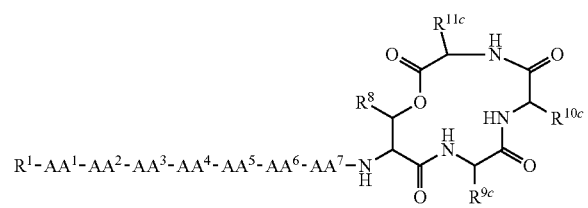

Figure 1:
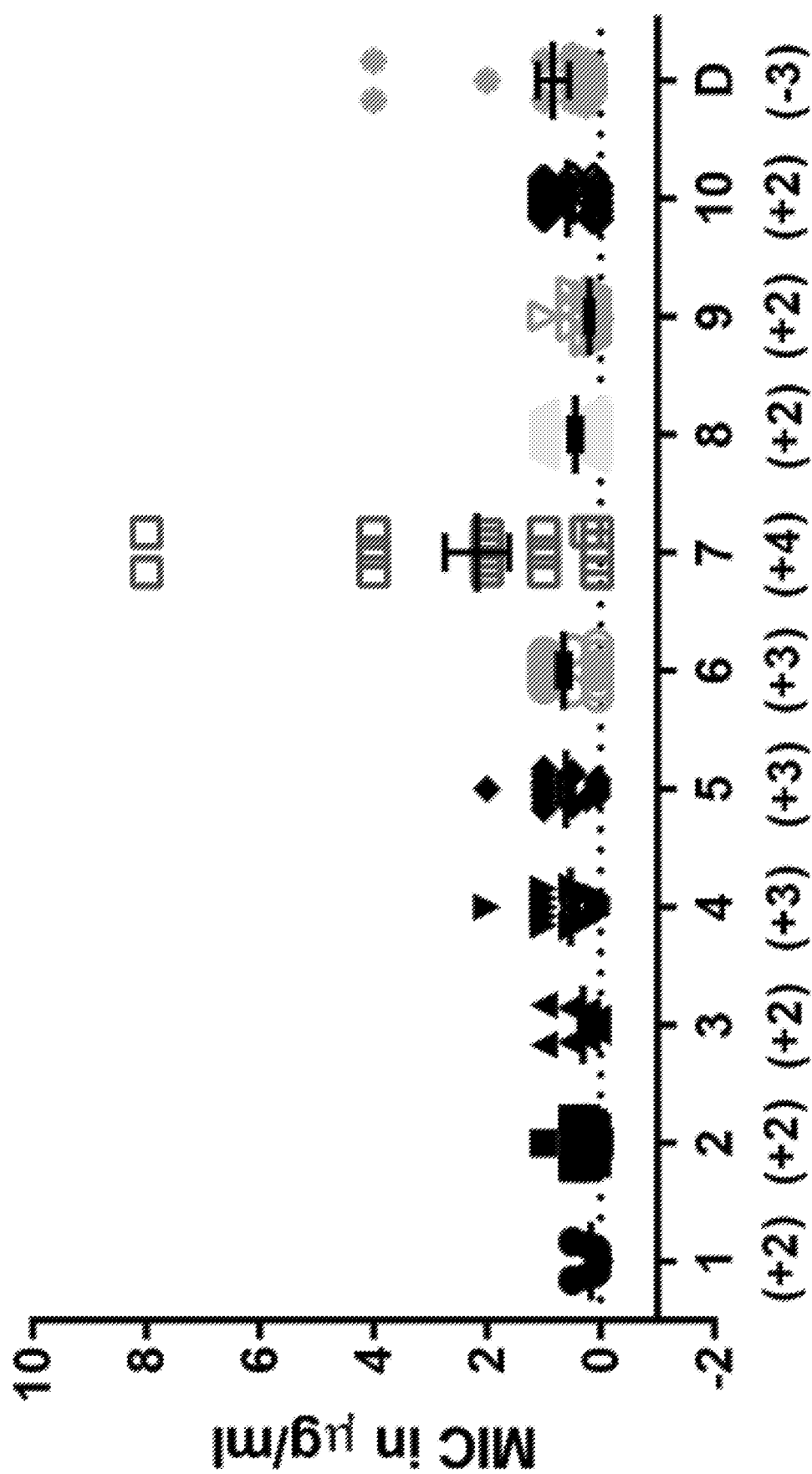

16 Claims, 5 Drawing Sheets
Specification includes a Sequence Listing.

(56) References Cited

OTHER PUBLICATIONS

Kahrstrom, C., "Antimicrobials: A new drug for resistant bugs," *Nature reviews. Microbiology*, 13(3): 126-7, 2015.
Kali, A., "Teixobactin: a novel antibiotic in treatment of gram positive bacterial infections," *Journal of clinical and diagnostic research: JCDR*, 9(3): DL01, 2015.
Kang J. et al, "Teixobactin: a novel antibiotic in treatment of gram positive bacterial infections," *Bioorganic & Medicinal Chemistry*, 9(3): 4990-4995, 2017.
Katsnelson, A., "New Twist on Antibiotic Hunt Hits Pay Dirt," *Nature reviews. Drug discovery*, 14(3): 153, 2015.
Kotic, M., "New Antibiotic, Unexpected Antiviral, IP7 in Cancer, and Better Dyes," *Chemistry & Biology (Oxford, United Kingdom)*, 22(2), 159-160, 2015.
Lewis, K. "Antimicrobials to combat drug tolerance and resistance." *Abstracts of Papers, 250th ACS National Meeting and Exposition*, 2015, BIOL-108.
Ling L.L et al., "A new antibiotic kills pathogens without detectable resistance," *Nature*, 517(7535): 455-459, 2015.
Parmar A., et al., "Defining the molecular structure of teixobactin analogues and understanding their role in antibacterial activities," *Chem. Commun.*, 53(12): 2016-2019, 2017.
Parmar A. et al., "Design and Syntheses of Highly Potent Teixobactin Analogues against *Staphylococcus aureus*, Methicillin-Resistant *Staphylococcus aureus*(MRSA), and Vancomycin-Resistant Enterococci (VRE) in Vitro and in Vivo," *J. Med. Chem.*, 61(5): 2009-2017, 2018.
Parmar A. et al., "Efficient total syntheses and biological activities of two teixobactin analogues," *Chem. Commun.*, 52(36): 6060-6063, 2016.
Parmer A. et al., "Syntheses of potent teixobactin analogues against methicillin-resistant *Staphylococcus aureus* (MRSA) through the replacement of 1-allo-enduracididine with its isoteres," *Chem. Commun.*, 53(55): 7788-7791, 2017.
Parmar A. et al., "Teixobactin analogues reveal enduracididine to be non-essential for highly potent antibacterial activity and lipid II binding," *Chem. Sci.*, 8(12): 8183-8192, 2017.
Piddock, L., "Teixobactin, the first of a new class of antibiotics discovered by iChip technology?," *The Journal of antimicrobial chemotherapy*, 70(10): 2679-80, 2015.
Sanchez de Badajoz E., "[New horizon in the fight against bacterial resistance]," *Archives espanoles de urologia*, 68(5): 464-5, 2015.
Sanchez de Badajoz E., "[New horizon in the fight against bacterial resistance]," *Archives espanoles de urologia*, 68(5): 464-5, 2015. Machine Translation.
Schumacher C. E. et al., "Synthesis and biological evaluation of novel teixobactin analogues," *Org. and Biomol. Chem.*, 15(41): 8755-8760, 2017.
Tetsch, L., "Teixobactin: Reservemunition aus dem Boden.," *Biologie in Unserer Zeit*, 45(3): 141-143, 2015.
Tetsch, L., "Teixobactin: Reservemunition aus dem Boden.," *Biologie in Unserer Zeit*, 45(3): 141-143, 2015. Machine Translation.
Tschiche, A. et al., "Polyglycerol-based amphiphilic dendrons as potential siRNA carriers for in vivo applications†," *J. Mater. Chem. B*, 2: 2153-2167, 2014.
Von Nussbaum, F., "Multiple attack on bacteria by the new antibiotic teixobactin," *Angew. Chem. Int Ed*, 54(23): 6684, 2015.
Wu C. et al., "Synthesis and structure—activity relationship studies of teixobactin analogues," *RSC Adv.*, 7: 1923-1926, 2017.
Yang H. et al., "Elucidation of the Teixobactin Pharmacophore," *ACS Chem. Biol.*, 11(7): 1823-1826, 2016.
Yang H. et al., "X-ray crystallographic structure of a teixobactin analogue reveals key interactions of the teixobactin pharmacophore," *Chem. Commun.*, 53(18): 2772-2775, 2017.
Zong Y. et al., "Developing Equipotent Teixobactin Analogues against Drug-Resistant Bacteria and Discovering a Hydrophobic Interaction between Lipid II and Teixobactin," *J. Med. Chem.*, 61(8): 3409-3421, 2018.
Gunjal et al., "Teixobactin: A Paving Stone toward a New Class of Antibiotics?", *J. Med. Chem.*, 63(21):12171-12195, 2020.
Hathout et al., "Kurstakins : A New class of Lipopeptides Isolated from Bacillus thuringiensis" *J. Nat. Prod.*, 63:1492-1496, 2000.
Kuiper et al., "Characterization of two Pseudomonas putida lipopeptide biosurfactants, putisolvin I and II, which inhibi biofil,m formation and break down exisiting biofilms", *Molecular Microbiology*, 51(1):97-113, 2004.
Online encyclopaedia extract for "amino acid".
Kuiper, I. et al., "Characterization of two *Pseudomonas putida* lipopeptide biosurfactants, putisolvin I and II. which inhibit biofilm formation and break down existing biofilms," *Molecular Microbiology*, 51.1 (2004): 97-113.

SEQUENCE LISTING

<160> NUMBER OF SEQ ID NOS: 22

<210> SEQ ID NO 1
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(7)
<223> OTHER INFORMATION: Xaa can be any naturally occurring amino acid

<400> SEQUENCE: 1

Xaa Xaa Xaa Xaa Xaa Xaa Xaa
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: Xaa can be any naturally occurring amino acid

<400> SEQUENCE: 2

Xaa Xaa Xaa Xaa Xaa Xaa
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Thr Ala Arg Glu
1

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

His Phe Ile Ser Gln Ile Ile Ser Thr Ala Arg Glu
1               5                   10

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Lys Ala Arg Glu
1

<210> SEQ ID NO 6
<211> LENGTH: 12
<212> TYPE: PRT

```
<213> ORGANISM: Artificial sequence
<220> FEATURE:
<223> OTHER INFORMATION: Synthetic peptide

<400> SEQUENCE: 6

His Phe Ile Ser Gln Ile Ile Ser Lys Ala Arg Glu
1               5                   10

<210> SEQ ID NO 7
<211> LENGTH: 8
<212> TYPE: PRT
<213> ORGANISM: Artificial sequence
<220> FEATURE:
<223> OTHER INFORMATION: Synthetic peptide

<400> SEQUENCE: 7

Ile Ser Gln Ile Ile Ser Thr Ala
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Phe Ile Ser Arg Ile Ile Ser Thr Ala
1               5

<210> SEQ ID NO 9
<211> LENGTH: 11
<212> TYPE: PRT
<213> ORGANISM: Artificial sequence
<220> FEATURE:
<223> OTHER INFORMATION: Synthetic peptide

<400> SEQUENCE: 9

Phe Ile Ser Gln Ile Ile Ser Cys Ala Arg Cys
1               5                   10

<210> SEQ ID NO 10
<211> LENGTH: 7
<212> TYPE: PRT
<213> ORGANISM: Artificial sequence
<220> FEATURE:
<223> OTHER INFORMATION: Synthetic peptide

<400> SEQUENCE: 10

Phe Ile Ser Gln Ile Ile Ser
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic peptide

<400> SEQUENCE: 11

Ala Ile Ser Gln Ile Ile Ser
1               5

<210> SEQ ID NO 12
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 12

Phe Ala Ser Gln Ile Ile Ser
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic peptide

<400> SEQUENCE: 13

Phe Ile Ala Gln Ile Ile Ser
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Phe Ile Ser Ala Ile Ile Ser
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Phe Ile Ser Gln Ala Ile Ser
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Phe Ile Ser Gln Ile Ala Ser
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

Phe Ile Ser Gln Ile Ile Ala
1               5

<210> SEQ ID NO 18
<211> LENGTH: 7
<212> TYPE: PRT
<213> ORGANISM: Artificial sequence
<220> FEATURE:
```

```
<223> OTHER INFORMATION: Synthetic peptide

<400> SEQUENCE: 18

Phe Ile Arg Gln Ile Ile Ser
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Phe Ile Ser Arg Ile Ile Ser
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Phe Ile Arg Arg Ile Ile Ser
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide

<400> SEQUENCE: 21

Phe Ile Arg Glu Ile Ile Ser
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic peptide

<400> SEQUENCE: 22

Phe Ile Lys Gln Ile Ile Ser
1               5
```

ANTIBACTERIAL PRODUCTS

This application is a national phase application under 35 U.S.C. § 371 of International Application No. PCT/GB2018/050605, filed Mar. 9, 2018, which claims priority to United Kingdom Application Nos. 1703753.2, filed Mar. 9, 2017, and 1714389.2, filed Sep. 7, 2017. The entire text of each of the above referenced disclosures is specifically incorporated herein by reference.

INCORPORATION OF SEQUENCE LISTING

The sequence listing that is contained in the file named "EPCLP0069US_v2_ST25.txt", which is 5 KB in size and was created on Sep. 13, 2021, is filed herewith by electronic submission and is incorporated by reference herein.

FIELD OF THE INVENTION

This invention relates to a series of novel compounds with antibacterial activity, and methods of making said compounds. The compounds have been developed as readily-accessible synthetic analogues of the naturally-occurring depsipeptide antibacterial Teixobactin. The novel compounds display potent antibacterial activity and may be useful in treating and preventing bacterial infections. The novel compounds may also be covalently bonded to a delivery agent, which is capable of binding to certain components of bacterial cells, serving to anchor the antibacterial compound and increase its effectiveness.

BACKGROUND

We are currently facing a worldwide pandemic of multi-drug resistant bacteria, arising from the long-term use of antibacterials. Antibacterial overavailability and poor prescribing practices have allowed exposure to sub-optimal concentrations of antibacterials, promoting the evolution of environmental resistance mechanisms in bacteria.

There is therefore a continuing need to develop new compounds and strategies for combating unwanted bacterial growth, particularly in bacteria that are resistant to existing drugs.

Teixobactin is a recently-discovered depsipeptide antibiotic that acts through a novel mechanism of action (Ling L. L et al., *Nature*, 2015, 517, 455-459). Teixobactin inhibits bacterial cell wall synthesis by binding to precursors of essential cell wall components. As such, it is likely to induce resistance at a considerably slower rate than antibacterials that act at intracellular protein targets.

Teixobactin's unusual structure comprises D-amino acid residues, and an L-allo-enduracididine residue. The manufacture of Teixobactin in a commercial scale is difficult and expensive, in part due to the presence of the L-allo-enduracididine residue.

Various analogues of Teixobactin have been described in the literature, including in Wu C., et al., *RSC Adv.*, 2017, 7, 1923-1926; Yang H., et al., *ACS Chem. Biol.* 2016, 11, 1823-1826; Abdel Monaim S. A. H., *ACS Omega* 2016, 1, 1262-1265; Parmar A., et al., *Chem. Commun.* 2017, 53, 2016-2019; Parmar A., et al., *Chem. Commun.* 2016, 52, 6060-6063; Jad Y. E., et al., *Org. Lett.*, 2015, 17 (24), pp 6182-6185; and Yang H. Chem. Commun., 2017, DOI: 10.1039/C7CC00783C advanced online publication.

The inventors have now found a new range of analogues of Teixobactin that is easily-accessible and displays potent antimicrobial activity, and have developed robust processes for their synthesis.

The listing or discussion of an apparently prior published document in this specification should not necessarily be taken as an acknowledgement that the disclosure of the document is part of the state of the art or is common general knowledge.

DESCRIPTION OF THE INVENTION

According to a first aspect of the invention, there is provided a compound of formula IA, IB or IC, (SEQ ID NO: 1)

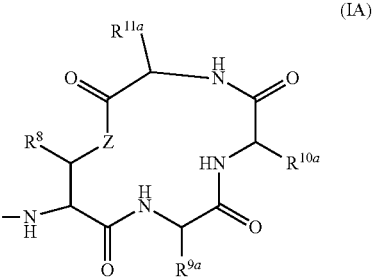

(IA)

(SEQ ID NO: 1)

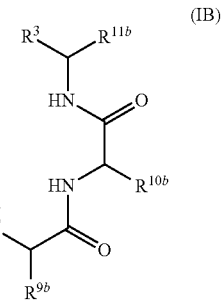

(IB)

(SEQ ID NO: 1)

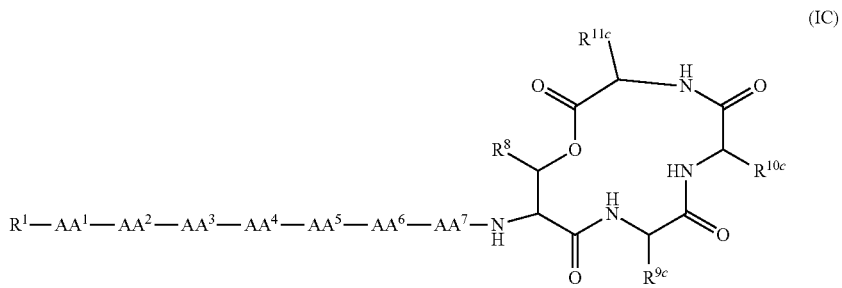

(IC)

or a pharmaceutically-acceptable salt, solvate or clathrate thereof, wherein:
- $R^1$ represents H, $C_{1-6}$ alkyl, $C_{1-6}$ acyl, benzyl or benzoyl;
- $AA^1$, $AA^2$ and $AA^5$ to $AA^7$ each independently represents an amino acid (including a proteinogenic amino acid or a non-proteinogenic amino acid);
- $AA^3$ and $AA^4$ each independently represents an amino acid (including a proteinogenic amino acid or a non-proteinogenic amino acid), diaminopropanoic acid, diaminobutanoic acid, or ornithine;
- $R^8$ represents hydrogen or $C_{1-4}$ alkyl;
- $R^{9a}$, $R^{9b}$, and $R^{9c}$ represent an amino acid side chain (including the side chain of a proteinogenic amino acid or a non-proteinogenic amino acid), —$CH_2$—$NH_2$, —$(CH_2)_2$—$NH_2$ or —$(CH_2)_3$—$NH_2$;
- $R^{10a}$ represents a fragment of formula -$L^1$-$L^2$-$L^3$-$X^1$, a hydrophobic proteinogenic amino acid side chain, a hydrophobic non-proteinogenic amino acid side chain, a polar uncharged amino acid side chain, a negatively charged amino acid side chain, hydrogen, or $R^{10a}$ is linked to the adjacent nitrogen atom to form a proline ring;
- $R^{11a}$ represents an amino acid side chain (including the side chain of a proteinogenic amino acid or a non-proteinogenic amino acid);
- Z is —O— or —NH—;
- $L^1$ represents a linear or branched $C_{1-12}$ alkylene linker;
- $L^2$ is selected from the group consisting of —O—, —N($X^a$)—, —[N($X^a$)$_2$]$^+$—, —C(O)—, —OC(O)—, —C(O)O—, —NHC(O)—, —C(O)N($X^a$)—, —OC(O)N($X^a$)—, —NHC(O)O—, or —NHC(O)N($X^a$)—;
- $X^a$ represents hydrogen or -$L^3$-$X^1$;
- $L^3$ represents a direct bond or a linear or branched $C_{1-12}$ alkylene linker;
- each $X^1$ is independently selected from the group consisting of —C(O)—$C_{1-12}$ alkyl, —C(O)—$NH_2$, —C(S)—$NH_2$, a fragment of formula Q, and a $C_{1-12}$ alkyl group optionally substituted by one or more $X^2$ substituents;
- wherein the fragment of formula Q is:

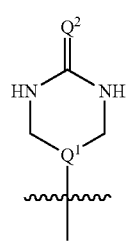

in which $Q^1$ represents either CH or N, and $Q^2$ represents O, S or NH;
- each $X^2$ independently represents —$NH_2$, —OH, —NHC(O)$NH_2$, —NHC(S)$NH_2$, —NHC(=NH)$NH_2$, or a 3- to 12-membered heterocyclyl group;
- or -$L^2$-$L^3$-$X^1$ together represent a fragment of formula Q:
- $R^{10b}$ represents an amino acid side chain, a —$C_{1-6}$ alkyl-$NH_2$ group, a —$C_{1-6}$ alkyl-NH—C(=NH)—$NH_2$ group or a fragment of formula -$L^1$-$L^2$-$L^3$-$X^1$ (wherein $L^1$, $L^2$, $L^3$ and $X^1$ are as defined above);
- $R^{11b}$ represents —C(O)$NH_2$;
- $R^3$ represents —$CH_2$—SH, and $R^2$ represents —$CH_2$—$NH_2$, —$(CH_2)_2$—$NH_2$, —$(CH_2)_3$—$NH_2$ or the side chain of an amino acid selected from the list consisting of threonine, cysteine, serine, lysine, tyrosine, aspartic acid, and glutamic acid;
- $R^2$ and $R^3$ are linked to form a linking group;
- wherein the linking group is a —$C_{1-6}$ alkylene-Q-$C_{1-6}$ alkylene- group in which Q represents a functional group selected from the list consisting of —O—, —OC(O)—, —C(O)O—, —C(O)N(R')—, —N(R')C(O)—, —S—, —S—S— and —C(O)—; R' represents H or $C_{1-4}$ alkyl; and
- the $C_{1-6}$ alkylene groups in the linking group are linear alkylene groups which may be the same or different and are optionally substituted with one or more substituents selected from the group consisting of —OH, —SH, —$SC_{1-4}$ alkyl, —$OC_{1-4}$ alkyl, —$NH_2$, —C(O)OH, —C(O)—$NH_2$, —C(O)$OC_{1-4}$ alkyl and a $C_{1-4}$ alkyl group, which latter group (i.e. the $C_{1-4}$ alkyl group) is optionally substituted with one or more substituents selected from the list consisting of —OH, —SH, —$SC_{1-4}$ alkyl, —$NH_2$, —C(O)OH, —C(O)—$NH_2$, —C(O)$OC_{1-4}$ alkyl and phenyl;
- $R^{10c}$ represents an amino acid side chain or a L-allo-enduracididine group;
- $R^{11c}$ represents an amino acid side chain;
- wherein, for compounds of formula IC, at least one of $AA^1$ to $AA^7$ is replaced by an amino acid of formula —NH—CH($R^c$)—C(O)—, and/or at least one of $R^{9c}$ and $R^{11c}$ alternatively represents $R^c$, wherein $R^c$ represents a fragment of formula -$L^1$-$L^2$-$L^3$-$X^1$ as defined above;
- optionally wherein the compound of formula IA, IB or IC is covalently bonded to a delivery agent, which is either capable of covalently bonding to one or more structures on a bacterial cell membrane or comprises a hydrophilic portion capable of otherwise binding to one or more structures on a bacterial cell membrane.

Such compounds, salts, solvates and clathrates are referred to hereinafter as the "compounds of the invention".

By "pharmaceutically-acceptable salt" we mean an acid addition or base addition salt suitable for use in pharmaceuticals. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, trifluoroacetic, citric, malic, lactic, fumaric, benzoic, glycolic, gluconic, succinic and arylsulphonic acids; and from metals such as sodium, magnesium, or preferably, potassium and calcium. Particularly preferred salts include those derived from acetic, trifluoroacetic, hydrochloric and tartaric acids.

By "solvate" we mean a solid form wherein the relevant compound (e.g. a compound of formula IA, IB or IC) is associated with one or more solvent molecules. The term solvate includes hydrates and other solvates of pharmaceutically-acceptable solvents. A preferred solvent for solvate formation is DMSO.

By "clathrate" we mean a solid form wherein the relevant compound (e.g. a compound of formula IA, IB or IC) forms a lattice that contains a guest molecule (e.g. a pharmaceutically-acceptable solvent) within the lattice structure.

By "amino acid" and "residue" (for example D-phenylalanine "residue") we mean the dehydrated portion of an amino acid present in polypeptide chains and represented by the following formula

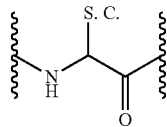

wherein S. C. represents an amino acid side chain. For the avoidance of doubt, the term "amino acid" includes non-proteinogenic amino acids unless otherwise specified.

By "amino acid side chain" or "side chain of an amino acid" we mean the group attached to the position a to the carboxyl and amino groups in α-amino acids, including non-proteinogenic α-amino acids and particularly proteinogenic amino acids. The skilled person will understand that the most common natural amino acids are known by their trivial names and will be aware of the side chain groups present in these amino acids.

"Proteinogenic" amino acids are the 22 amino acids that may be naturally encoded or naturally found in the genetic code of organisms. "Non-proteinogenic" amino acids are those not naturally encoded or found in the genetic code of any organism. The set of non-proteinogenic amino acids is generally considered to include all organic compounds with an amine ($-NH_2$) and a carboxylic acid ($-COOH$) functional group linked via a single additional carbon atom, as well as a side chain and a hydrogen bound to that single additional carbon atom, but excluding selenocysteine, pyrrolysine and the 20 standard amino acids that are incorporated into proteins during translation. Non-proteinogenic amino acids include those amino acids that are intermediates in biosynthesis, those that are post-translationally formed in proteins, and those that possess a physiological role (e.g. components of bacterial cell walls, neurotransmitters and toxins). References to hydrophobic non-proteinogenic amino acid side chains are references to hydrophobic side chains (particularly those formed primarily of alkyl and/or aryl groups in the absence of polar groups) which are capable of being bound to an amino acid backbone. References to polar non-proteinogenic amino acid side chains are references to polar side chains (particularly those comprising a hydroxyl group or an amide functional group (e.g. wherein one or more of said groups is bound to the amino acid via a linear, branched, cyclic or part cyclic $C_{1-8}$ alkylene group)) which are capable of being bound to an amino acid backbone Various structural features, such as $L^2$ and Q represent linking groups which form a bridge between two separate portions of the molecule. In each case, such linking groups include $-OC(O)-$. For $L^2$, the left-hand hyphen in such linking groups represents the point of attachment to $L^1$, and the right-hand hyphen in such linking groups represents the point of attachment to $L^3$. For Q, the left-hand hyphen in such linking groups represents the point of attachment to the alkylene linker that is bound to the carbon atom at $R^2$, and the right-hand hyphen in such linking groups represents the point of attachment to the alkylene linker that is bound to the carbon atom at $R^3$.

The delivery agent may be a delivery agent fragment of formula II to X as hereinafter defined, and may be covalently bonded to a compound of formula IA, IB or IC at any position on the molecule. As such, for the avoidance of doubt, a delivery agent may be included in all of the definitions of substituents listed hereinabove and, may also be appended to any other region of the molecule, such as to any one of the amino acid residues $AA^1$ to $AA^7$. The optimum point of attachment of the delivery agent may be determined by the skilled person.

A preferred point of attachment for the delivery agent is to the N-terminus of the peptide sequence. Thus, in one embodiment, $R^1$ may also be a delivery agent. For compounds of formula IA (and IAA), other preferred points of attachment for the delivery agent include the groups represented by $R^{9a}$, $R^{10a}$, and $R^{11a}$. For compounds of formula IB, other preferred points of attachment for the delivery agent include the groups represented by $R^{9b}$, $R^{10b}$, and $R^{11b}$. For compounds of formula IC, other preferred points of attachment for the delivery agent include the groups represented by $R^{9c}$, $R^{10c}$, and $R^{11c}$.

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated. Unless otherwise specified, alkyl and alkoxy groups may also be substituted with one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two)

of carbon atoms, be unsaturated. Unless otherwise specified, alkylene groups may also be substituted with one or more halo atoms.

The term "aryl", when used herein, includes $C_{6-10}$ aryl groups such as phenyl, naphthyl and the like. When substituted, aryl groups are preferably substituted with between one and three substituents.

The term "acyl" as used herein refers to alkyl groups having a carbonyl group attached to the carbon which forms the point of attachment to the rest of the molecule.

When the stereochemistry of a chiral centre is not explicitly defined herein (i.e. by the use of wedged/hashed bonds) it should be understood that the stereocentre may be present in the R- or S-configuration, or a mixture of both configurations.

The skilled person will realise that all references herein to particular aspects of the invention include references to all embodiments and combinations of one or more embodiments that make up that aspect of the invention. Thus, all embodiments of particular aspects of the inventions may be combined with one or more other embodiments of that aspect of the invention to form further embodiments without departing from the teaching of the invention.

In one embodiment of the invention, Z represents —O—. For example, the compound of the invention may be a compound of formula IAA:

(SEQ ID NO: 1)

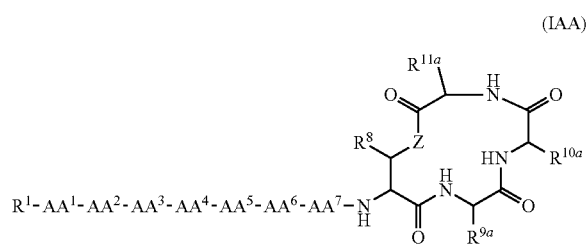

(IAA)

In one embodiment of the invention, particularly when the compound of the invention is a compound of formula IA (or IAA), $R^{10a}$ represents a fragment of formula -$L^1$-$L^2$-$L^3$-$X^1$.

$L^1$ preferably represents a $C_{1-6}$, or more preferably a $C_{1-4}$ linear or branched alkylene linker (e.g. methylene or n-butylene).

$L^2$ is preferably selected from the group consisting of —O—, —NH—, —N($X^1$)—, —[N($X^1$)$_2$]$^+$—, —OC(O)—, —C(O)O—, —NHC(O)—, —C(O)NH—, —OC(O)NH—, —NHC(O)O—, and —NHC(O)NH—. More preferably $L^2$ is selected from the group consisting of —NH—, —N($X^1$)— and, particularly, —OC(O)—, —C(O)O—, —NHC(O)—, —C(O)NH—, —OC(O)NH—, and —NHC(O)O—.

$L^3$ preferably represents a direct bond or a linear or branched $C_{1-6}$ alkylene linker. More preferably, $L^3$ represents a direct bond or a linear $C_{1-6}$ alkylene linker.

In one embodiment, each $X^1$ is independently selected from the group consisting of —C(O)—$C_{1-12}$ alkyl, —C(O)—NH$_2$, —C(S)—NH$_2$, a fragment of formula Q, and a $C_{1-12}$ alkyl group substituted by one or more $X^2$ substituents. In a particularly preferred embodiment of the invention, $X^1$ represents either a fragment of formula Q, or a $C_{1-12}$ alkyl group substituted by one or more (e.g. 2) $X^2$ substituents. In a further preferred embodiment of the invention, $X^1$ represents either a fragment of formula Q, or a $C_{1-6}$ (e.g. $C_{1-3}$) alkyl group substituted by at least two $X^2$ substituents.

Compounds in which a plurality of $X^2$ groups are present have been found to be particularly effective in inhibiting or killing bacteria.

In embodiments in which $X^1$ may represent a fragment of formula Q (particularly those in which $X^1$ represents either a fragment of formula Q, or a $C_{1-12}$ alkyl group substituted by one or more (e.g. 2) $X^2$ substituents), $Q^1$ preferably represents N.

In one embodiment, each $X^2$ independently represents —NH$_2$, —OH, —NHC(O)NH$_2$, —NHC(S)NH$_2$, —NHC(=NH)NH$_2$, or a 3- to 6-membered aromatic, saturated or part saturated heterocyclic ring containing one or two heteroatoms selected from O and N. Preferably, said heterocyclyl group is selected from piperidinyl, piperazinyl, morpholinyl, pyrrolidinyl, tetrahydrofuranyl, pyridinyl, pyrimidinyl, pyrazinyl, pyridazinyl, pyrrolyl, furanyl, pyrazolyl, imidazolyl, and oxazolyl, the most preferred of which is pyridine. More preferably, each $X^2$ independently represents —NH$_2$ or —OH.

In a preferred embodiment, $R^{10a}$ is a pendant group which contains at least two terminal guanidinyl, urea, thiourea, amino and/or hydroxyl groups (e.g. at least two $X^2$ groups). For example, $R^{10a}$ may represent -$L^1$-N($X^1$)$_2$, -$L^1$-[N($X^1$)$_3$]$^+$A$^-$ (in which A$^-$ is a suitable anion, such as a halide, sulfate, carbonate, phosphate, acetate or the like with the appropriate stiochiometry), or -$L^1$-$L^2$-$L^3$-$C_{1-6}$ alkyl in which said $C_{1-6}$ alkyl is substituted by two $X^2$ groups. In a particularly preferred embodiment, $R^{10a}$ is a pendant group which contains at least three terminal guanidinyl, urea, thiourea, amino and/or hydroxyl groups (e.g. at least three $X^2$ groups). In another preferred embodiment, $R^{10a}$ represents —$C_{1-4}$ alkylene-N($X^1$)$_2$ or —$C_{1-4}$ alkylene-$L^2$-$C_{1-6}$ alkyl in which said $C_{1-6}$ alkyl is substituted by two $X^2$ groups (optionally in which $L^2$ represents —NH—, —NHC(O)—, or —NHC(O)O). In the above-mentioned embodiments, $X^1$ preferably represents a $C_{1-4}$ alkyl group optionally substituted by one or more $X^2$ substituents. Also in such embodiments (including also those in which $X^1$ represents a $C_{1-4}$ alkyl group optionally substituted by one or more $X^2$ substituents), $X^2$ preferably represents a 4- to 6-membered heterocyclyl group (such as pyridine, piperidine, pyrrole or pyrrolidine) or, more preferably, represents —NH$_2$, —OH, —NHC(O)NH$_2$, —NHC(S)NH$_2$, or —NHC(=NH)NH$_2$.

In a further preferred embodiment, $R^{10a}$ is a pendant group which contains a cyclic thiourea, a cyclic urea or cyclic guanidine. For example, $R^{10a}$ may represent -$L^1$-$L^2$-$L^3$-$X^1$ in which $X^1$ (or -$L^2$-$L^3$-$X^1$) represents a fragment of formula Q. In such embodiments, $Q^1$ preferably represents N.

Particularly preferred groups which may be represented by $R^{10a}$ include those shown below:

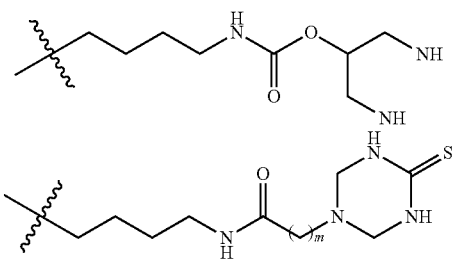

(wherein m represents from 1 to 6).

Other preferred groups which may be represented by $R^{10a}$ include $-L^1-N(X^1)_2$ and $-L^1-[N(X^1)_3]^+A^-$ in which $-N(X^1)_2$ represents:

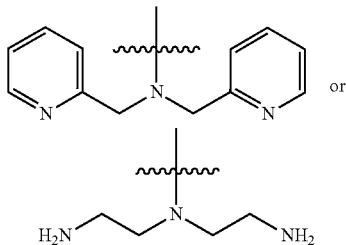

and $-[N(X^1)_3]^+$ represents:

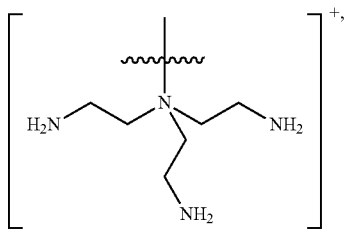

wherein the wavy line represents the point of attachment to $L^1$.

$R^{10a}$ may represent a hydrophobic amino acid side chain, a hydrophobic non-proteinogenic amino acid side chain, a polar uncharged amino acid side chain, a negatively charged amino acid side chain, hydrogen, or $C-R^{10a}$ may be linked to the adjacent nitrogen atom to form a proline ring (i.e. such that the $-N(H)-C(R^{10a})-$ fragment in the compounds of formula IA (or IB or IC) is modified to represent

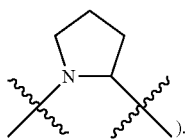

Suitable amino acid side chains that may be mentioned in the context of $R^{10a}$ include proteinogenic amino acid hydrophobic side chains (such as those of alanine (i.e. a methyl group), valine, isoleucine, leucine, methionine, phenylalanine, tyrosine and tryptophan), non-proteinogenic amino acid hydrophobic side chains (such as $C_{2-12}$ alkyl (e.g. ethyl, n-propyl, cyclopropyl, propenyl, n-butyl, tert-butyl, cyclobutyl, butenyl, pentyl, cyclopentyl, hexyl, cyclohexyl, heptyl, or octyl), $C_{1-12}$ alkylthiomethyl, phenyl, naphthyl, biphenyl, toluyl, or toluylmethyl), polar uncharged side chains (such as those of serine, threonine, asparagine and glutamine), negatively charged side chains (such as those of aspartic acid and glutamic acid) and others (such as cysteine, selenocysteine, glycine and proline). Compounds of formula IA, IB and IC in which the $R^{10a}$ group is hydrogen or preferably a hydrophobic side chain (including either a proteinogenic or non-proteinogenic hydrophobic amino acid side chain) have been found to be surprisingly effective in inhibiting or killing bacteria. Thus, in a preferred embodiment, $R^{10a}$ is a hydrophobic side chain. Most preferably $R^{10a}$ is a hydrophobic side chain in the L-configuration. Particular hydrophobic side chains that may be mentioned include $C_{1-6}$ alkyl groups (e.g. methyl, ethyl, propyl, butyl, pentyl, hexyl, cyclopentyl, cyclohexyl, phenyl, hydroxyphenyl, benzyl, indolylmethyl and $CH_3SCH_2CH_2-$).

In an embodiment of the invention, $R^1$ represents H, $C_{1-6}$ alkyl, $C_{1-6}$ acyl, benzyl, benzoyl or a delivery agent (e.g. a fragment of formula II to X, as defined hereinafter). Preferably, $R^1$ does not represent a delivery agent fragment of formula II to X, i.e. $R^1$ represents H, $C_{1-6}$ alkyl, $C_{1-6}$ acyl, benzyl or benzoyl.

In another embodiment, $R^1$ represents a delivery agent fragment of formula II to X as defined hereinafter or, preferably, H, $C_{1-4}$ alkyl, $C_{1-4}$ acyl, benzyl or benzoyl.

In a further embodiment $R^1$ represents a delivery agent fragment of formula I to X as defined hereinafter or, most preferably, H, methyl or acetyl.

In a particular embodiment, $AA^1$, $AA^2$ and $AA^5$ to $AA^7$ each independently represents a proteinogenic amino acid, and $AA^3$ and $AA^4$ each independently represents a proteinogenic amino acid, diaminopropanoic acid, diaminobutanoic acid, or ornithine.

The compounds of the invention are proposed as analogues of Teixobactin. Consequently, it is preferred that the sequence of amino acids represented by $AA^1$ to $AA^7$ (SEQ ID NO: 1) is structurally similar to the corresponding amino acid sequence in Teixobactin. Thus, in embodiments of the invention:

$AA^1$ may represent an L- or D-phenylalanine residue;
$AA^2$ may represent an L- or D-isoleucine residue;
$AA^3$ may represent an L- or D-serine residue;
$AA^4$ may represent an L- or D-glutamine residue;
$AA^5$ may represent an L-, L-allo-, D- or D-allo-isoleucine residue;
$AA^6$ may represent an L- or D-isoleucine residue; and/or
$AA^7$ may represent an L- or D-serine residue.

It has been surprisingly found that structural variation is tolerated to a much greater extent at positions represented by $AA^1$, $AA^3$ and $AA^4$ (as well as $R^{9a}$, $R^{9b}$ and $R^{9c}$). Thus, in a preferred embodiment, $AA^2$ represents an L-isoleucine residue, $AA^5$ represents a D-allo-isoleucine or D-isoleucine residue, $AA^6$ represents an L-isoleucine residue, and $AA^7$ represents an L-serine residue, whereas $AA^1$, $AA^3$ and $AA^4$ may be varied as described herein.

Whilst $AA^1$, $AA^3$ and $AA^4$ preferably represent a D-phenylalanine residue, an L-serine residue and a D-glutamine residue, respectively, i.e. in line with the structure of Teixobactin, other amino acids or similar structures may be substituted at these three positions. For example, $AA^3$ and $AA^4$ may each independently represent any hydrophobic amino acid (including a proteinogenic amino acid (such as alanine, valine, isoleucine, leucine, methionine, phenylalanine, tyrosine or tryptophan) or a non-proteinogenic amino acid (such as norvaline, cyclohexylglycine, cyclohexylalanine, phenylglycine, biphenylglycine, biphenylalanine, naphthylglycine or naphthylalanine)), any polar non-charged amino acid (including a proteinogenic amino acid (such as serine, threonine, asparagine, or glutamine) or a non-proteinogenic amino acid (such as one with a side chain comprising a hydroxy group or an amide functional group bound to the amino acid via a linear, branched, cyclic or part cyclic $C_{1-8}$ alkylene group)), any positively charged amino acid, diaminopropanoic acid, diaminobutanoic acid, or ornithine. $AA^1$ may represent any hydrophobic amino acid as described above in respect of $AA^3$ and $AA^4$. In a particular embodiment, $AA^3$ and $AA^4$ may represent L-arginine or, preferably, L-alanine at either or both of these positions. It is also preferred that, in embodiments in which a delivery agent is covalently bound to the compound of the invention, it is bound to the amino acid at $AA^1$, $AA^3$ or $AA^4$ (or at $R^{11a}$, $R^{11b}$ or $R^{11c}$ as is described hereinafter).

In a most preferred embodiment:
$AA^1$ represents a D-phenylalanine residue;
$AA^2$ represents an L-isoleucine residue;
$AA^3$ represents an L-serine residue;
$AA^4$ represents a D-glutamine residue;
$AA^5$ represents a D-allo-isoleucine or D-isoleucine residue;
$AA^6$ represents an L-isoleucine residue; and
$AA^7$ represents an L-serine residue.

In one embodiment, $R^8$ preferably represents hydrogen or a methyl group so as to form part of a serine or threonine residue. The group at $R^8$ may be present in either the R- or S-configuration, though it is preferred that it is present in the S-configuration (for example, so as to form part of a D-threonine residue) when $R^8$ is methyl.

In one embodiment, $R^{9a}$, $R^{9b}$, and $R^{9c}$ represent a proteinogenic amino acid side chain, $-CH_2-NH_2$, $-(CH_2)_2-NH_2$ or $-(CH_2)_3-NH_2$.

In another embodiment, $R^{9a}$, $R^{9b}$ and $R^{9c}$ preferably represent a hydrophobic proteinogenic or non-proteinogenic amino acid side chain (such as that of alanine (i.e. a methyl group), valine, isoleucine, leucine, methionine, phenylalanine, tyrosine, tryptophan, norvaline, cyclohexylglycine, cyclohexylalanine, phenylglycine, biphenylglycine, biphenylalanine, naphthylglycine or naphthylalanine), a side chain of a positively charged amino acid (such as that of histidine, lysine or arginine), a side chain of a polar non-charged proteinogenic or non-proteinogenic amino acid (such as that of serine, threonine, asparagine, or glutamine, or a hydroxy group or an amide functional group bound to the remainder of the molecule via a linear, branched, cyclic or part cyclic $C_{1-8}$ alkylene group) or $-CH_2-NH_2$, $-(CH_2)_2-NH_2$ or $-(CH_2)_3-NH_2$. Most preferably, $R^{9a}$, $R^{9b}$ and $R^{9c}$ represent a hydrophobic amino acid side chain. The groups at $R^{9a}$, $R^{9b}$ and $R^{9c}$ may be present in either the D- or L-configuration, though it is preferred that it is present in the L-configuration. Thus, for example, when $R^{9a}$, $R^{9b}$ or $R^{9c}$ represent a methyl group (i.e. the side chain of alanine), the chiral carbon to which $R^{9a}$, $R^{9b}$ or $R^{9c}$ is bound is preferably in the S-configuration (thus corresponding to the L-alanine that it present at this position for Teixobactin).

In one embodiment, $R^{11a}$ represents a proteinogenic amino acid side chain.

In another embodiment, $R^{11a}$ or $R^{11c}$ represents a hydrophobic proteinogenic or non-proteinogenic amino acid side chain (such as that of alanine (i.e. a methyl group), valine, isoleucine, leucine, methionine, phenylalanine, tyrosine, tryptophan, norvaline, cyclohexylglycine, cyclohexylalanine, phenylglycine, biphenylglycine, biphenylalanine, naphthylglycine or naphthylalanine). The group at $R^{11a}$ or $R^{11c}$ may be present in either the D- or L-configuration, though it is preferred that it is present in the L-configuration. Thus, for example, when $R^{11a}$ or $R^{11c}$ represents a butyl group (e.g. the side chain of isoleucine), the chiral carbon to which $R^{11a}$ or $R^{11c}$ is bound is preferably in the S-configuration (thus corresponding to the L-isoleucine that is present at this position for Teixobactin). It is also preferred that, in embodiments in which a delivery agent is covalently bound to the compound of the invention, that delivery agent is bound to the amino acid side chain at $R^{11a}$ or $R^{11c}$ or the $-C(O)NH_2$ group represented by $R^{11b}$ (or at $AA^3$ or $AA^4$ as is described hereinbefore).

Compounds of formula IB are based on Teixobactin but primarily involve modification, and possibly opening, of the cyclic portion of the macromolecule. Compounds of formula IB have been found to be particularly effective as antibacterial agents.

In embodiments of the invention in which the compound is a compound of formula IB, $R^{10b}$ may represent the side chain of arginine, lysine, histidine or allo-enduracididine, a $-C_{1-6}$ alkyl-$NH_2$ group, a $-C_{1-6}$ alkyl-NH—C(=NH)—$NH_2$ group, or any of the preferred groups defined hereinabove in respect of $R^{10a}$. References herein to the side chain of enduracididine are references the fragment 2-imino-4-imidazolidinylmethyl. The most preferred structure for $R^{10b}$ is the side chain of arginine (i.e. a $-C_3$ alkyl-NH—C(=NH)—$NH_2$ group).

Thus, in embodiments of the invention in which the compound is a compound of formula IB, $R^{10b}$ may represent the side chain of arginine, lysine, and histidine or enduracididine, a $-C_{1-6}$ alkyl-$NH_2$ group, a $-C_{1-6}$ alkyl-NH—C(=NH)—$NH_2$ group, or a fragment of formula $-L^1-L^2-L^3-X^1$ in which each $X^1$ is independently selected from the group consisting of $-C(O)-C_{1-12}$ alkyl, $-C(O)-NH_2$, $-C(S)-NH_2$, a fragment of formula Q, and a $C_{1-12}$ alkyl group substituted by one or more $X^2$ substituents. In a particularly preferred embodiment, $X^1$ represents either a fragment of formula Q, or a $C_{1-12}$ alkyl group substituted by one or more (e.g. 2) $X^2$ substituents. In a further preferred embodiment of the invention, $X^1$ represents either a fragment of formula Q, or a $C_{1-6}$ (e.g. $C_{1-3}$) alkyl group substituted by at least two $X^2$ substituents (optionally wherein each $X^2$ independently represents $-NH_2$, $-OH$, $-NHC(O)NH_2$, $-NHC(S)NH_2$, $-NHC(=NH)NH_2$).

In further embodiments of the invention in which the compound is a compound of formula IB, a preferred embodiment, $R^{10b}$ may represent the side chain of lysine or, preferably, arginine, or a pendant group which contains at least two terminal guanidinyl, urea, thiourea, amino and/or hydroxyl groups (e.g. at least two $X^2$ groups). For example, $R^{10b}$ may represent -$L^1$-N($X^1$)$_2$ or -$L^1$-$L^2$-$L^3$-$C_{1-6}$ alkyl in which said $C_{1-6}$ alkyl is substituted by two $X^2$ groups. In another preferred embodiment, $R^{10b}$ represents $-C_{1-4}$ alkylene-N($X^1$)$_2$ or $-C_{1-4}$ alkylene-$L^2$-$C_{1-6}$ alkyl in which said $C_{1-6}$ alkyl is substituted by two $X^2$ groups (optionally in which $L^2$ represents $-NH-$, $-NHC(O)-$, or $-NHC(O)O$). In the above-mentioned embodiments, $X^1$ preferably represents a $C_{1-4}$ alkyl group optionally substituted by one or more $X^2$ substituents. Also in such embodiments (including also those in which $X^1$ represents a $C_{1-4}$ alkyl group optionally substituted by one or more $X^2$ substituents), $X^2$ preferably represents a 4- to 6-membered heterocyclyl group (such as pyridine, piperidine, pyrrole or pyrrolidine) or, more preferably, represents $-NH_2$, $-OH$, $-NHC(O)NH_2$, $-NHC(S)NH_2$, or $-NHC(=NH)NH_2$.

In embodiments in which $R^2$ and $R^3$ are not linked, $R^2$ may preferably represent the side chain of an amino acid selected from the list consisting of threonine, cysteine, serine, or lysine; more preferably the side chain of threonine or cysteine; and most preferably the side chain of cysteine. In such embodiments, both $R^2$ and $R^3$ represents $-CH_2-SH$.

Preferred groups represented by Q include $-OC(O)-$, $-C(O)O-$, $-NHC(O)-$, $-C(O)NH-$ or $-S-S-$.

In embodiments in which $R^2$ and $R^3$ are linked, preferably the alkylene groups in the linking group are linear $C_{1-4}$ alkylene groups, which may be the same or different and are optionally substituted with one or more substituents selected from the group consisting of $-OH$, $-SH$, $-SC_{1-4}$ alkyl, —OC$_{1-4}$ alkyl —NH$_2$, —COOH, —C(O)—NH$_2$, —COOC$_{1-4}$ alkyl and a C$_{1-4}$ alkyl group, which latter group (i.e. the C$_{1-4}$ alkyl group) is optionally substituted with one or more substituents selected from the list consisting of —OH, —SH, —SC$_{1-4}$ alkyl, —NH$_2$, —COOH, —C(O)—NH$_2$, —COOC$_{1-4}$ alkyl and phenyl.

In further embodiments, the alkylene groups in the linking group are optionally substituted by one or more substituents selected from the group consisting of —OH, —SH, —SMe, —OMe, —OEt, —NH$_2$, —COOH, —C(O)—NH$_2$, —COOMe, COOEt, and a C$_{1-4}$ alkyl group, which latter group (i.e. the C$_{1-4}$ alkyl group) is optionally substituted with one or more substituents selected from the list consisting of —OH, —SH, —SMe, —NH$_2$, —COOH, —C(O)—NH$_2$ and —COOMe, —COOEt.

In a further embodiment, the alkylene groups in the linking group (i.e. the linking group formed when R$^2$ and R$^3$ are linked) are optionally substituted by C$_{1-4}$ alkyl groups.

In a particular embodiment, the alkylene groups in the linking group are C$_{1-4}$ alkylene groups, optionally substituted by one or more methyl groups.

In a further embodiment, there is provided a compound of formula IB, wherein the linking group is —CH$_2$-Q-CH$_2$—.

In a particular embodiment Q represents —S—S—.

In a further embodiment, there is provided a compound of the invention, wherein when R$^2$ and R$^3$ are linked, the linking group is selected from the group consisting of:

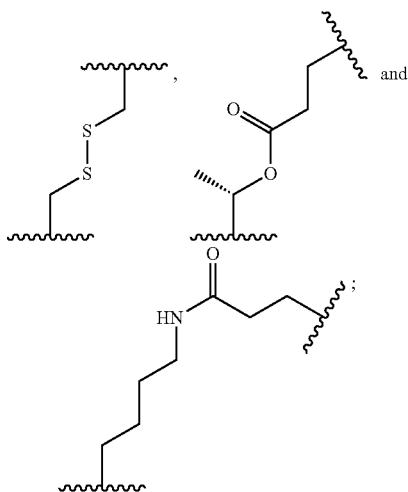

wherein the wavy line at the bottom of each structure indicates the point of attachment to the carbon atom at R$^2$ and the wavy line at the top of the structure indicates the point of attachment to the carbon atom at R$^3$.

In a further embodiment there is provided a compound of the invention, wherein the cyclic structure comprising the linking group formed by the linkage of R$^2$ and R$^3$ is a 14- to 18-membered ring, for example a 14- to 16-membered ring and preferably a 14-membered ring.

By "[number]-membered ring" (e.g. 16-membered ring), we mean a cyclic structure containing the specified number of ring-constituting atoms, i.e. a ring in which said number represents the number of skeleton atoms forming said ring.

In embodiments of the invention in which the compound is a compound of formula IB, AA$^1$ may represent an L- or D-phenylalanine residue;
AA$^2$ may represent an L- or D-isoleucine residue;
AA$^3$ may represent an L- or D-serine residue;
AA$^4$ may represent an L- or D-glutamine residue;
AA$^5$ may represent an L-, L-allo-, D- or D-allo-isoleucine residue;
AA$^6$ may represent an L- or D-isoleucine residue; and/or
AA$^7$ may represent an L- or D-serine residue.

In a preferred embodiment, there is provided a compound of formula IB, wherein:

AA$^1$ represents a D-phenylalanine residue;
AA$^2$ represents an L-isoleucine residue;
AA$^3$ represents an L-serine residue;
AA$^4$ represents a D-glutamine residue;
AA$^5$ represents a D-allo-isoleucine residue;
AA$^6$ represents an L-isoleucine residue; and
AA$^7$ represents an L-serine residue.

In still further preferred embodiments of compounds of formulae IA, IB and IC, AA$^2$ represents an L-isoleucine residue, AA$^5$ represents a D-allo-isoleucine or D-isoleucine residue, AA$^6$ represents an L-isoleucine residue, AA$^7$ represents an L-serine residue, AA$^1$ represents a hydrophobic amino acid, and AA$^3$ and AA$^4$ each independently represent a hydrophobic amino acid, a polar non-charged amino acid, a positively charged amino acid, diaminopropanoic acid, diaminobutanoic acid or ornithine (optionally wherein AA$^3$ represents an L-serine residue and/or AA$^4$ represents a D-glutamine residue), and:

(i) R$^{10a}$ represents a fragment of formula -L$^1$-L$^2$-L$^3$-X$^1$ in which each X$^1$ is independently selected from the group consisting of —C(O)—C$_{1-12}$ alkyl, —C(O)—NH$_2$, —C(S)—NH$_2$, a fragment of formula Q, and a C$_{1-12}$ alkyl group substituted by one or more X$^2$ substituents; and R$^{10b}$ represents the side chain of arginine, lysine, histidine or allo-enduracididine, a —C$_{1-6}$ alkyl-NH$_2$ group, a —C$_{1-6}$ alkyl-NH—C(=NH)—NH$_2$ group, or a fragment of formula R$^{10a}$;

(ii) R$^{10a}$ represents a fragment of formula -L$^1$-L$^2$-L$^3$-X$^1$ in which each X$^1$ represents either a fragment of formula Q, or a C$_{1-6}$ (e.g. C$_{1-3}$) alkyl group substituted by one or more (e.g. 2) X$^2$ substituents, optionally wherein each X$^2$ independently represents —NH$_2$, —OH, —NHC(O)NH$_2$, —NHC(S)NH$_2$, —NHC(=NH)NH$_2$; and R$^{10b}$ represents the side chain of arginine or lysine, a —C$_{1-3}$ alkyl-NH$_2$ group, a —C$_{2-4}$ alkyl-NH—C(=NH)—NH$_2$ group, or a fragment of formula R$^{10a}$; or (iii) R$^{10a}$ represents either of the structures shown below:

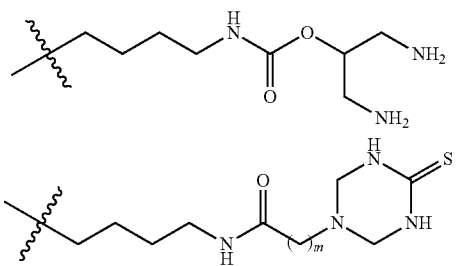

wherein m represents from 1 to 6, and R$^{10b}$ represents the side chain of arginine or either of the structures shown above.

In these and other embodiments, it is preferred that Z represents —O— and it is most preferred that R$^1$, R$^8$, R$^{9a}$, R$^{9b}$ and R$^{9c}$ each represent methyl, and R$^{11a}$ and R$^{11c}$ represent the side chain of isoleucine.

Preferred compounds of formula IC are those in which:

(SEQ ID NO: 1)

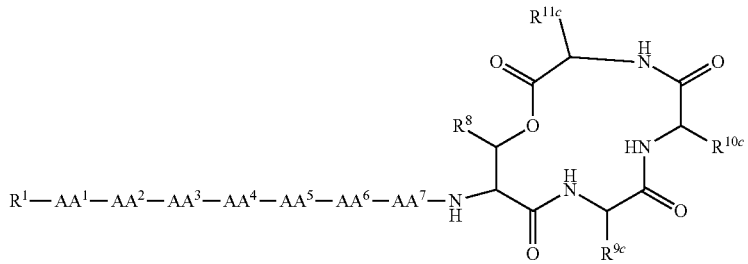

(IC)

$R^1$ represents H, $C_{1-6}$ alkyl, $C_{1-6}$ acyl, benzyl or benzoyl;
$AA^1$ to $AA^7$ each independently represents an amino acid or a —NH—CH($R^0$)—C(O)— group;
$R^8$ represents hydrogen or $C_{1-4}$ alkyl;
$R^{9c}$ represent $R^c$ or an amino acid side chain;
$R^{10c}$ represents an amino acid side chain (e.g. a side chain of arginine or lysine) or a L-allo-enduracididine group;
$R^{11c}$ represents $R^c$ or an amino acid side chain; and
$R^c$ represents a fragment of formula -$L^1$-$L^2$-$L^3$-$X^1$ as defined above;
provided that at least one of $AA^1$ to $AA^7$, $R^{9c}$ and $R^{11c}$ contains a group represented by $R^c$. Preferably only one of $AA^1$ to $AA^7$, $R^{9c}$ and $R^{11c}$ contains a group represented by $R^c$.

It has been found that structural changes can be made at the $AA^3$ and $AA^4$ groups of Teixobactin without significantly reducing the antibacterial efficacy of the resulting compound. Thus, preferred positions at which the mandatory $R^c$ substituent may be located are $R^{9c}$ and $R^{11c}$, and particularly $AA^3$ and $AA^4$.

Particular compounds of formula IC that may be mentioned include those in which:
(i) $R^c$ is a fragment of formula -$L^1$-$L^2$-$L^3$-$X^1$ which contains a fragment of formula Q or at least two terminal guanidinyl, urea, thiourea, amino and/or hydroxyl groups (e.g. at least two $X^2$ groups);
(ii) $R^c$ is a fragment of formula -$L^1$-$L^2$-$L^3$-$X^1$ in which $X^1$ represents either a fragment of formula Q, or a $C_{1-6}$ (e.g. $C_{1-3}$) alkyl group substituted by at least two $X^2$ substituents; or
(iii) $R^c$ is a fragment of formula -$L^1$-$L^2$-$L^3$-$X^1$ in which $X^1$ represents a $C_{1-6}$ (e.g. $C_{1-3}$) alkyl group substituted by at least two substituents selected from the group consisting of —$NH_2$, —OH, —NHC(O)$NH_2$, —NHC(S)$NH_2$ and —NHC(=NH)$NH_2$.

In embodiments (i) to (iii) above, particularly preferred compounds are those in which:
$L^1$ represents a linear or branched $C_{1-4}$ alkylene linker;
$L^2$ is selected from the group consisting of —O—, —N($X^a$)—, —[N($X^a$)$_2$]$^+$—, —C(O)—, —OC(O)—, —C(O)O—, —NHC(O)—, —C(O)N($X^a$)—, —OC(O)N($X^a$)—, —NHC(O)O—, or —NHC(O)N($X^a$)—;
$X^a$ represents hydrogen or -$L^3$-$X^1$; and
$L^3$ represents a direct bond.

It is most preferred that the compound of formula IA, IB or IC is not covalently bonded to a delivery agent. However, according to an alternative embodiment, a compound of the invention is covalently bound to a delivery agent which is a fragment of formula II:

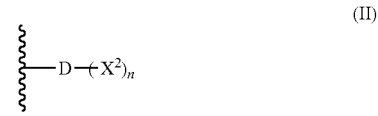

(II)

wherein D represents a dendrimer fragment to which the $X^2$ groups shown are attached, $X^2$ represents —$NH_2$, boronic acid or a boronic acid derivative; and n is 2 or more (e.g. from 2 to 20); and wherein the wavy line indicates the point of attachment to the compound of formula IA, IB or IC.

By "delivery agent" we mean any substance which facilitates the binding of an antibacterial agent to a portion of a bacterial cell (preferably in the region of the bacterial cell wall), and which can thereby anchor the antibacterial agent in the vicinity of the biological target (e.g. an enzyme that is important for cellular activity).

Unless otherwise stated, terms such as "binding", "bound", etc., refer to the interaction between molecules or chemical structures which serve to hold those molecules or chemical structures in close proximity to one another. In the context of the present invention, the term "binding", unless otherwise stated, particularly refers to the binding that occurs as a result of interactions between permanent dipoles or more preferably as a result of hydrogen bonding between the molecular structures involved.

By the phrase "hydrophilic portion which is capable of binding to one or more structures", we include a molecular fragment which is more soluble in water or other polar solvents (e.g. protic solvents such as alcohols) than in oil or other hydrophobic solvents (e.g. hydrocarbons). The phrase specifically includes any structure which is capable of binding to one or more structures in bacterial cell membranes by way of one or more hydrogen bonds and/or electrostatic interactions (i.e. ionic bonds).

Delivery Agents

Particular delivery agents that may be mentioned include those which are capable of binding to one or more structures on a bacterial cell membrane via the formation of one or more covalent bonds with said structures, via the formation of one or more hydrogen bonds with said structures, or through electrostatic interactions between oppositely charged regions on the delivery agent and the bacterial cell membrane (i.e. a form of ionic bonding). In particular embodiments, the delivery agents are able to bind to the bacterial cell membrane via one or more such covalent bonds, a plurality of hydrogen bonds and/or a plurality of such electrostatic interactions. For example, the delivery agent moiety may be capable of forming 1, 2, 3, 4, 5, 6, 7, 8, 9 or more separate covalent bonds or hydrogen bonds with said structures, thereby greatly enhancing the extent to which the delivery agent is anchored to the cell wall. Delivery agents which are capable of forming at least 4, at least 6, or at least 8 of such linkages (particularly hydrogen bonding linkages) are preferred.

Covalent bonds between the delivery agent and the one or more structures on the bacterial cell membrane may be formed, for example, where the delivery agent comprises a boronic acid component or a pharmaceutically-acceptable salt thereof. Where such boronic acids or boronic acid derivatives are present, covalent bonding may occur between the boron atoms of the delivery agent and 1,2- and 1,3-diol groups within the saccharides on the surface of the bacterial cell.

Hydrogen bonds between the delivery agent and the one or more structures on the bacterial cell membrane may be formed through interactions of the delivery agent with saccharides on the surface of the bacterial cell, and particularly with other structures such as phosphate groups or sulphate groups in the lipopolysaccharides or phospholipids of the cell membrane. Functional groups that are capable of participating in hydrogen bonding are well known to the skilled person. Particular functional groups that may be mentioned in this respect include primary amines, amidines (including guanidines) and amides (including ureas), as well as pharmaceutically-acceptable salts thereof. Still further particular functional groups that should be mentioned include primary amines, amidines, guanidines, amides and ureas (and pharmaceutically-acceptable salts thereof).

In embodiments in which the delivery agent binds to the bacterial cell wall by way of one or more electrostatic interactions (optionally in combination with one or more hydrogen bonding interactions), the delivery agent may carry a plurality of positively charged regions. Such positively charged regions are able to interact with the negatively charged phosphate groups that are present in the phospholipids and lipopolysaccharides of the cell membranes. The positively charged regions on the delivery agent may be present due to the delivery agent molecule being provided in the form of a salt, or the delivery agent may exist as a zwitterion under physiological conditions. Accordingly, positive charges may be present as a result of the reaction of a free base form of the delivery agent with an acid to form an acid addition salt. Particular delivery agents that may be mentioned include those which contain a plurality (e.g. at least 4, at least 6, or at least 8 charged regions) of such charged regions.

Particular delivery agents that may be mentioned therefore include those which comprise one or more functional groups selected from the list consisting of boronic acids, boronic acid derivatives, primary amines, guanidines, and pharmaceutically-acceptable acid addition salts thereof. For example, the delivery agent may comprise one or more functional groups selected from the list consisting of boronic acids, boronic acid derivatives, primary amines, guanidines, and pharmaceutically-acceptable acid addition salts thereof, and when the delivery agent is a compound of formula II, $X^2$ may represent a boronic acid group, a boronic acid derivative, a primary amine, a guanidine, or a pharmaceutically-acceptable acid addition salt of any such groups.

Where the delivery agent comprises one or more primary amine groups, it is preferred that the delivery agent is provided as an acid addition salt (thus containing one or more $—NH_3^+$ groups). Particular delivery agents that may be mentioned in this respect include delivery agents which are not covalently bonded to the antibacterial agent, and which comprise a polypeptide or a polypeptide derivative, or a pharmaceutically-acceptable salt thereof.

In other embodiments of the invention, the delivery agent comprises a plurality of said functional groups, particularly where the functional groups are intended to interact with the cell membrane via electrostatic or hydrogen bonding interactions. For example, the delivery agent may comprise 2, 3, 4, 5, 6, 7, 8, 9 or more of said functional groups. Delivery agents which comprise larger numbers of such functional groups are believed to be capable of binding more strongly to the structures in the bacterial cell wall, and thereby improve the antibacterial properties of a compound of formula IA, IB or IC.

In a particular embodiment of the invention, the functional groups are independently selected from the list consisting of boronic acids, boronic acid derivatives, primary amines, amidines, guanidines, amides, ureas, and acid addition salts thereof.

In certain embodiments, the delivery agent comprises a dendrimer-like structure. For example, compounds of formula IA, IB or IC contain a delivery agent of formula II comprising a dendrimer fragment at the position denoted as D. The term "dendrimer" is well known in the art, and refers to structures containing a branching, tree-like architecture. Preferably, such dendrimer structures are generally acyclic (e.g. they do not contain any cyclic structures having more than 6 members (i.e. the largest ring structures that may be present in the dendrimers are 6-membered rings such as phenyl groups)) or the dendrimer structure may be completely acyclic. A preferred delivery agent is an organic molecule (or a salt thereof) containing a dendrimer fragment (i.e. a fragment containing multiple, tree-like branches), and each of the branches of that dendrimer fragment may be linked to a relevant functional group. Thus, a single delivery agent may contain a plurality of functional groups capable of binding to a bacterial cell membrane via covalent bonds, hydrogen bonds and/or electrostatic interactions along the lines described above.

Particular delivery agents that may be mentioned include those which contain a dendrimer fragment. For example, delivery agents that may be mentioned include those of formula III:

(III)

or a pharmaceutically-acceptable salt thereof, wherein $D^1$ represents a dendrimer fragment to which the $NH_2$ groups shown above are attached; and n1 is 2 or more (e.g. from 2 to 20), and wherein the wavy line indicates the point of attachment to the compound of formula IA, IB or IC.

Other delivery agents that may be mentioned include those of formula IV and V:

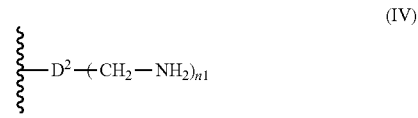

(IV)

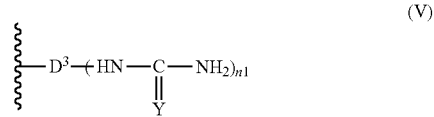

(V)

or a pharmaceutically-acceptable salt thereof, wherein $D^2$ and $D^3$ each represent a dendrimer fragment to which the groups shown in parentheses are attached; Y represents O, NH or S; and each n1 is 2 or more (e.g. from 2 to 20), wherein the wavy line indicates the point of attachment to the compound of formula IA, IB or IC.

Further delivery agents that may be mentioned include those of formulae VI to VIII:

(VI)
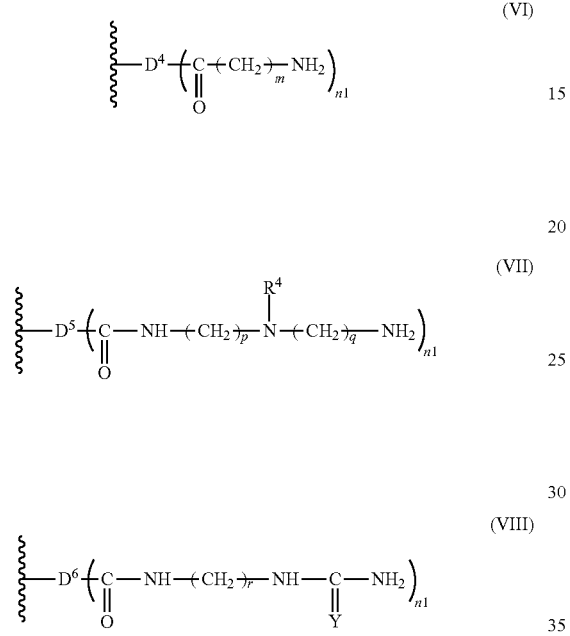
(VII)

(VIII)

wherein each of $D^4$ to $D^6$ represents a dendrimer fragment to which the groups shown in parentheses are attached; Y represents O, NH or S; each n1 is 2 or more (e.g. from 2 to 20); m, p, q and r each independently represent from 1 to 8 (e.g. from 1 to 6); $R^4$ represents a $C_{1-6}$ alkyl group, and wherein the wavy line indicates the point of attachment to the compound of formula IA, IB or IC.

Dendrimer fragments $D^1$ to $D^6$ may be polyglycerol-based structures or may be dendron-based structures. Particular dendrimer fragments that $D^1$ to $D^6$ (preferably $D^4$ to $D^6$) may represent include those of formulae A to E:

A
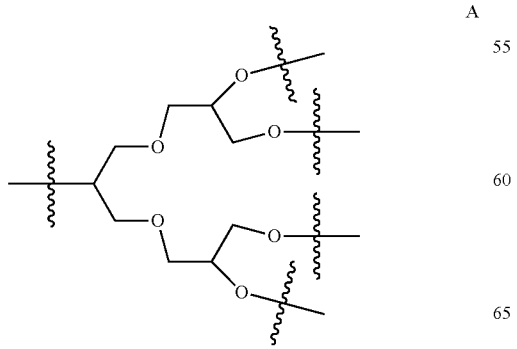

B
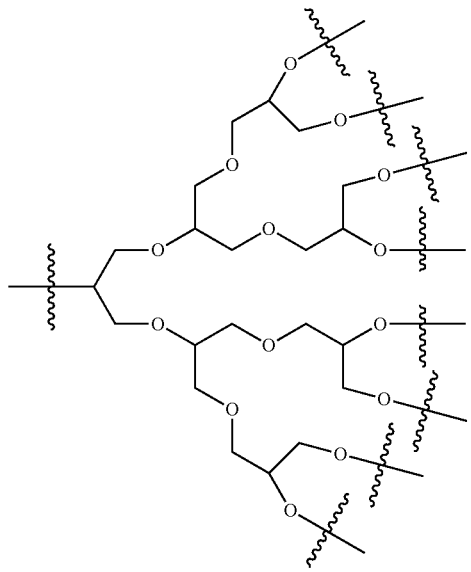

C
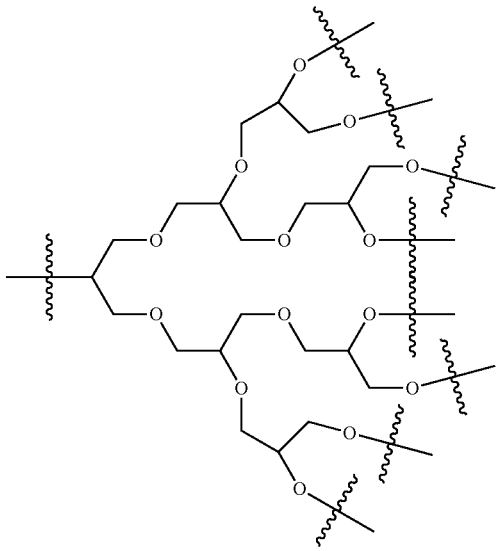

D
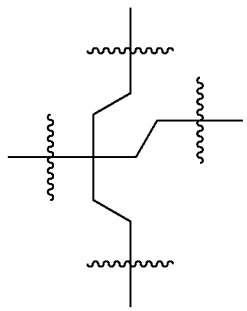

E

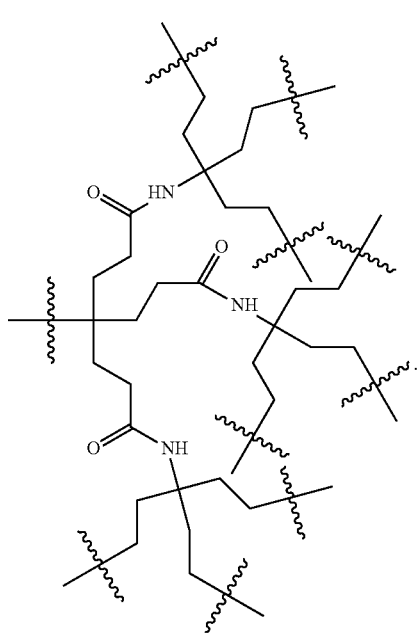

For each of the dendrimers of formulae A to E, the single wavy line on the left-hand side of the structures as shown corresponds to the point of attachment to the compound of formula IA, IB or IC. The remaining wavy lines indicate the points of attachment of the plurality of amine-, X- or boronic acid-containing portions of the delivery agent (i.e. the bracketed portions in formulae I to VIII).

In fragments of formulae III to V, particular dendrimer fragments that $D^1$ to $D^3$ may represent include those of formulae A to E as defined above wherein the dendrimer fragments are linked to the plurality of amine-containing portions of the delivery agent (i.e. the bracketed portions in formulae III to V) by way of direct bonds or, preferably, additional linker groups. Additional linker groups that may be mentioned in this respect include ester linkages (i.e. —C(O)—O—), amide linkages (i.e. —C(O)—NH—), sulfonamide linkages (i.e. —S(O)$_2$—NH—), ether linkages (i.e. —O—), amine linkages (i.e. —N(R$^x$)— in which R$^x$ represents hydrogen or a $C_{1-6}$ alkyl group), a $C_{1-12}$ (e.g. $C_{1-6}$) alkylene linkage, or a plurality of such linkages in combination. In compounds of formulae III to V which contain multiple such additional linker groups, the additional linker groups may be the same or different.

Particular preferred delivery agents include:
(i) fragments of formula VI in which $D^4$ represents a dendrimer fragment of any one of formula A to E (particularly formula C);
(ii) fragments of formula VII in which $D^5$ represents a dendrimer fragment of any one of formula A to E (particularly formula A or B);
(iii) fragments of formula VIII in which $D^6$ represents a dendrimer fragment of any one of formula A to E (particularly formula D or E).

Other dendrimer structures will be known to the skilled person. For example, various dendrimers that are known to the skilled person include those disclosed in J. Mater. Chem. B, 2012, 2, 2153-2167. The disclosures in that document show that such dendrimer compounds may have low toxicities.

Other delivery agents that may be mentioned include those of formulae IXa, IXb, and X:

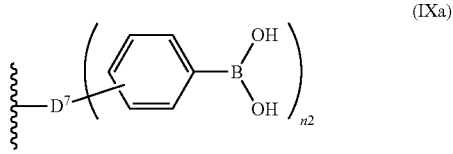

(IXa)

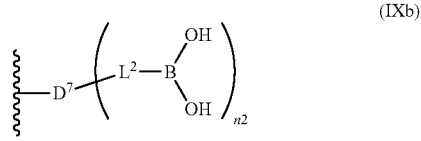

(IXb)

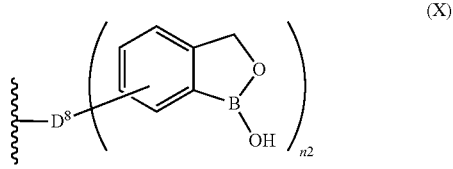

(X)

wherein $L_2$ represents an aliphatic linker (e.g. a $C_{1-6}$ alkyl chain); $D^7$ and $D^8$ independently represent a direct bond or a dendrimer fragment to which the boron-containing groups shown are attached; n2 is 1 or more (e.g. from 2 to 20); and optionally wherein $D^7$ and $D^8$ are attached to the boronic acid portions of the compound of formula IXa and X, or boric acid portions of the compound of formula IXb, via a linker group; and wherein the wavy line indicates the point of attachment to the compound of formula IA, IB or IC.

In embodiments of compounds of formula IA, IB or IC containing delivery agent fragments of formula IXa, IXb or X, the dendrimer fragments that are represented by $D^7$ and $D^8$ may be polyglycerol-based structures or dendron-based structures as defined above in respect of dendrimer fragments $D^1$ to $D^6$. Similarly, particular dendrimer fragments that $D^7$ and $D^8$ may represent include those of formulae A to E as defined above.

In compounds of formula IA, IB or IC containing delivery agent fragments of formula IXa, IXb or X, the linker group that may be present in the delivery agent may comprise one or more groups selected from the list comprising $C_{1-10}$ alkyl, —NH—, —O—, —C(O)—O—, and —C(O)—NH— (wherein the amide and ester linkers may each be attached in either of the two possible orientations). For example, the linker group may be a —(CH$_2$)$_2$—NH—(CH$_2$)$_8$—C(O)—NH— group.

Particular delivery agents that may be mentioned include those which contain a dendrimer fragment. That is, particular delivery agents that may be mentioned include fragments of formulae III, IXa, IXb and X, or pharmaceutically-acceptable salts thereof (e.g. fragments of formulae IV, V, IXa, IXb and X or pharmaceutically-acceptable salts thereof, or most preferably fragments of formulae VI, VII, VIII, IXa, IXb and X or pharmaceutically-acceptable salts thereof).

The delivery agent may also comprise a polypeptide or a polypeptide derivative, or a pharmaceutically-acceptable salt thereof. It is preferred (though not essential) that, when the delivery agent is a polypeptide or polypeptide derivative, or a pharmaceutically-acceptable salt thereof, then the polypeptide contains at least two residues selected from the group consisting of arginine and lysine. The amino acid residues may be provided in their naturally occurring stereochemical configuration (e.g. the L-configuration), or the alternative stereochemical configuration. It is preferred that the amino acid residues are provided in their naturally occurring stereochemical configuration.

In embodiments in which the delivery agent is a polypeptide, a polypeptide derivative or a pharmaceutically-acceptable salt thereof (e.g. a polypeptide, or a pharmaceutically-acceptable salt thereof), preferably the polypeptide contains at most 20 (e.g. no more than 15) amino acid residues. Particular polypeptides that may be mentioned include acyclic polypeptides (e.g. acyclic polypeptides containing at most 20 amino acid residues). For example, polypeptides of particular interest include those which contain at least four, at least six or at least eight arginine or lysine residues. In all cases, the amino acids that form the polypeptides that may be used in the delivery agents may be in either the D or L forms.

Other polypeptides and polypeptide derivatives of particular interest include compounds containing a sequence of at most 20 (e.g. between 5 and 15) amino acid residues. Polypeptide derivatives include polypeptide compounds which contain non-peptide moieties at one or both ends of the peptide chain. Alternatively or additionally, polypeptide derivatives include polypeptide compounds in which one or more of the amino acids is optionally provided in a chemically modified form. Examples of such modifications include replacing one or more —NH₂ groups on side chains on said amino acids (e.g. the side chains of lysine or arginine) with amides and derivatives thereof (e.g. amides, ureas, thioamides or thioureas).

In a further embodiment, the polypeptide derivative may consist of from one to six amino acids selected from the group consisting of arginine and lysine, optionally together with a suitable linker to bond the polypeptide derivative to the antibacterial compound of formula IA, IB or IC. Polypeptides and polypeptide derivatives which contain higher positive charge have been found to have increased effectiveness in enhancing the antibacterial potential (i.e. reducing the minimum inhibitory concentration) of existing antibacterial agents when the two agents are provided in combination. Therefore, in a preferred embodiment, the polypeptide or polypeptide derivative is a polypeptide-containing compound that bears a positive charge of at least 3 units. Particularly preferred embodiments include those in which the polypeptide or polypeptide derivative is a polypeptide-containing compound that bears a positive charge of at least 5 (e.g. at least 6) units.

The positive charge may be nominally determined by counting the number of lysine and arginine amino acids that are present in the polypeptide (each such amino acid providing one unit of positive charge). Other amino acids having side chains that are positively charged may also be mentioned in this respect.

An example of a polypeptide delivery agent that may be mentioned is:

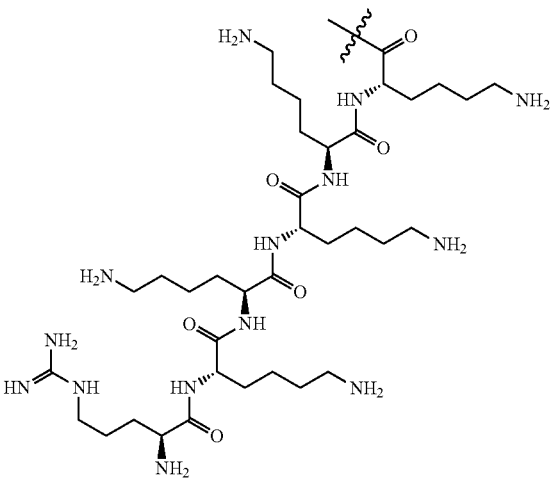 [SMILES: *C(=O)[C@H](CCCCN)NC(=O)[C@H](CCCCN)NC(=O)[C@H](CCCCN)NC(=O)[C@H](CCCCN)NC(=O)[C@H](CCCCN)NC(=O)[C@@H](N)CCCNC(=N)N]

In a further embodiment, there is provided a compound of the invention, wherein R¹ represents a delivery agent of formula II to X as hereinabove defined.

In a further embodiment, the compound of the invention is selected from the group consisting of:

(SEQ ID NO: 9)

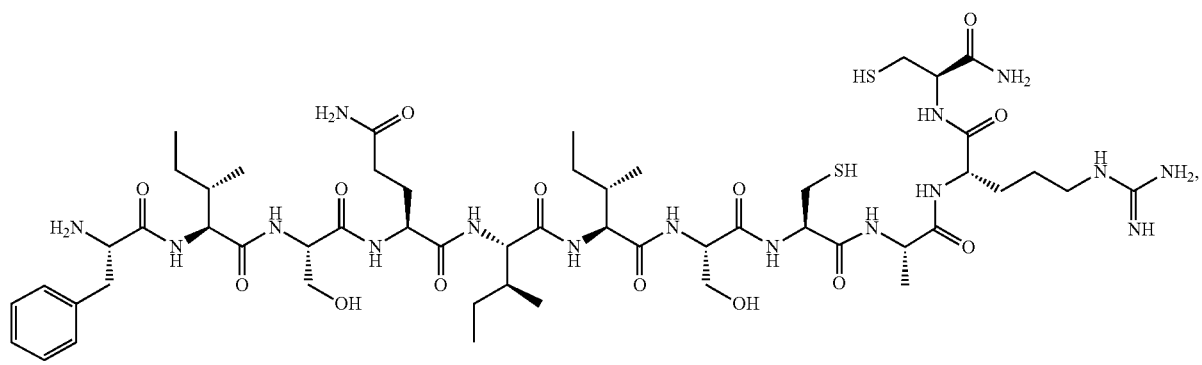

(SEQ ID NO: 9)
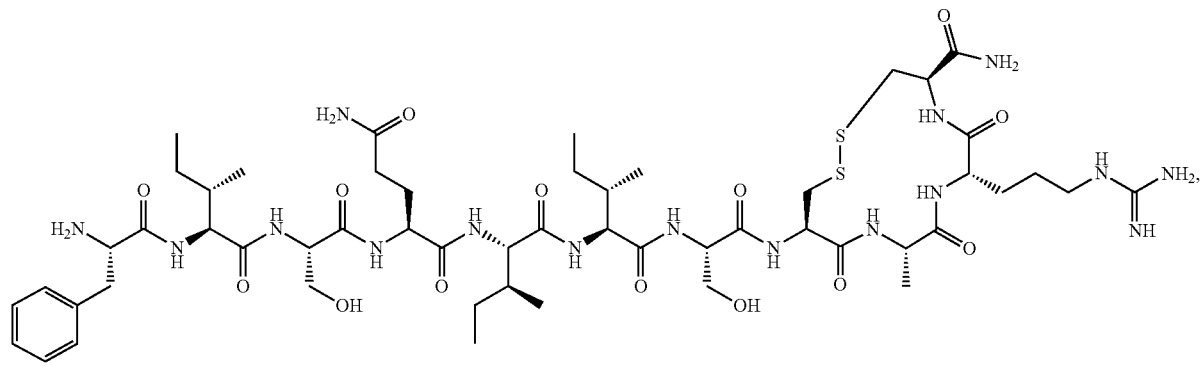
(SEQ ID NO: 9)
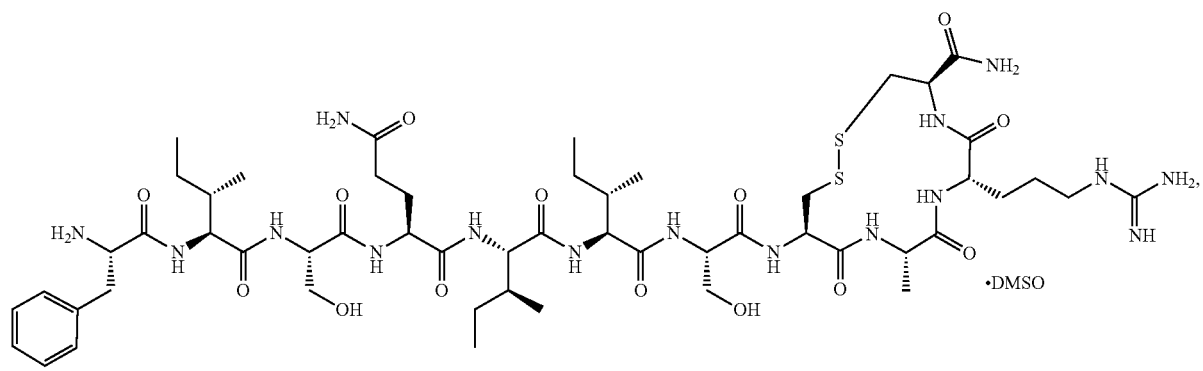
(SEQ ID NO: 10)
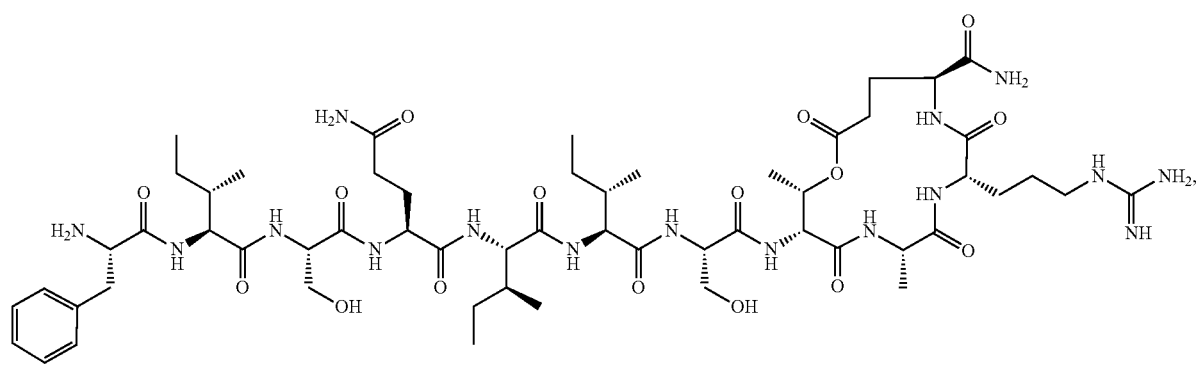
(SEQ ID NO: 10)
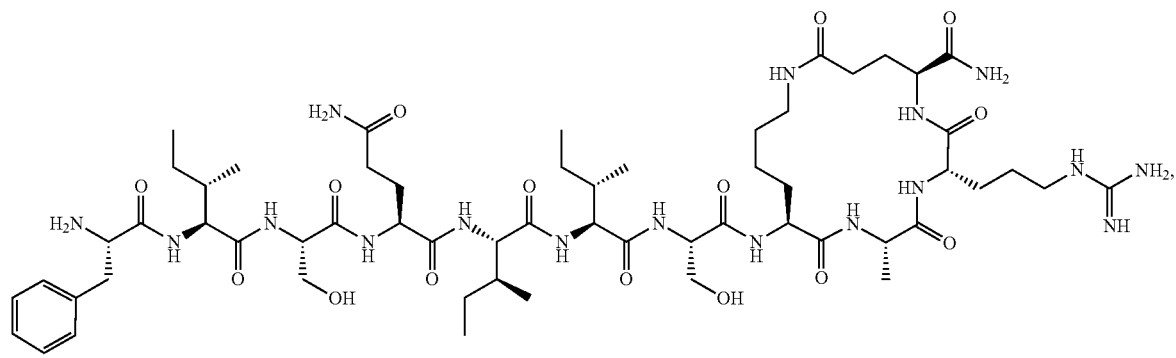

(SEQ ID NO: 11)
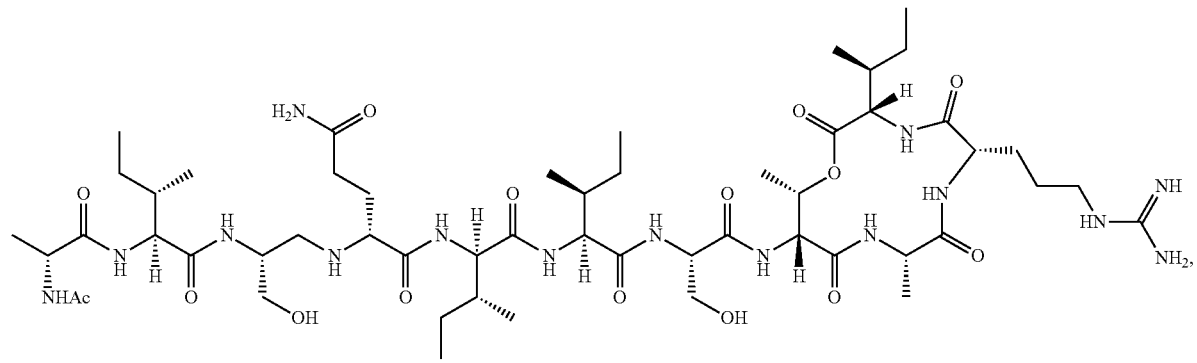
(SEQ ID NO: 12)
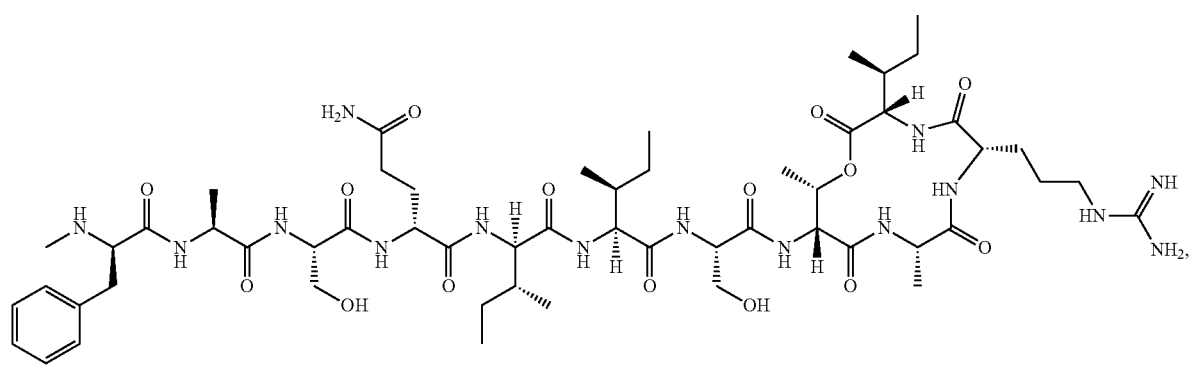
(SEQ ID NO: 13)
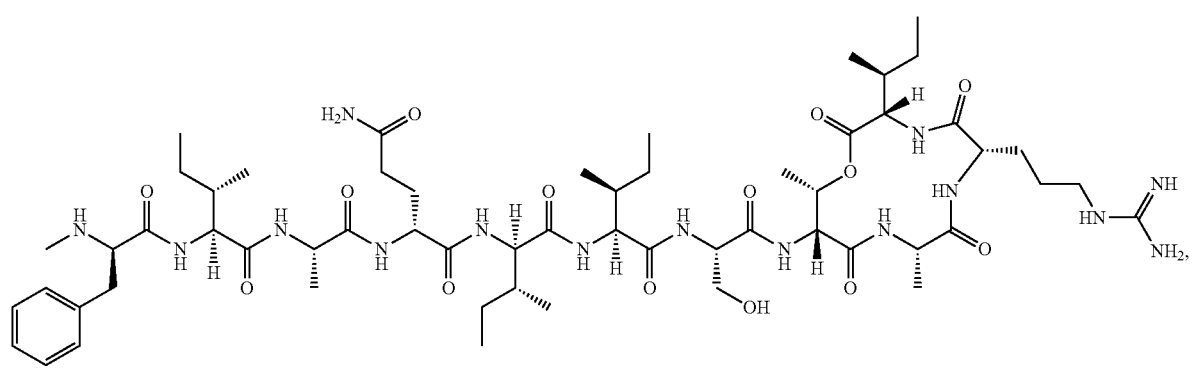
(SEQ ID NO: 14)
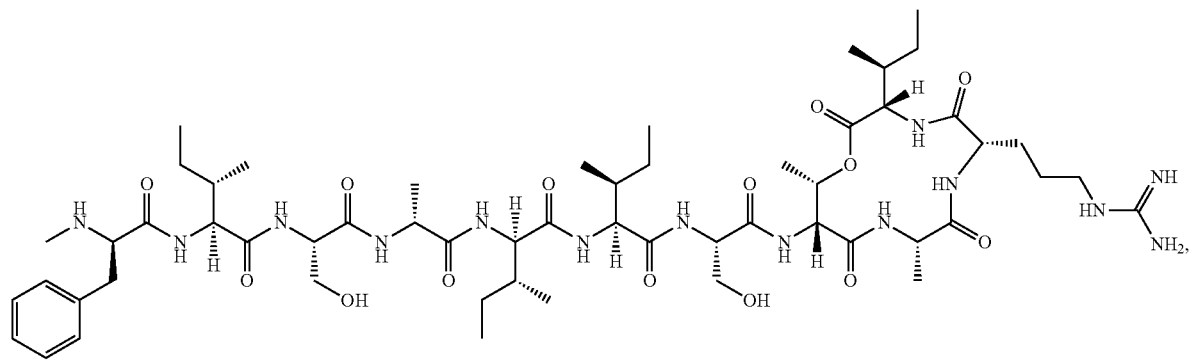

(SEQ ID NO: 15)
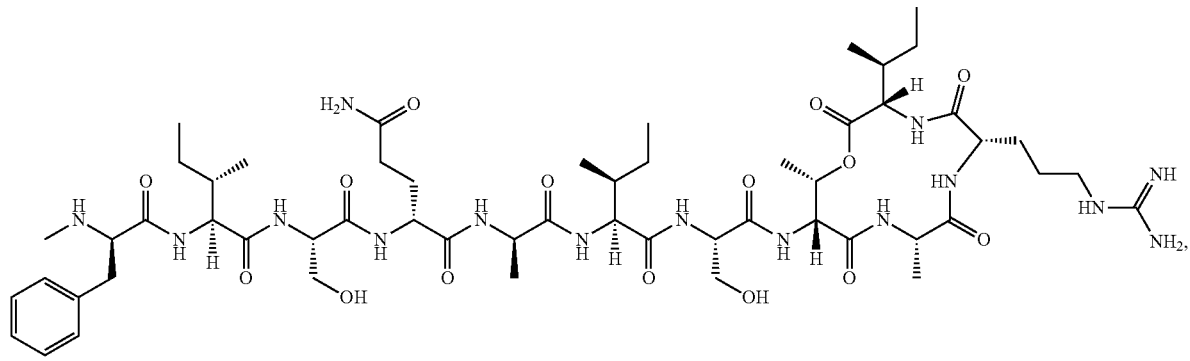
(SEQ ID NO: 16)
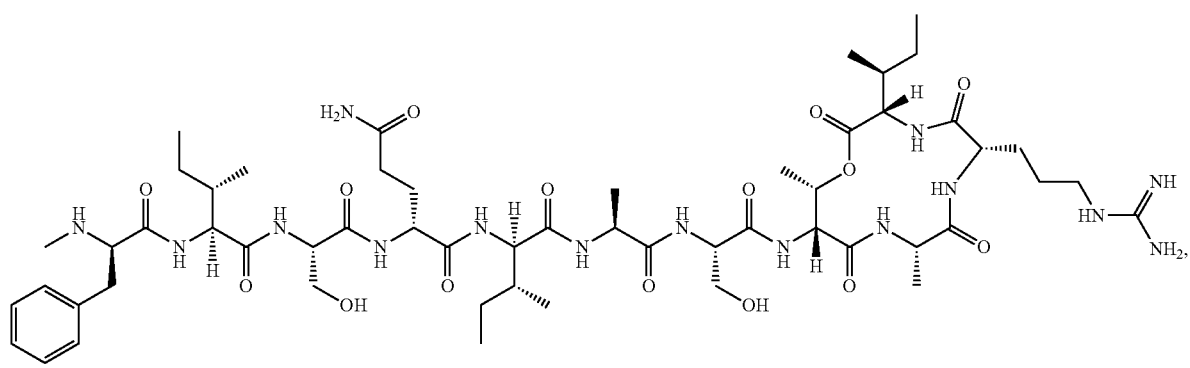
(SEQ ID NO: 10)
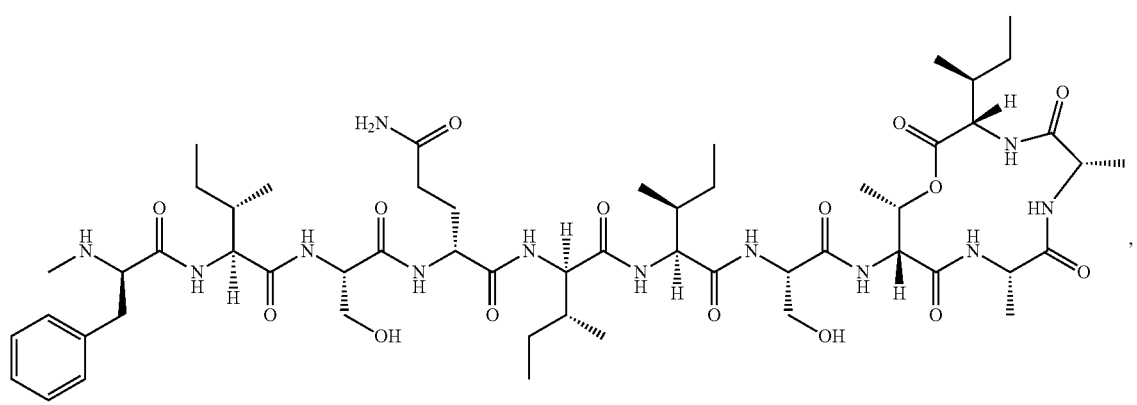
(SEQ ID NO: 10)
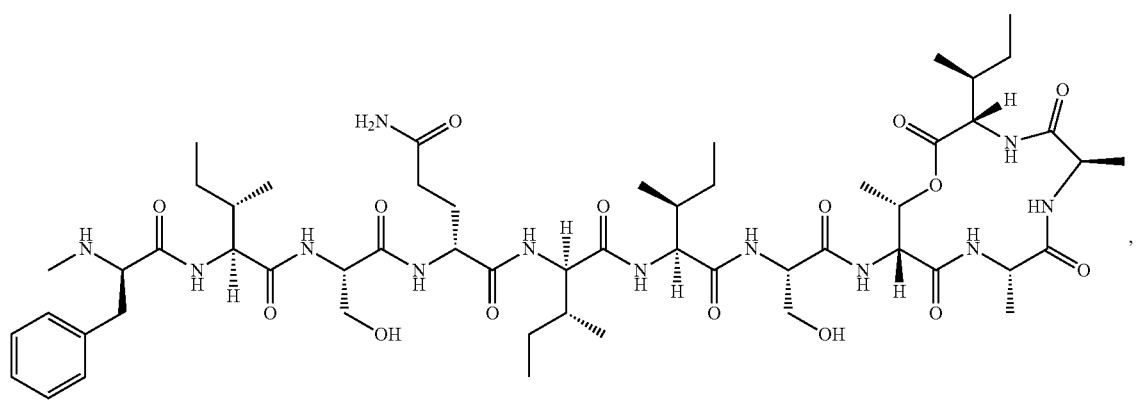

-continued
(SEQ ID NO: 10)
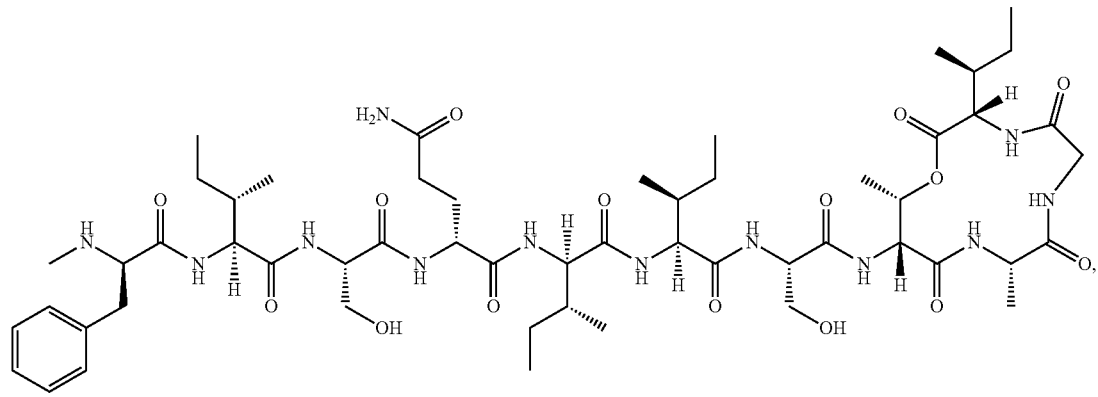
(SEQ ID NO: 10)
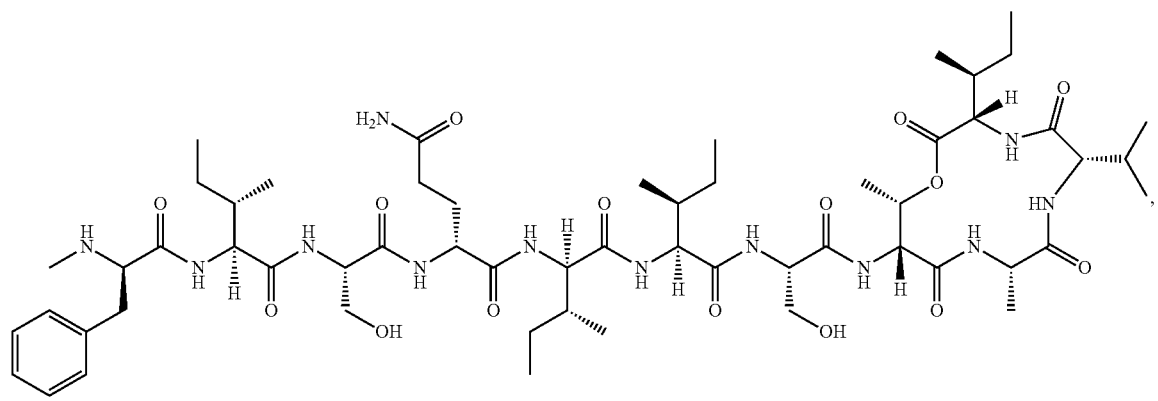
(SEQ ID NO: 10)
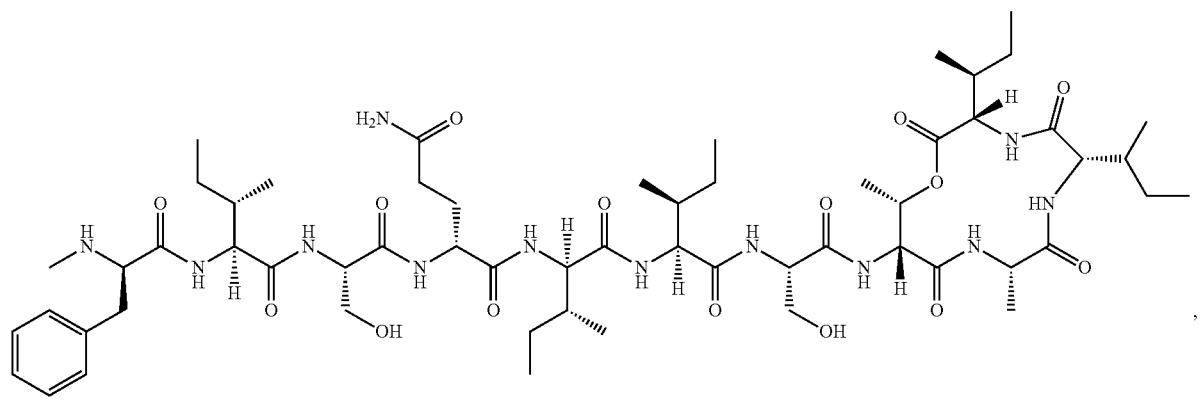

(SEQ ID NO: 10)
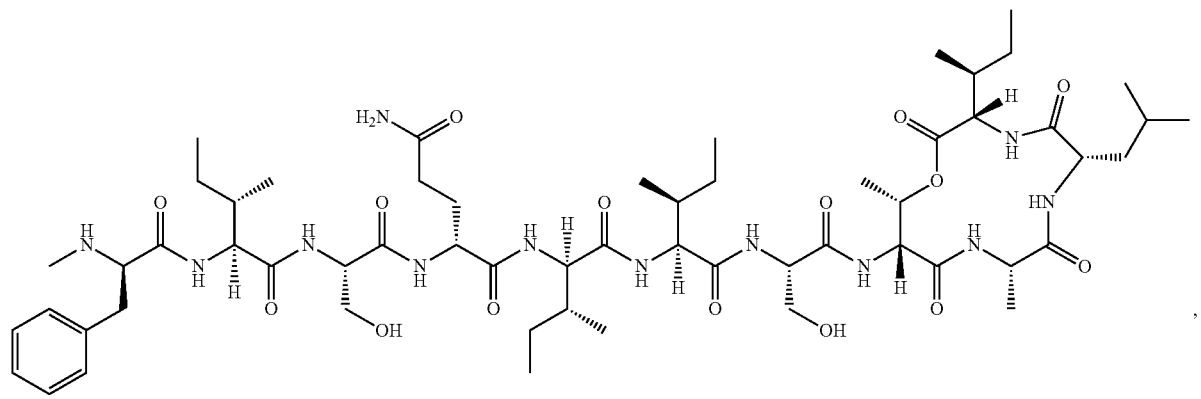
(SEQ ID NO: 10)
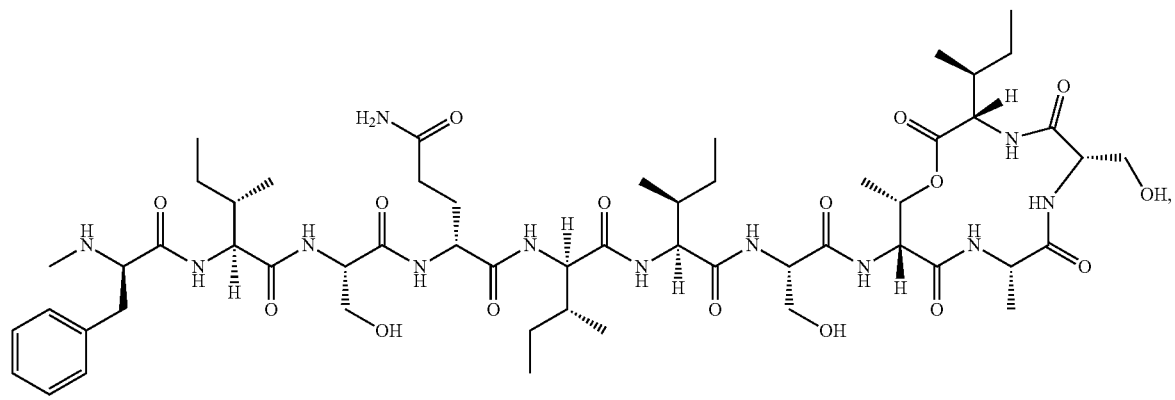
(SEQ ID NO: 10)
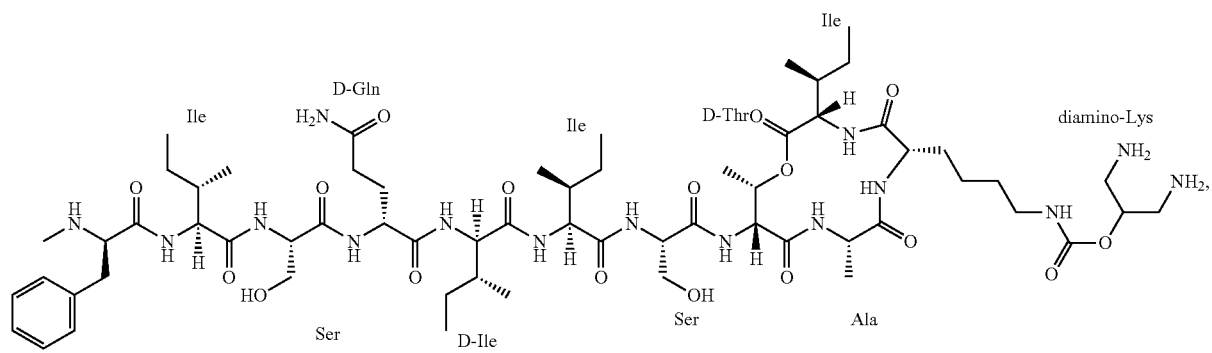
(SEQ ID NO: 10)
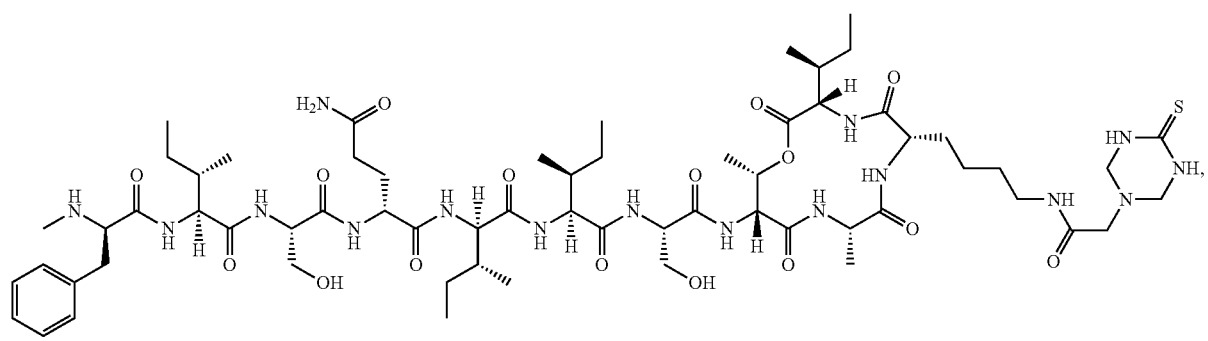

(SEQ ID NO: 10)
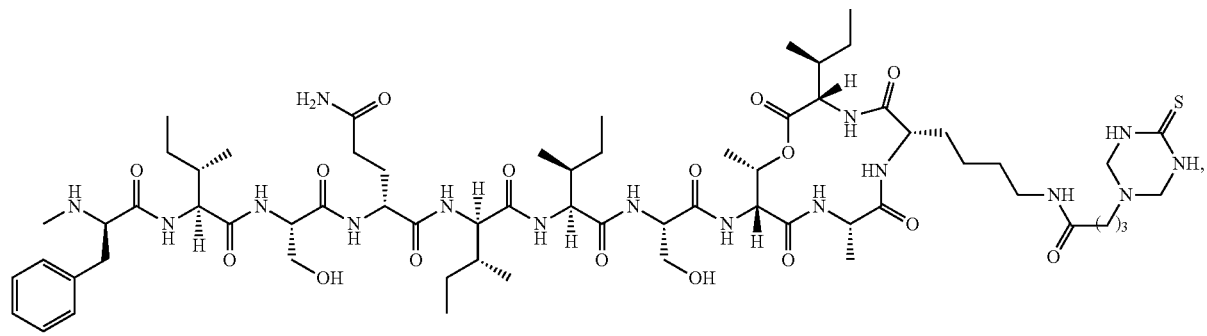
(SEQ ID NO: 10)
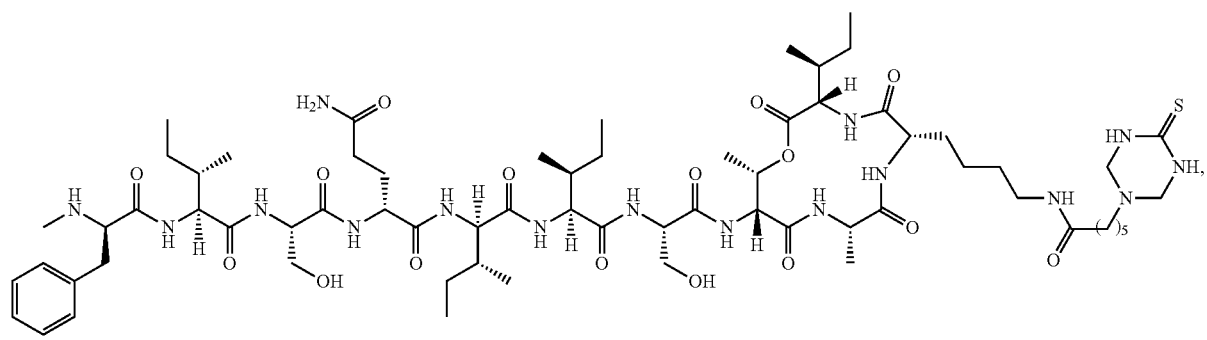
(SEQ ID NO: 18)
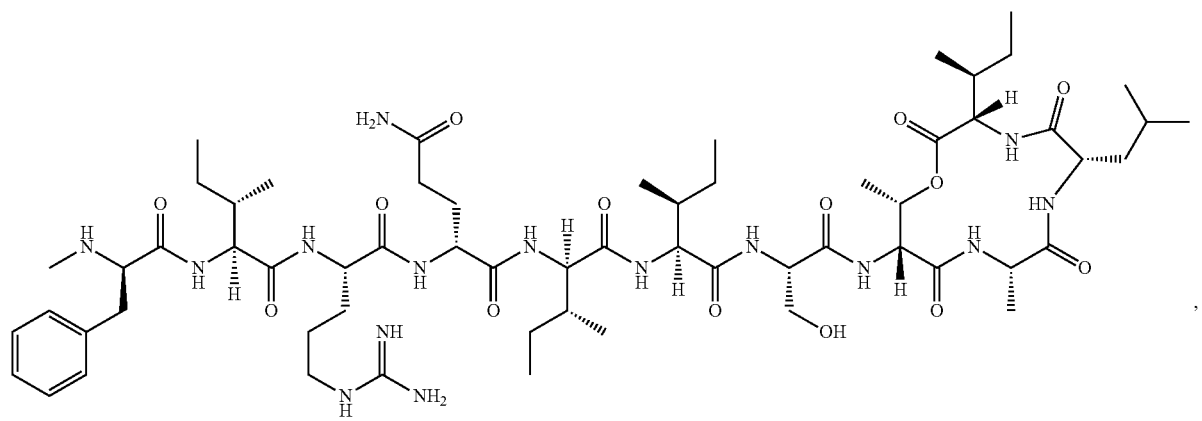
(SEQ ID NO: 19)
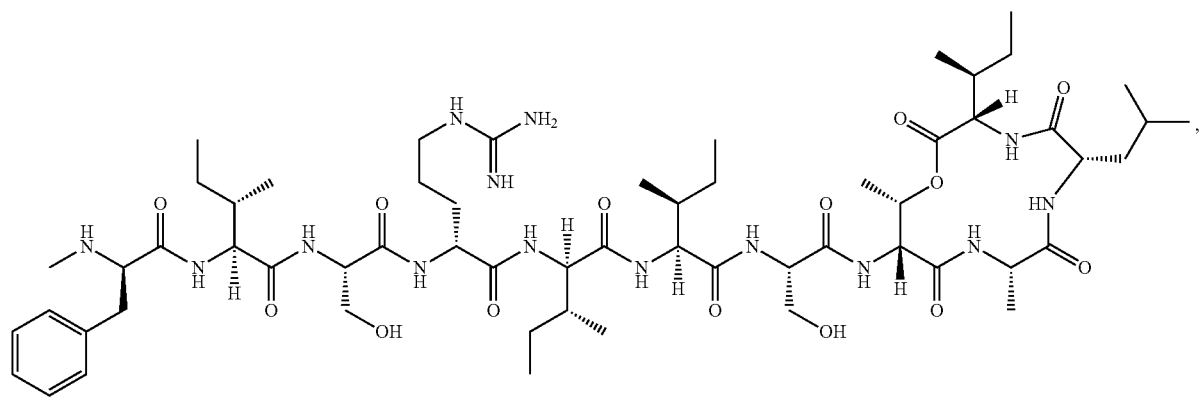

(SEQ ID NO: 10)
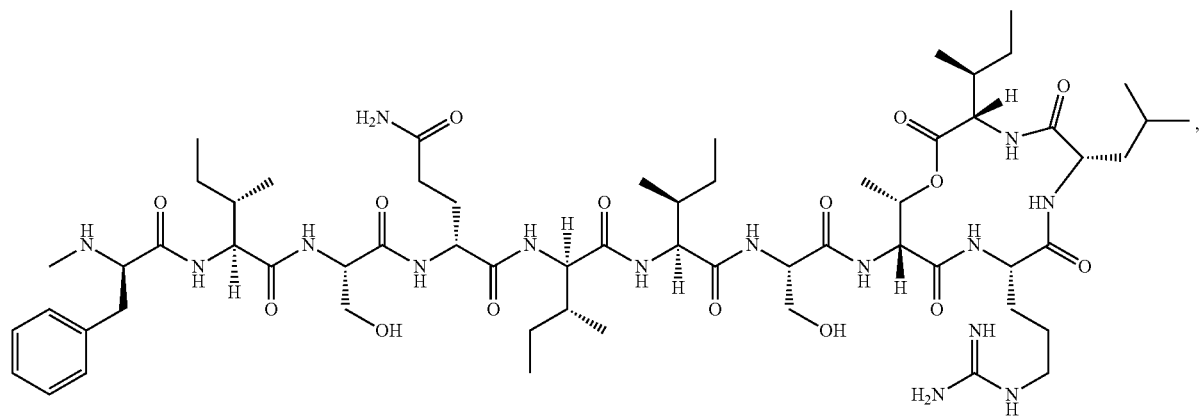
(SEQ ID NO: 20)
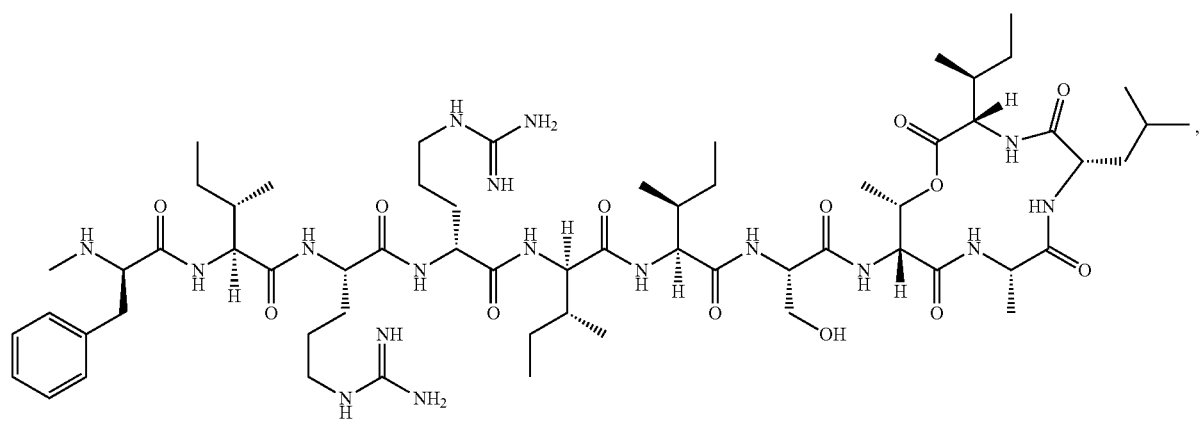
(SEQ ID NO: 21)
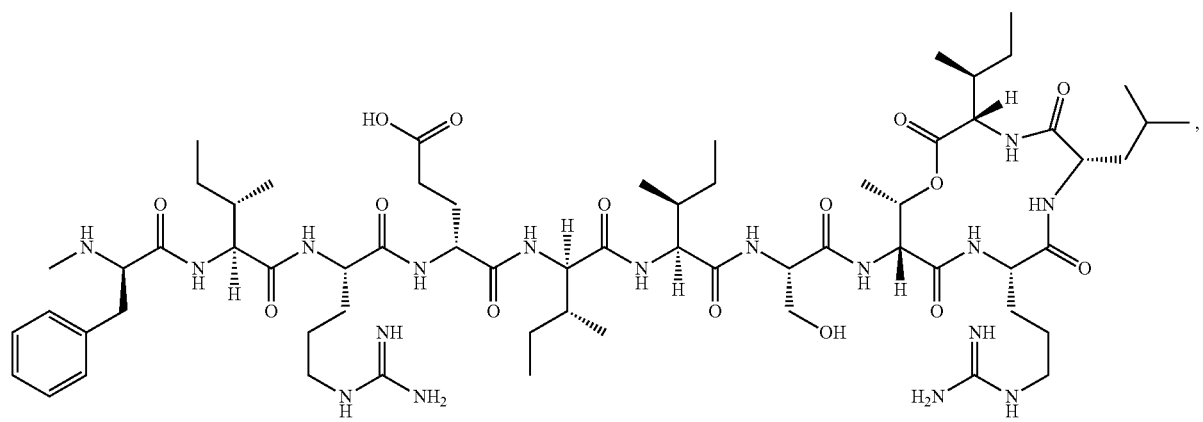

-continued
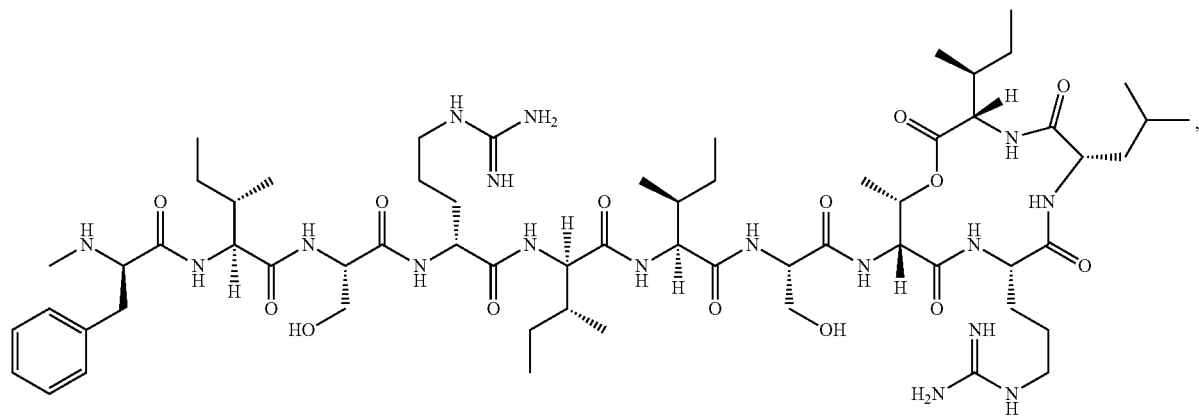
(SEQ ID NO: 19)
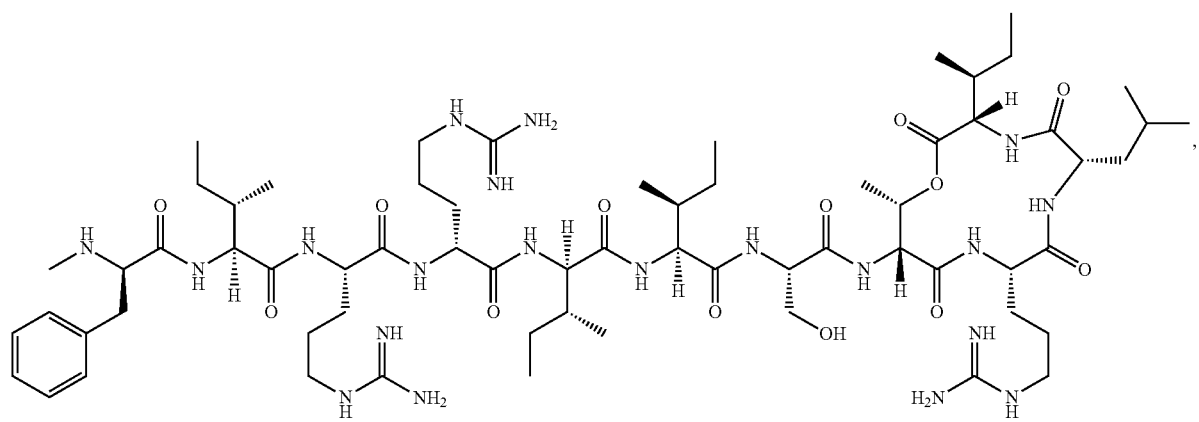
(SEQ ID NO: 20)
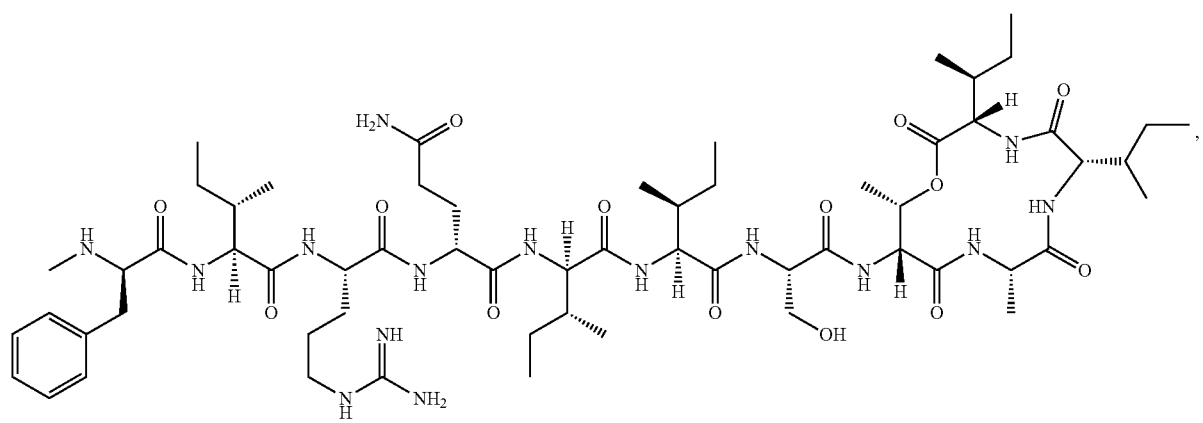
(SEQ ID NO: 18)

(SEQ ID NO: 19)
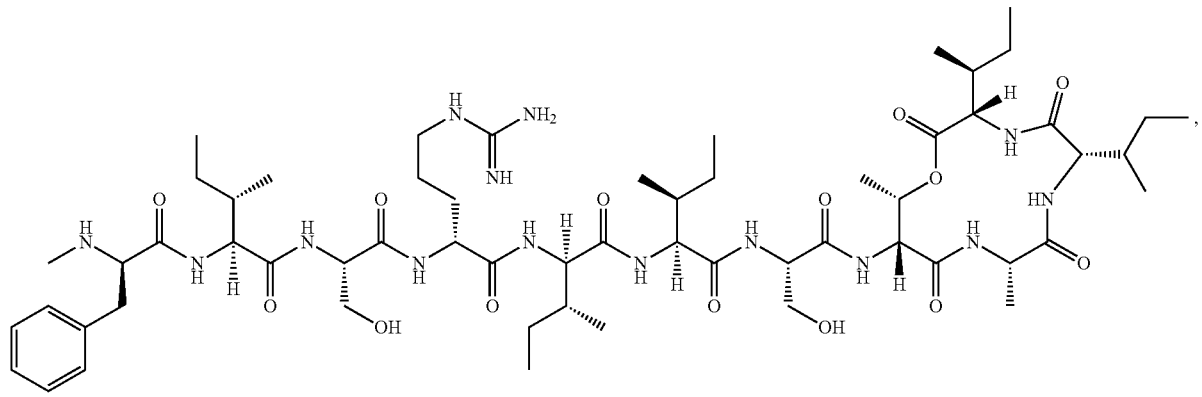
(SEQ ID NO: 10)
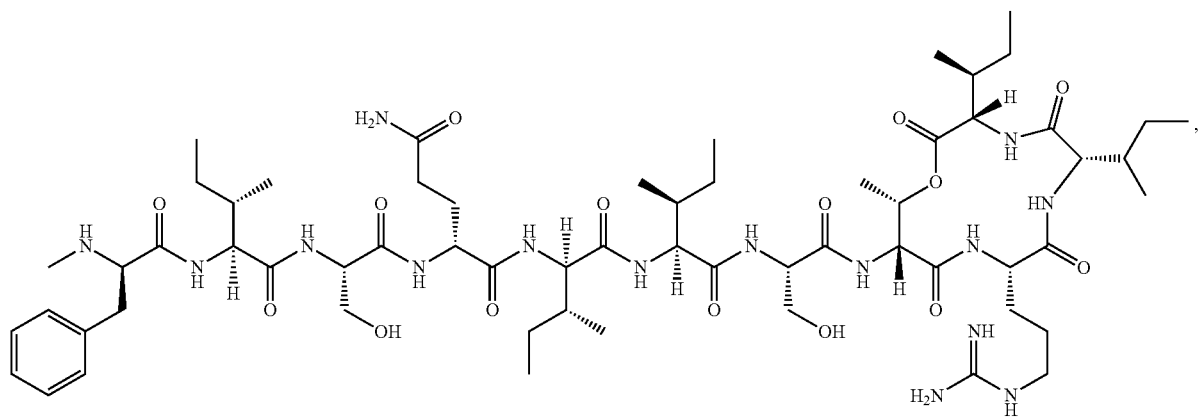
(SEQ ID NO: 20)
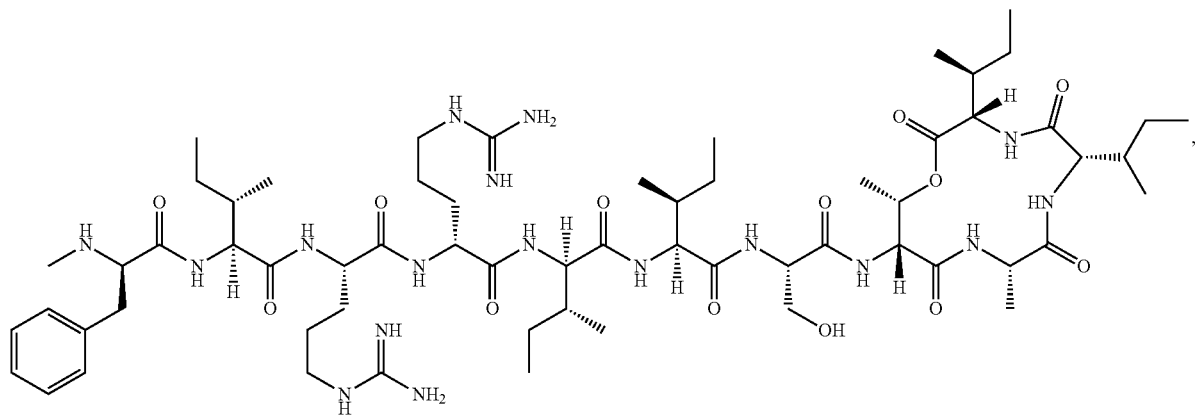

(SEQ ID NO: 10)
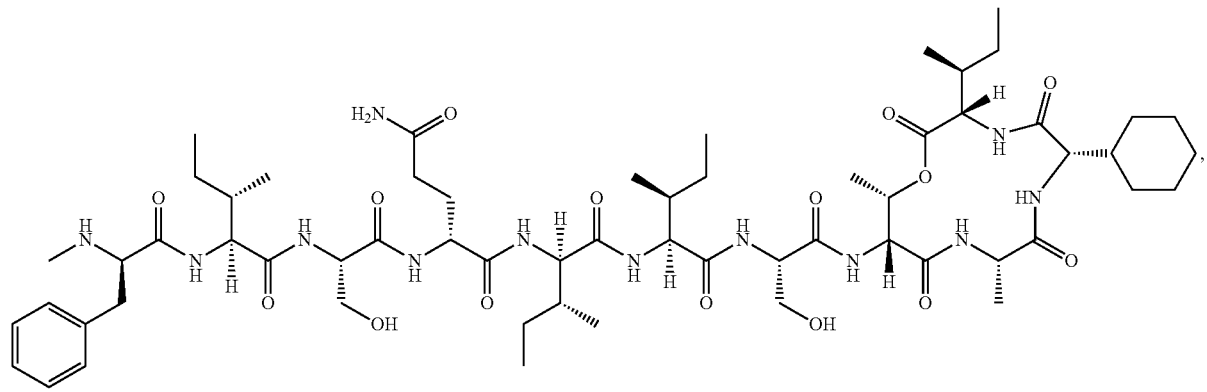
(SEQ ID NO: 18)
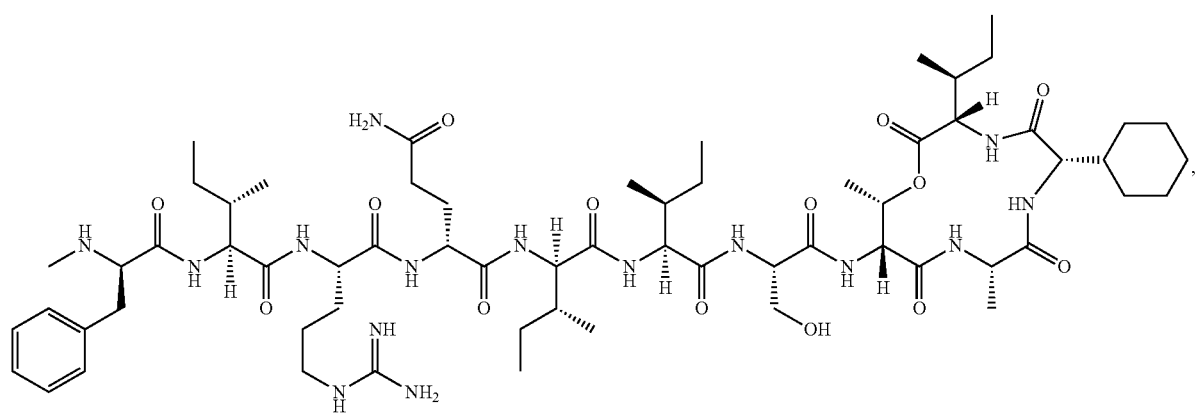
(SEQ ID NO: 19)
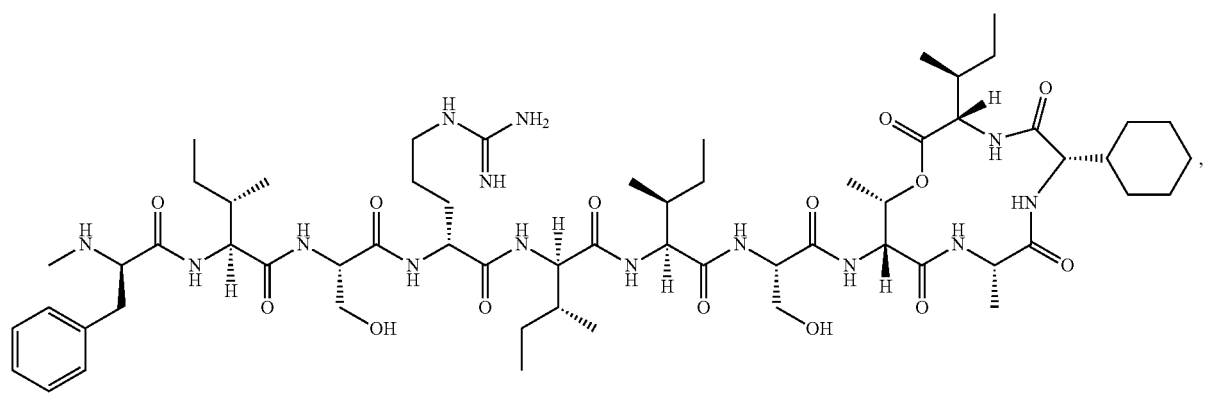

(SEQ ID NO: 10)
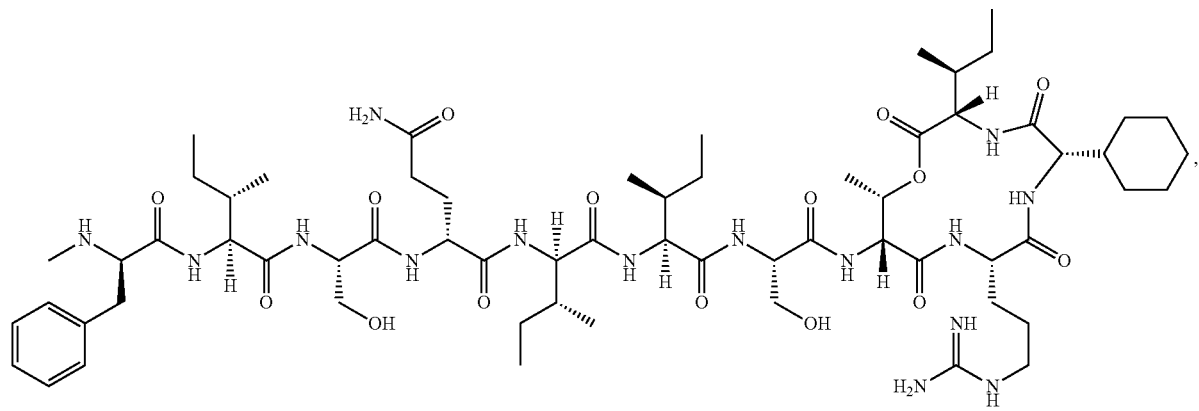
(SEQ ID NO: 20)
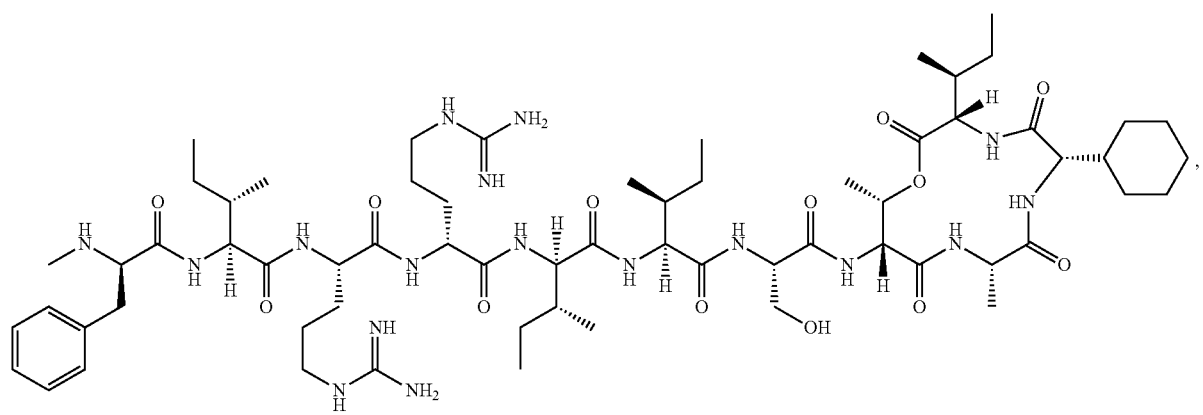
(SEQ ID NO: 21)
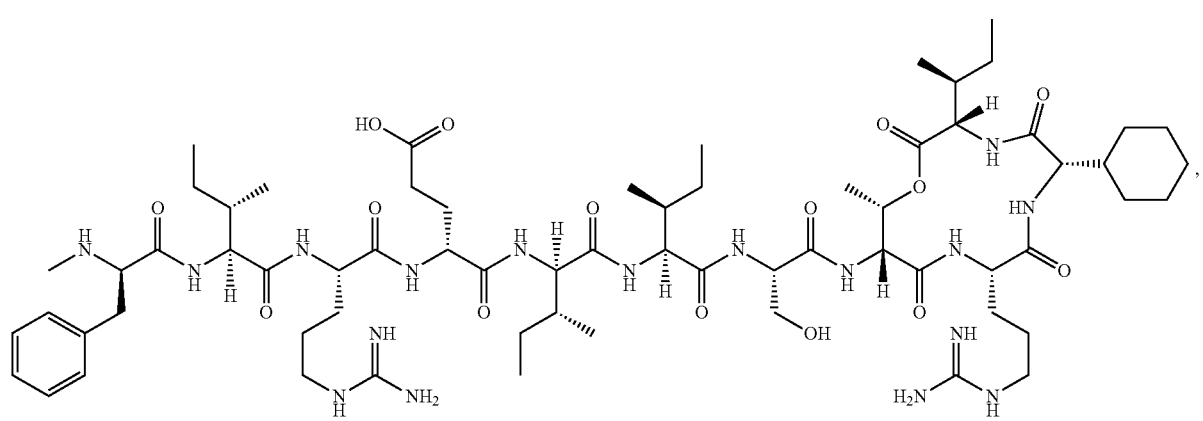

(SEQ ID NO: 19)
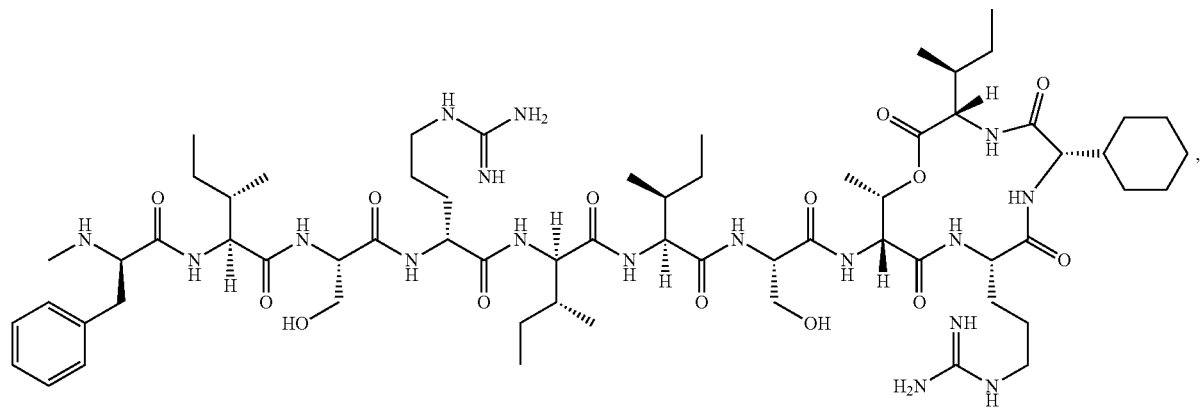
(SEQ ID NO: 20)
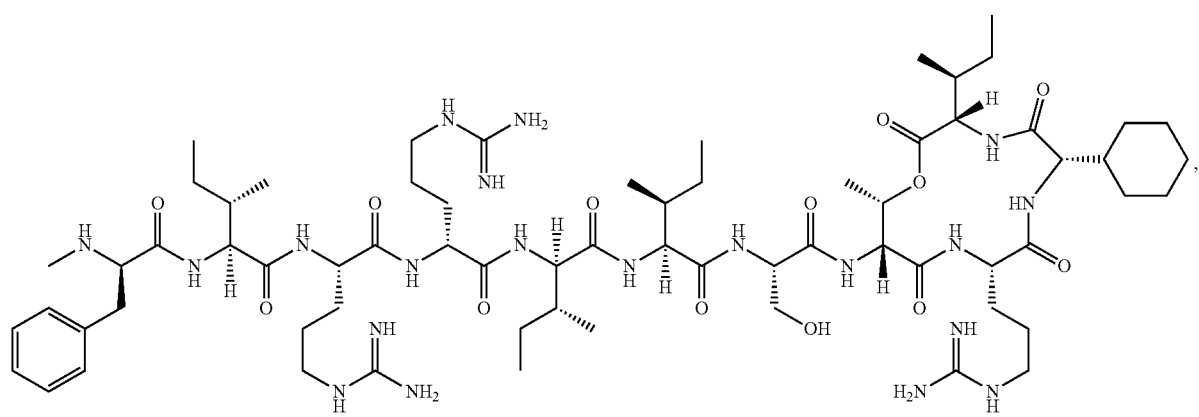
(SEQ ID NO: 10)
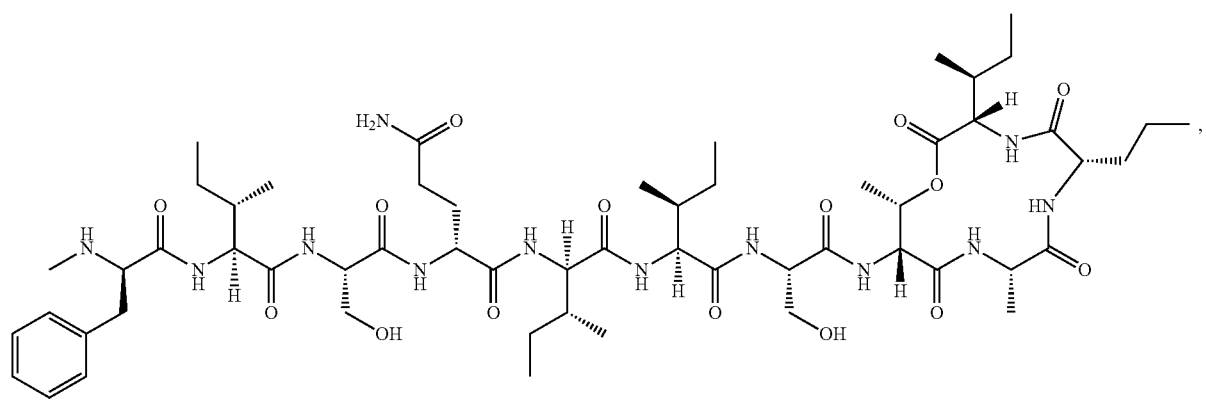

(SEQ ID NO: 18)
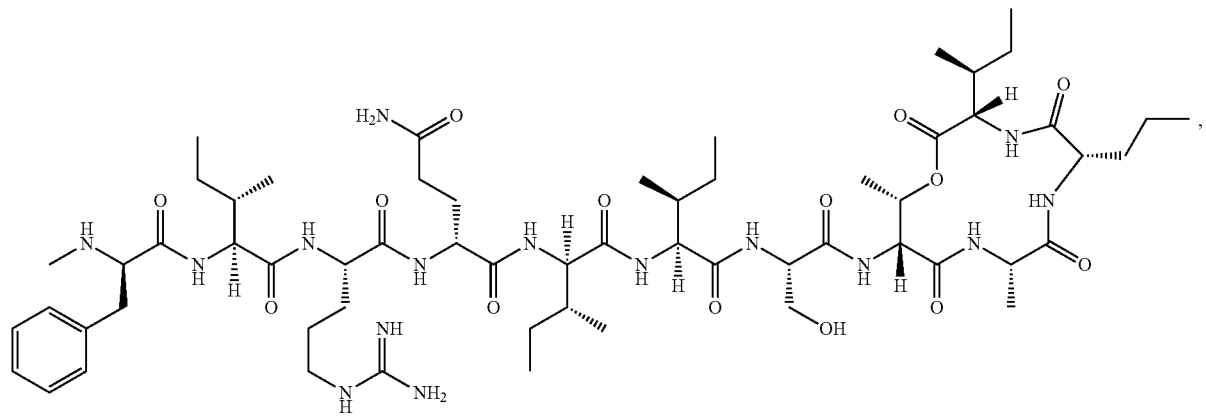
(SEQ ID NO: 19)
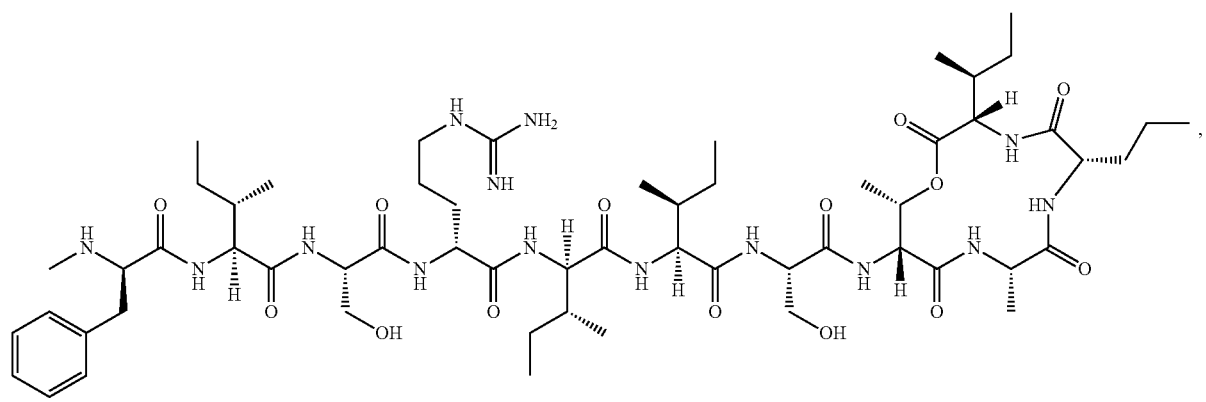
(SEQ ID NO: 10)
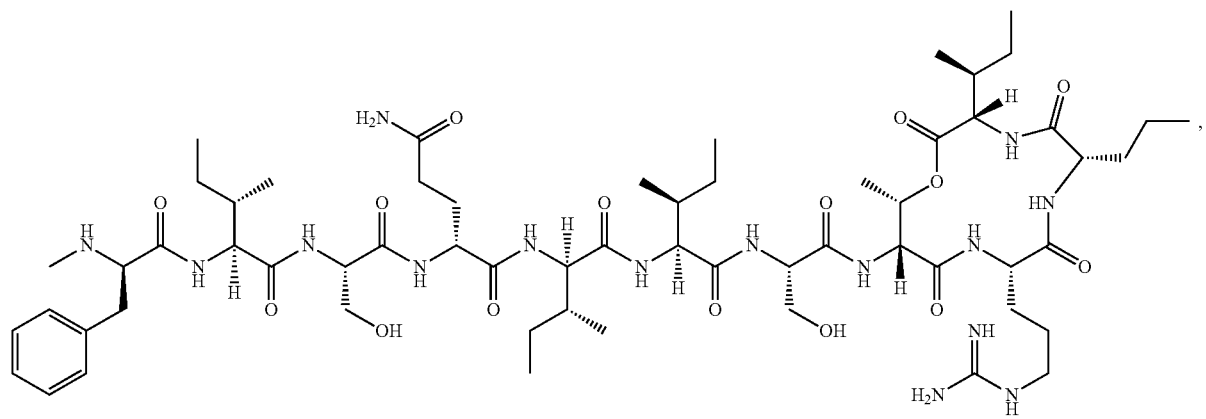

(SEQ ID NO: 20)
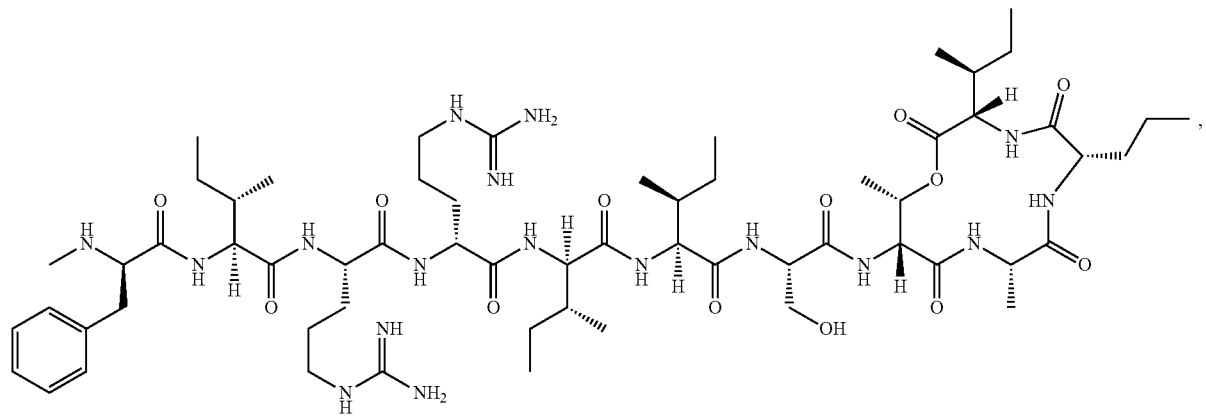
(SEQ ID NO: 21)
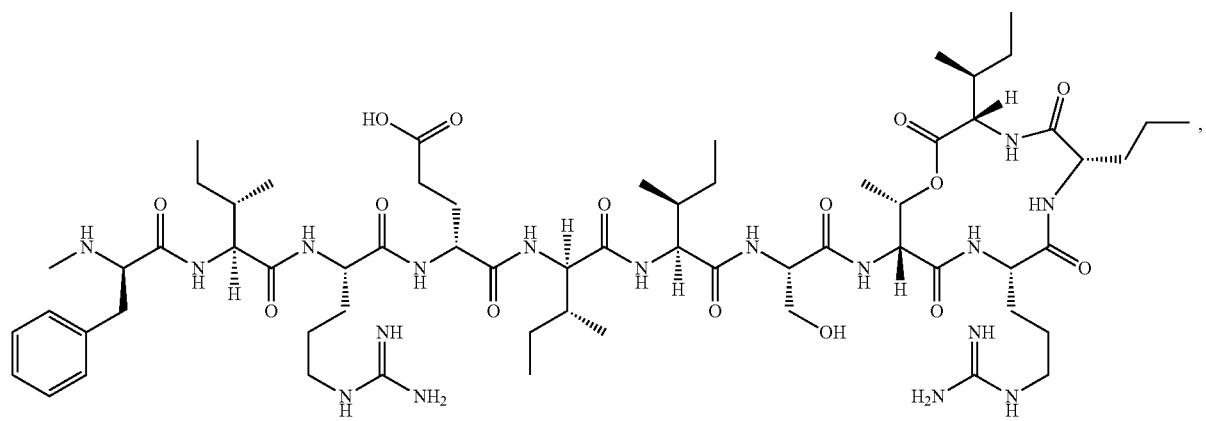
(SEQ ID NO: 19)
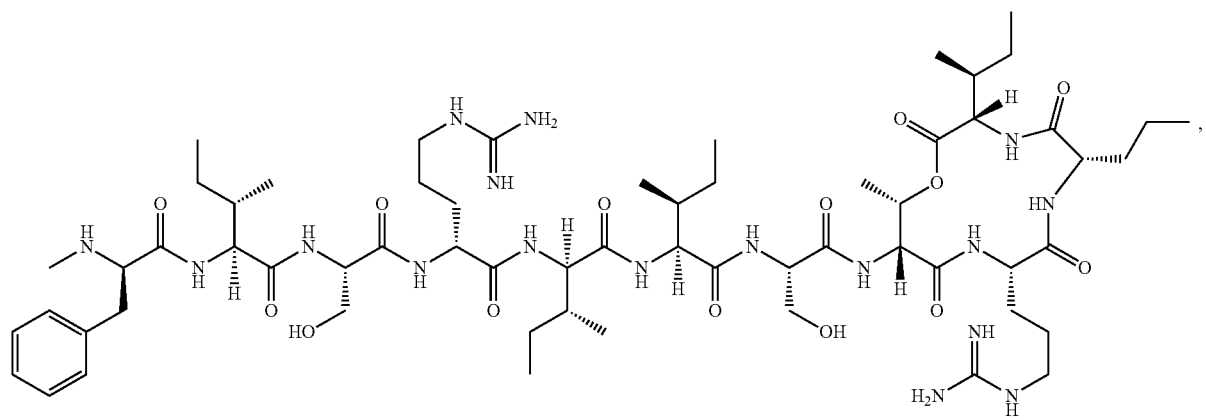

-continued
(SEQ ID NO: 20)
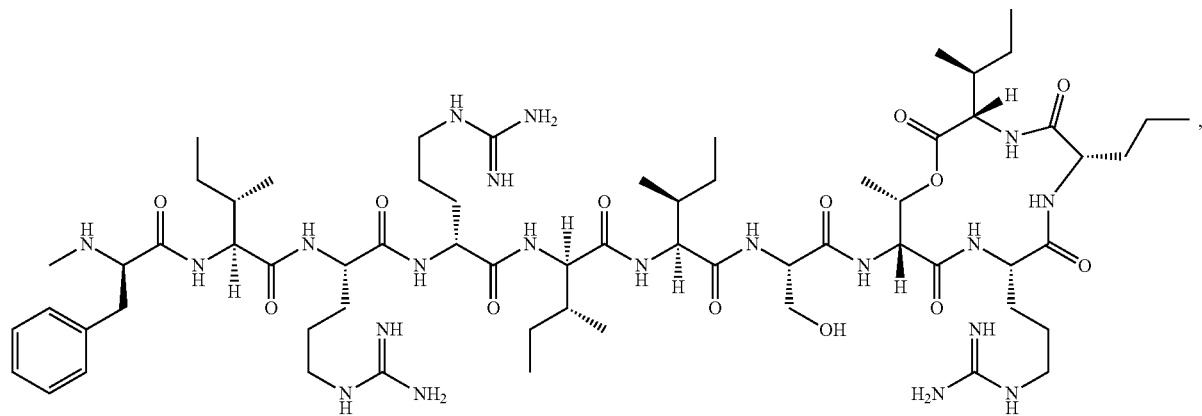
(SEQ ID NO: 19)
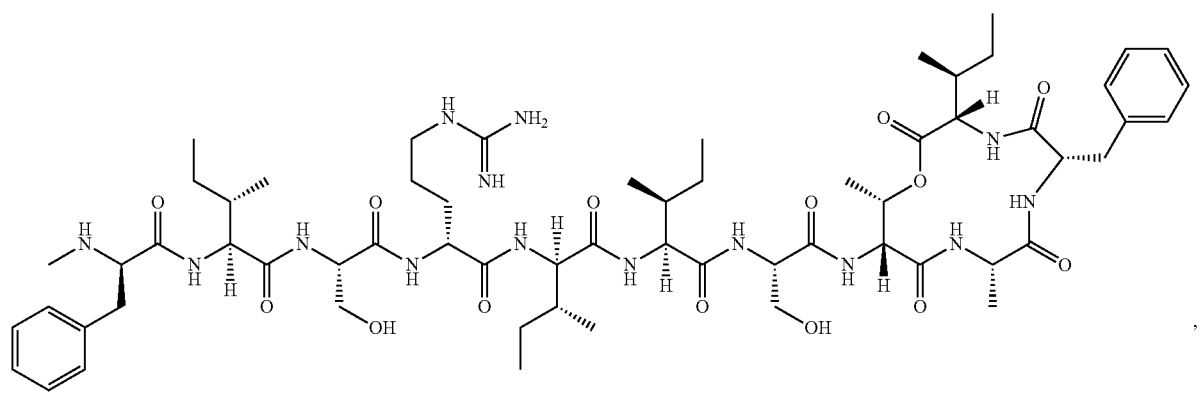
(SEQ ID NO: 19)
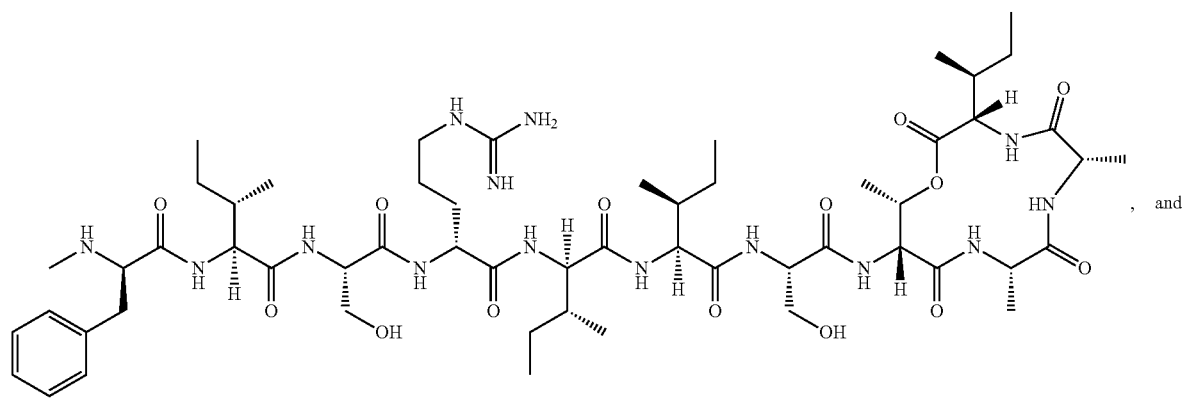
, and (SEQ ID NO: 22)

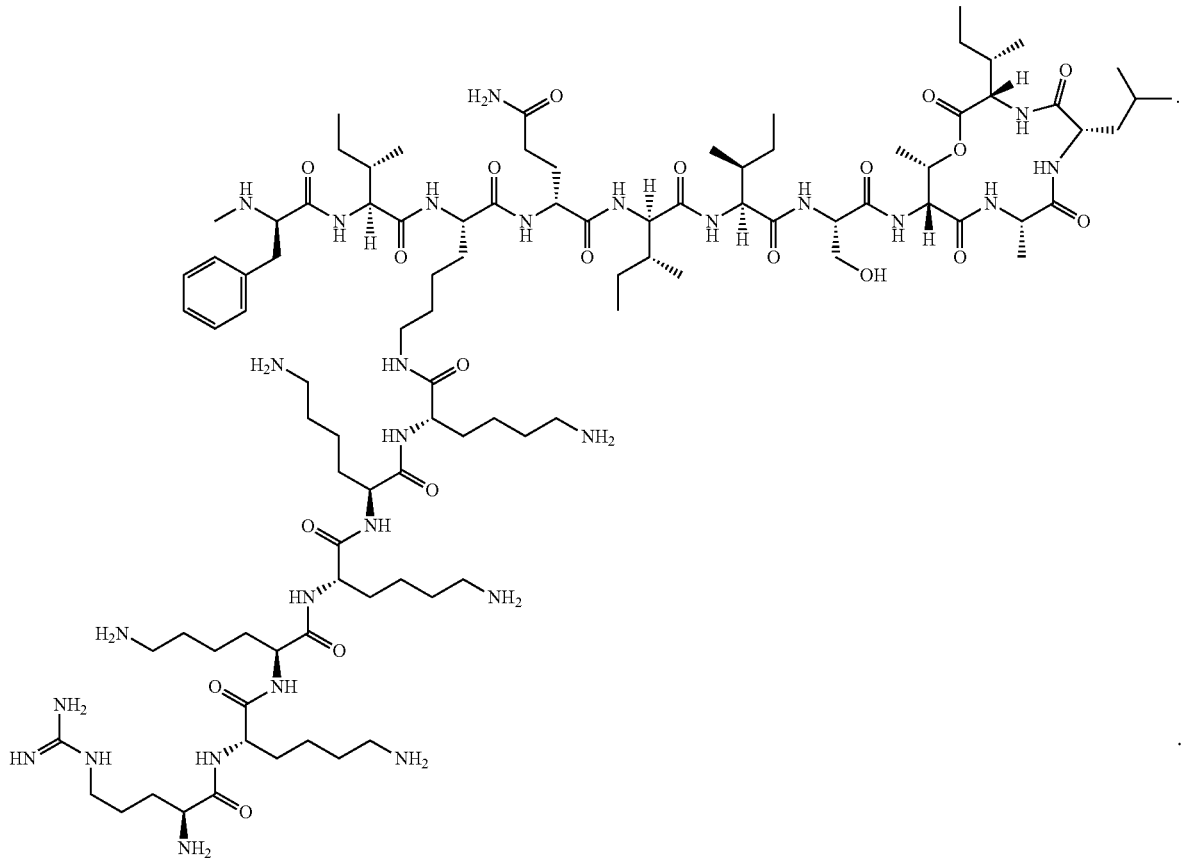

Preparation

The compounds of the invention may be prepared in accordance with techniques known to those skilled in the art, for example as described hereinafter.

Thus, according to a second aspect of the invention there is provided a process for the preparation of a compound of formula IA, IB or IC, which comprises:

(i) for compounds of formula IB in which $R^{10b}$ represents a —$C_{1-6}$-alkyl-NHC(=NH)NH$_2$ group (e.g. an arginine side chain), deprotection of a compound of formula XI, (SEQ ID NO: 1)

wherein $AA^1$ to $AA^7$, $R^1$ to $R^3$, $R^{9b}$ and $R^{11b}$ are as hereinbefore defined (and $AA^1$ to $AA^7$ are optionally protected); in the presence of an acid (such as trifluroacetic acid, hydrochloric acid or p-toluenesulfonic acid), for example under conditions known to a person skilled in the art (such as in the presence of a suitable organic solvent (e.g. dioxane, THF, MeCN, diethyl ether, EtOAc, DCM or DMF));

in a particularly preferred embodiment the deprotection of a compound of formula XI is performed in the presence of trifluroacetic acid, triisopropylsilane and water;

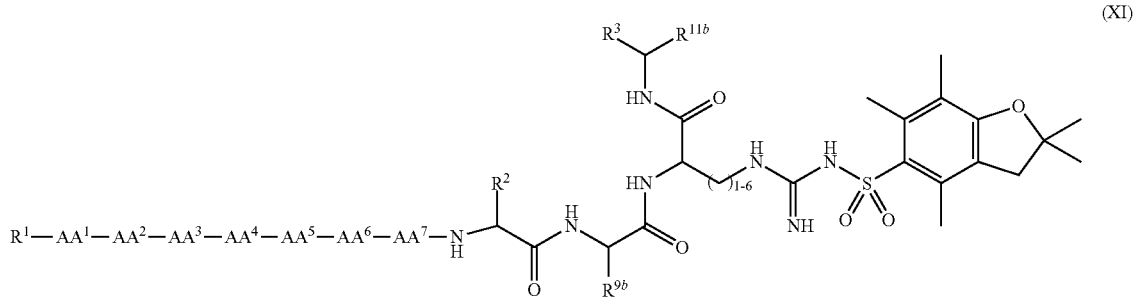

(XI)

optionally deprotection of a compound of formula XI is performed on a solid support and/or in combination with cleavage of the amino acid sequence from the solid support;

(ii) deprotection of a compound of formula IA, IB or IC in which one or more hydroxyl groups is protected with an ether protecting group (such as a tert-butyl, benzyl, allyl, or methoxymethyl ether, preferably a tert-butyl ether), which deprotection may be performed in the presence of an acid (such as trifluoroacetic acid, hydrochloric acid or p-toluenesulfonic acid), for example under conditions known to a person skilled in the art (such as in the presence of a suitable organic solvent (e.g. dioxane, THF, MeCN, diethyl ether, EtOAc, DCM or DMF));

(iii) deprotection of a compound of formula IA, IB or IC in which one or more primary amide groups is protected with a trityl-based group (e.g. a dimethoxy trityl group, a monomethoxy trityl group or an unsubstituted trityl group), which deprotection may be performed in the presence of an acid (such as trifluroacetic acid, hydrochloric acid or p-toluenesulfonic acid), for example under conditions known to a person skilled in the art (such as in the presence of a suitable organic solvent (e.g. dioxane, THF, MeCN, diethyl ether, EtOAc, DCM or DMF));

in a particularly preferred embodiment the deprotections of steps (ii) and (iii) are performed in the presence of trifluroacetic acid, triisopropylsilane and water;

optionally the deprotections of steps (ii) and (iii) are performed on a solid support and/or in combination with cleavage of the amino acid sequence from the solid support;

(iv) for compounds of formula IB in which $R^2$ and $R^3$ are linked and Q represents —S—S—, oxidation of a compound of formula XII, (SEQ ID NO: 1)

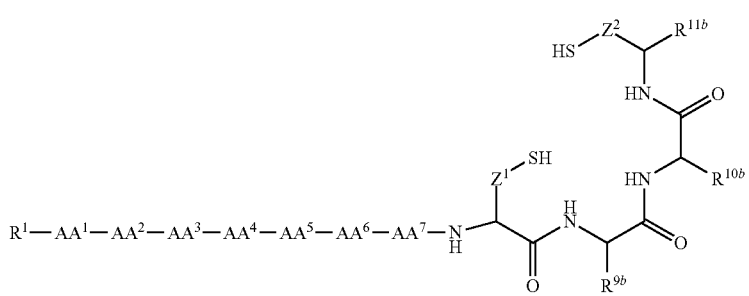

wherein $AA^1$ to $AA^7$ are as defined hereinabove and are optionally protected, $R^1$, $R^{9b}$, $R^{10b}$ and $R^{11b}$ are as defined hereinabove, $Z^1$ and $Z^2$ each independently represent a linear $C_{1-6}$ alkylene group, optionally substituted as defined in hereinabove in respect of the linear $C_{1-6}$ alkylene groups that form part of the linker group; using a suitable oxidising agent, such as oxygen, hydrogen peroxide or 1,3-dibromo-5,5-dimethylhydantoin (DBDMH), for example under conditions known to a person skilled in the art (such as in the presence of a suitable organic solvent (e.g. dioxane, THF, MeCN, diethyl ether, EtOAc, DCM, DMF, water, DMSO or mixtures thereof));

optionally the oxidation of a compound of formula XII is performed on a solid support;

(v) for compounds of formula IA, IB or IC, reaction of a compound of formula XIIIA, XIIIB or XIIIC, (SEQ ID NO: 2)

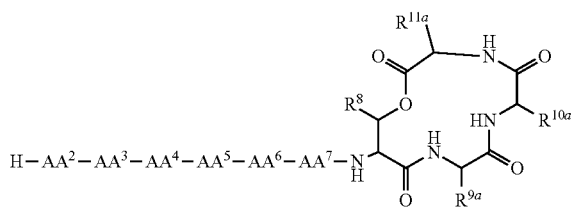

(SEQ ID NO: 2)

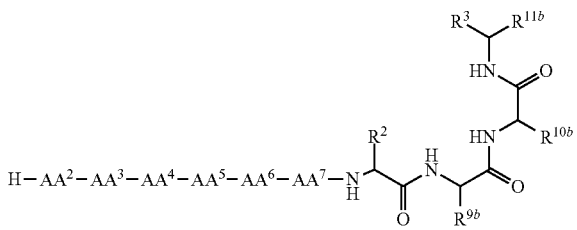

-continued (SEQ ID NO: 2)

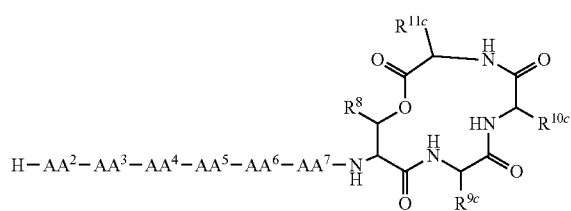

wherein AA² to AA⁷ are as defined hereinabove and are optionally protected; and Z, $R^2$, $R^3$, $R^8$, $R^{9a}$, $R^{9b}$, $R^{9c}$, $R^{10a}$, $R^{10b}$, $R^{10}$, $R^{11a}$, $R^{11b}$ and $R^{11c}$ are as defined hereinabove, in a process comprising the steps of:

a) reacting the compound of formula XIIIA, XIIIB or XIIIC with a compound of formula XIV

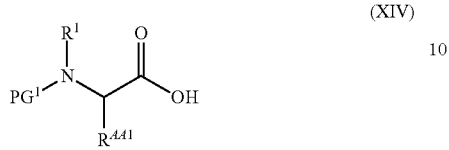

(XIV)

wherein $R^1$ is as defined hereinabove, $R^{AA1}$ is the side chain of the desired AA¹ amino acid (optionally in protected form), and $PG^1$ represents an optional suitable protecting group (such as a carbamate protecting group, including Boc, CBz or preferably Fmoc), with a suitable peptide coupling reagent; (such as a uronium coupling reagent (for example HATU and TBTU); a benzotriazole coupling reagent (for example HOBt or HOAt), a carbodiimide coupling reagent (for example EDCI, DIC or DCC) or an (imino)cyanoacetate coupling reagent (for example ethyl (hydroxyimino)cyanoacetate (Oxyma)) or combinations thereof), for example under conditions known to a person skilled in the art (such as in the presence of a suitable organic solvent (e.g. dioxane, THF, MeCN, diethyl ether, EtOAc, DCM or DMF) and a suitable base (e.g. trimethylamine, triisopropylethylamine or pyridine), at a temperature of e.g. between room temperature and 50° C.); followed by b) removal of the protecting group $PG^1$ if present, which may be performed under acidic or basic conditions as appropriate, (e.g. in the presence of piperidine);

(vi) for compounds of formula IA or IC, reaction of a compound of formula (XVA) or formula (XVC), (SEQ ID NO: 1)

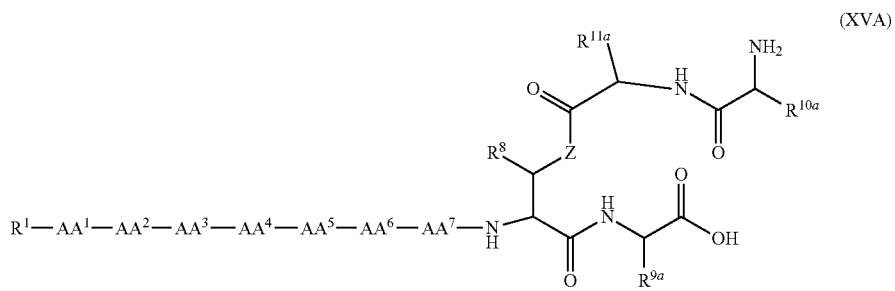

(XVA)

(SEQ ID NO: 1)

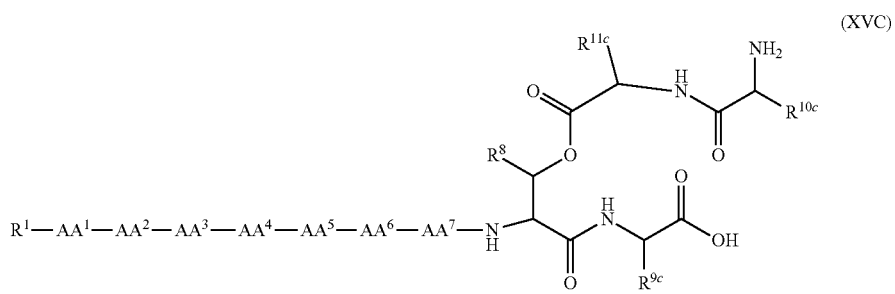

(XVC)

wherein AA¹ to AA⁷ are as defined hereinabove and are optionally protected, and Z, $R^1$, $R^8$, $R^{9a}$, $R^{9c}$, $R^{10a}$, $R^{10c}$, $R^{11a}$ and $R^{11c}$ are as hereinabove defined, with a suitable peptide coupling reagent; (such as a uronium coupling reagent (for example HATU and TBTU); a benzotriazole coupling reagent (for example HOBt or HOAt), a carbodiimide coupling reagent (for example EDCI, DIC or DCC) or an (imino)cyanoacetate coupling reagent (for example ethyl (hydroxyimino)cyanoacetate (Oxyma)) or combinations thereof), under conditions described above; or (vii) for compounds of formula IB in which $R^{11b}$ represents —C(O)NH₂, cleavage of a solid phase resin from a compound of formula XVI, (SEQ ID NO: 1)

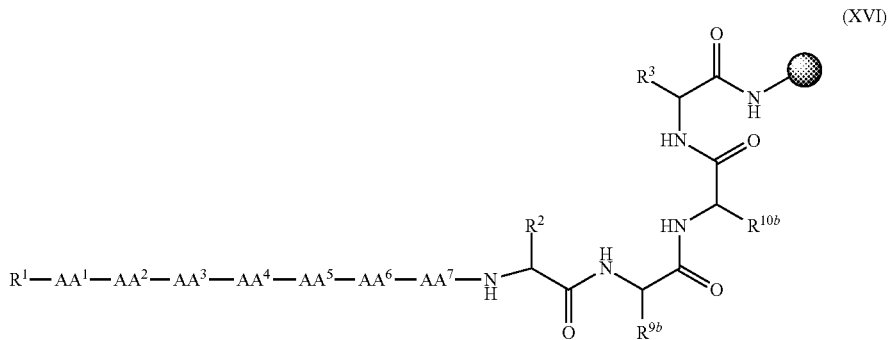

(XVI)

wherein AA$^1$ to AA$^7$ are as defined hereinabove and are optionally protected; R$^1$, R$^2$, R$^3$, R$^{9b}$ and R$^{10b}$ are as described hereinabove; and 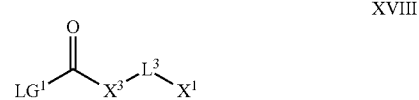 represents a suitable solid phase resin (for example Rink amide resin (e.g. ChemMatrix® Rink amide resin)); in the presence of an acid (such as trifluroacetic acid, hydrochloric acid or p-toluenesulfonic acid), for example under conditions known to a person skilled in the art (such as in the presence of a suitable organic solvent (e.g. dioxane, THF, MeCN, diethyl ether, EtOAc, DCM or DMF));

in a particularly preferred embodiment the removal of the solid phase resin from a compound of formula XVI is performed in the presence of trifluroacetic acid, triisopropylsilane and water;

(viii) for compounds of formula IA or IB in which R$^{10a}$ or R$^{10b}$, as appropriate, represents -L$^1$-L$^2$-L$^3$-X$^1$ in which L$^2$ represents —NHC(O)—NHC(O)O— or —NHC(O)NH—, reaction of a compound of formula XVIIA or XVIIB, wherein Z, R$^1$, AA$^1$ to AA$^7$, R$^2$, R$^3$, R$^8$, R$^{9a}$, R$^{9b}$, R$^{11a}$, R$^{11b}$ and L$^1$ are as hereinbefore defined, with a compound of formula XVIII,

XVIII $$\underset{LG^1}{\overset{O}{\|}}\overset{}{C}-X^3-L^3-X^1$$

wherein X$^3$ represents a direct bond, —O— or —NH—, as necessary, L$^3$ and X$^1$ are as hereinbefore defined (or wherein X$^1$ is in a protected form), and LG$^1$ represents hydrogen or a suitable leaving group, such as an N-hydroxysuccinimide group, under suitable conditions known the person skilled in the art, for example the conditions described above in respect of step (v) or in the presence of a suitable base (e.g. DIPEA, trimethylamine, triisopropylethylamine or pyridine).

The processes described in steps (i) to (viii) are referred to hereinafter as "the processes of the invention".

(SEQ ID NO: 1)

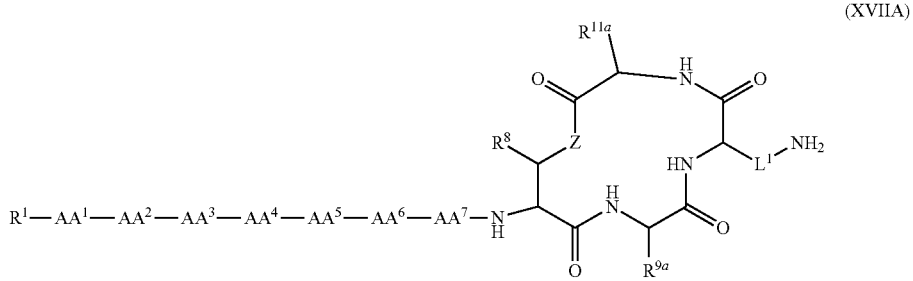

(XVIIA)

(SEQ ID NO: 1)

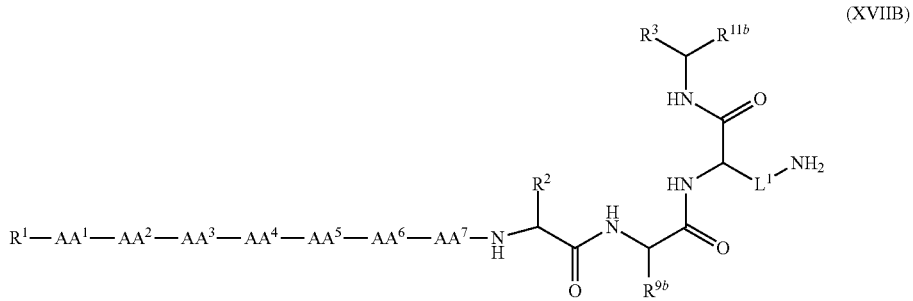

(XVIIB)

By "performed on a solid support" we mean that the relevant processes are carried out with the peptide sequence covalently bonded to a solid phase resin (for example a polysterene or polyethylene glycol resin (e.g. a ChemMatrix® resin)). The point of attachment to the solid phase resin may be at the N-terminus or, preferably at the C-terminus of the peptide sequence or a precursor thereof. The peptide sequence will normally be bound to the resin through either an amide or ester linkage, wherein either the carbonyl portion or amine portion is derived from the C-terminus or N-terminus amino acid residue as appropriate.

The skilled person will be able to determine appropriate solid phase resins for use in the processes of the invention and the most appropriate point of attachment of the resin to the peptide sequence for a given process. Suitable resins include the commercially available resins Rink amide resin and 2-chlorotrityl resin, both of which may be attached to the C-terminus of a peptide sequence, via an amide or ester linkage respectively.

Cleavage of the peptide sequence from Rink amide resin and 2-chlorotrityl resin can be achieved under acidic conditions. Cleavage from Rink amide resin results in a primary amide group at the C-terminus of a peptide sequence, and cleavage from 2-chlorotrityl resin results in the carboxylic acid group being restored at the C-terminus.

For compounds of formula IB in which $R^2$ and $R^3$ are linked and $R^{11b}$ represents $-C(O)NH_2$, the macrocyclic moiety is typically formed by linkage of two amino acid side chains, which allows the solid phase resin to be attached to the C-terminus of one of the ring-forming amino acid residues and thus for macrocyclisation to be performed prior to cleavage from the solid phase resin. The use of Rink amide resin for the synthesis of these compounds also allows for the cleavage to be performed under the same acidic conditions as deprotection of many commonly-employed protecting groups. Collectively, these factors allow for the highly-efficient synthesis of Teixobactin analogues, which display potent antibacterial activity. The presence of a primary amide group (resulting from the cleavage of the Rink amide resin) on the macrocyclic ring appears to be well-tolerated in terms of biological efficacy, even though such a group is not present in Teixobactin.

In further embodiments of the processes of the invention, any two or more of the deprotections of steps (i), (ii), (iii) may be performed concurrently, and any one or more of these deprotections may also be performed concurrently with the cleavage of step (vii). For example, the global deprotection and cleavage from the solid support of a compound of formula (XIX), wherein $AA^1$, $AA^2$, $AA^5$, $AA^6$, $R^1$, $R^2$, $R^3$, $R^{9b}$, $PG^2$, $PG^3$ and ● are as defined hereinabove.

Protecting groups that may be removed concurrently include alcohol and primary amide protecting groups that can be removed under acidic conditions (for example ether protecting groups (e.g. tert-butyl) and trityl amide protecting groups). These groups may also be removed concurrently with the 2,2,4,6,7-pentamethyldihydrobenzofurane (Pbf) group for the protecting of guanidinyl groups (drawn explicitly in inter alia formula XIX), and with cleavage of the peptide sequence, or a precursor thereto, from Rink amide or 2-chlorotrityl resin.

With reference to synthetic processes, by "performed concurrently" we mean that the relevant two or more transformations are achieved under a single set of reaction conditions.

Other specific transformation steps that may be employed in the synthesis of compounds of formula IA, IB or IC include:
(a) peptide coupling, which may for example be facilitated by a suitable peptide coupling reagent such as any of the coupling reagents and conditions as described in step (v) as hereinabove;
(b) ester formation, which may for example be facilitated by suitable carboxylic acid activating agents (e.g. carbodiimides such as DIC, DCC and EDCI and/or DMAP), for example under conditions known to a person skilled in the art (such as in the presence of a suitable organic solvent (e.g. dioxane, THF, MeCN, diethyl ether, EtOAc, DCM or DMF));
(c) macrocycle formation, including:
1. ester formation, for example the preparation of a compound of formula XX,

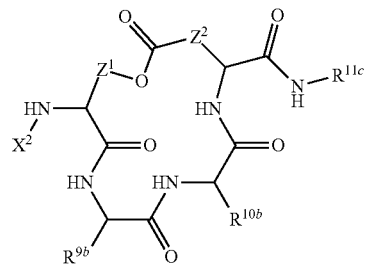

(XX)

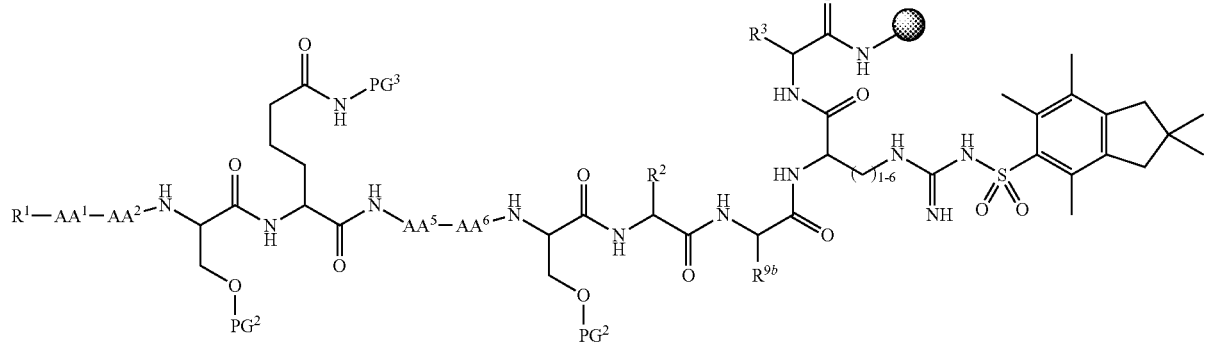

(XIX)

wherein $R^{9b}$, $R^{10b}$, $Z^1$ and $Z^2$ are as hereinbefore defined (and $R^{10b}$ is optionally a protected amino acid side chain);

$R^{11c}$ represents H or a solid phase resin (for example, Rink amide or 2-chlorotrityl resin);

$X^2$ represents H, a suitable protecting group (such as a carbamate protecting group, including Boc, CBz or preferably Fmoc) or a group consisting of one or more of the amino acid residues $AA^7$ to $AA^1$ as defined hereinabove, which are optionally protected, wherein the N-terminus of the group of one or more amino acids is bound to a suitable protecting group (such as a carbamate protecting group, including Boc, CBz or preferably Fmoc); and by reacting a compound of formula XXI,

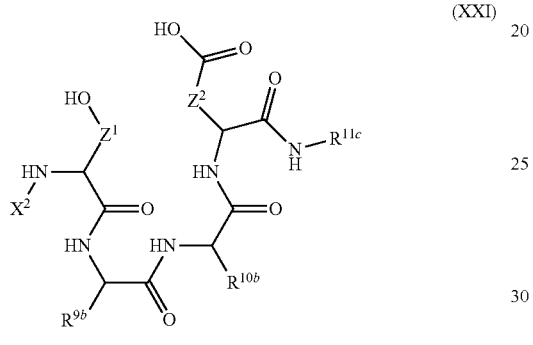

(XXI)

wherein $R^{9b}$, $R^{10b}$, $R^{11c}$, $X^2$, $Z^1$ and $Z^2$ are as hereinbefore defined for a compound of formula XX;

in the presence of a suitable carboxylic acid activating agent (e.g. a carbodiimide such as DIC, DCC and EDCI and/or DMAP), for example under conditions known to a person skilled in the art (such as in the presence of a suitable organic solvent (e.g. dioxane, THF, MeCN, diethyl ether, EtOAc, DCM or DMF));

2. amide formation, for example the preparation of a compound of formula XXII;

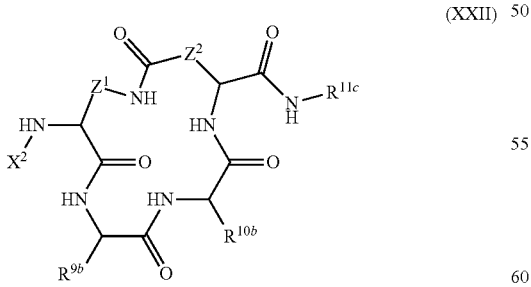

(XXII)

wherein $R^{9b}$, $R^{10b}$, $R^{11c}$, $X^2$, $Z^1$ and $Z^2$ are as defined in respect of a compound of formula XX; by reacting a compound of formula XXIII

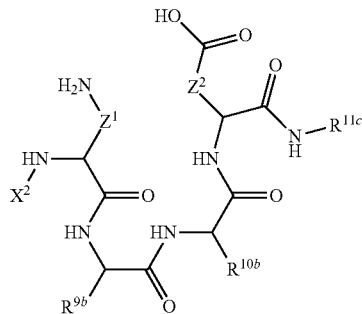

(XXIII)

wherein $R_{9b}$, $R^{10b}$, $R^{11c}$, $X^2$, $Z^1$ and $Z^2$ are as defined in respect of a compound of formula XX; for example, under the conditions described for step (v) a) hereinabove;

3. disulphide formation, for example the preparation of a compound XXIV;

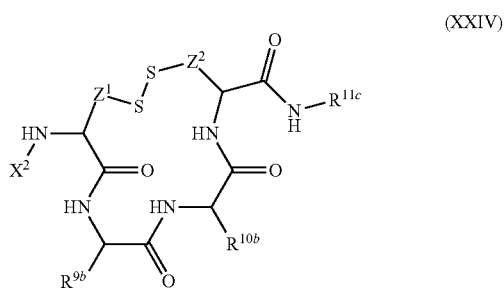

(XXIV)

wherein $R^{9b}$, $R^{10b}$, $R^{11c}$, $X^2$, $Z^1$ and $Z^2$ are as defined in respect of a compound of formula XX;

by oxidising a compound of formula XXV

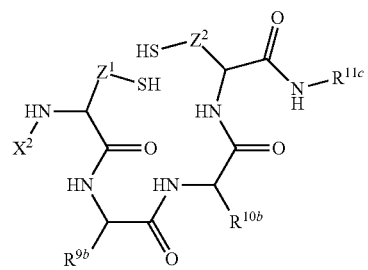

(XXV)

wherein $R^{9b}$, $R^{10b}$, $R^{11c}$, $X^2$, $Z^1$ and $Z^2$ are as defined for a compound of formula XX; with a suitable oxidising agent, such as oxygen, hydrogen peroxide or 1,3-dibromo-5,5-dimethylhydantoin (DBDMH), for example under conditions known to a person skilled in the art (such as in the presence of a suitable organic solvent (e.g. dioxane, THF, MeCN, diethyl ether, EtOAc, DCM, DMF, water, DMSO or mixtures thereof));

(d) protection of reactive functional groups, for example hydroxyl groups, primary or secondary amines, guanidines, carboxylic acids and primary or secondary amides, with suitable protecting groups, for example carbamate protecting groups (e.g Boc, CBz, Fmoc or Alloc groups), ether protecting groups (e.g. tert-butyl ethers) or trityl amide protecting groups; details of suitable protecting groups and methods for their incorporation can be found in P. G. M. Wuts and T. W. Greene *Protective Groups in Organic Synthesis*, 4$^{th}$ edition, 2006, Wiley, 2006;

(e) deprotection of protected hydroxyl groups, primary or secondary amines, carboxylic acids, guanidines and primary or secondary amides; suitable procedures for the removal (i.e. deprotection) of protecting groups can be found in P. G. M. Wuts and T. W. Greene *Protective Groups in Organic Synthesis*. 4$^{th}$ edition, 2006, Wiley, 2006;

(f) cleavage of peptide compounds from solid phase resins (such as Rink amide ChemMatrix® resin and 2-chlorotrityl resin), for example in the presence of a suitable acid;

(g) preparation of delivery agent fragments of formula II to X, which may be prepared according to the procedures described in Tschiche et al. *J. Mater. Chem. B*, 2014, 2, 2153-2167 and WO 2016/034894;

(h) incorporation of a delivery agent fragment of formula I to X into a compound of formula IA, IB or IC.

Compounds of the invention may be prepared by methods analogous to those listed above, together with those that are known to those skilled in the art. Compounds of formula IA, IB or IC may be prepared using processes involving solid (such as solid-phase peptide synthesis SPPS) or solution phase organic synthesis, as appropriate, using conditions that are known to those skilled in the art.

Persons skilled in the art will appreciate that, in order to obtain compounds of formula IA, IB or IC (etc.) in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the 5 sequence for accomplishing the synthesis and whether each step should be performed in solution or on solid phase. A recent review of suitable protecting groups for amino acids is provided by Isidro-Llobet et al. *Chem. Rev.* 2009, 109, 2455-2504.

Advantageously, removal of protecting groups and cleavage from solid phase resins should be performed towards the end (preferably as the final step) of a synthetic route in order to maximise the efficiency of a synthetic process.

Uses and Pharmaceutical Preparations

The compounds of the invention are useful because they possess pharmacological activity. They are therefore indicated as pharmaceuticals.

Thus, according to a third aspect of the invention there is provided a pharmaceutical composition comprising a compound of the invention in combination with a pharmaceutically-acceptable adjuvant diluent or carrier. Such formulations are referred to hereinafter as the "formulations of the invention".

According to a fourth aspect of the invention, there is provided the compounds of the invention or the formulations of the invention for use in medicine.

The use of compounds or formulations of the invention in medicine includes their use as pharmaceuticals (both for human and veterinary use). The compositions of the present invention may also be useful in other fields of industry. For example, the compositions may be useful as plant protection products (i.e. in agriculture), in cosmetic products (e.g. in creams, toothpaste, lotions and ointments), and hygiene and sterilisation procedures (e.g. in scientific laboratories).

In this respect, fifth, sixth, seventh and eighth aspects of the invention provide, respectively:

(a) a compound or formulation of the invention, as hereinbefore defined, for use in treating or preventing a bacterial infection in a subject;

(b) use of a compound or formulation of the invention, as hereinbefore defined, in the manufacture of a medicament for treating or preventing a bacterial infection in a subject;

(c) a method of treating or preventing a bacterial infection, which method comprises administration of a therapeutically effective amount of a compound or formulation of the invention as hereinbefore defined to a subject in need thereof;

(d) use (e.g. ex vivo use) of a compound or formulation of the invention to kill bacteria.

When used herein, the terms "bacteria" (and derivatives thereof, such as "bacterial infection") includes references to organisms (or infections due to organisms) of the following classes and specific types:

Gram-positive cocci, such as

Staphylococci (e.g. *Staph. aureus, Staph. epidermidis, Staph. saprophyticus, Staph. auricularis, Staph. capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi, Staph. s. coagulans, Staph. sciuri, Staph. simulans, Staph. warneri* and *Staph. xylosus*) and Streptococci (e.g.

beta-haemolytic, pyogenic streptococci (such as *Strept. agalactiae, Strept. canis, Strept. dysgalactiae, Strept. dysgalactiae equisimilis, Strept. equi, Strept. equi zooepidemicus, Strept. iniae, Strept. porcinus* and *Strept. pyogenes*), microaerophilic, pyogenic streptococci (*Streptococcus "milleri"*, such as *Strept. anginosus, Strept. constellatus, Strept. constellatus pharyngidis* and *Strept. intermedius*), oral streptococci of the "*mitis*" (alpha-haemolytic-*Streptococcus "viridans"*, such as *Strept. mitis, Strept. oralis, Strept. sanguinis, Strept. cristatus, Strept. gordonii* and *Strept. parasanguinis*), "*salivarius*" (non-haemolytic, such as *Strept. salivarius* and *Strept. vestibularis*) and "*mutans*" (tooth-surface streptococci, such as *Strept. criceti, Strept. mutans, Strept. ratti* and *Strept. sobrinus*) groups,

*Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus;*

Enterobacteriaceae, such as
- *Escherichia coli,*
- *Enterobacter* (e.g. *Enterobacter aerogenes, Enterobacter agglomerans* and *Enterobacter cloacae*)
- *Citrobacter* (such as *Citrob. freundii* and *Citrob. divernis*),
- *Hafnia* (e.g. *Hafnia alvei*),
- *Erwinia* (e.g. *Erwinia persicinus*),
- *Morganella morganii,*
- *Salmonella* (*Salmonella enterica* and *Salmonella typhi*),
- *Shigella* (e.g. *Shigella dysenteriae, Shigella flexneri, Shigella boydii* and *Shigella sonnei*),
- *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*),
- *Proteus* (e.g. *Pr. mirabilis, Pr. rettgeri* and *Pr. vulgaris*),
- *Providencia* (e.g. *Providencia alcalifaciens, Providencia rettgeri* and *Providencia stuartii*),
- *Serratia* (e.g. *Serratia marcescens* and *Serratia liquifaciens*), and
- *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fennelliae*);

*Acinetobacter* (e.g. *A. baumanii, A. calcoaceticus, A. haemolyticus, A. johnsonii, A. junii, A. lwoffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*);

*Bacteroides fragilis;*

*Peptococcus* (e.g. *Peptococcus niger*);

*Peptostreptococcus;*

*Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. carnis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);

*Mycoplasma* (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

*Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes;*

*Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae;*

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);

*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

*Rickettsia* (e.g. *Ricksettsii* or *Coxiella burnetii*);

*Legionella* (e.g. *Legionalla anisa, Legionalla birminghamensis, Legionalla bozemanii, Legionalla cincinnatiensis, Legionalla dumoffii, Legionalla feeleii, Legion-* alla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis and Legionalla wadsworthii);

Moraxella catarrhalis;

Stenotrophomonas maltophilia;

Burkholderia cepacia;

Francisella tularensis;

Gardnerella (e.g. Gardneralla vaginalis and Gardneralla mobiluncus);

Streptobacillus moniliformis;

Flavobacteriaceae, such as Capnocytophaga (e.g. Capnocytophaga canimorsus, Capnocytophaga cynodegmi, Capnocytophaga gingivalis, Capnocytophaga granulosa, Capnocytophaga haemolytica, Capnocytophaga ochracea and Capnocytophaga sputigena);

Bartonella (Bartonella bacilliformis, Bartonella clarridgeiae, Bartonella elizabethae, Bartonella henselae, Bartonella quintana and Bartonella vinsonii arupensis);

Leptospira (e.g. Leptospira biflexa, Leptospira borgpetersenii, Leptospira inadai, Leptospira interrogans, Leptospira kirschneri, Leptospira noguchii, Leptospira santarosai and Leptospira weilii);

Spirillium (e.g. Spirillum minus);

Bacteroides (e.g. Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus and Bacteroides vulgatus);

Prevotella (e.g. Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis and Prevotella zoogleoformans);

Porphyromonas (e.g. Porphyromonas asaccharolytica, Porphyromonas cangingivalis, Porphyromonas canons, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii and Porphyromonas macacae);

Fusobacterium (e.g. F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans and F. varium);

Chlamydia (e.g. Chlamydia trachomatis);

Chlamydophila (e.g. Chlamydophila abortus (Chlamydia psittaci), Chlamydophila pneumoniae (Chlamydia pneumoniae) and Chlamydophila psittaci (Chlamydia psittaci));

Leuconostoc (e.g. Leuconostoc citreum, Leuconostoc cremoris, Leuconostoc dextranicum, Leuconostoc lactis, Leuconostoc mesenteroides and Leuconostoc pseudomesenteroides);

Gemella (e.g. Gemella bergeri, Gemella haemolysans, Gemella morbillorum and Gemella sanguinis); and Ureaplasma (e.g. Ureaplasma parvum and Ureaplasma urealyticum).

Thus, compounds of the invention may be used to kill any of the above-mentioned bacterial organisms.

Particular bacteria that may be mentioned in this respect include:

Bacillaceae, such as Bacillus anthracis, Bacillus subtilis, Bacillus thuringiensis, Bacillus stearothermophilus and Bacillus cereus;

Staphylococci, such as Staph. aureus (either Methicillin-sensitive (i.e. MSSA) or Methicillin-resistant (i.e. MRSA)) and Staph. epidermidis;

Acinetobacter (e.g. A. baumanii, A. calcoaceticus, A. haemolyticus, A. johnsonii, A. junii, A. lwoffi and A. radioresistens);

Enterobacteriaceae, such as Escherichia coli, Klebsiella (e.g. Klebs. pneumoniae and Klebs. oxytoca) and Proteus (e.g. Pr. mirabilis, Pr. rettgeri and Pr. vulgaris); or Pseudomonas (e.g. Ps. aeruginosa, Ps. maltophilia (Stenotrophomonas maltophilia), Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida and Ps. stutzeri).

Particular bacterial infections that may be mentioned in relation to the fifth to eighth aspects of the invention include infections with:

Bacillaceae, such as Bacillus anthracis, Bacillus subtilis, Bacillus thuringiensis, Bacillus stearothermophilus and Bacillus cereus;

Staphylococci, such as Staph. aureus (either Methicillin-sensitive (i.e. MSSA) or Methicillin-resistant (i.e. MRSA)) and Staph. epidermidis;

Acinetobacter (e.g. A. baumanii, A. calcoaceticus, A. haemolyticus, A. johnsonii, A. junii, A. lwoffi and A. radioresistens);

Enterobacteriaceae, such as Escherichia coli, Klebsiella (e.g. Klebs. pneumoniae and Klebs. oxytoca) and Proteus (e.g. Pr. mirabilis, Pr. rettgeri and Pr. vulgaris); or Pseudomonas (e.g. Ps. aeruginosa, Ps. maltophilia (Stenotrophomonas maltophilia), Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida and Ps. stutzeri).

The compounds of the present invention are particularly advantageous as, when covalently bonded to a delivery agent, they are capable of inhibiting the growth, survival and reproduction of Gram negative bacteria, something which few existing antibacterial agents are able to do effectively. Thus, in particular embodiments of all of the methods disclosed herein, the bacteria are Gram negative bacteria.

In this respect, particular conditions that the compounds and formulations of the invention can be used to treat include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, bacilliary dysentry, bacterial conjunctivitis, bacterial keratitis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, empymea, endocarditis, endometritis, enteric fever, enteritis, epididymitis, epiglottitis, erysipclas, erysipeloid, erythrasma, eye infections, furuncles, Gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, Ritter's disease, salmonellosis, salpingitis, septic arthritis, septic infections, septicameia, sinusitis, skin infections (e.g. skin granulomas), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis.

Further conditions that may be mentioned in this respect include infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* or *Enterococcus faecium*.

The compounds and formulations of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compounds and formulations may be administered at varying doses.

Suitable daily doses for the compounds and formulations of the invention in therapeutic treatment of humans are in the range of about 1 to about 2000 mg/m$^2$.

The most effective mode of administration and dosage regimen for the compounds and formulations of the invention depends on several factors, including the particular condition being treated, the extent and localisation of that condition in the patient being treated, as well as the patient's state of health and their reaction to the compound being administered. Accordingly, the dosages of the compounds and formulations of the invention should be adjusted to suit the individual patient. Methods for determining the appropriate dose for an individual patient will be known to those skilled in the art.

Additionally, compositions of the invention may have the advantage that they may be more efficacious than, be less toxic than, have a broader range of activity than, be more potent than, produce fewer side effects than, or have other useful pharmacological properties over compositions known in the prior art. In particular, compositions of the invention may have the advantage that they are less toxic than compositions known in the prior art due to a reduction in the detrimental effects that the delivery agents may have on cell membrane (of the host organisms).

The use of certain compounds and formulations of the invention in medicine is, to the knowledge of the inventors, novel. In certain embodiments of the invention, the subject of the treatment or prevention methods is a mammal, particularly a human.

Figure 2:
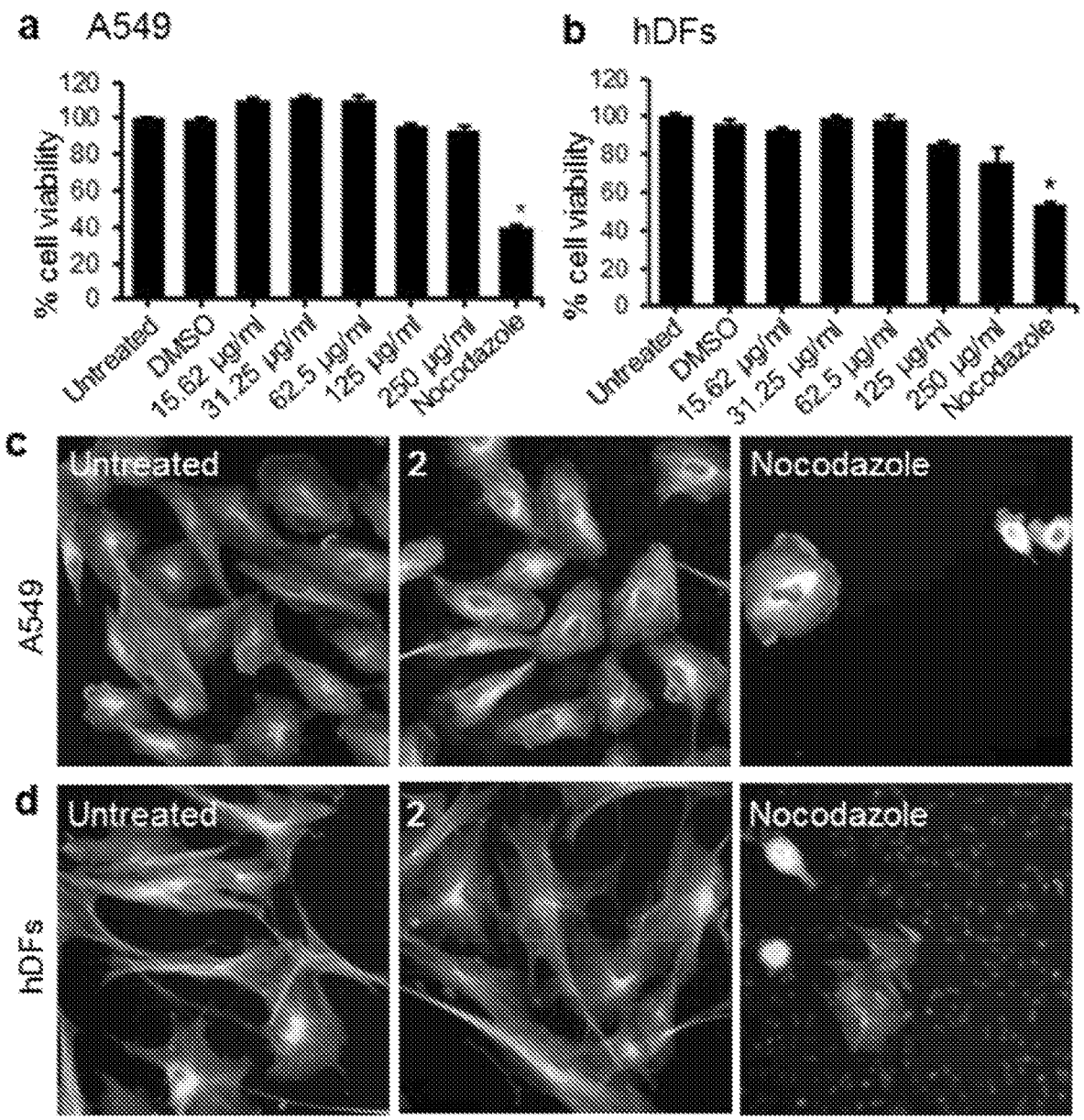
Figure 3:
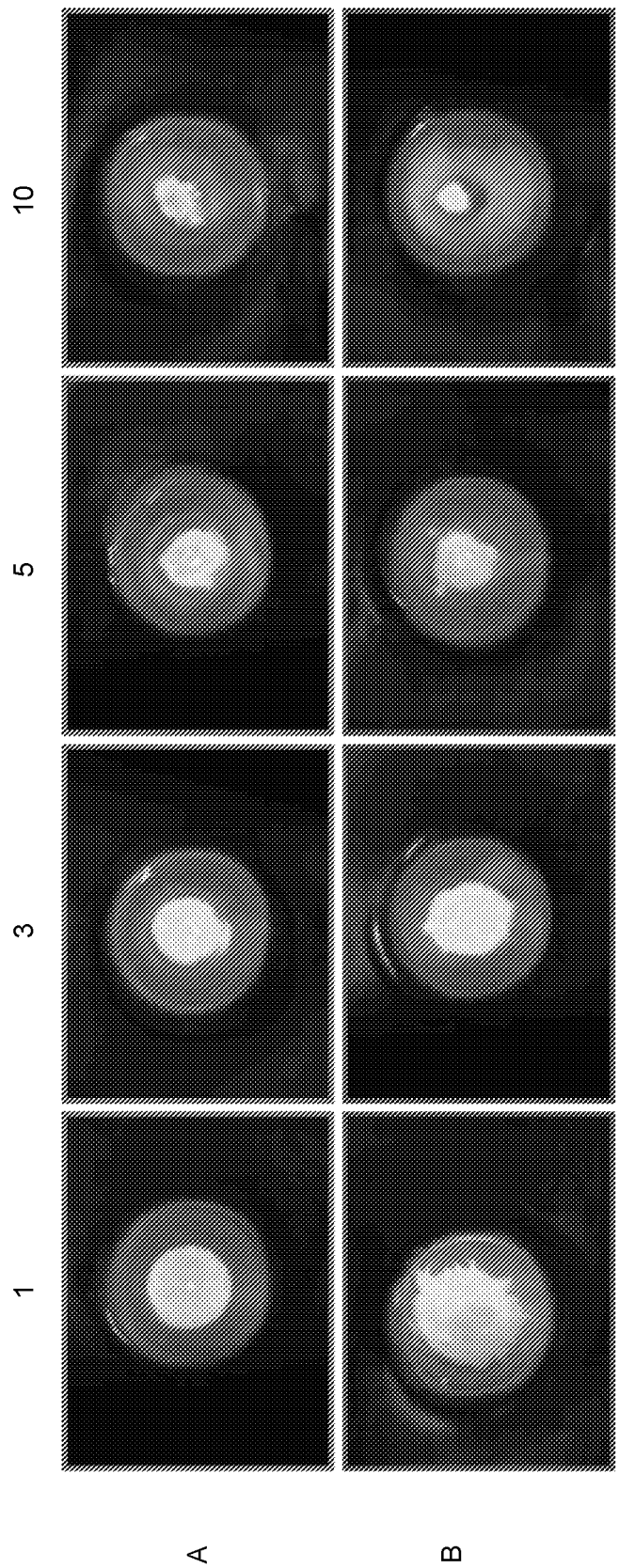
Figure 4:
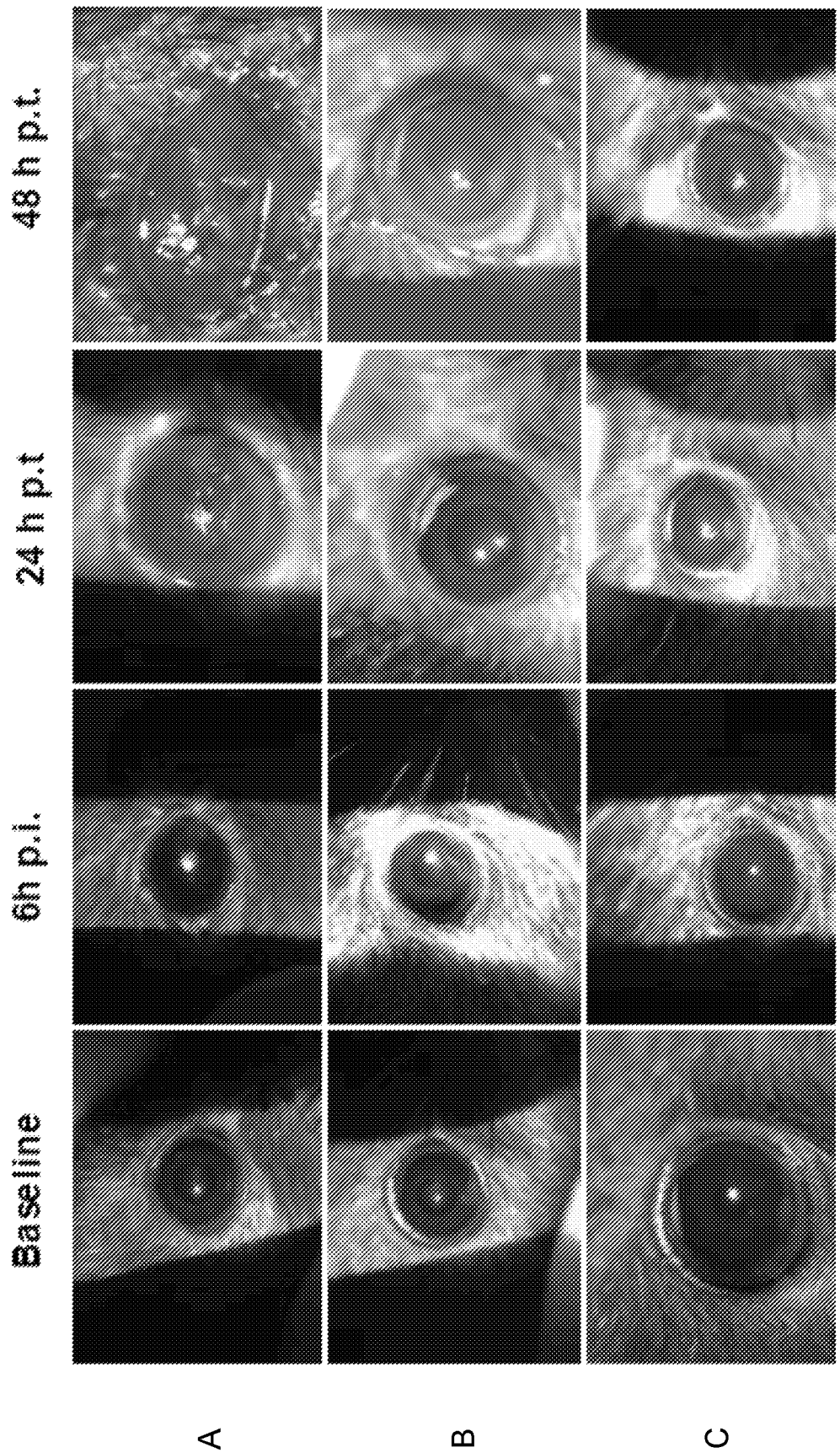
Figure 5:
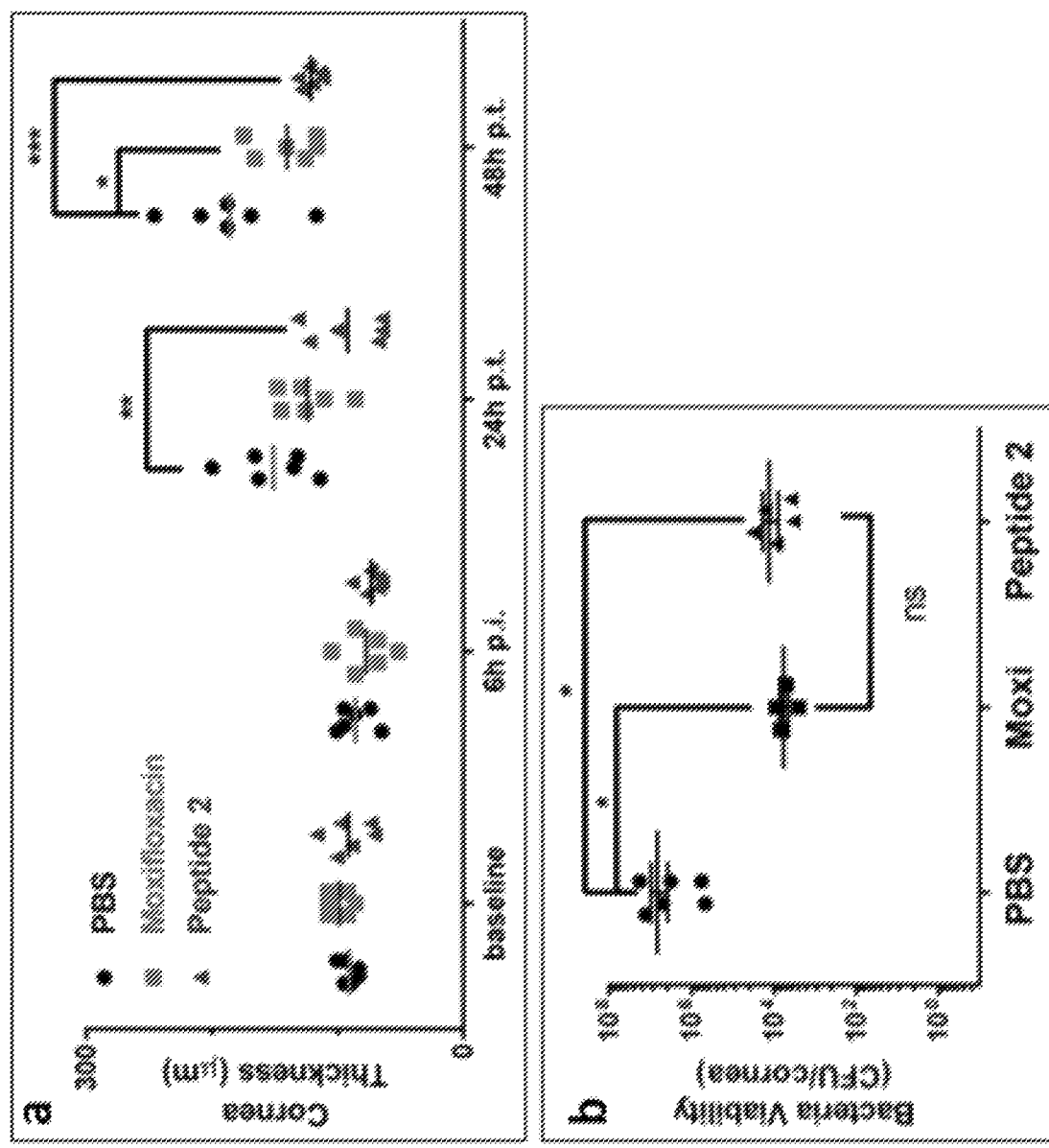

The invention is illustrated by the following examples in which:

FIG. 1 shows the MIC distribution of Compounds 25 to 34 (denoted by numbers 1 to 10, respectively in the figure) against 19 different Gram-positive pathogens. The teixobactin analogue daptomycin (labelled as D) was used as the comparator drug. Note the increase in MIC distribution as the overall net charge on the teixobactin analogues was increased. The number in parentheses indicates the overall net charge of the peptides;

FIG. 2 shows the cytotoxicity evaluation of Compound 26 in A549 lung epithelial cell line and human primary dermal fibroblasts (hDFs). Representative images of cells treated with either Compound 26 (62.5 µg/ml for 24 h) or nocodazole (10 µg/ml, toxicity control) are shown;

FIG. 3 shows representative slit lamp fluorescence images showing the time-dependent changes in wound closure of the cornea after application of: (A) PBS (2 eyes) or (B) 0.3% Compound 26 (4 eyes). The images were taken on days 1, 3, 5 and 10. The wounded cornea was stained fluorescein to observe epithelial defects and imaged by slit lamp biomicroscopy;

FIG. 4 shows the slit lamp examination of mice infected with *S. aureus* ATCC 29213 strains. Mice were treated with: (A) vehicle; (B) Compound 26; or (C) moxifloxacin; and FIG. 5 shows (a) changes in corneal thickness (CT) of mice before and after infections and treatment with vehicle alone, Compound 26 (denoted as "Peptide 2" in the figure) or moxifloxacin; and (b) bacterial bioburden in the infected corneal after 48 h treatment with the same materials. Values represent colony counts from individual cornea and bars represent mean CFU/tissue±standard errors of the mean.

The invention will now be described in more detail by reference to the following non-limiting Examples.

EXAMPLES

MIC Testing

For MIC testing all peptides were dissolved in DMSO (according to the method of L. L. Ling, et al., *Nature* 2015, 517, 455-459). Bacteria were grown on Mueller Hinton broth (oxoid). All incubations were at 37° C. Dilutions were carried out using Mueller Hinton. 100 µl of autoclaved Mueller Hinton broth was added to wells 2-12 on a 96-well plate. 200 µl of the peptide was added to well one at a concentration of 512 µg/ml. 100 µl of peptide in well one was taken up and pipetted into well two. The mixture was then mixed via pipetting before 100 µl was taken up and pipetted into well three. This process was repeated up to well 11. Once peptide was added to well 11 100 µl was taken up and then discarded ensuring the well 12 had no peptide present. Each well was then inoculated with 100 µl of bacteria that had been diluted to an OD600 nm of 0.1. This was repeated three times. The 96-well plates were then incubated for 24 hours. The MIC was determined to be the lowest concentration at which there was no growth visible. Results are tabulated in the Examples.

Materials

Fmoc-D-Ile-OH, Fmoc-D-Thr(Trt)-OH, Fmoc-ε-Ahx-OH and oxyma pure were purchased from Merck Millipore. All L Amino acids, 1-[Bis(dimethylamino)methylene]-1H-1,2,3-triazolo[4,5-b]pyridinium 3-oxid hexafluorophosphate (HATU), Fmoc-D-Gln(Trt)-OH, Boc-D-Nmethylphenyl-OH, Fmoc-D-Thr-OH, Boc-Asp(OtBu)-OH, Fmoc-Glu (OAll)-OH, Fmoc-Lys(Alloc)-OH, Bis-Boc-pyrazolocarboxamidine, Diisoproplycarbodiimide and Triisopropylsilane were purchased from Fluorochem.

The protecting groups for the amino acids are Bu for Glu, Boc for Pro, Tyr, Lys, Trp, Pbf for Arg and Trt for Gln unless specified otherwise. Diisopropylethylamine, supplied as extra dry, redistilled, 99.5% pure, was purchased from Sigma Aldrich. Dimethylformamide (DMF) peptide synthesis grade and Trifluoroacetic acid (TFA) was purchased from Rathburn chemicals.

Petroleum ether, Diethyl ether, i-PrOH, MeOH (HPLC grade), and Acetonitrile (HPLC grade) were purchased from Fisher Scientific. Water with the Milli-Q grade standard was obtained in-house from an ELGA Purelab Flex system. 2-Chlorotritylchloride resin (manufacturer's loading: 1.20 mmol/g) was obtained from Fluorochem. Rink amide Chemmatrix resin (manufacturer's loading=0.49 mmol/g) was obtained from Biotage. All chemicals were used without further purification.

General Procedure for Peptide Synthesis

Peptide syntheses were performed using standard Fmoc Solid Phase Peptide Synthesis (SPPS) protocols on a 2-Chlorotritylchloride resin, loading=1.20 mmol/g or a Rink Amide Chemmatrix Resin, loading=0.49 mmol/g using a Biotage Initiator+Alstra fully automated microwave peptide synthesizer. All amino acid couplings were performed using 5 eq. Amino Acid with 5 eq. DIC/Oxyma in DMF as a coupling cocktail by irradiating at 70° C. for 5 min. Fmoc deprotection was performed using 20% piperidine in DMF.

Peptide cleavage was performed using TFA/TIS/$H_2O$=95:2.5:2.5 (3 mL/100 mg resin) for 1 h. Peptides were precipitated using cold $Et_2O$ (−20° C.) by adding approximately 5× volume of the TFA used for cleavage and centrifuging at 7000 rpm at 0° C.

All peptides/conjugates were analysed on a Thermo Scientific Dionex Ultimate 3000 RP-HPLC equipped with a Phenomenex Gemini NX C18 110 Å (150×4.6 mm) column using the following buffer systems: A: 0.1% HCOOH in milliQ water. B: MeCN using a flow rate of 1 ml/min. The column was flushed with 100% A for 5 min prior to an injection and was flushed for 5 min with 95% B and 5% A after the run was finished.

Peptides were analysed using the following gradient: 95% A for 2 min. 5-95% B in 15 min. 95% B for 5 min. 95% A for 4 min.

Peptides and conjugates were purified using the same gradient as mentioned above, on a Thermo Scientific Dionex Ultimate 3000 RP-HPLC with a flow rate of 5 mL/min using a Phenomenex Gemini NX C18 110 Å (150×10 mm) semi-prep column.

Abbreviations
AA amino acid
Boc butyloxycarbonyl
DCM dichloromethane
DIC N,N'-diisopropylcarbodiimide
DIPEA N,N-diisopropylethylamine
DMAP 4-dimethylaminopyridine
DMF dimethyl formamide
DMSO dimethyl sulfoxide
Eq equivalents
Fmoc fluorenylmethyloxycarbonyl
GABA gamma-aminobutyric acid
H hours
HATU 1-[bis(dimethylamino)methylene]-1H-1,2,3-triazolo[4,5-b]pyridinium 3-oxid hexafluorophosphate
HOSu 1-hydroxypyrrolidine-2,5-dione (N-hydroxysuccinimide)
HPLC high performance liquid chromatography
LC liquid chromatography
MeCN acetonitrile
mQ Milli q water (deionised water)
MS mass spectrometry
Pbf 2,2,4,6,7-pentamethyldihydrobenzofurane
PG protecting group
SPPS solid-phase peptide synthesis
TFA trifluoroacetic acid
TIS triisopropylsilane
UV ultraviolet Example 1—Synthesis of Compounds 1, 2 and 3

Compound 1

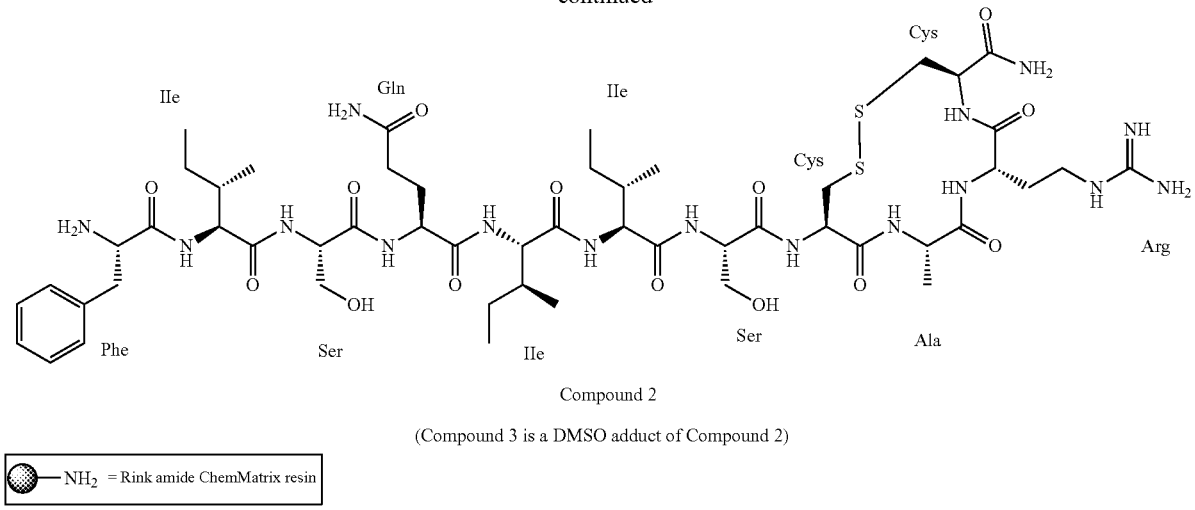

Compound 2

(Compound 3 is a DMSO adduct of Compound 2)

Synthesis of Compounds 1, 2 & 3: a. Fmoc-AA(PG)-OH (AA=amino acid, PG=protecting group), DIC/Oxyma microwave couplings followed by 20% piperidine in DMF. b. TFA:TIS:H$_2$O=95:2.5:2.5, 1 h. c: DMSO:mQ=1:3 (peptide concentration 1 mM) in air, 12 h.

Steps a and b. Commercially available Rink amide Chem-matrix resin (manufacturer's loading=0.49 mmol/g) was swelled in DMF and through automated standard SPPS Compound 1 was synthesized using the general procedure described hereinabove.

Step c. Crude Compound 1 was then dissolved in DMSO: mQ water=1:3 while maintaining a peptide concentration of 1 mM and was stirred for 12 h at r.t. in air to yield Compounds 2 (~60%) & 3 (~40%). Compounds 2 and 3 were purified using semi-prep RP-HPLC using the protocols described hereinabove.

Example 2—Synthesis of Compound 4

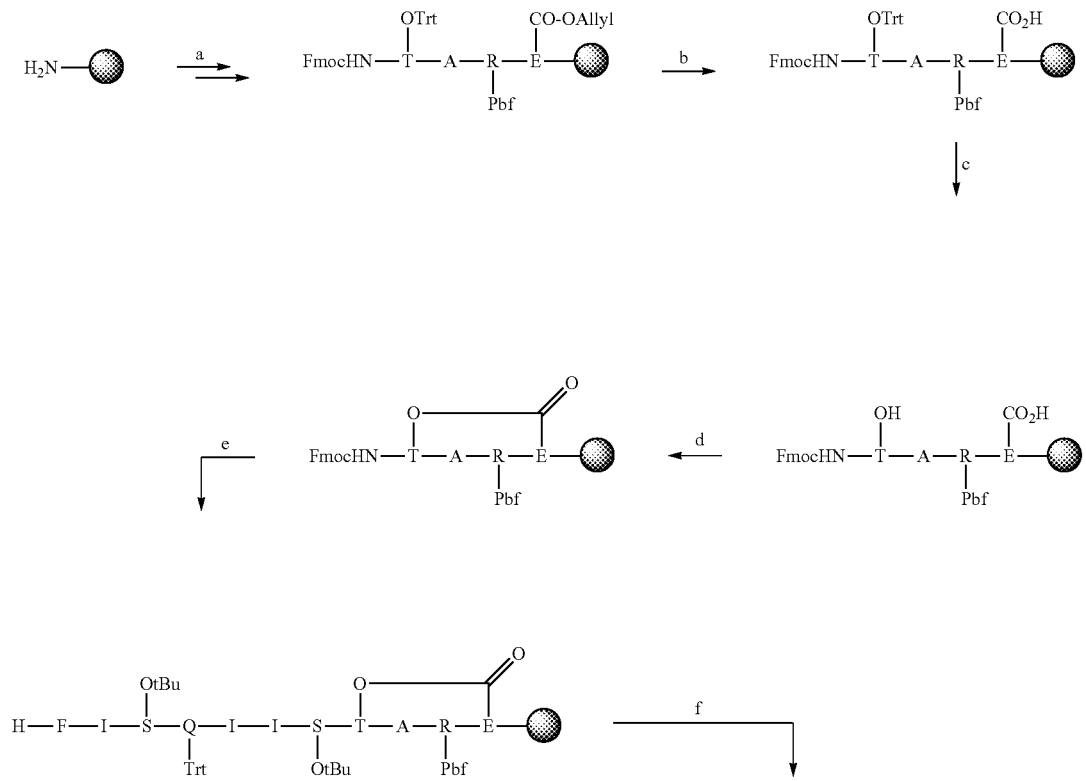

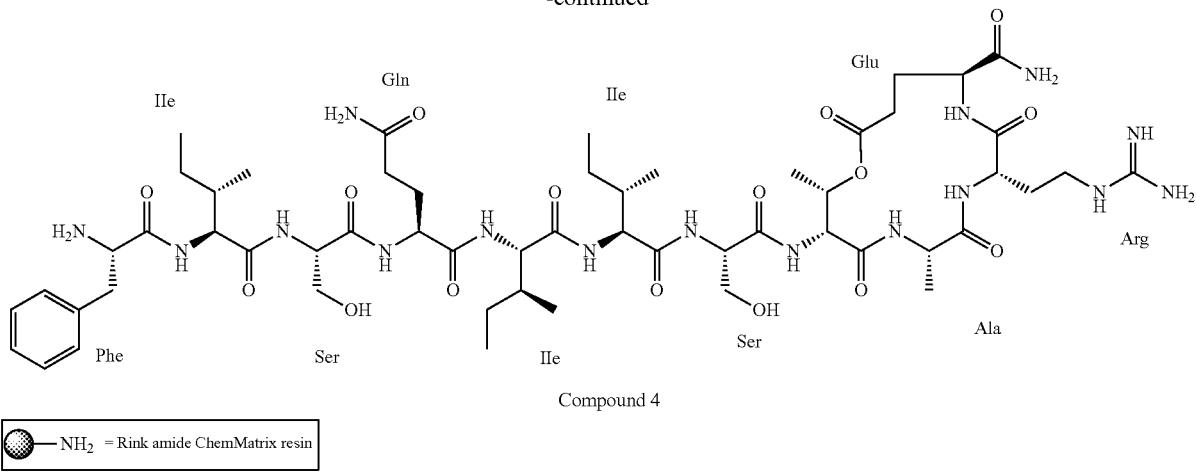

Compound 4

●—NH₂ = Rink amide ChemMatrix resin (TARE = SEQ ID NO: 3; HFISQIISTARE = (SEQ ID NO: 4)

Synthesis of Compound 4: a. Fmoc-AA(PG)-OH (AA=amino acid, PG=protecting group), HATU/DIPEA followed by 20% piperidine in DMF. b. [Pd(PPh₃)₄]⁰ (0.2 eq.)+24 eq. PhSiH₃ in DCM, 2×1 h. c. 24×30 s TFA:TIS:DCM=2:5:93. d. 2.5 eq. DIC/12 eq. DMAP in DMF, overnight. e. Fmoc-AA(PG)-OH (AA=amino acid, PG=protecting group), DIC/Oxyma microwave couplings followed by 20% piperidine in DMF. f. TFA:TIS:H₂O=95:2.5:2.5, 1 h.

Step a. Commercially available Rink amide Chemmatrix resin (manufacturer's loading=0.49 mmol/g) was swelled in DMF and through automated standard SPPS residues Fmoc-Glu(OAll)-OH, Fmoc-Arg(Pbf)-OH, Fmoc-Ala-OH and Fmoc-D-Thr(Trt)-OH were coupled in succession using the general protocol described hereinabove.

Step b. The Allyl protecting group of Glu was removed using 0.2 eq. [Pd(PPh³)]⁰ and 24 eq. PhSiH₃ in dry DCM under argon for 1 h. This procedure was repeated twice and the resin was washed thoroughly with DCM and DMF to remove any Pd stuck to the resin.

Step c. The resin was swelled in DCM. The Trt protecting group of Thr was then removed using 24×30 s bursts of 2% TFA+5% TIS in DCM.

Step d. Esterification was performed using 2.5 eq. DIC+ 12 eq. DMAP in DMF by shaking the resin overnight.

Step e. The subsequent amino acids were coupled using the protocols described hereinabove.

Step f. Cleavage, precipitation and HPLC purification were performed using the protocols described hereinabove (10% overall recovery after HPLC purification).

Example 3—Synthesis of Compound 5

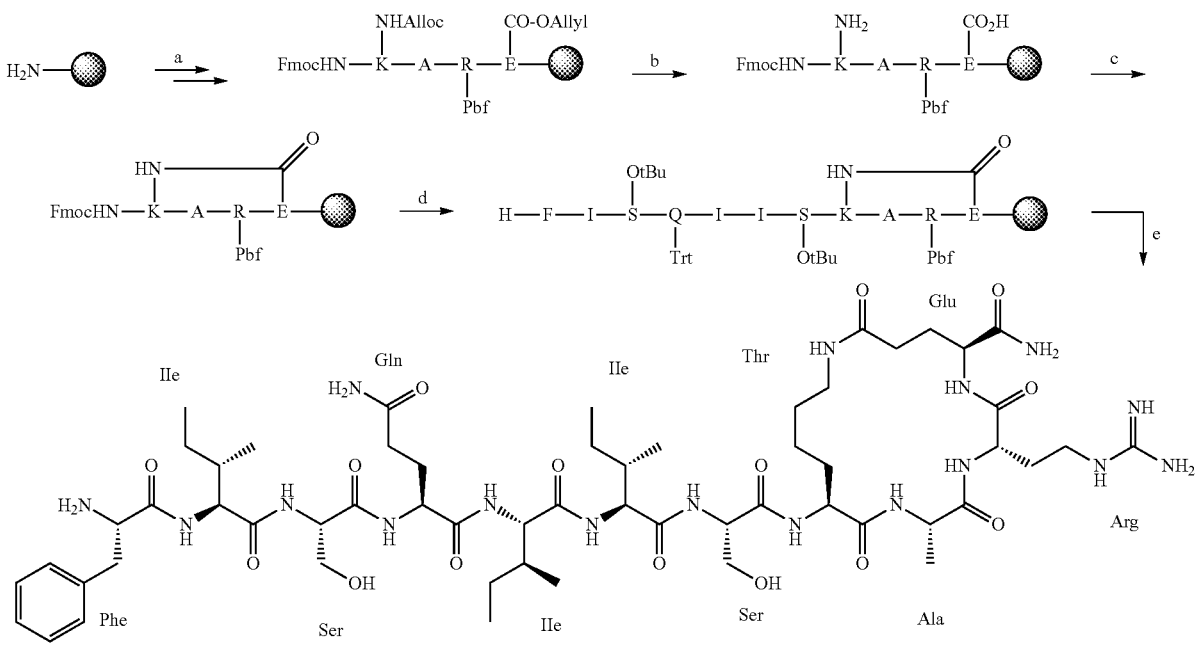

Compound 5

-continued

◯—NH₂ = Rink amide ChemMatrix resin (KARE = (SEQ ID NO: 5); HFISQIISKARE = (SEQ ID NO: 6))

Synthesis of Compound 5: a. Fmoc-AA(PG)-OH (AA=amino acid, PG=protecting group), HATU/DIPEA followed by 20% piperidine in DMF. b. [Pd(PPh₃)₄]⁰ (0.4 eq.)+48 eq. PhSiH₃ in DCM, 2×1 h. c. 2 eq. HATU/8 eq. DIPEA, overnight. d. Fmoc-AA(PG)-OH (AA=amino acid, PG=protecting group), DIC/Oxyma microwave couplings followed by 20% piperidine in DMF. e. TFA:TIS:H₂O=95:2.5:2.5, 1 h.

Step a. Commercially available Rink amide Chemmatrix resin (manufacturer's loading=0.49 mmol/g) was swelled in DMF and through automated standard SPPS residues Fmoc-Glu(OAll)-OH, Fmoc-Arg(Pbf)-OH, Fmoc-Ala-OH and Fmoc-Lys(Alloc)-OH were coupled in succession using the general protocols described hereinabove.

Step b. The Allyl protecting group of Glu and the Alloc protecting group of Lys were removed using 0.4 eq. [Pd(PPh₃)]⁰ and 48 eq. PhSiH₃ in dry DCM under argon for 1 h. This procedure was repeated twice and the resin was washed thoroughly with DCM and DMF to remove any Pd stuck to the resin.

Step c. Amide bond formation was performed using 2 eq. of HATU with 8 eq. of DIPEA in DMF by shaking the resin overnight.

Step d. The subsequent amino acids were coupled using the general protocols described hereinabove.

Step e. Cleavage, precipitation and HPLC purification were performed using the general protocols described hereinabove (50% overall recovery after purification).

Reference Example 4: Synthesis of Reference Compound 6

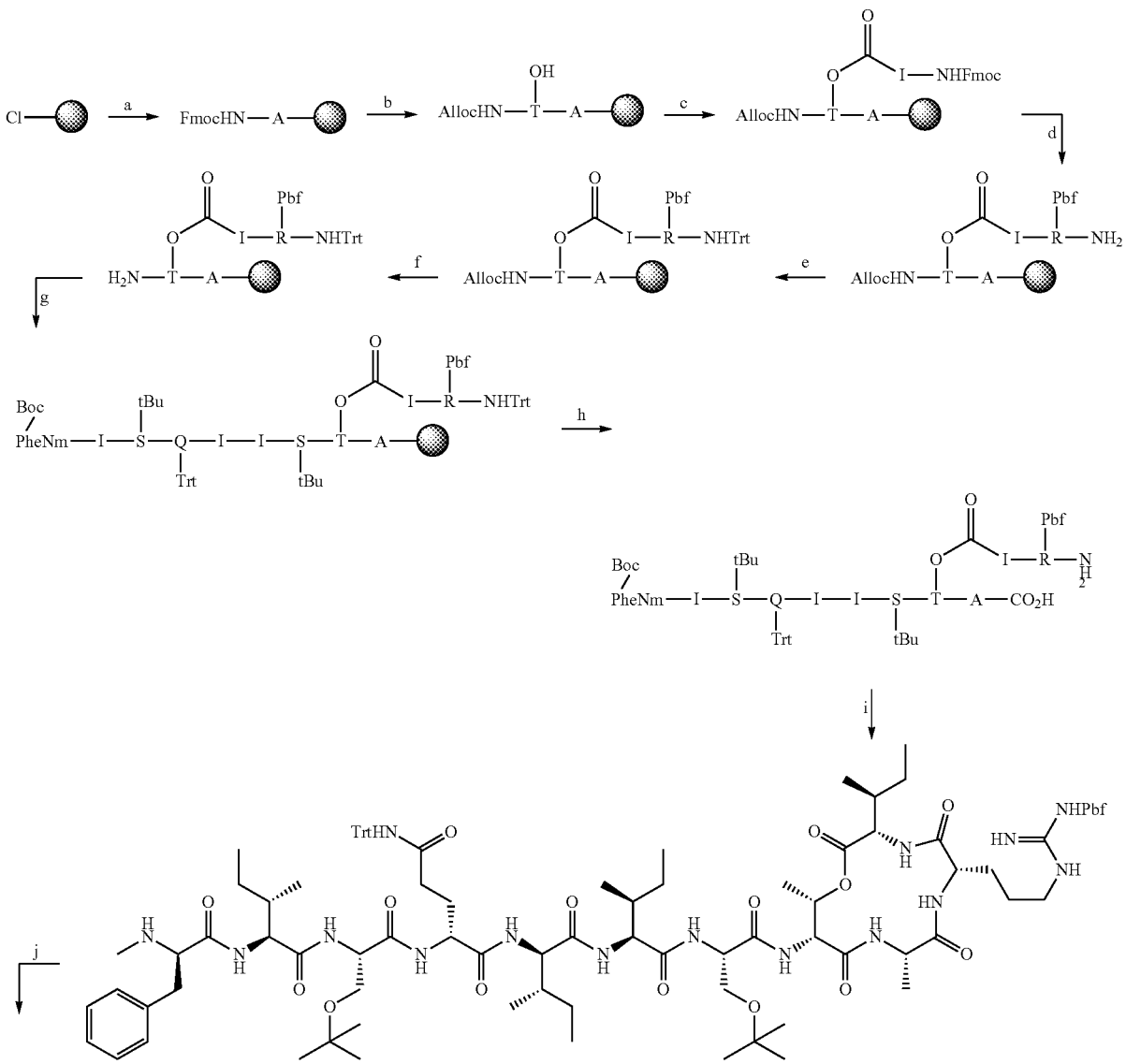

-continued

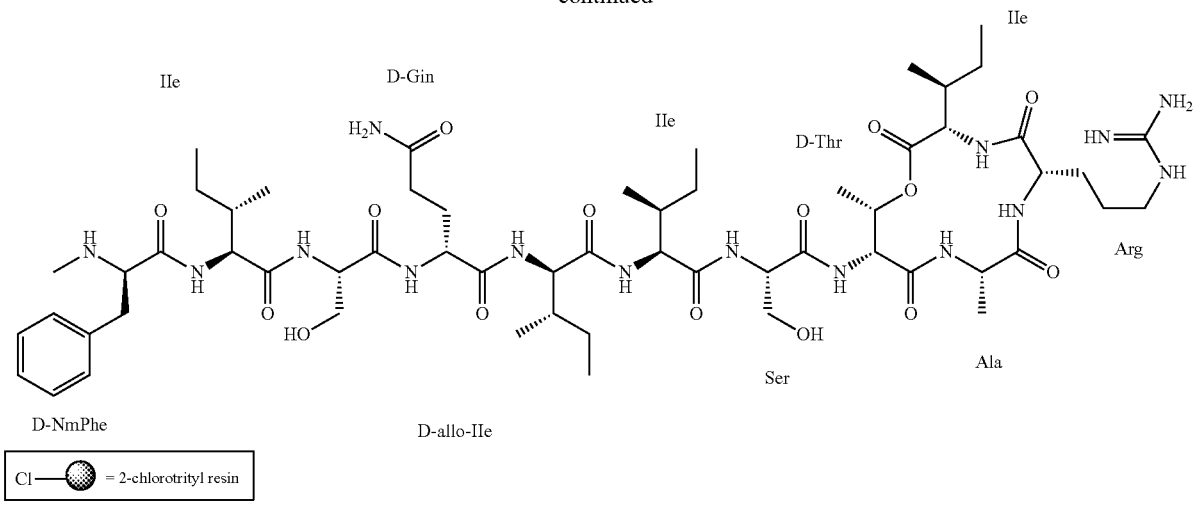

(ISQIISTA = (SEQ ID NO: 7))

Synthesis of Compound 6: a. 4 eq. Fmoc-Ala-OH/8 eq. DIPEA in DCM, 3 h. b. 20% piperidine in DMF followed by 3 eq. AllocHN-D-Thr-OH, 3 eq. HATU/6 eq. DIPEA. c. 10 eq. Fmoc-Ile-OH, 10 eq. DIC, 5 mol % DMAP in DMF, 2 h followed by capping with $Ac_2O$/DIPEA 10% in DMF d. 4 eq. Fmoc-Arg(Pbf)-OH, 4 eq. HATU/8 eq. DIPEA in DMF, 1 h followed by 20% piperidine in DMF e. 10 eq. Trt-Cl, 15% $Et_3N$ in DCM, 1 h. f. $[Pd(PPh_3)_4]^0$ (0.2 eq.)+24 eq. $PhSiH_3$ in DCM, 2×1 h. g. Fmoc-AA(PG)-OH (AA=amino acid, PG=protecting group), HATU/DIPEA followed by 20% piperidine in DMF. h. TFA:TIS:DCM=2:5:93, 2 h. i. 1 eq. HATU/10 eq. DIPEA in DMF, 1 h, monitored on HPLC. j. TFA:TIS:$H_2O$=95:2.5:2.5, 1 h.

Step a. Commercially available 2-Chlorotrityl chloride resin (manufacturer's loading=1.2 mmol/g) was swelled in DCM in a reactor. To this resin was added 4 eq. Fmoc-Ala-OH/8 eq. DIPEA in DCM and the reactor was shaken for 3 h. The loading determined by UV absorption of the piperidine-dibenzofulvene adduct was calculated to be 0.68 mmol/g.

Step b. The fmoc protecting group was removed using 20% piperidine in DMF following the general procedure described hereinabove above. AllocHN-D-Thr-OH was then coupled to the resin by adding 3 eq. of the AA, 3 eq. HATU and 6 eq. DIPEA in DMF and shaking for 3 h at r.t.

Step c. Esterification was performed using 10 eq. of Fmoc-Ile-OH, 10 eq. DIC and 5 mol % DMAP in DCM and shaking the reaction for 2 h. This was followed by capping the unreacted alcohol using 10% $Ac_2O$/DIPEA in DMF and shaking for 30 min.

Step d. Fmoc-Arg(Pbf)-OH was coupled using 4 eq. of AA, 4 eq. HATU and 8 eq. DIPEA in DMF and shaking for 1 h followed by Fmoc deprotection using 20% piperidine in DMF as described in the general protocols hereinabove.

Step e. The N terminus of Arg was protected using 10 eq. Trt-Cl and 15% $Et_3N$ in DCM and shaking for 1 h. The protection was verified by the Ninhydrin colour test.

Step f. The Alloc protecting group of D-Thr was removed using 0.2 eq. $[Pd(PPh^3)]^0$ and 24 eq. $PhSiH_3$ in dry DCM under argon for 1 h. This procedure was repeated twice and the resin was washed thoroughly with DCM and DMF to remove any Pd stuck to the resin.

Step g. All amino acids were coupled using 4 eq. AA, 4 eq. HATU and 8 eq. DIPEA. Deprotection cycles were performed using the general protocol described hereinabove. Each coupling and deprotection cycle were checked by the Ninhydrin colour test.

Step h. The peptide was cleaved off from the resin without cleaving off the protecting groups for the amino acid side chains using TFA:TIS:DCM=2:5:93 and shaking for 2 h.

Step i. The solvent was evaporated and the peptide was redissolved in DMF to which 1 eq. HATU and 10 eq. DIPEA were added and the reaction was stirred for 1 h to perform the cyclization. The reaction was monitored on HPLC till all starting material had been consumed.

Step j. The side-chain protecting groups were then cleaved off using TFA:TIS:$H_2O$=95:2.5:2.5 by stirring for 1 h. The peptide was precipitated using cold $Et_2O$ (−20° C.) and centrifuging at 7000 rpm to obtain the crude white solid (44% overall yield, 70% purity). HPLC purification yielded the compound also as a white solid (50% recovery, 10% overall yield).

Example 5—Mass Spectrometry Data for Compounds 1 to 5 and Reference Compound 6

LC-MS data for Compounds 1 to 5 and Reference Compound 6 were collected on an Agilent 1100 Series instrument with a Phenomenex Kinetex C18 100 Å column (150×4.6 mm, 5 μm at 35° C.) connected to an ESMSD type VL mass detector with a flow rate of 1.5 ml/min was used with the following solvent systems: (A): 0.1% HCOOH in $H_2O$ and (B) MeCN. The column was flushed with 100% A for 2 min, then a gradient from 0 to 100% B over 6 min was used, followed by 2 min of flushing with 100% B. Results are shown in Table 1.

TABLE 1

Mass spectrometry data for Compounds 1 to 5 and Reference Compound 6

| Compound No. | Chemical formula | Mass calculated. | Mass observed. |
|---|---|---|---|
| 1. | $C_{53}H_{90}N_{16}O_{14}S_2$ | 1238.63 | 1239.45 [M + H$^+$] |
| 2. | $C_{53}H_{88}N_{16}O_{14}S_2$ | 1236.61 | 1237.35 [M + H$^+$] |
| 3. | $C_{53}H_{88}N_{16}O_{14}S_2$ | 1236.61 | 1314.3 [M + DMSO + H$^+$] |

TABLE 1-continued

Mass spectrometry data for Compounds 1 to 5 and Reference Compound 6

| Compound No. | Chemical formula | Mass calculated. | Mass observed. |
|---|---|---|---|
| 4. | $C_{56}H_{92}N_{16}O_{16}$ | 1244.69 | 1322.55 [M + DMSO + H$^+$] |
| 5. | $C_{58}H_{97}N_{17}O_{15}$ | 1271.74 | 636.9 [M/2 + H$^+$] |
| 6. | $C_{59}H_{97}N_{15}O_{16}$ | 1271.72 | 1272.60 [M + H$^+$] |

Example 6—Activity of Compounds 1 to 4 and Reference Compound 6 Against *Staphylococcus aureus*

Minimum inhibitory concentrations for various compounds against *S. aureus* are shown in Table 2.

TABLE 2

MIC values

| Compound no. | MIC (μg/ml) against *S. aureus* |
|---|---|
| 1 | 32 |
| 2 | 8 |
| 3 | 4 |
| 4 | 32 |
| 6 | 64 |

Example 7—Synthesis of Compounds 7 to 20

The general synthesis of Teixobactin derivatives in which the amino acid at position 10 (the L-allo-enduracididine amino acid) is replaced with another amino acid is detailed in Example 4, and is described in A. Parmar, et al., Chem. Commun. 2016, 52, 6060-6063.

Compounds 7 to 20 (including Reference Compound 13) were prepared by methods analogous to that method. Compounds 7 to 12 form a series of alanine derivatives of Teixobactin.

The structures of compounds 7 to 20 (including Reference Compound 13) are, respectively, as follows:

(SEQ ID NO: 11)

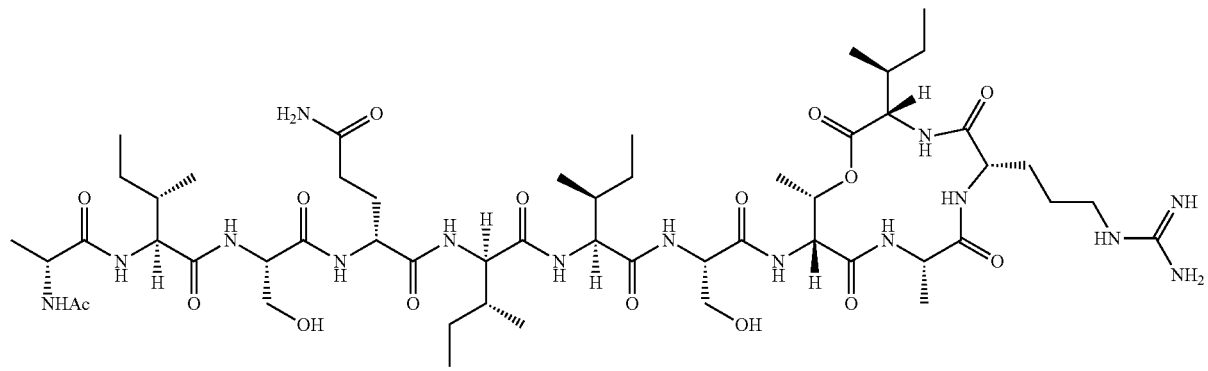

(SEQ ID NO: 12)

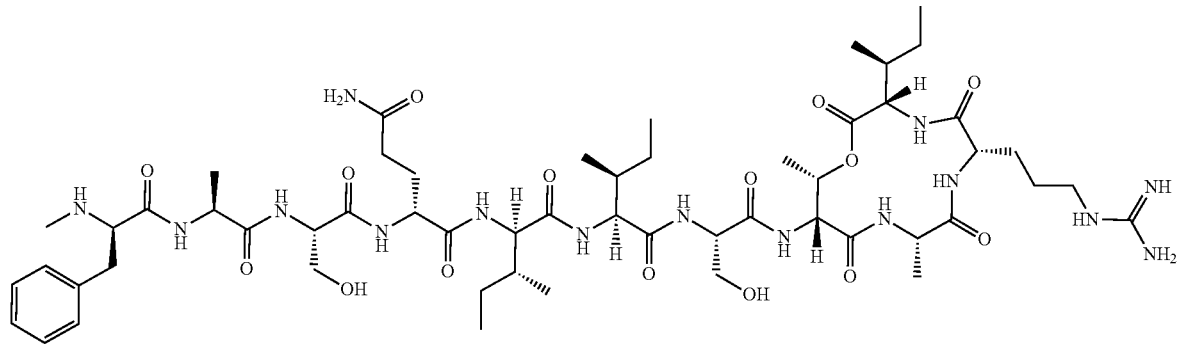

(SEQ ID NO: 13)
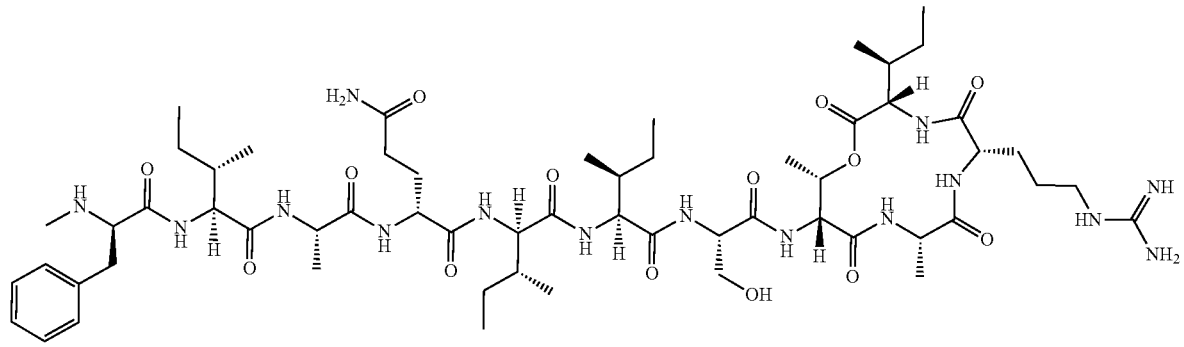
(SEQ ID NO: 14)
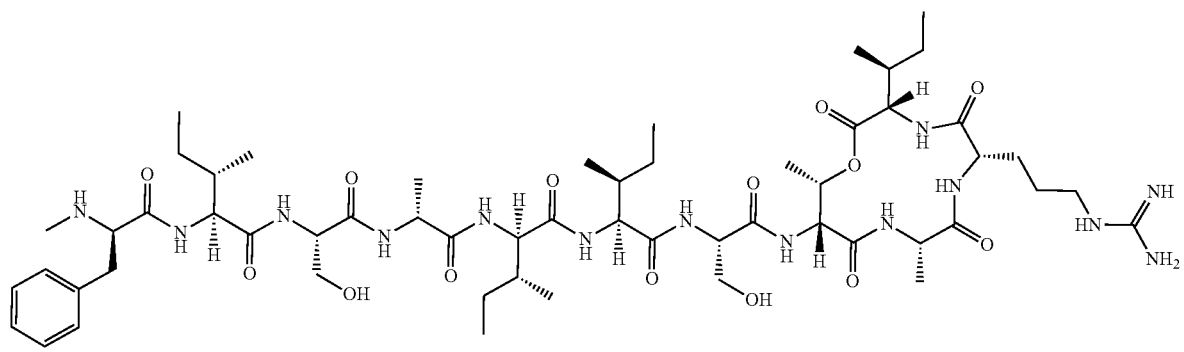
(SEQ ID NO: 15)
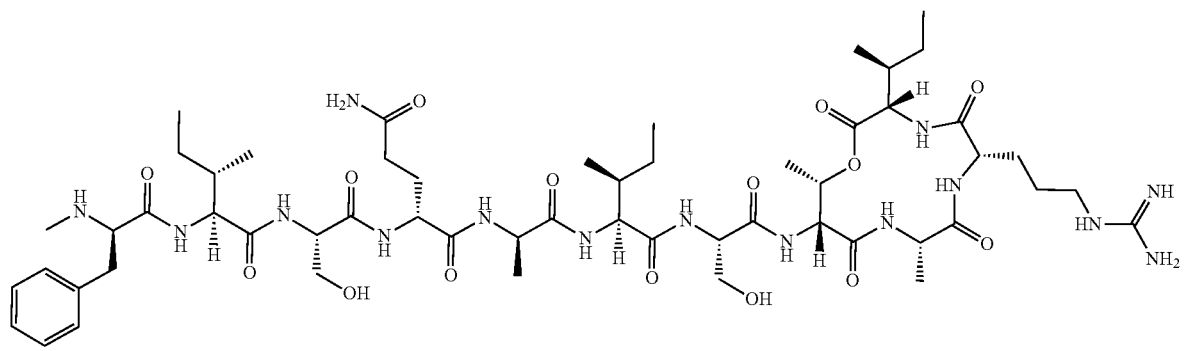
(SEQ ID NO: 16)
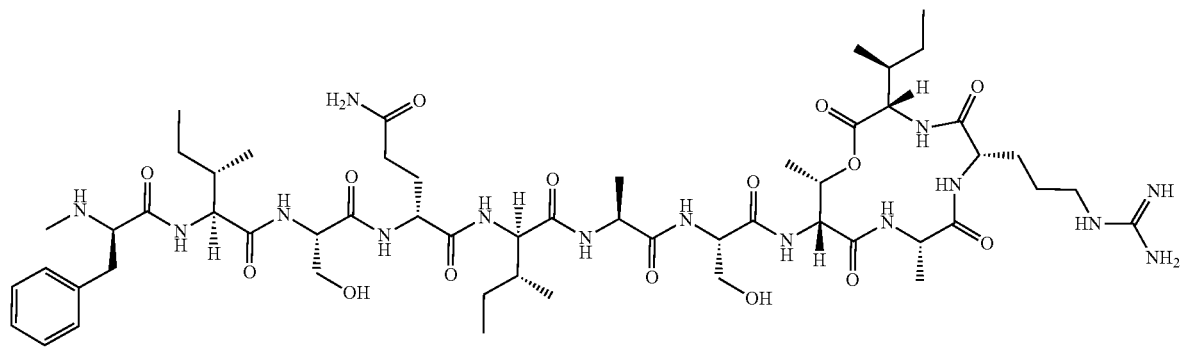

(SEQ ID NO: 17)
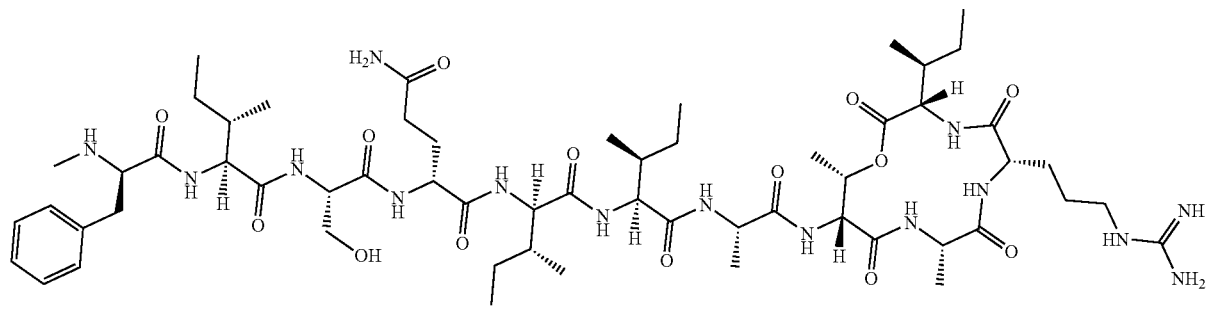
(SEQ ID NO: 10)
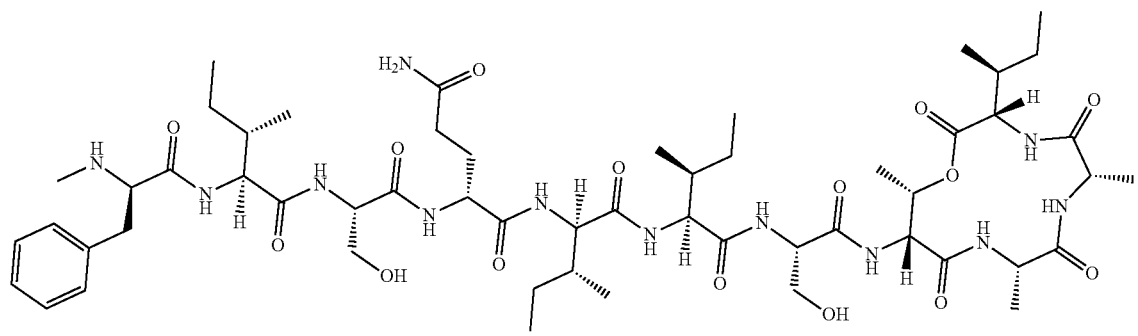
(SEQ ID NO: 10)
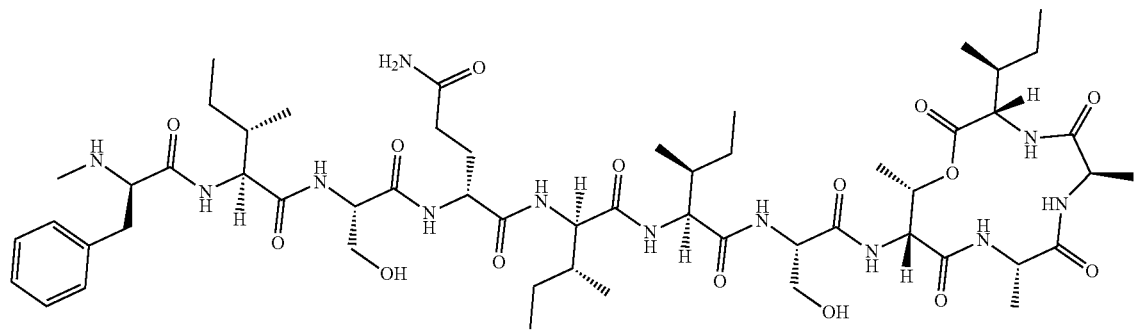
(SEQ ID NO: 10)
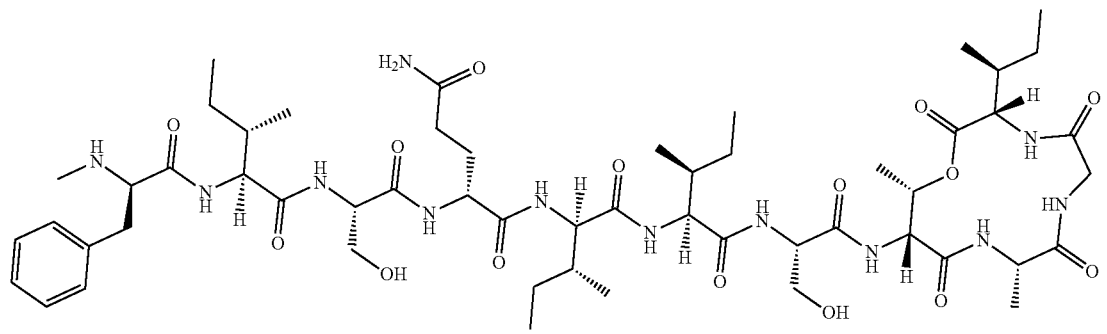

(SEQ ID NO: 10)
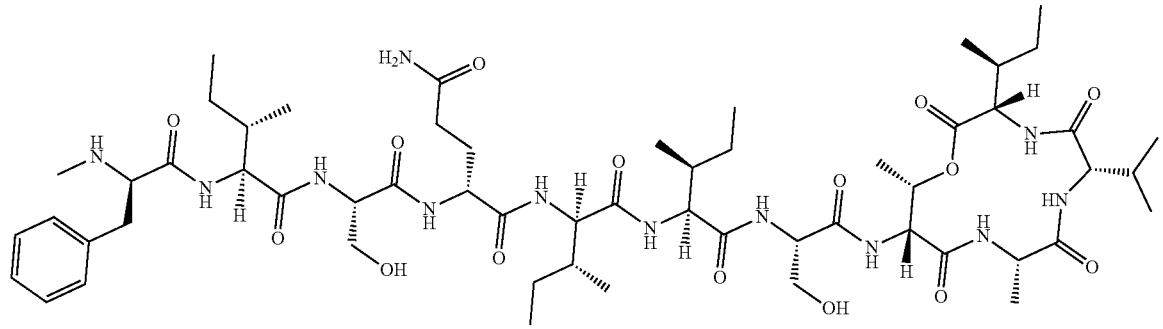
(SEQ ID NO:10)
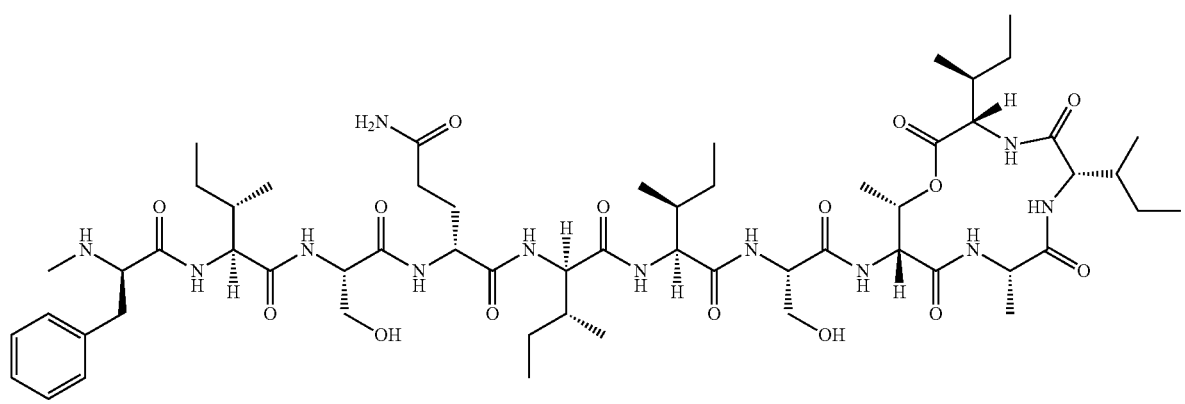
(SEQ ID NO:10)
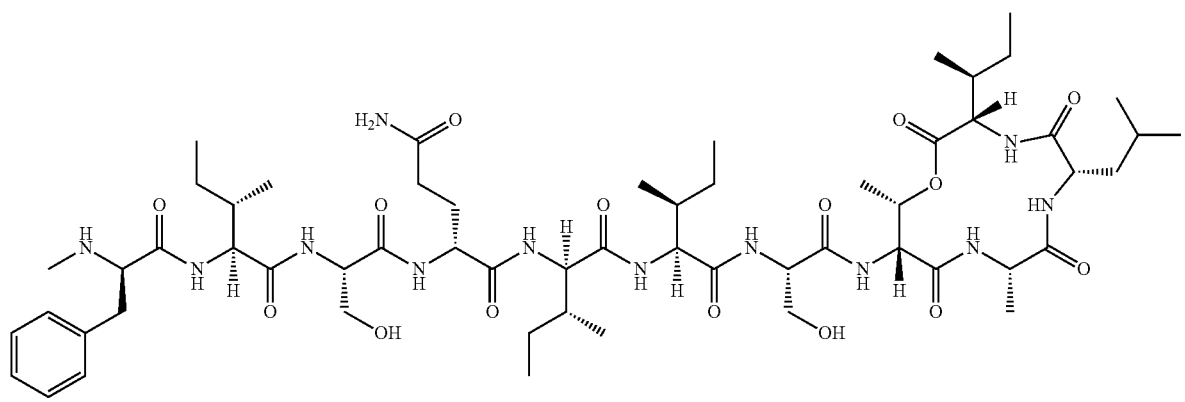
(SEQ ID NO:10)
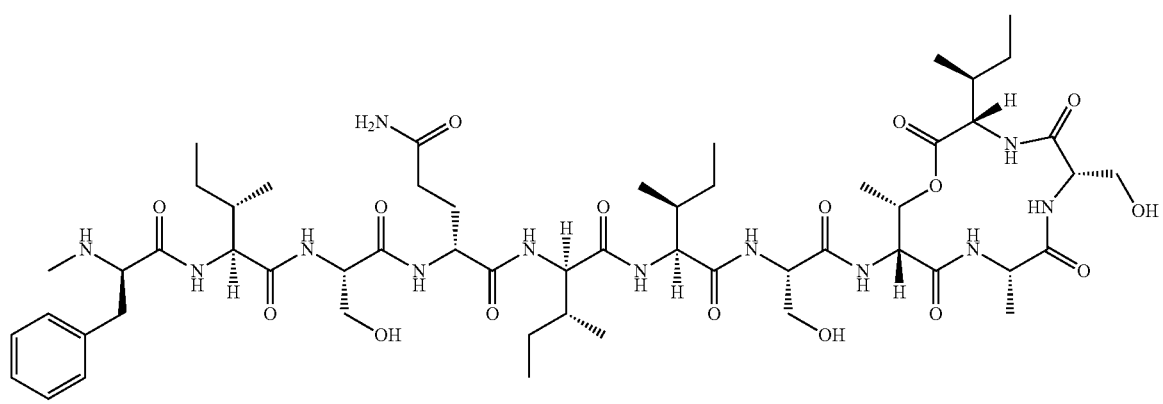

Example 8—Mass Spectrometry Data for Compounds 7 to 20

LC-MS data were collected on an Agilent 1100 Series instrument with a Phenomenex Kinetex C18 100 Å column (150×4.6 mm, 5 μm at 35° C.) connected to an ESMSD type VL mass detector with a flow rate of 1.5 ml/min was used with the following solvent systems: (A): 0.1% HCOOH in H$_2$O and (B) MeCN. The column was flushed with 100% A for 2 m %, then a gradient from 0 to 100% B over 6 min was used, followed by 2 min of flushing with 100% B. Results are shown in Table 3.

TABLE 3

Mass spectrometry data for Compounds 7 to 20

| Compound Number | Code | Chemical formula | Exact Mass | Mass found [M + H$^+$] | Overall yield [%] |
|---|---|---|---|---|---|
| 7 | f1a | $C_{53}H_{93}N_{15}O_{16}$ | 1195.69 | 1196.4 | 12 |
| 8 | I2A | $C_{55}H_{91}N_{15}O_{15}$ | 1201.68 | 1202.4 | 10 |
| 9 | S3A | $C_{58}H_{97}N_{15}O_{14}$ | 1227.73 | 1228.5 | 11 |
| 10 | q4a | $C_{56}H_{94}N_{14}O_{14}$ | 1186.71 | 1187.4 | 12 |
| 11 | i5a | $C_{55}H_{91}N_{15}O_{15}$ | 1201.68 | 1202.4 | 11 |
| 12 | I6A | $C_{55}H_{91}N_{15}O_{15}$ | 1201.68 | 1202.4 | 12 |
| 13* | S7A | $C_{58}H_{97}N_{15}O_{14}$ | 1227.73 | 1228.5 | 12 |
| 14 | R10A | $C_{55}H_{90}N_{12}O_{15}$ | 1158.66 | 1159.5 | 13 |
| 15 | R10a | $C_{55}H_{90}N_{12}O_{15}$ | 1158.66 | 1159.5 | 10 |
| 16 | R10G | $C_{54}H_{88}N_{12}O_{15}$ | 1144.65 | 1145.6 | 2 |
| 17 | R10V | $C_{57}H_{94}N_{12}O_{15}$ | 1186.70 | 1187.6 | 24 |
| 18 | R10I | $C_{58}H_{96}N_{12}O_{15}$ | 1200.71 | 1201.5 | 10 |
| 19 | R10L | $C_{58}H_{96}N_{12}O_{15}$ | 1200.71 | 1201.5 | 20 |
| 20 | R10S | $C_{55}H_{90}N_{12}O_{16}$ | 1174.66 | 1175.6 | 21 |

*Reference compound

Example 9—Activity of Compounds 7 to 20 Against MRSA and *Mycobacterium smegmatis*

Minimum inhibitory concentrations for various compounds against MRSA are shown in Table 4A.

TABLE 4A

MIC values

| Compound No. | Name | MIC (MRSA*) (μg/mL) | MIC (μg/mL) Mycobacterium smegmatis |
|---|---|---|---|
| 7 | f1a | >128 | NT |
| 8 | I2A | >128 | NT |
| 9 | S3A | 1-2 | NT |
| 10 | q4a | 2-4 | NT |
| 11 | i5a | 64-128 | NT |
| 12 | I6A | >128 | NT |
| 13* | S7A | 16-32 | NT |
| 14 | R10A | 1-2 | 2 |
| 15 | R10a | 32 | NT |
| 16 | R10G | 2 | NT |
| 17 | R10V | 0.5 | NT |
| 18 | R10I | 0.25 | NT |
| 19 | R10L | 0.25 | NT |
| 20 | R10S | 16 | NT |
| * | Argio-Teixobactin | 2 | NT |
| * | Teixobactin | 0.25 | NT |

Small letters denote D amino acids.
MIC: Minimum Inhibitory Concentration.
NT: Not tested.
*MRSA ATCC 33591.
*Reference Compound We have performed an alanine scan of the Arg$_{10}$-teixobactin analogue via the synthesis of 14 analogues. The studies reveal that replacement of residues D-NMe-Phe$_1$, L-Ile$_2$, D-allo-Ile$_5$, L-Ile$_6$ and L-Ser, with Alanine (Compounds 7, 8, 11 and 12 and Reference Compound 13) results in a significant loss in antibacterial activity. However, the replacement of L-Ser$_3$ and D-Gln$_4$ with L-Ala and D-Ala respectively (Compounds 9 and 10) results in a comparable MIC value as that of the Arg$_{10}$-teixobactin analogue (Reference Compound 6). Contrary to the current understanding, we further observe that replacing the Arg$_{10}$ residue with non-polar residues such as Ile and Leu results in analogues which give exceptionally high biological activity, identical to that of Teixobactin against MRSA. Importantly, both Leu$_{10}$-teixobactin (Compound 19) and Ile$_{10}$-teixobactin (Compound 18) are made up of commercially available simpler building blocks rather than the synthetically challenging enduracididine. It thus seems that the presence of an amino acid with a cationic side chain such as enduracididine, arginine or lysine is not essential for biological activity. NMR studies have also revealed that the mutants S3A, Q4A and R10A (Compounds 9, 10 and 14) are more unstructured towards the N-termini but highly structured towards the C termini due to the close-by ring. Surprisingly, Gly$_{10}$-teixobactin (Compound 16) shows identical activity to Arg$_{10}$-teixobactin (Reference Compound 6) proving that a complete removal of the chiral center at position 10 is tolerated provided the configuration of the remaining residues is intact. Compounds 14, 17, 18 and 19, along with Arg$_{10}$-teixobactin and vancomycin/daptomycin as controls, were tested against an extended panel of Gram positive bacteria (Table 4B) to provide a more comprehensive overview of the biological activity of these molecules.

TABLE 4B

MIC and MBC (in μg/mL) of the teixobactin analogues 14,17,18 and 19, Arg$_{10}$-teixobactin and daptomycin control against an extended panel of Gram positive bacteria.

| Strain | Compound | 14 | 17 | 18 | 19 | Arg$_{10}$-teixobactin | Vancomycin | Daptomycin |
|---|---|---|---|---|---|---|---|---|
| MRSA1 | MIC | 4 | 1 | 0.25 | 0.25 | 1 | 2 | 0.5 |
|  | MBC | 16 | 4 | 1 | 2 | 2 | — | — |
| MRSA 2 | MIC | 1 | 0.5 | <0.0625 | <0.0625 | 0.125 | 2 | 0.5 |
|  | MBC | 4 | 4 | <0.0625 | <0.0625 | 0.5 | — | — |
| MRSA 3 | MIC | 1 | 0.25 | <0.0625 | <0.0625 | 0.5 | 2 | 0.5 |
|  | MBC | 2 | 2 | 0.125 | <0.0625 | 1 | — | — |

TABLE 4B-continued

MIC and MBC (in µg/mL) of the teixobactin analogues 14,17,18 and 19, Arg$_{10}$-teixobactin and daptomycin control against an extended panel of Gram positive bacteria.

| Strain | Compound | 14 | 17 | 18 | 19 | Arg$_{10}$-teixobactin | Vancomycin | Daptomycin |
|---|---|---|---|---|---|---|---|---|
| Staph. aureus | MIC | 1 | 0.25 | <0.0625 | <0.0625 | 0.25 | 4 | 0.25 |
|  | MBC | 2 | 1 | 0.125 | 0.125 | 1 | — | — |
| VRE 1 | MIC | 4 | 0.5 | <0.0625 | 0.25 | 2 | >4 | 0.5 |
| VRE 2 | MIC | 4 | 0.5 | <0.0625 | 0.25 | 2 | >4 | 0.5 |
| M. smegmatis | MIC | 1-2 | 1 | 0.5 | 1 | 1-2 | >64 | — |

Strain information: MRSA 1: MRSA ATCC 700699, MRSA 2: MRSA DR 42412 (sputum), MRSA 3: MRSA DM21455 (eye). MRSA 2 and MRSA 3 are clinical isolates.
*Staphylococcus aureus* ATCC 29213, *Enterococcus faecalis* (VRE 1: VRE ATCC 700802, VRE 2: VRE ATCC 29212). *M. smegmatis* ATCC 607. Culture Media: Mueller Hinton Broth.

Example 10—Synthesis of Compound 21 (Diamino$_{10}$-Teixobactin)

The diamino linker was synthesized for Diamino$_{10}$-Teixobactin using the procedure below.

Synthesis of Diamino NHS Linker

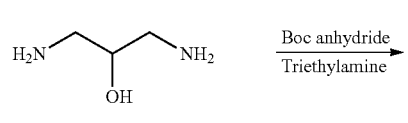

1,3-diaminopropan-2-ol

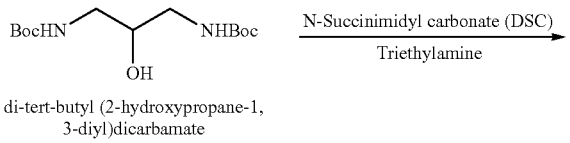

di-tert-butyl (2-hydroxypropane-1,3-diyl)dicarbamate

di-tert-butyl (2-hydroxypropane-1,3-diyl)dicarbamate di-tert-butyl (2-((((2,5-dioxopyrrolidin-1-yl)oxy)carbonyl)oxy)propane-1,3-diyl)dicarbamate 1,3-diaminopropan-2-ol (200 mg, 2.22 mmols) was dissolved in 20 ml methanol and triethylamine (20 ml) was added dropwise. Boc anhydride (3eq) was then added and heated at 50° C. for 20 min and 1 hr at room temperature. This was monitored by TLC (9:1) DCM:methanol. After completion saturated solution of NaHCO$_3$ was added (40 ml) and extracted with ethyl acetate. The solvent was evaporated in vacuo and used in the next step without purification.

Di-tert-butyl (2-hydroxypropane-1,3-diyl)dicarbamate (800 mg, 2.76 mmols) was dissolved in 30 ml acetonitrile. N-succinimidyl carbonate (DSC) (1.4 g, 5.52 mmols) was added and dropwise addition of trimethylamine (1.1 ml, 8.28 mmols) was added leaving the reaction to stir overnight. After completion of the reaction, the solvent was evaporated and purified on silica with DCM:methanol (9:1) to achieve di-tert-butyl (2-((((2,5-dioxopyrrolidin-1-yl)oxy)carbonyl)oxy)propane-1,3-diyl)dicarbamate, 76% yield. The compound was characterized by mass spectrometry.

Synthesis of Diamino₁₀-Teixobactin (FISQIIS=SEQ ID NO: 10)

Synthesis Scheme for the Diamino Teixobactin Compound (Compound 21)

Lys₁₀-Teixobactin was synthesised using protocols described in A. Parmar, et al., *Chem. Commun.* 2016, 52, 6060-6063. Lys₁₀-Teixobactin (5 mg, 0.0041 mmols) was dissolved in 100 μL of DMSO and 75 μL of Dipea was added. Di-tert-butyl (2-((((2,5-dioxopyrrolidin-1-yl)oxy)carbonyl)oxy)propane-1,3-diyl)dicarbamate (2.65 mg, 0.00615 mmols) was dissolved in 50 μl and added to the Lys₁₀-Teixobactin solution. This was stirred for 10 min and then quenched with acetic acid 100 μl and monitored by HPLC. This was then purified by reverse phase and freeze dried to yield the BOC protected compound.

Example 11—Synthesis of Compounds 22 to 24

General Synthesis of Cyclic Thioureas

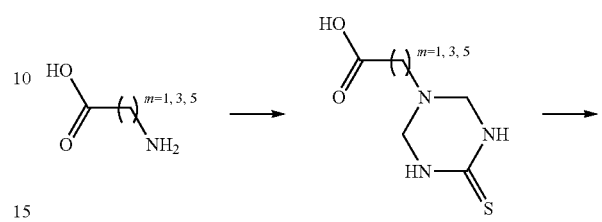

(SEQ ID NO: 10)

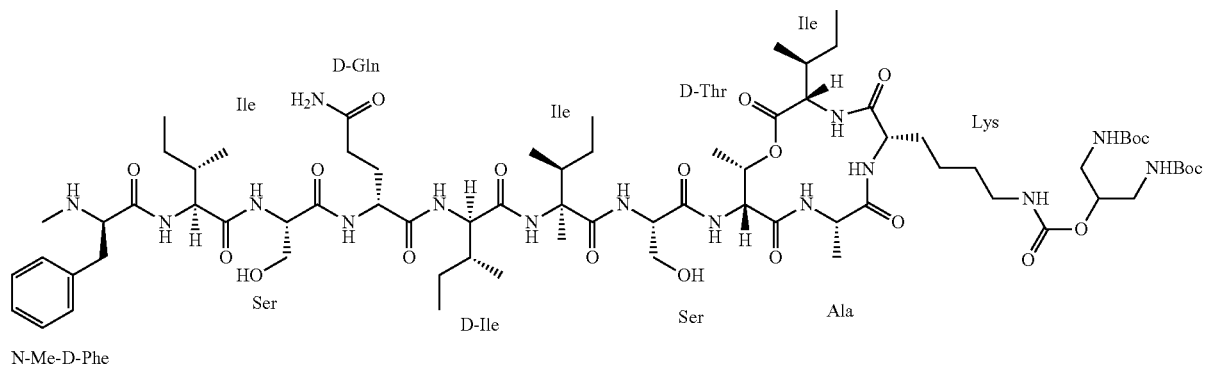

To Boc-diamino₁₀-Teixobactin was added neat formic acid and allowed to stir for 1 hr monitoring by HPLC. Water was then added and freeze dried to yield the Teixobactin diamino compound (Compound 21). The compound was characterized by mass spectrometry Exact Mass 1331.78 Mass found [M+H⁺] 1332.5.

(SEQ ID NO: 10)

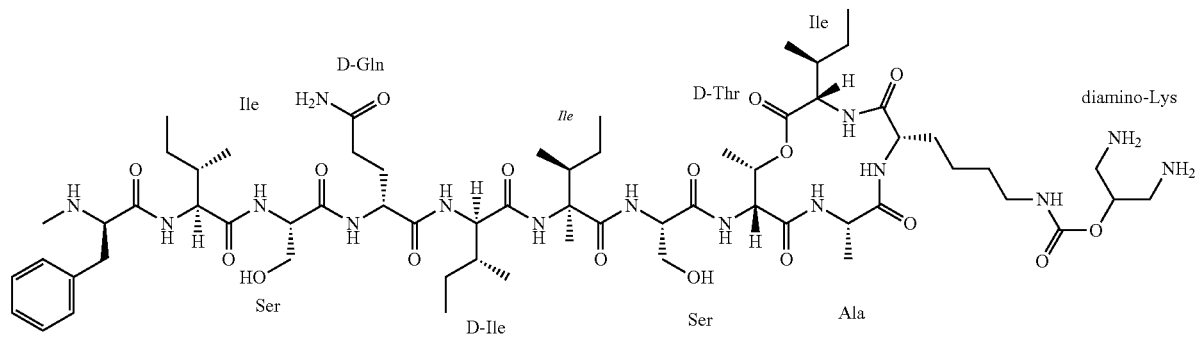

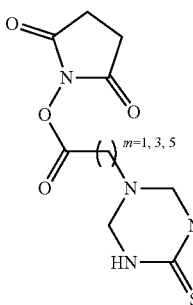

General Scheme for the Synthesis and Activation of Cyclic Thioureas

To a mixture of 3.80 g (100 mmol) of thiourea and 7.5 ml of 37% aqueous formaldehyde (93.4 mmol) was added at vigorous stirring 100 mmol of glycine/Gamma amino butyric acid/6-Aminohexanoic acid, and stirring was continued for another 20 min until it dissolved. The reaction was then left standing at room temperature. A day later, the precipitate was filtered off and recrystallized from a mixture of 2-propanol-water (1:1). Yields: 50-75%

Activation of Thioureas.

To 1 eq. Thiourea derivative (10 mg) dissolved in 500 μL of DMF 0.98 eq. HOSu (N-hydroxysuccinimide) and 0.98 eq. of DCC was added and stirred for 2 hrs until precipitation of cyclohexyl urea was complete. The precipitate was filtered off and discarded.

TABLE 5

List of thiourea derivatives synthesized

| Compound No. | Value of 'm' | Name |
|---|---|---|
| 25 | 1 | Gly-thiourea |
| 26 | 3 | GABA-thiourea |
| 27 | 5 | Ahx-thiourea |

TABLE 6

Mass analysis of analogues 22-24

| Compound No. | Analogue | Chemical Formula | Exact Mass | Mass found [M + H$^+$] |
|---|---|---|---|---|
| 22 | Gly-thiourea-Lys$_{10}$-teixobactin | $C_{63}H_{104}N_{16}O_{16}S$ | 1372.75 | 1373.55 |
| 23 | GABA-thiourea-Lys$_{10}$-teixobactin | $C_{65}H_{108}N_{16}O_{16}S$ | 1400.78 | 1401.45 |
| 24 | Ahx-thiourea-Lys$_{10}$-teixobactin | $C_{67}H_{112}N_{16}O_{16}S$ | 1428.82 | 1429.5 |

General Synthesis of Cyclic Thiourea-Containing Teixobactin Derivatives. (FISQIIS=SEQ ID NO: 10)

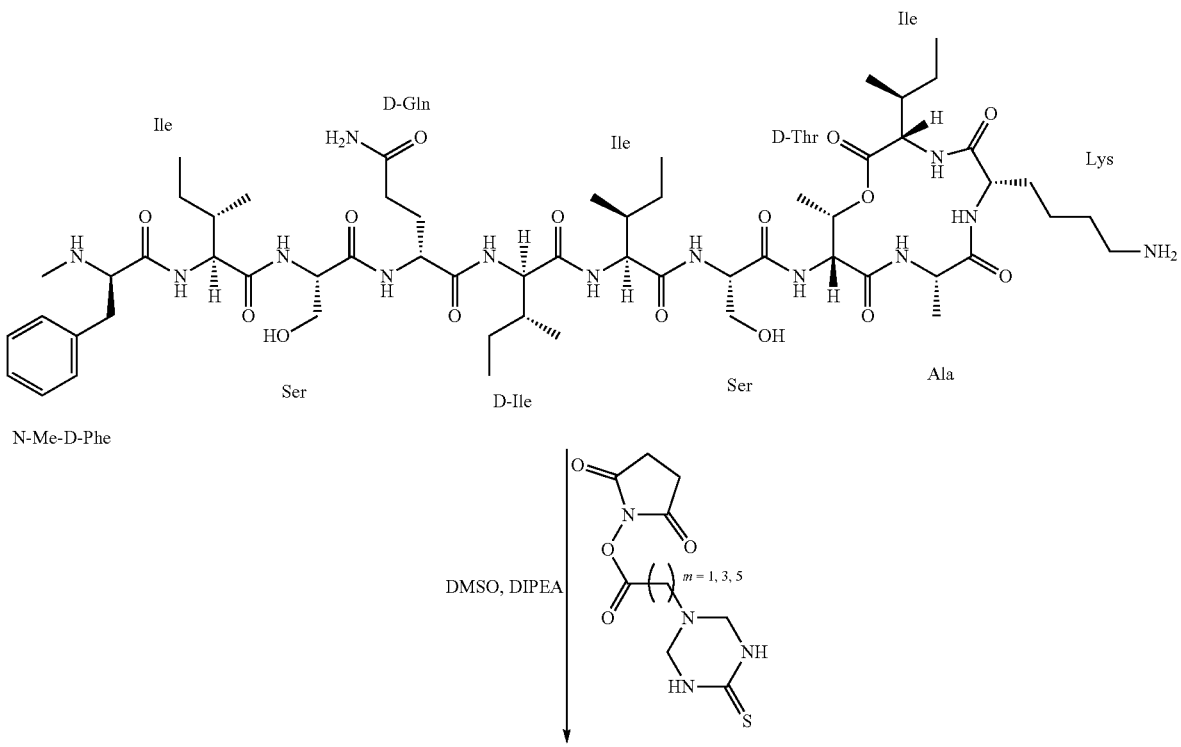

-continued

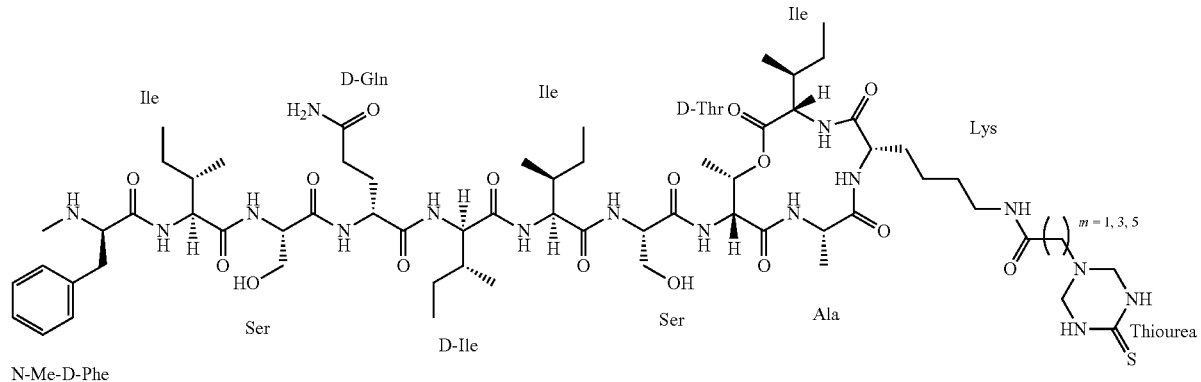

General Scheme for Synthesis of Thiourea-Containing Teixobactin (Compounds 22 to 24)

Lys$_{10}$-Teixobactin was synthesized using our previously described procedure (Parmar, A. et al. *Chem. Commun.* 52, 6060-6063 (2016)). Lys$_{10}$-Teixobactin (3 mg, 0.0025 mmol) was dissolved in 100 μL of DMSO and 50 μL of DIPEA was added. 60 μL of activated thiourea prepared as described above was added to the solution. This was stirred for 15 min and then acetonitrile was added dropwise until the solution was clear. The reaction mixture was analysed on RP-HPLC followed by RP-HPLC purification and freeze dried to yield the thiourea-containing Teixobactin derivatives (Compounds 22 to 24).

Example 12—Activity of Compounds 21 to 24 Against *S. aureus*, MRSA and *Mycobacterium smegmatis*

TABLE 7

MIC: Minimum Inhibitory Concentration.

| Compound No. | Name | MIC (MRSA*) (μg/mL) | MIC (μg/mL) *Mycobacterium smegmatis* |
|---|---|---|---|
| 21 | Diamino Teixobactin | 0.25 | 0.5 |

*MRSA ATCC 33591

TABLE 8

MIC: Minimum Inhibitory Concentration.

| Compound. No. | Value of 'm' | Name | MIC against *S. aureus* ATCC 25923 (μg/mL) |
|---|---|---|---|
| 22 | 1 | Gly-thiourea-Lys$_{10}$-Teixobactin | 2 |
| 23 | 3 | GABA-thiourea-Lys$_{10}$-Teixobactin | 2 |
| 24 | 5 | Ahx-thiourea-Lys$_{10}$-Teixobactin | 2 |

Example 13

The general synthesis of Teixobactin derivatives in which the amino acid at position 10 (the L-allo-enduracididine amino acid) is replaced with another amino acid is detailed in Example 4, and is described in A. Parmar, et al., *Chem. Commun.* 2016, 52, 6060-6063.

Compounds 25 to 53 are variants of Teixobactin in which the amino acid at position 10 is replaced with leucine, isoleucine, cyclohexylglycine, norvaline, phenylalanine or alanine, and from none to three of the amino acids at positions 3, 4 and 9 are replaced with arginine. These compounds were prepared by methods analogous to the method in Example 4. A detailed method for Compound 26 is provided in Example 14.

The structures of compounds 25 to 53 are, respectively, as follows:

(SEQ ID NO: 18)
Compound 25
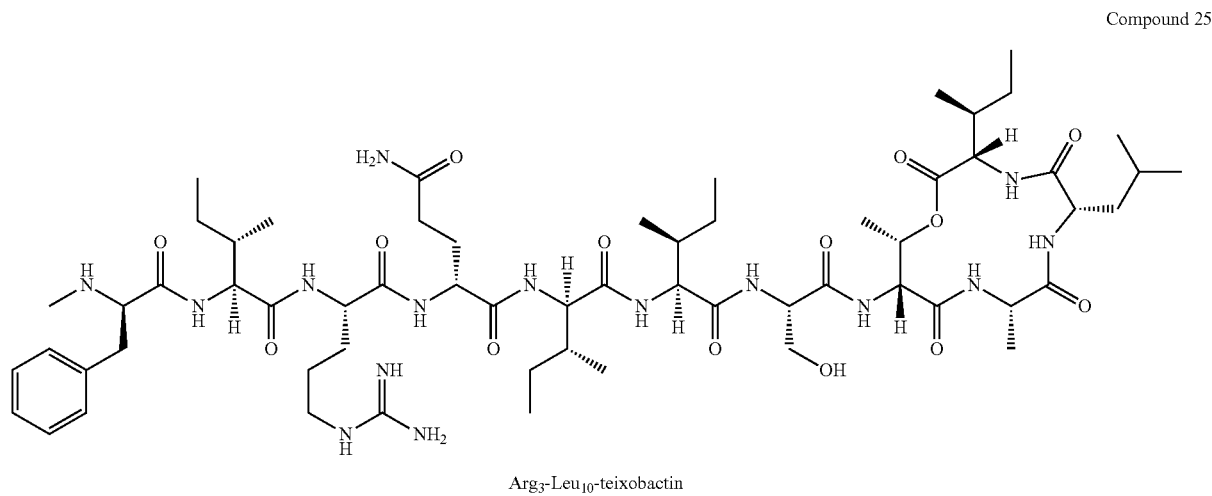
Arg$_3$-Leu$_{10}$-teixobactin
(SEQ ID NO: 19)
Compound 26
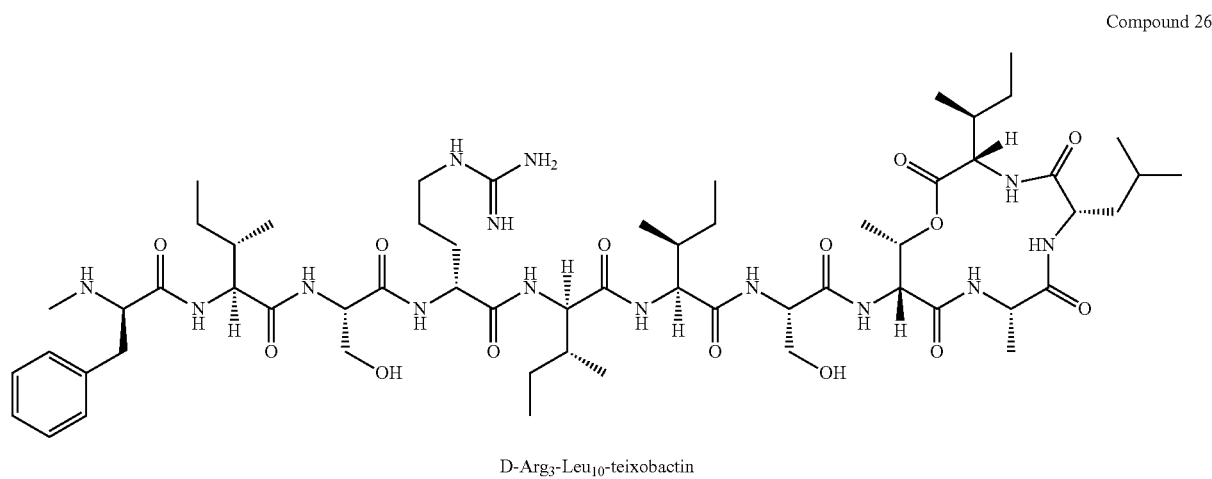
D-Arg$_3$-Leu$_{10}$-teixobactin
(SEQ ID NO: 10)
Compound 27
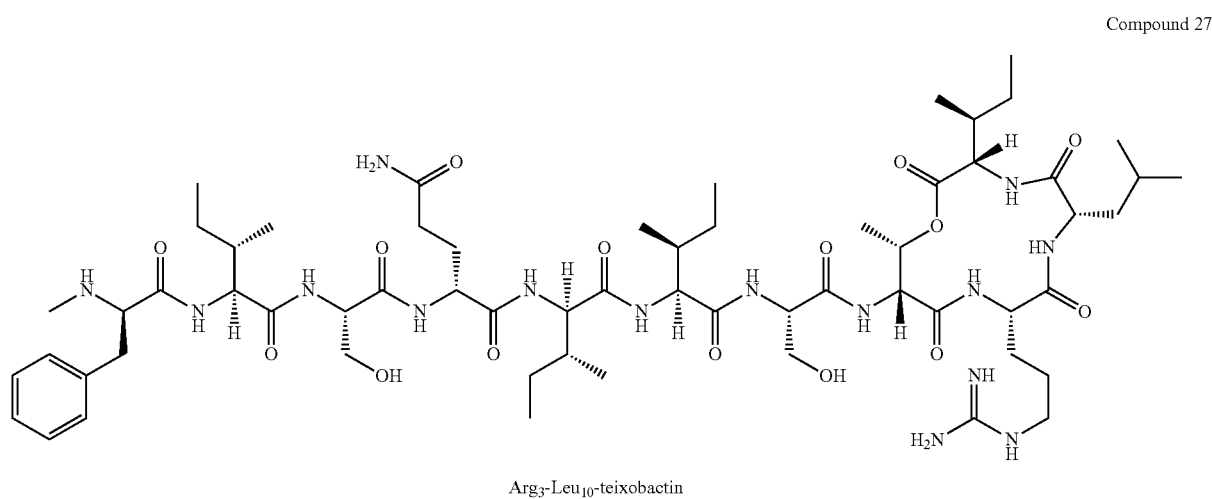
Arg$_3$-Leu$_{10}$-teixobactin -continued
(SEQ ID NO: 20)
Compound 28
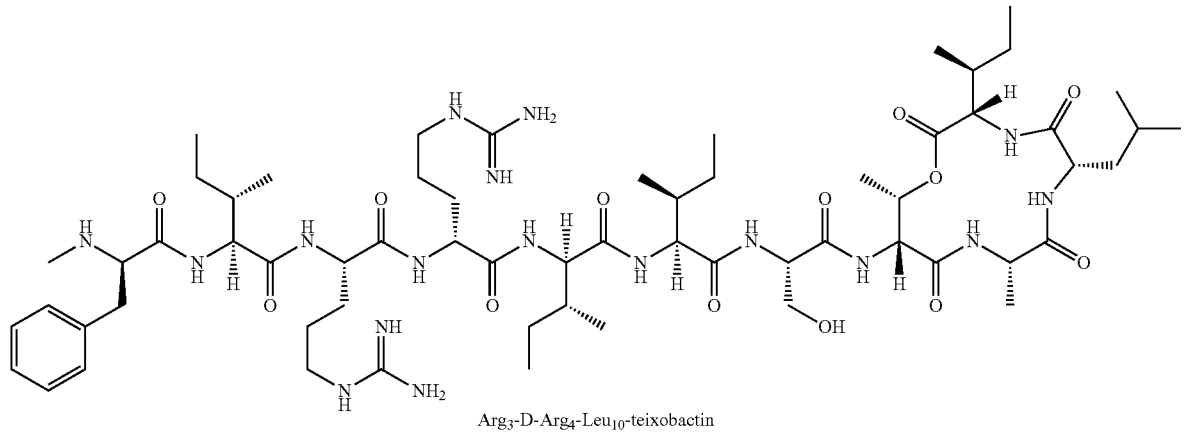
Arg₃-D-Arg₄-Leu₁₀-teixobactin
(SEQ ID NO: 21)
Compound 29
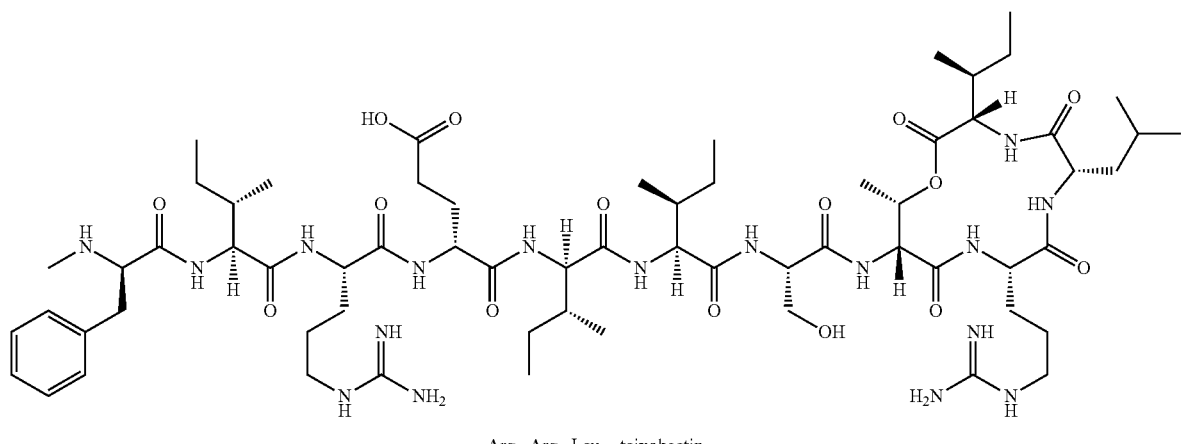
Arg₃-Arg₉-Leu₁₀-teixobactin
(SEQ ID NO: 19)
Compound 30
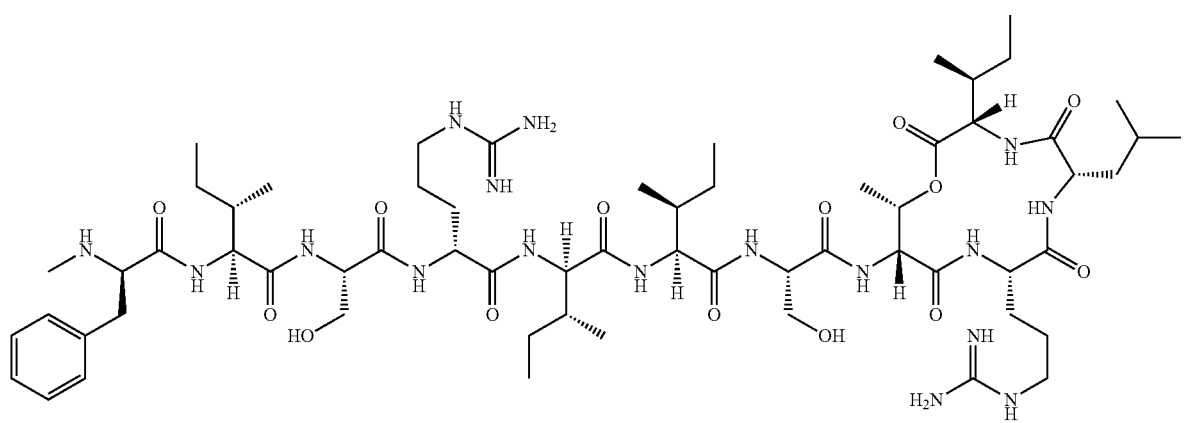
D-Arg₄-Arg₉-Leu₁₀-teixobactin (SEQ ID NO: 20)
Compound 31
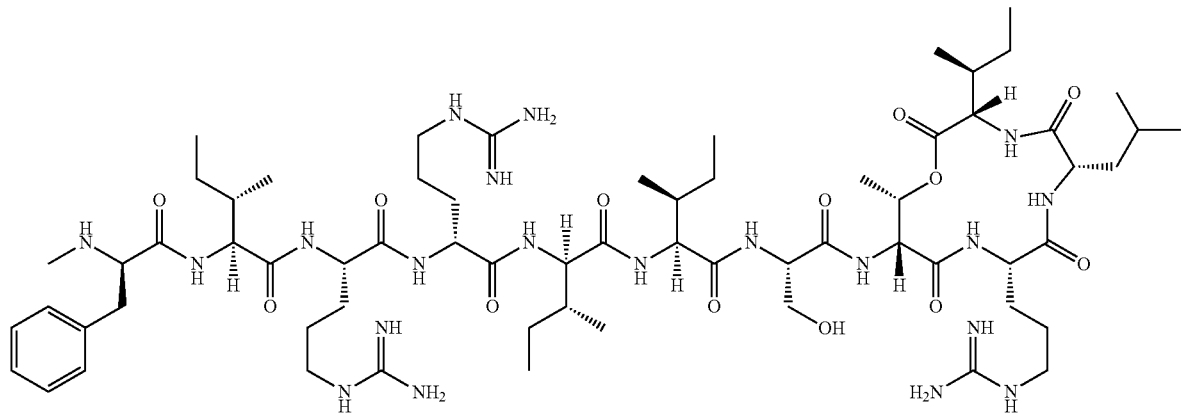
Arg$_3$-D-Arg$_4$-Leu$_{10}$-teixobactin
(SEQ ID NO: 18)
Compound 32
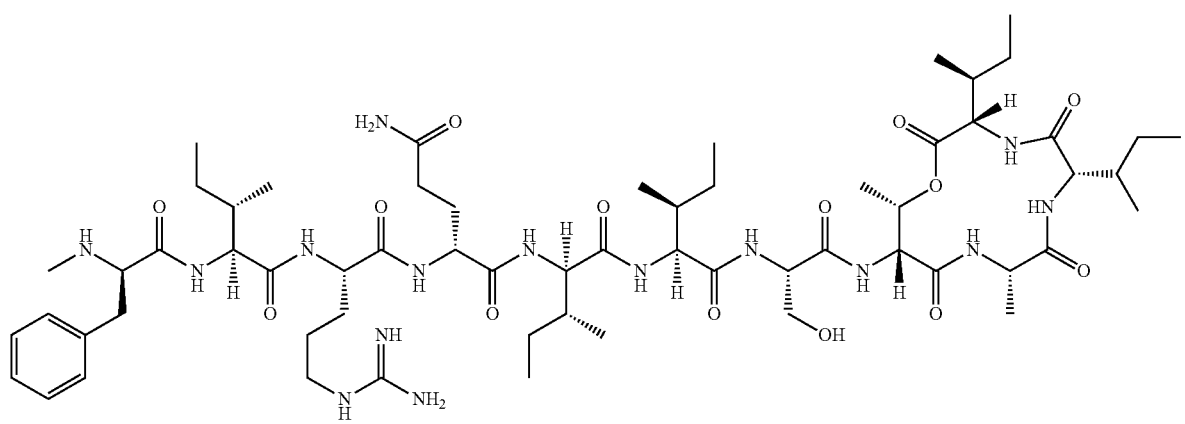
Arg$_3$-Ile$_{10}$-teixobactin
(SEQ ID NO: 19)
Compound 33
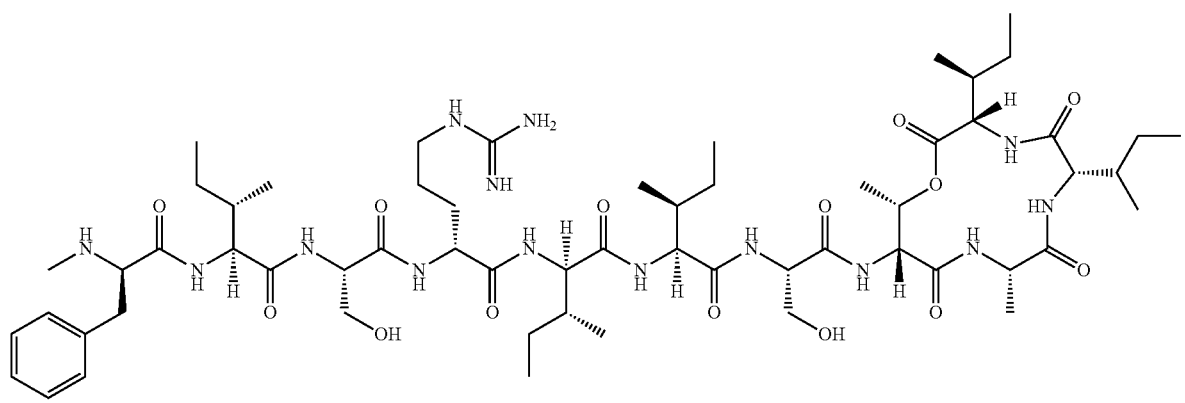
D-Arg$_4$-Ile$_{10}$-teixobactin (SEQ ID NO: 10)
Compound 34
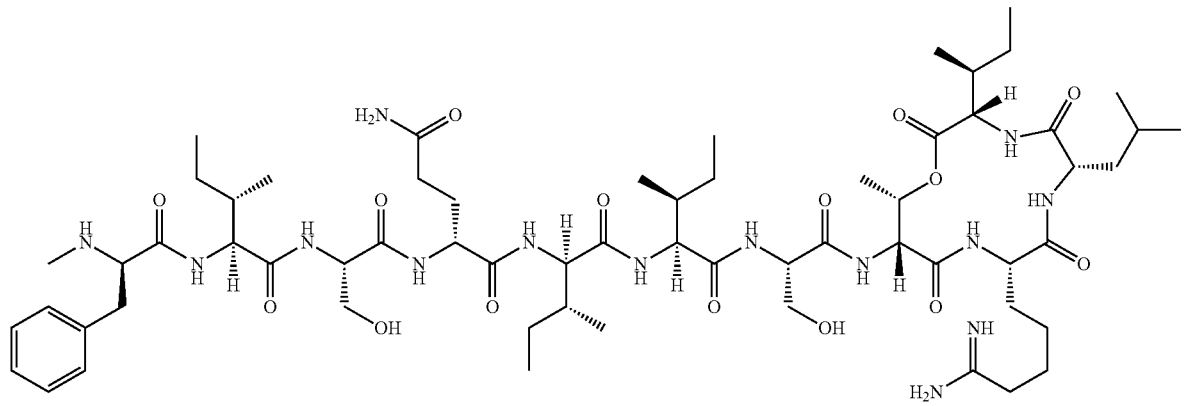
Arg₉-Leu₁₀-teixobactin
(SEQ ID NO: 20)
Compound 35
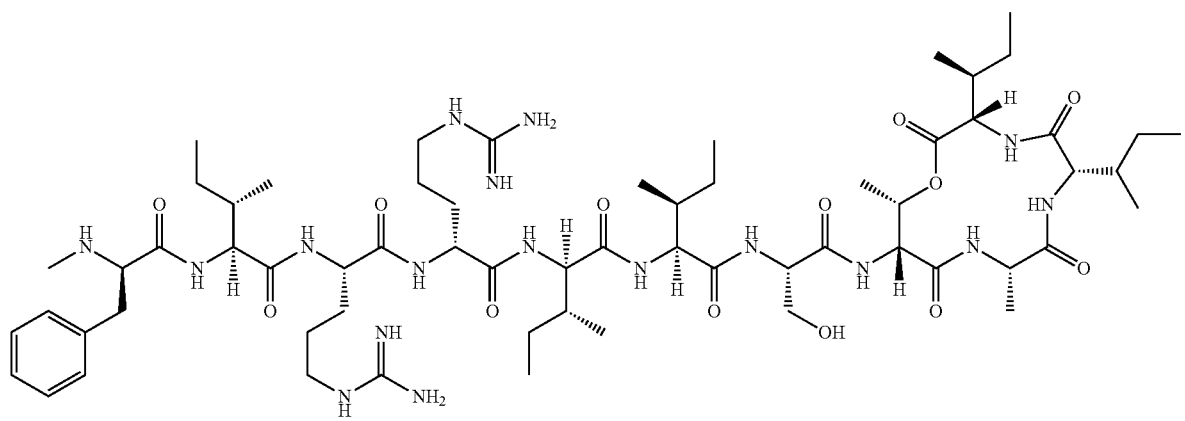
Arg₃-D-Arg₄-Ile₁₀-teixobactin
(SEQ ID NO: 10)
Compound 36
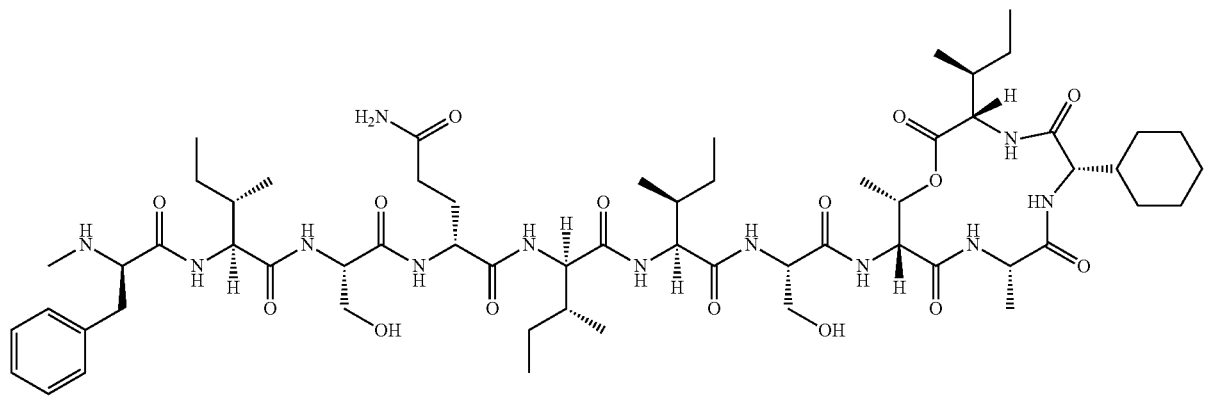
Chg₁₀-teixobactin -continued
(SEQ ID NO: 18)
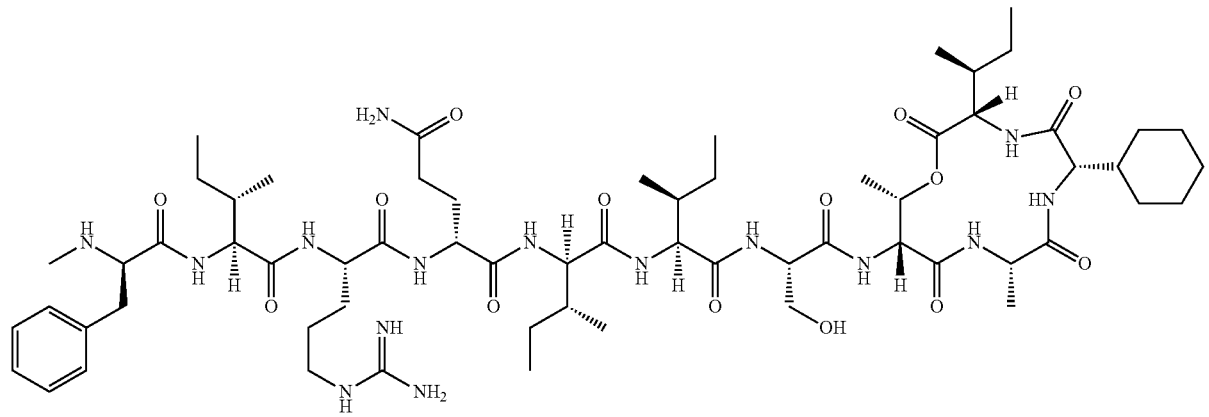
Compound 37
Arg₃-Chg₁₀-teixobactin
(SEQ ID NO: 19)
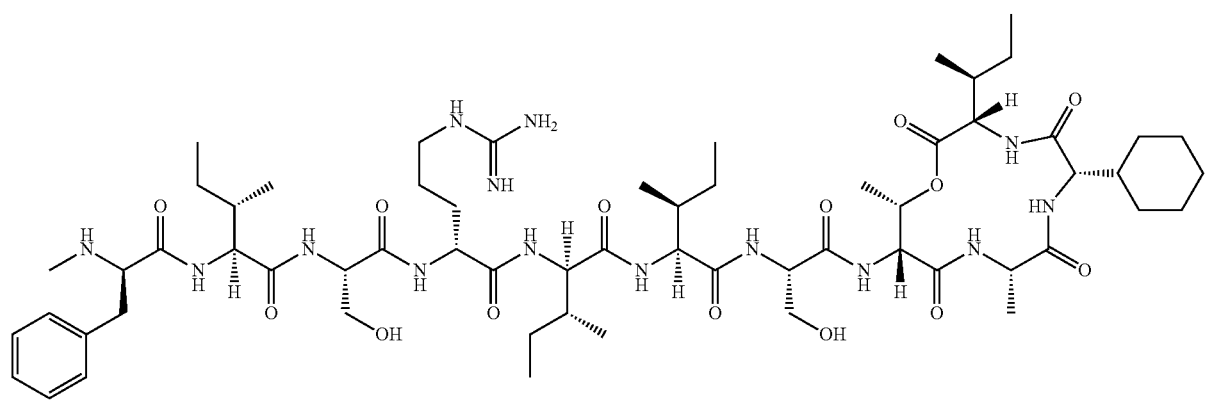
Compound 38
D-Arg₄-Chg₁₀-teixobactin
(SEQ ID NO: 10)
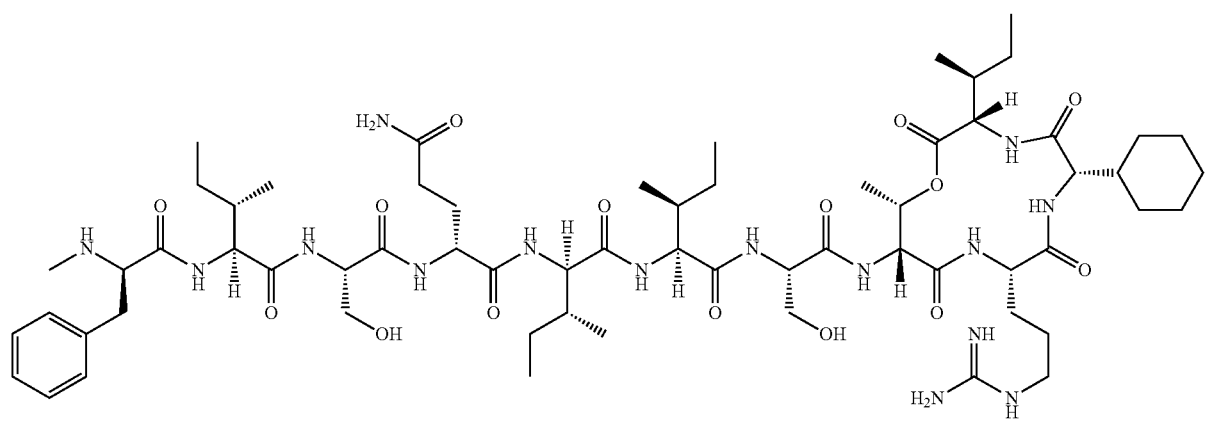
Compound 39
Arg₉-Chg₁₀-teixobactin -continued
(SEQ ID NO: 20)
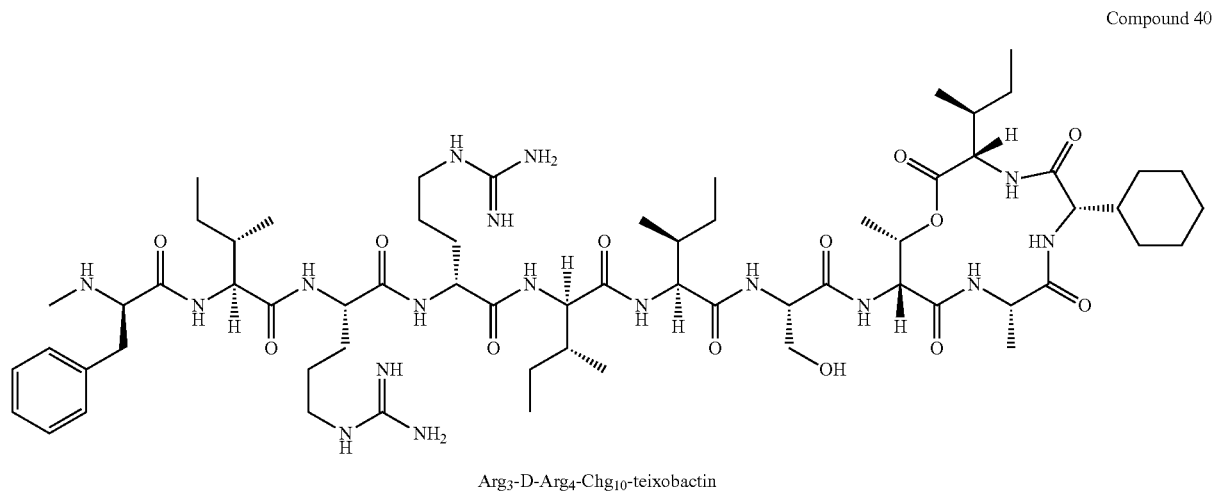
Compound 40
Arg₃-D-Arg₄-Chg₁₀-teixobactin
(SEQ ID NO: 21)
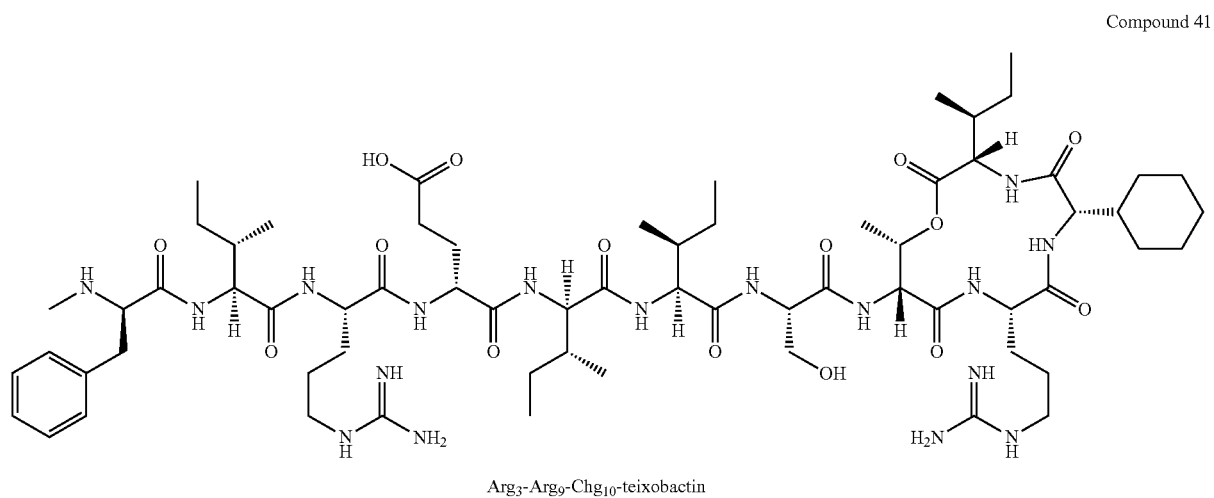
Compound 41
Arg₃-Arg₉-Chg₁₀-teixobactin
(SEQ ID NO: 19)
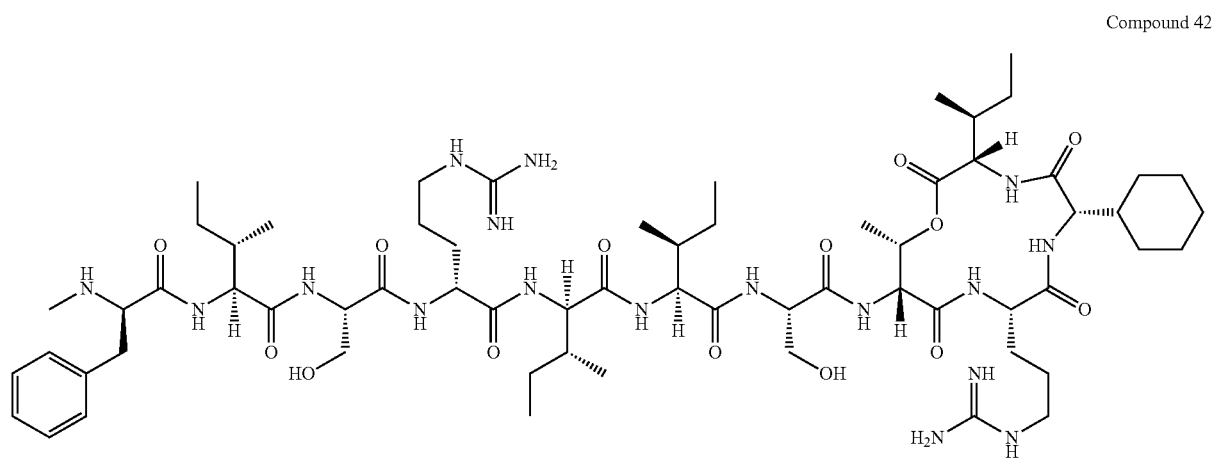
Compound 42
D-Arg₄-Arg₉-Chg₁₀-teixobactin -continued
(SEQ ID NO: 20)
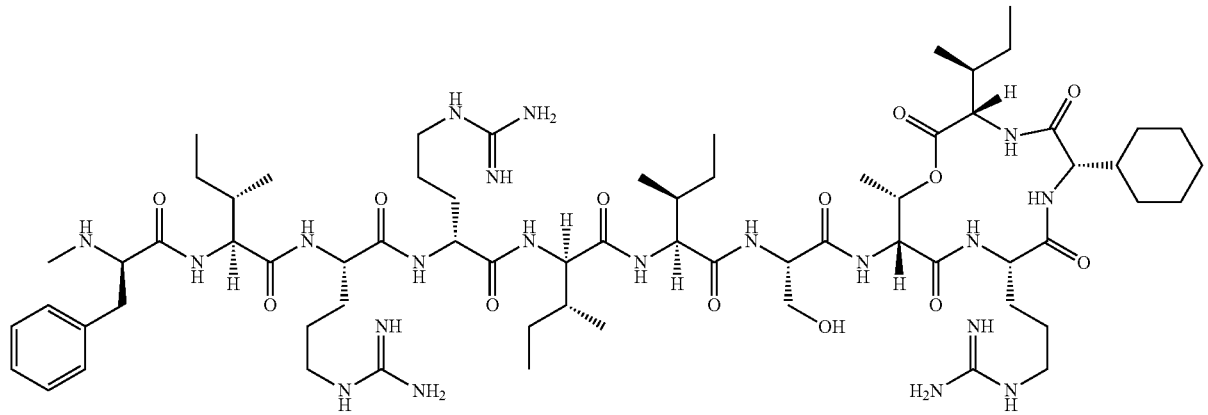
Arg₃-D-Arg₄-Arg₉-Chg₁₀-teixobactin
Compound 43
(SEQ ID NO: 10)
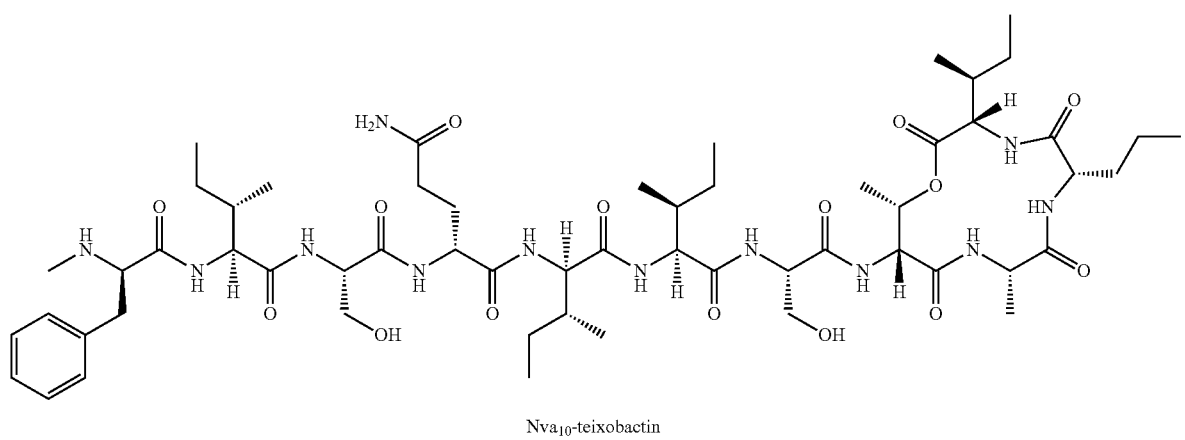
Nva₁₀-teixobactin
Compound 44
(SEQ ID NO: 18)
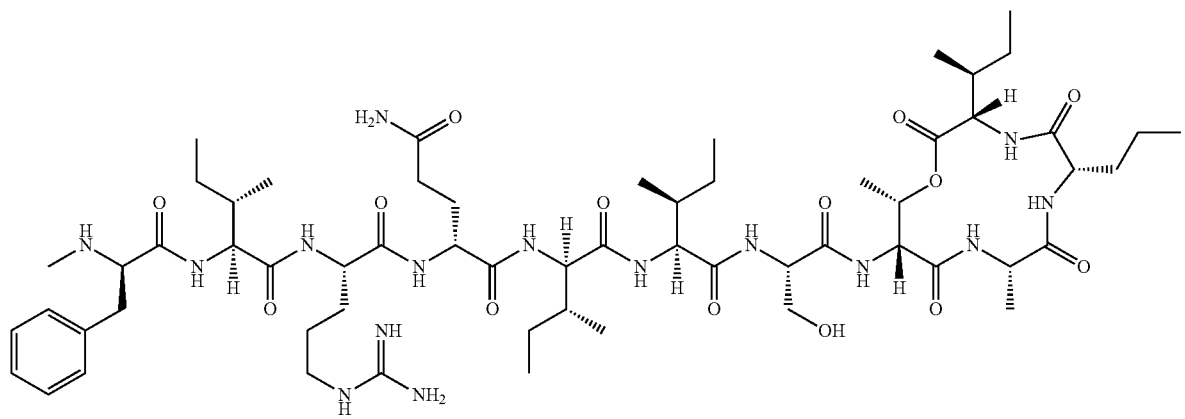
Arg₃-Nva₁₀-teixobactin
Compound 45

-continued
(SEQ ID NO: 19)
Compound 46
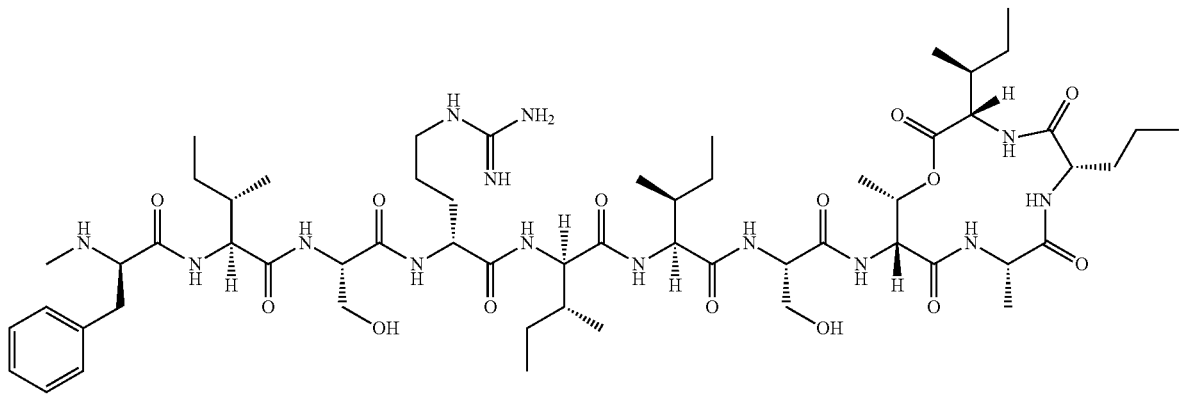
D-Arg₄-Nva₁₀-teixobactin
(SEQ ID NO: 10)
Compound 47
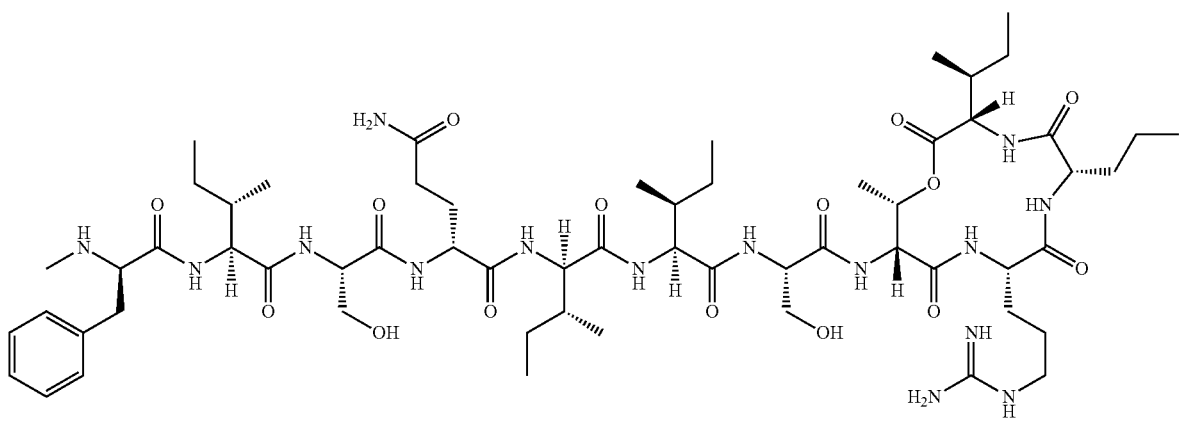
Arg₉-NVa₁₀-teixobactin
(SEQ ID NO: 20)
Compound 48
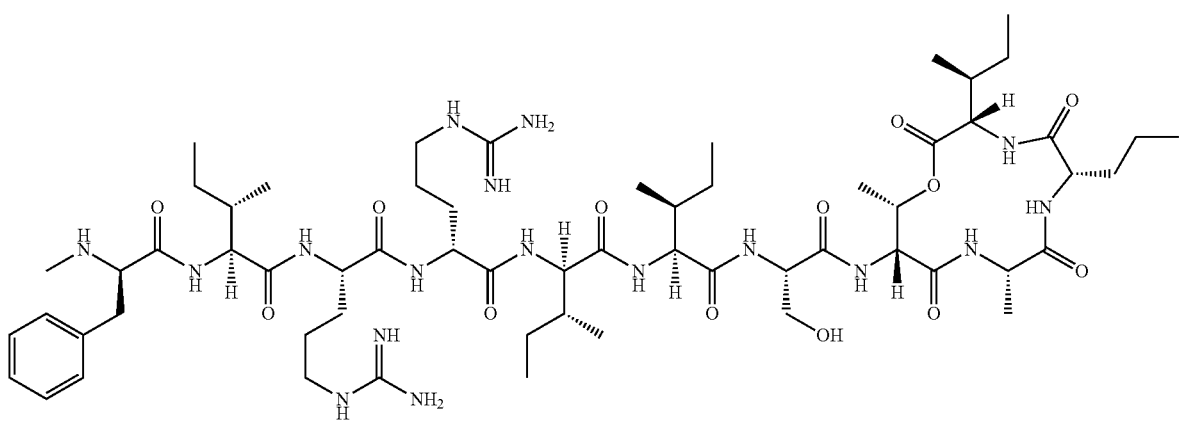
Arg₃-D-Arg₄-Nva₁₀-teixobactin -continued
(SEQ ID NO: 21)
Compound 49
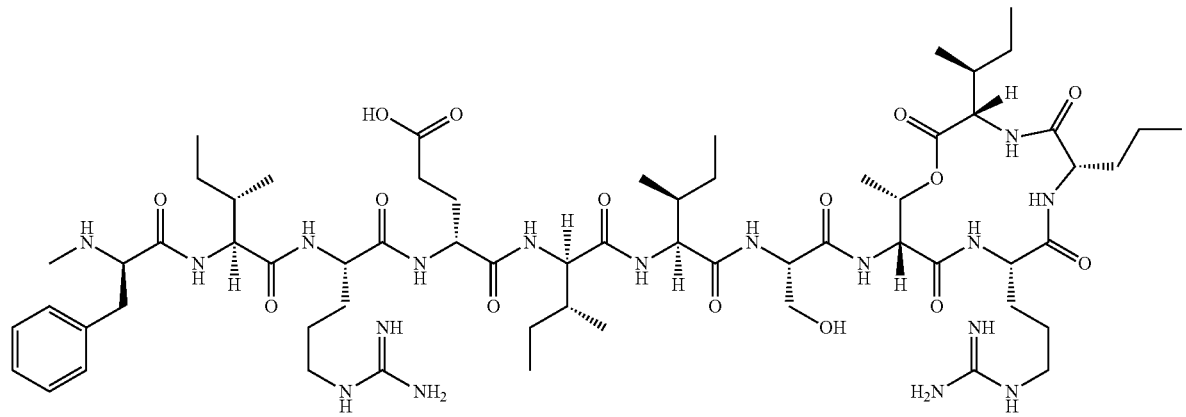
Arg₃-Arg₉-Nva₁₀-teixobactin
(SEQ ID NO: 19)
Compound 50
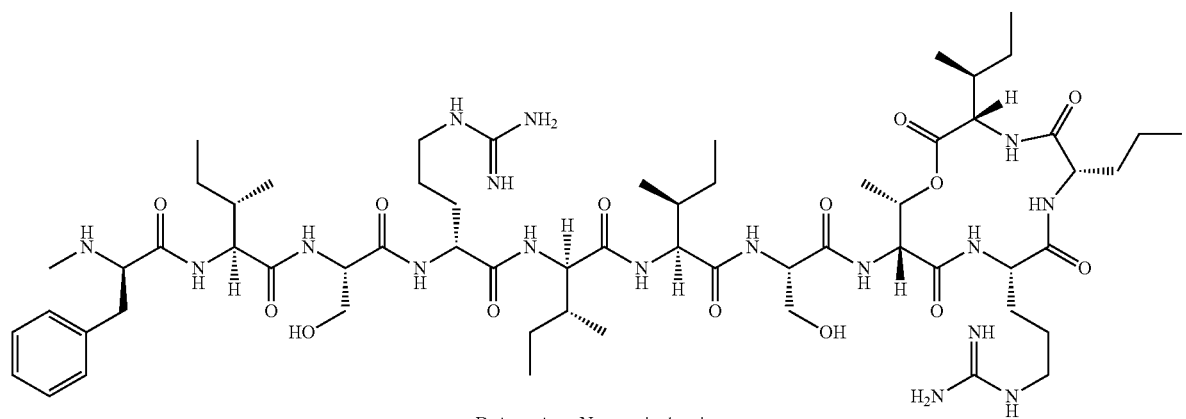
D-Arg₄-Arg₉-Nva₁₀-teixobactin
(SEQ ID NO: 20)
Compound 51
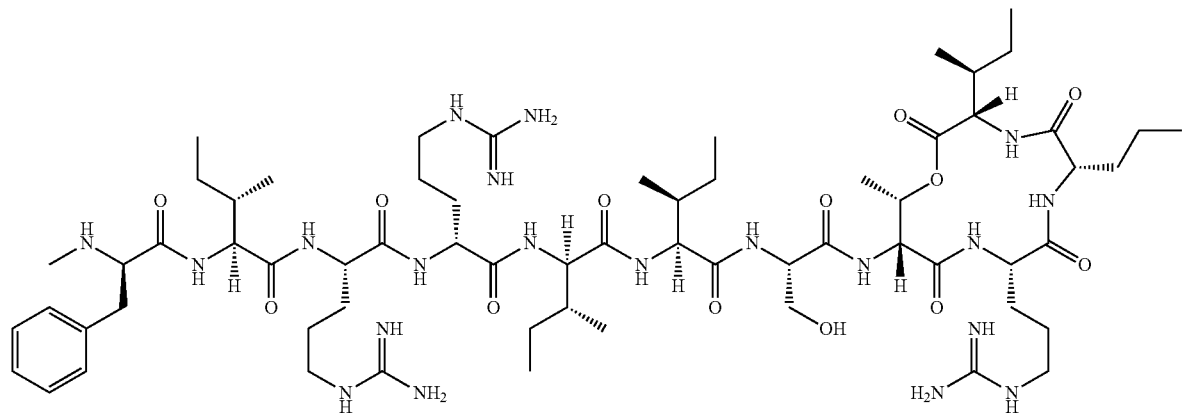
Arg₃-D-Arg₄-Arg₉Nva₁₀-teixobactin -continued
(SEQ ID NO: 19)
Compound 52
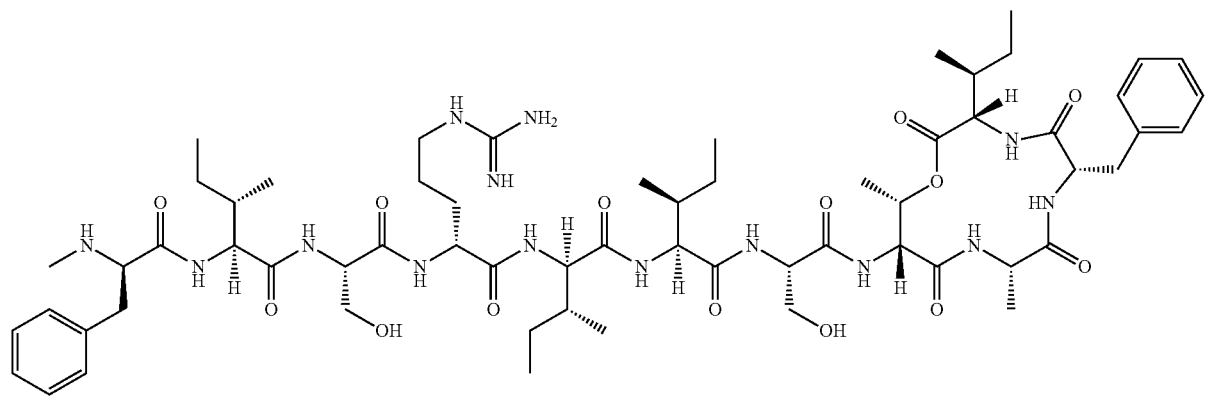
D-Arg$_4$-Phe$_{10}$-teixobactin
(SEQ ID NO: 19)
Compound 53
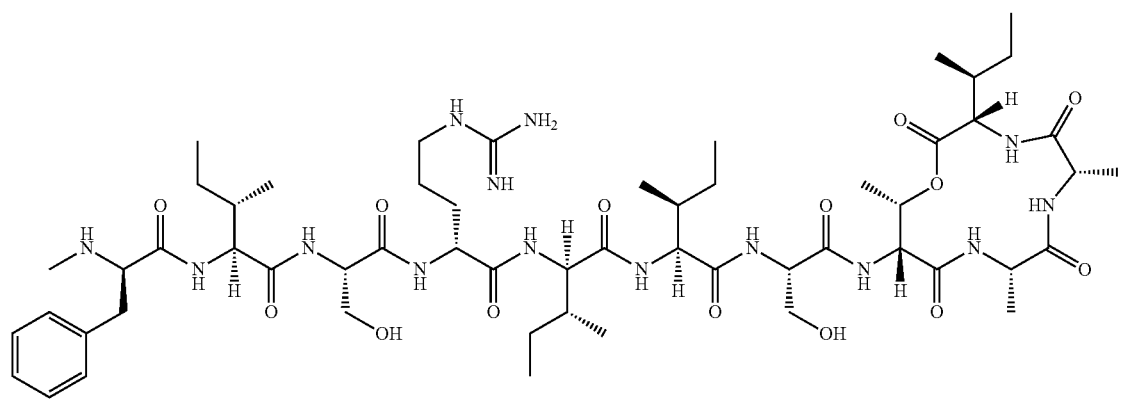
D-Arg$_4$-Phe$_{10}$-teixobactin
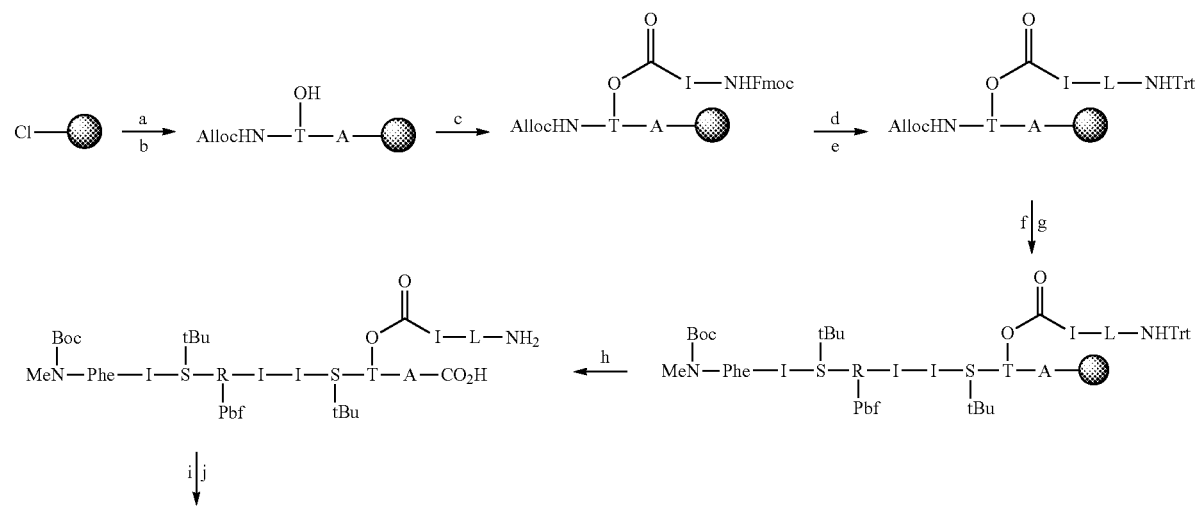

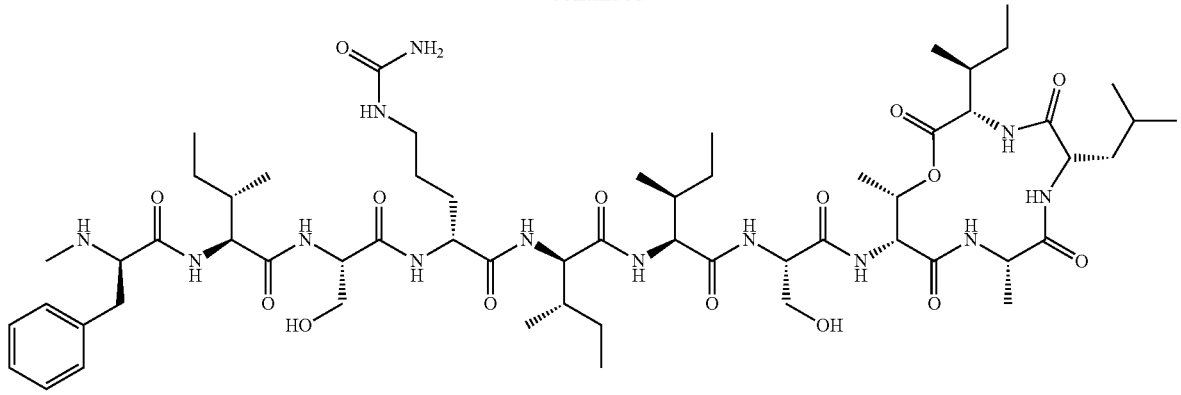

Synthesis of D-Arg$_4$-Leu$_{10}$-teixobactin (Compound 26) starting from 2-chlorotritylchloride resin: a. 4 eq. Fmoc-Ala-OH/8 eq. DIPEA in DCM, 3 h. b. 20% piperidine in DMF followed by 3 eq. AllocHN-D-Thr-OH, 3 eq. HATU/6 eq. DIPEA, 1.5 h c. 10 eq. Fmoc-Ile-OH, 10 eq. DIC, 5 mol % DMAP in DCM, 2 h followed by capping with Ac$_2$O/DIPEA 10% in DMF, 20% piperidine in DMF d. 4 eq. Fmoc-Leu-OH, 4 eq. HATU/8 eq. DIPEA in DMF, 1 h followed by 20% piperidine in DMF e. 10 eq. Trt-Cl, 15% Et$_3$N in DCM, 1 h. f. 0.2 eq. [Pd(PPh$_3$)$_4$]$^0$+24 eq. PhSiH$_3$ in dry DCM, 1×20 min, 1×45 min. g. 4 eq. Fmoc/Boc-AA(PG)-OH (AA=amino acid, PG=protecting group), 4 eq. DIC/Oxyma (μwave, 10 min) followed by 20% piperidine in DMF (3 min, 10 min). h. TFA:TIS:DCM=2:5:93, 1 h. i. 1 eq. HATU/10 eq. DIPEA in DMF, 30 min. j. TFA:TIS:H$_2$O=95:2.5:2.5, 1 h.

Step a. Commercially available 2-chlorotrityl chloride resin (manufacturer's loading=1.2 mmol/g, 170 mg resin) was swelled in DCM in a reactor. To this resin was added 4 eq. Fmoc-Ala-OH/8 eq. DIPEA in DCM and the reactor was shaken for 3 h. The loading determined by UV absorption of the piperidine-dibenzofulvene adduct was calculated to be 0.6 mmol/g, (170 mg resin, 0.102 mmol). Any unreacted resin was capped with MeOH:DIPEA:DCM=1:2:7 by shaking for 1 h.

Step b. The Fmoc protecting group was deprotected using 20% piperidine in DMF by shaking for 3 min, followed by draining and shaking again with 20% piperidine in DMF for 10 min. AllocHN-D-Thr-OH was then coupled to the resin by adding 3 eq. of the AA, 3 eq. HATU and 6 eq. DIPEA in DMF and shaking for 1.5 h at room temperature.

Step c. Esterification was performed using 10 eq. of Fmoc-Ile-OH, 10 eq. DIC and 5 mol % DMAP in DCM and shaking the reaction for 2 h. This was followed by capping the unreacted alcohol using 10% Ac$_2$O/DIPEA in DMF shaking for 30 min and Fmoc was removed using protocol described earlier in step (b).

Step d. Fmoc-Leu-OH was coupled using 4 eq. of AA, 4 eq. HATU and 8 eq. DIPEA in DMF and shaking for 1 h followed by Fmoc deprotection using 20% piperidine in DMF as described earlier.

Step e. The N terminus of Leu was protected using 10 eq. Trt-Cl and 15% Et$_3$N in DCM and shaking for 1 h. The protection was verified by the Ninhydrin colour test.

Step f. The Alloc protecting group of D-Thr was removed using 0.2 eq. [Pd(PPh$_3$)]$^0$ and 24 eq. PhSiH$_3$ in dry DCM under argon for 20 min. This procedure was repeated again increasing the time to 45 min and the resin was washed thoroughly with DCM and DMF to remove any Pd stuck to the resin.

Step g. All amino acids were coupled using 4 eq. Amino Acid, 4 eq. DIC/Oxyma using a microwave peptide synthesizer. Coupling time was 10 min. Deprotection cycles were performed as described earlier.

Step h. The peptide was cleaved from the resin without cleaving off the protecting groups of the amino acid side chains using TFA:TIS:DCM=2:5:93 and shaking for 1 h.

Step i. The solvent was evaporated and the peptide was redissolved in DMF to which 1 eq. HATU 5 and 10 eq. DIPEA were added and the reaction was stirred for 30 min to perform the cyclization.

Step j. The side-chain protecting groups were then cleaved off using TFA:TIS:H$_2$O=95:2.5:2.5 by stirring for 1 h. The peptide was precipitated using cold Et$_2$O (−20° C.) and centrifuging at 7000 rpm to obtain a white solid. This solid was further purified by RP-HPLC.

The overall yields for Compounds 25 to 34 after HPLC purifications were typically in the range of 13-22%. All teixobactin analogues 25 to 34 were characterized by HRMS (ESI) in positive mode (see table below). Compound 26 was also characterised by NMR. The homogeneity of HPLC purified fractions were analyzed by mass spectroscopy. All the teixobactin analogues used were purified to >95% purity as indicated by HPLC.

TABLE 9

Compound number, name, chemical formula, mass calculated, and mass observed for Compounds 25 to 34.

| Comp. | Name | Chemical formula | Mass Calc. (Da) | Mass obs. (Da) |
|---|---|---|---|---|
| 25 | Arg$_3$-Leu$_{10}$-teixobactin | C$_{61}$H$_{104}$N$_{15}$O$_{14}$ | 1270.7887 | 1270.7913 |
| 26 | D-Arg$_4$-Leu$_{10}$-teixobactin | C$_{59}$H$_{101}$N$_{14}$O$_{14}$ | 1229.7622 | 1229.7650 |
| 27 | Arg$_9$-Leu$_{10}$-teixobactin | C$_{61}$H$_{104}$N$_{15}$O$_{15}$ | 1286.7836 | 1286.7843 |
| 28 | Arg$_3$-D-Arg$_4$-Leu$_{10}$-teixobactin | C$_{62}$H$_{108}$N$_{17}$O$_{13}$ | 1298.8313 | 1298.8325 |
| 29 | Arg$_3$-Arg$_9$-Leu$_{10}$-teixobactin | C$_{64}$H$_{111}$N$_{18}$O$_{14}$ | 1355.8527 | 1355.8606 |
| 30 | D-Arg$_4$-Arg$_9$-Leu$_{10}$-teixobactin | C$_{62}$H$_{108}$N$_{17}$O$_{14}$ | 1314.8262 | 1314.8263 |

TABLE 9-continued

Compound number, name, chemical formula, mass calculated, and mass observed for Compounds 25 to 34.

| Comp. | Name | Chemical formula | Mass Calc. (Da) | Mass obs. (Da) |
|---|---|---|---|---|
| 31 | $Arg_3$-D-$Arg_4$-$Arg_9$-$Leu_{10}$-teixobactin | $C_{65}H_{115}N_{20}O_{13}$ | 1383.8952 | 1383.8943 |
| 32 | $Arg_3$-$Ile_{10}$-teixobactin | $C_{61}H_{104}N_{15}O_{14}$ | 1270.7887 | 1270.7896 |
| 33 | D-$Arg_4$-$Ile_{10}$-teixobactin | $C_{59}H_{101}N_{14}O_{14}$ | 1229.7622 | 1229.7607 |
| 34 | $Arg_9$-$Ile_{10}$-teixobactin | $C_{61}H_{104}N_{15}O_{15}$ | 1286.7836 | 1286.7780 |

Example 15—Activity of Compounds 25 to 53 Against MRSA

Minimum inhibitory concentrations for Compounds 25 to 53 against MRSA are shown in Table 10.

TABLE 10

MIC: Minimum Inhibitory Concentrations

| Compound No. | Name | MIC (MRSA) (µg/mL) |
|---|---|---|
| 25 | $Arg_3$-$Leu_{10}$-teixobactin | 0.125 |
| 26 | D-$Arg_4$-$Leu_{10}$-teixobactin | 0.125 |
| 27 | $Arg_9$-$Leu_{10}$-teixobactin | 0.125 |
| 28 | $Arg_3$-D-$Arg_4$-$Leu_{10}$-teixobactin | 0.25 |
| 29 | $Arg_3$-$Arg_9$-$Leu_{10}$-teixobactin | 1 |
| 30 | D-$Arg_4$-$Arg_9$-$Leu_{10}$-teixobactin | 1 |
| 31 | $Arg_3$-D-$Arg_4$-$Arg_9$-$Leu_{10}$-teixobactin | 1 |
| 32 | $Arg_3$-$Ile_{10}$-teixobactin | 0.25 |
| 33 | D-$Arg_4$-$Ile_{10}$-teixobactin | 0.125 |
| 34 | $Arg_9$-$Ile_{10}$-teixobactin | 0.25 |
| 35 | $Arg_3$-D-$Arg_4$-$Ile_{10}$-teixobactin | 0.5 |
| 36 | $Chg_{10}$-teixobactin | 0.25 |
| 37 | $Arg_3$-$Chg_{10}$-teixobactin | 0.5 |
| 38 | D-$Arg_4$-$Chg_{10}$-teixobactin | 0.5 |
| 39 | $Arg_9$-$Chg_{10}$-teixobactin | 1 |
| 40 | $Arg_3$-D-Arg4-$Chg_{10}$-teixobactin | 1 |
| 41 | $Arg_3$-$Arg_9$-$Chg_{10}$-teixobactin | 0.5 |
| 42 | D-$Arg_4$-$Arg_9$-$Chg_{10}$-teixobactin | 0.5 |
| 43 | $Arg_3$-D-$Arg_4$-$Arg_9$-$Chg_{10}$-teixobactin | 64 |
| 44 | $Nva_{10}$-teixobactin | 0.5 |
| 45 | $Arg_3$-$Nva_{10}$-teixobactin | 1 |
| 46 | D-$Arg_4$-$Nva_{10}$-teixobactin | 0.25 |
| 47 | $Arg_9$-$Nva_{10}$-teixobactin | 0.5 |
| 48 | $Arg_3$-D-$Arg_4$-$Nva_{10}$-teixobactin | >64 |
| 49 | $Arg_3$-$Arg_9$-$Nva_{10}$-teixobactin | 0.5 |
| 50 | D-$Arg_4$-$Arg_9$-$Nva_{10}$-teixobactin | 0.5 |
| 51 | $Arg_3$-D-$Arg_4$-$Arg_9$-$Nva_{10}$-teixobactin | 64 |
| 52 | D-$Arg_4$-$Phe_{10}$-teixobactin | 2 |
| 53 | D-$Arg_4$-$Ala_{10}$-teixobactin | 4 |

Example 16—In Vitro Antibacterial Studies

The antimicrobial potency of teixobactin analogue Compounds 25 to 34 was assessed against MRSA ATCC 33591. The $Leu_{10}$-teixobactin and natural teixobactin were included as benchmarks for activity. The six analogues 25 to 27 and 32 to 34 with two cationic charges have hydrophobic-hydrophilic balances similar to natural teixobactin (two cationic charges). These analogues showed comparable potency (MIC 0.125-0.25 µg/ml) to natural teixobactin (MIC 0.25 µg/ml). Compounds 28 to 30 each possess three cationic charges. Interestingly, Compound 28 showed comparable antimicrobial activity (MIC 0.25 µg/ml) to natural teixobactin. However, Compounds 29 and 30 showed 4 times reduced antibacterial activity (MIC 1 µg/ml) than natural teixobactin or $Leu_{10}$-teixobactin. Compound 31 with four cationic charges also showed reduced antibacterial activity (MIC 1 µg/ml).

Compounds 25 to 34 were further assessed against a panel of antibiotic-resistant and antibiotic susceptible Gram-positive pathogens and comparator antibiotics, daptomycin (FIG. 1). The MIC results indicate that the synthetic analogues are potent against the various strains tested, but their MIC distribution differs significantly. Interestingly, a wider distribution of MIC values was observed as the overall net charge of the peptide was increased.

Notably, the MIC values for *Staphylococcus* were not altered whereas a significant increase in *Enterococcus* was observed with four cationic charges (Compound 31, MIC 2-8 µg/ml). Similar trends have been reported for teixobactin analogues, whereby increases in positive charges give increases in MICs against *Staphylococcus aureus* ATCC 29213. Herein, for example, $Lys_3$-D-$Lys_4$-$Lys_{10}$-teixobactin (four cationic charges) has a reported MIC of 8 µg/ml against *Staphylococcus aureus* ATCC 29213; whereas, we observed an MIC of 1 µg/ml (8 times improvement) for $Arg_3$-D-$Arg_4$-$Arg_9$-$Leu_{10}$-teixobactin (Compound 31, four cationic charges) against the same bacterial strain.

The inclusion of 3 arginines in the above case likely perturbs the amphiphilic character of the teixobactin, resulting in a decrease in activity. The six analogues 25 to 27 and 32 to 34 with two cationic charges showed comparable antibacterial potency to Leu10-teixobactin. Importantly, the hydrophobic-hydrophilic balance of these analogues was similar to natural teixobactin (two cationic charges). The analogues 28 to 30 with three cationic charges also showed comparable antibacterial potency to $Leu_{10}$-teixobactin. All synthesized analogues showed good potency against a broad panel of bacteria. The nine analogues 25 to 30 and 32 to 34 showed drug like profiles such as high antibacterial potency with optimal balance of hydrophobicity and hydrophilicity. The minimum bactericidal concentrations (MBC) of teixobactin analogues against *S. aureus*/MRSA strains (Table 11) has been further determined. Compound 26 displayed highly potent bactericidal properties, as its MBC values did not increase above 4 times the MIC against the tested strains. Compound 26 was found inactive against *Pseudomonas aeruginosa* (Gram negative bacteria). In view of narrow MIC distribution values and bactericidal properties, attention was focused on Compound 26 and further investigated its biological properties.

TABLE 11

MIC values (μg/ml) of compounds 25 to 34 against a broad panel of bacteria.
*Enterococcus faecalis*, VRE 1001-1002, 1004, 1008 are clinical isolates.
MRSA 42412, MRSA 21455 and MRSA 1003 are clinical isolates.

| | Compound No. | 25 | 26 | 27 | 28 | 29 | 30 |
|---|---|---|---|---|---|---|---|
| | Strain | | | | | | |
| 1 | *Staphylococcus saprophyticus* ATCC BAA 750 | <0.0625 | <0.0625 | <0.0625 | <0.0625 | <0.0625 | <0.0625 |
| 2 | *Staphylococcus saprophyticus* ATCC 15305 | <0.0625 | <0.0625 | <0.0625 | <0.0625 | <0.0625 | <0.0625 |
| 3 | *Staphylococcus saprophyticus* ATCC 49453 | <0.0625 | <0.0625 | <0.0625 | <0.0625 | <0.0625 | <0.0625 |
| 4 | *Staphylococcus saprophyticus* ATCC 49907 | <0.0625 | <0.0625 | <0.0625 | <0.0625 | <0.0625 | <0.0625 |
| 5 | VRE 1001 | 0.25 | 0.5 | 0.5 | 1 | 0.5 | 1 |
| 6 | VRE 1002 | 0.5 | 1 | 1 | 1 | 1 | 1 |
| 7 | VRE 1004 | <0.0625 | 0.25 | 0.25 | 0.5 | 0.5 | 1 |
| 8 | VRE 1008 | 0.125 | 0.5 | 0.25 | 0.5 | 0.5 | 1 |
| 9 | VRE ATCC 700802 | 0.5 | 0.5 | 0.5 | 2 | 1 | 1 |
| 10 | VRE ATCC 29212 | 0.5 | 0.5 | 1 | 1 | 1 | 1 |
| 11 | MRSA ATCC 700699 | 0.5 | 0.25 | 0.5 | 0.5 | 1 | 1 |
| 12 | MRSA 42412 | <0.0625 | 0.0313 | <0.0625 | 0.25 | 0.25 | 1 |
| 13 | MRSA 21455 | 0.03125 | 0.0313 | 0.25 | 0.5 | 1 | 1 |
| 14 | MRSA 1003 | <0.0625 | 0.5 | 0.25 | 1 | 2 | 0.5 |
| 15 | SA29213 | 0.25 | <0.0625 | 0.5 | 0.25 | 1 | 1 |
| 16 | SA4299 | 0.125 | — | 0.25 | 0.25 | 0.5 | 0.5 |
| 17 | SE12228 | <0.0625 | <0.0625 | <0.0625 | <0.0625 | <0.0625 | <0.0625 |
| 18 | *Bacillus Cereus* ATCC 11788 | <0.0625 | 0.5 | 0.25 | 1 | 1 | 1 |
| 19 | *Bacillus Subtilis* ATCC 6633 | <0.0625 | 0.125 | <0.0625 | <0.0625 | <0.0625 | <0.0625 |

| | Compound No. | 31 | 32 | 33 | 34 | Daptomycin |
|---|---|---|---|---|---|---|
| | Strain | | | | | |
| 1 | *Staphylococcus saprophyticus* ATCC BAA 750 | <0.0625 | <0.0625 | <0.0625 | <0.0625 | — |
| 2 | *Staphylococcus saprophyticus* ATCC 15305 | 0.25 | <0.0625 | <0.0625 | <0.0625 | — |
| 3 | *Staphylococcus saprophyticus* ATCC 49453 | <0.0625 | <0.0625 | <0.0625 | <0.0625 | — |
| 4 | *Staphylococcus saprophyticus* ATCC 49907 | <0.0625 | <0.0625 | <0.0625 | <0.0625 | — |
| 5 | VRE 1001 | 2 | 1 | 0.5 | 1 | — |
| 6 | VRE 1002 | 8 | 1 | 1 | 1 | — |
| 7 | VRE 1004 | 4 | 1 | 0.5 | 1 | — |
| 8 | VRE 1008 | 8 | 1 | 0.5 | 1 | — |
| 9 | VRE ATCC 700802 | 4 | 1 | 0.25 | 1 | 0.25 |
| 10 | VRE ATCC 29212 | 4 | 1 | 0.25 | 1 | 0.25 |
| 11 | MRSA ATCC 700699 | 2 | 1 | 0.25 | 1 | 0.25 |
| 12 | MRSA 42412 | 2 | 0.125 | <0.0625 | 0.125 | <0.0625 |
| 13 | MRSA 21455 | 2 | 0.25 | 0.03125 | 0.5 | <0.0625 |
| 14 | MRSA 1003 | 2 | 0.125 | <0.0625 | 0.5 | — |
| 15 | SA29213 | 1 | 0.5 | 0.0625 | 1 | — |
| 16 | SA4299 | 1 | 0.125 | <0.0625 | 1 | — |
| 17 | SE12228 | <0.0625 | <0.0625 | <0.0625 | <0.0625 | — |
| 18 | *Bacillus Cereus* ATCC 11788 | 1 | 0.125 | <0.0625 | 0.5 | — |
| 19 | *Bacillus Subtilis* ATCC 6633 | <0.0625 | <0.0625 | <0.0625 | 0.125 | — |

Example 17—Resistance Studies and Time Dependent Killing of Bacteria: Compound 26

D-Arg$_4$-Leu$_{10}$-teixobactin (Compound 26) was evaluated for single step resistance in *S. aureus* ATCC 29213 and MRSA ATCC 33591. Mutants of *S. aureus* ATCC 29213 or MRSA ATCC 33591 resistant to teixobactin analogue 26 (5×, 10×, 20×MIC) could not be obtained. The calculated frequency of resistance to Compound 26 was found to be <10$^{-10}$ which is comparable to teixobactin. A lack of resistance in preliminary studies against 26 is promising in the development of drug like molecules against resistant bacteria. Time-kill kinetics studies of D-Arg$_4$-Leu$_{10}$-teixobactin 26 against *S. aureus* ATCC 29213 was investigated to ascertain if the chemical modifications retained the bactericidal properties. The exposure of bacterial inoculum to 0.5 µg/ml or 1 µg/ml of Compound 26 resulted in ≥2 log$_{10}$ decrease in bacterial viability at 8 h, which is comparable with previous reports of teixobactin analogues and teixobactin.

Example 18—In Vitro Cytotoxicity Studies

It was important to evaluate the cytotoxicity of Compound 26 on mammalian cells prior to in vivo studies. The cytotoxicity of Compound 26 in human lung epithelial cell line A549 and primary dermal fibroblasts (hDFs) was determined. Both of these cell culture models are already established for evaluation of cytotoxicity of antimicrobial peptides. An MTS assay indicated that both mammalian cell-types exposed to various concentrations of the peptide retained significant metabolic activity (≥80% viability, FIG. 2 *a,b*), even at a concentration that was ~900 times (250 µg/ml) higher than the average MIC (0.27 µg/ml) values, indicating excellent cell selectivity of the teixobactin analogues. High content images indicated the absence of any cytoskeletal and nuclear disruption upon exposure of both epithelial and fibroblasts cells to Compound 26 (FIG. 2 *c,d*), establishing its non-cytotoxic properties. The morphology of mammalian cells exposed to Compound 26 appeared similar to the untreated cells. However, exposure of cells to an antineoplastic agent (nocodazole, used as a control) resulted in substantial loss of adhered cells, confirming its cytotoxicity.

Both A549 cells (a) and hDFs (b) were treated with increasing concentrations of Compound 26 (ranging from 15.62 µg/ml to 250 µg/ml) for 24 h. The stock solution of Compound 26 (500 µg/ml) was prepared fresh by directly dissolving Compound 26 in cell culture medium and used. Cells were treated with dimethyl sulfoxide (DMSO, 0.1% v/v) or nocodazole (5 µg/ml dissolved in DMSO) as controls. At the end of the treatment period, metabolic activities of cells were quantified by MTS-based cell viability assay. Data represents mean±SEM of three independent triplicate experiments, *p>0.05. After 24 h treatment with Compound 26, A549 cells (c) and hDFs (d) were fixed, fluorescently stained with rhodamine-phalloidin (red), alexa fluor 488 conjugated anti-α-tubulin (green) and Hoechst 33342 (blue) and imaged using IN Cell Analyzer 2200 automated microscope. Representative images of cells treated with Compound 26 (62.5 µg/ml for 24 h) or nocodazole (10 µg/ml, toxicity control) are shown in FIG. 2 *c,d*.

Example 19—In Vivo Toxicity Studies

The in vivo toxicity of Compound 26 in a rabbit corneal damage model was examined. A 50 µl of 0.3% (w/v) solution was applied topically (4 times/day) to the circularly debrided cornea and reepithelialisation was monitored by fluorescein staining. Vehicle alone served as control. FIG. 3 shows the decrease in fluorescein staining with time for both control wounds and wounds treated with Compound 26. There was no significant difference in wound closure between PBS treated wounds or wounds treated with Compound 26. The lack of any delay in the reepithelialisation and wound closure for the injured cornea treated with Compound 26 suggests good biocompatibility of the peptide.

Example 20—In Vivo Antibacterial Efficacy of D-Arq$_4$-Leu$_{10}$-Teixobactin in Bacterial Keratitis Model The in vivo efficacy of Compound 26 in the mice-eye model of *S. aureus* keratitis was examined. *S. aureus* is one of the major etiological agents for bacterial keratitis and the toxic secretions produced by this microorganism have been implicated in corneal melt, leading to significant morbidity and vision loss. Scarified cornea of the mice were infected with *S. aureus* ATCC 29213 inoculum (15 µl of 6×10$^6$ CFU/ml) after scratching the corneal epithelium with scalpel blade. At 6 h post infections (p.i.), the infected cornea were treated with vehicle (PBS), Compound 26 (0.3% w/v in PBS) and moxifloxacin (0.3%). A total of 8 doses were applied and the progression of the infection was monitored by slit lamp examination, anterior segment optical coherent tomography (AS-OCT) and microbiological enumeration of the bacterial bioburden. Mice cornea treated with PBS had severe clinical presentation indicated by chemosis, significant presence of hypopyon like materials and corneal infiltrates (FIG. 4).

Note the significant presence of corneal haze and mucopurulent discharge in PBS treated cornea whereas Compound 26 or moxifloxacin treated cornea remained clear and no signs of corneal defects. Notably, infected cornea treated with Compound 26 or a fluoroquinalone antibiotic, had similar clinical appearance progression, as indicated by lack of any conjunctival chemosis and corneal infiltrates. These results indicate that Compound 26 halted the progression of *S. aureus* infections and the activity was comparable to moxifloxacin.

To determine the effect of treatments on tissue severity, the corneal thickness from various groups was determined (FIG. 5*a*). The baseline corneal thickness of mice (93.8±2.9 µm) decreased moderately (79.0±3.4 µm) after de-epithelialization followed by *S. aureus* infection (6 h p.i.). Treatment of the infected cornea with vehicle alone (PBS) resulted in substantial increase in corneal thickness after 24 h (151.7±12.7 µm) and 48 h (186.2±17.5 µm), indicating corneal edema after infection. Infected cornea treated with Compound 26 had a mean corneal thickness of 92.3±12.5 µm and 121.7±3.2 µm after 24 h and 48 h post treatment (p.t.), respectively. For the moxifloxacin-treated cornea the mean corneal thickness was 124.2±9.4 µm after 24 h p.t. and 140.3±10.3 µm after 48 h p.t. These results suggested that Compound 26 treatment resulted in significant decrease in corneal edema after *S. aureus* infections when compared PBS treated or moxifloxacin-treated groups.

FIG. 5*a*: Note that the CT values for Compound 26 treated cornea approached the baseline values after 48 h p.t., which was absent in the case of PBS-/Moxifloxacin-treated corneas. Note that a significant decrease in corneal edema was observed for infected cornea treated with Compound 26 compared to untreated cornea (p, 0.01 two-way ANOVA) as early after 3 doses which decreased further after 8 doses (p, 0.001). The results indicated a marked decrease in the severity (due to infections) after treatment with Compound 26 when compared to standard antibiotic treatment.

Bacterial enumeration of the corneal tissues harvested after 8 dosages confirmed the in vivo efficacy of Compound 26 (FIG. 5*b*). All the infected cornea that received PBS treatment contained significant presence of bacteria, varying from 4.7×10$^5$-1.3×10$^7$ CFU/tissue. The mean log$_{10}$ CFU/ tissue±standard error of the mean for PBS treated cornea was 6.51±0.27. Five out of six cornea treated with Compound 26 had detectable bacterial colonies. The mean $\log_{10}$ CFU/tissue for Compound 26 treated cornea was 3.97±0.19. Four infected corneas treated with moxifloxacin contained detectable bacterial colonies with a mean $\log_{10}$ CFU/tissue of 3.7±0.24 was observed. These results confirmed that Compound 26 had a similar antibacterial effect as an established antibiotic in decreasing the bacterial bioburden, thus demonstrating its potential as a safe therapeutic for topical applications.

Example 21—Leu$_{10}$-Teixobactin-3-(S3K-K5R) Conjugate (Compound 54)

(SEQ ID NO: 22)

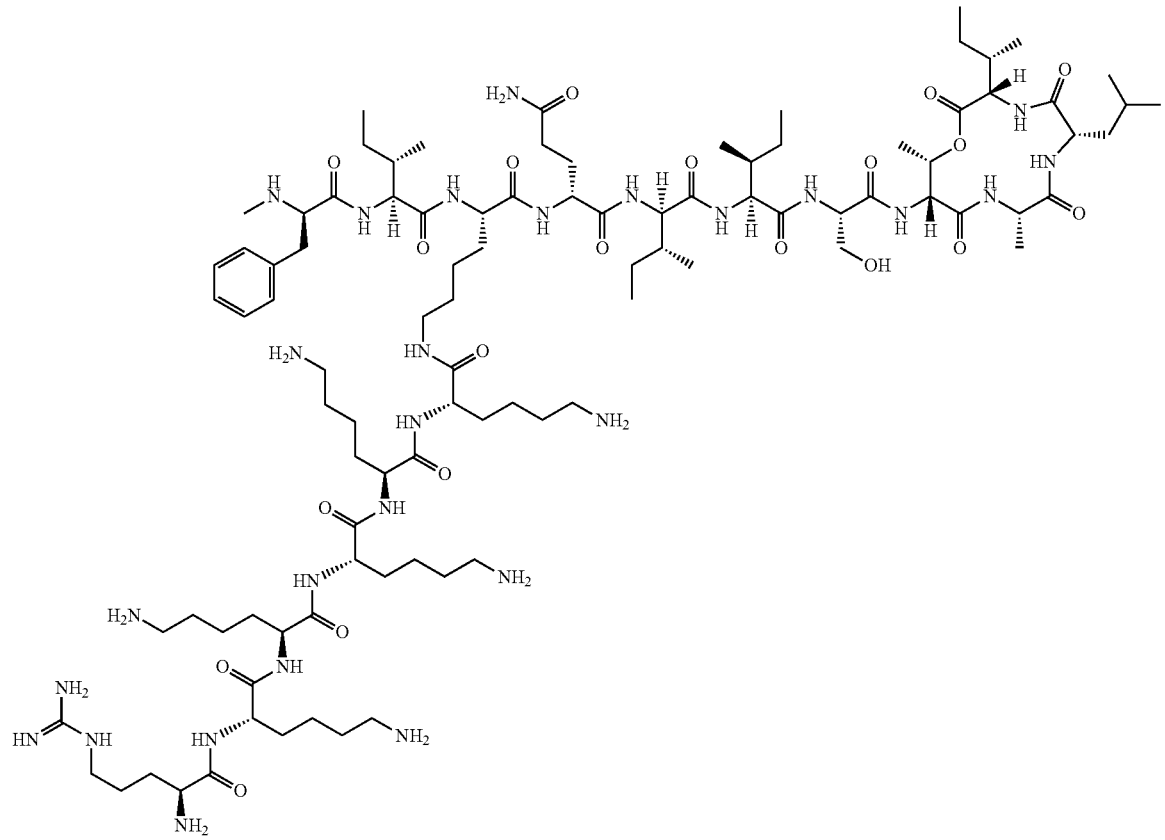

Compound 54 (Leu$_{10}$-Teixobactin-3-(S3K-K5R) conjugate, above) was prepared by a method analogous to the method for preparing Compound 26 (see Example 14). Calculated mass: 2038.3507; Found mass: 2039.33.

Example 22—Activity of Compound 54 Against MRSA, *E. coli* and *A. baumannii*

Minimum inhibitory concentrations for Compound 54 against MRSA, *E. coli* and *A. baumannii* are shown in Table 12.

TABLE 12

| MIC: Minimum Inhibitory Concentrations (μg/ml) | | | |
|---|---|---|---|
| | MRSA | Ecoli | A baumannii |
| Compound 54 | 8 | 16 | 2 |

The invention claimed is:
1. A compound of formula IA,

(SEQ ID NO: 1)

$R^1-AA^1-AA^2-AA^3-AA^4-AA^5-AA^6-AA^7-$ (IA)

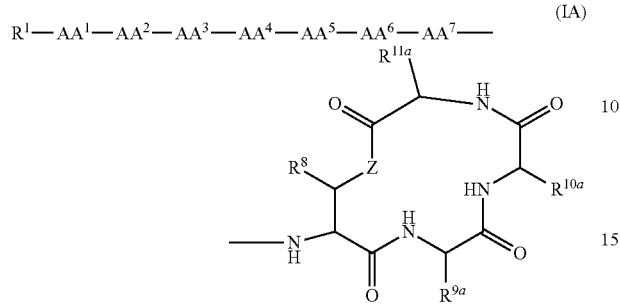

or a pharmaceutically-acceptable salt, solvate or clathrate thereof, wherein:
$R^1$ represents H, $C_{1-6}$ alkyl, $C_{1-6}$ acyl, benzyl or benzoyl;
$AA^1$, $AA^2$ and $AA^5$ to $AA^7$ each independently represents a proteinogenic or non-proteinogenic amino acid;
$AA^3$ and $AA^4$ each independently represents a proteinogenic or non-proteinogenic amino acid, diaminopropanoic acid, diaminobutanoic acid, or ornithine;
$R^8$ represents hydrogen or $C_{1-4}$ alkyl;
$R^{9a}$, represents a proteinogenic or non-proteinogenic amino acid side chain, $-CH_2-NH_2$, $-(CH_2)_2-NH_2$ or $-(CH_2)_3-NH_2$;
$R^{10a}$ represents a side chain of an amino acid selected from the group consisting of valine, isoleucine, leucine, methionine, phenylalanine, tyrosine and tryptophan, a hydrophobic non-proteinogenic amino acid side chain, hydrogen, or $R^{10a}$ is linked to the adjacent nitrogen atom to form a proline ring;
$R^{11a}$ represents a proteinogenic or non-proteinogenic amino acid side chain;
Z is $-O-$ or $-NH-$;
optionally wherein the compound of formula IA is covalently bonded to a delivery agent, which is either capable of covalently bonding to one or more structures on a bacterial cell membrane or comprises a hydrophilic portion capable of otherwise binding to one or more structures on a bacterial cell membrane.

2. The compound according to claim 1, wherein $AA^1$ represents a D-phenylalanine residue, $AA^2$ represents an L-isoleucine residue, $AA^5$ represents a D-allo-isoleucine or D-isoleucine residue, $AA^6$ represents an L-isoleucine residue, and $AA^7$ represents an L-serine residue.

3. The compound according to claim 1, wherein the delivery agent is a fragment of formula II,

wherein D represents a dendrimer fragment to which the $X^2$ groups shown are attached, $X^2$ represents $-NH_2$, boronic acid or a boronic acid derivative; and n is 2 or more (e.g. from 2 to 20); and
wherein the wavy line indicates the point of attachment to the compound of formula IA;
or wherein the delivery agent is a polypeptide or polypeptide derivative, or a pharmaceutically-acceptable salt thereof, which polypeptide or polypeptide derivative contains at least two residues selected from the group consisting of arginine and lysine.

4. The compound according to claim 1, wherein the delivery agent comprises one or more functional groups, which are independently selected from the list consisting of boronic acids, boronic acid derivatives, primary amines, amidines, guanidines, amides, ureas, and acid addition salts thereof.

5. The compound according to claim 1, wherein the delivery agent is a fragment of any one of formula III to VIII

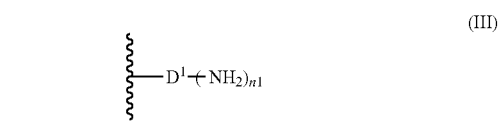

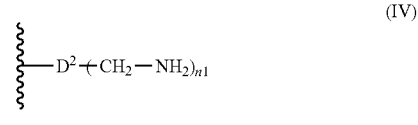

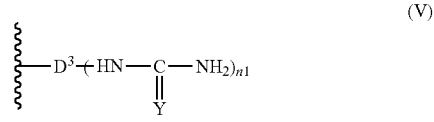

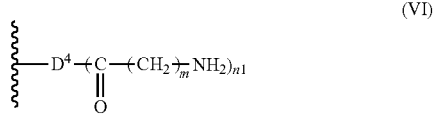

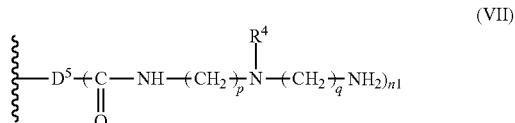

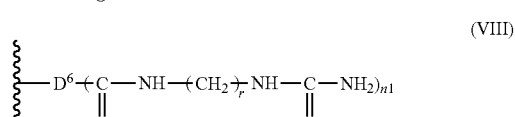

wherein $D^1$ to $D^6$ each represent a dendrimer fragment to which the groups shown in parentheses are attached; Y represents O, NH or S; each n1 is 2 or more (e.g. from 2 to 20); m, p, q and r each independently represent from 1 to 8; and $R^4$ represents a $C_{1-6}$ alkyl group; or
wherein the delivery agent is a fragment of formula IXa, IXb or X;

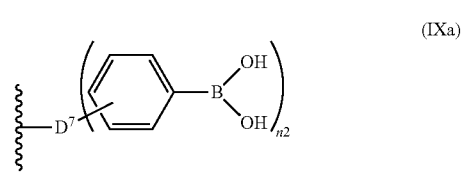

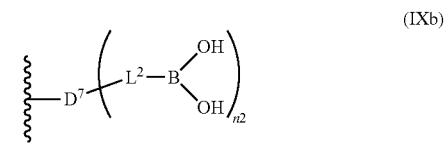

-continued

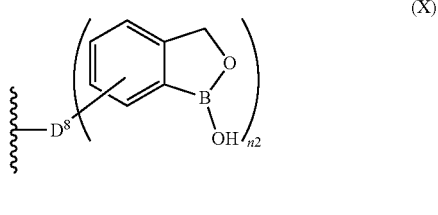
(X)

wherein each $L_2$ represents an aliphatic linker (e.g. a $C_{1-6}$ alkyl chain); $D^7$ and $D^8$ independently represent a direct bond or a dendrimer fragment to which the boron-containing groups shown are attached, n2 is 1 or more, and optionally wherein $D^7$ and $D^8$ are attached to the boronic acid or boric acid portions of the compound of formula IXa, IXb and X via a linker group.

6. The compound according to claim 5, wherein the delivery agent is a fragment of any one of formula III to VIII, IXa, IXb or X, and $D^1$ to $D^8$ independently represent a dendrimer fragment of any one of formula A to E:

A

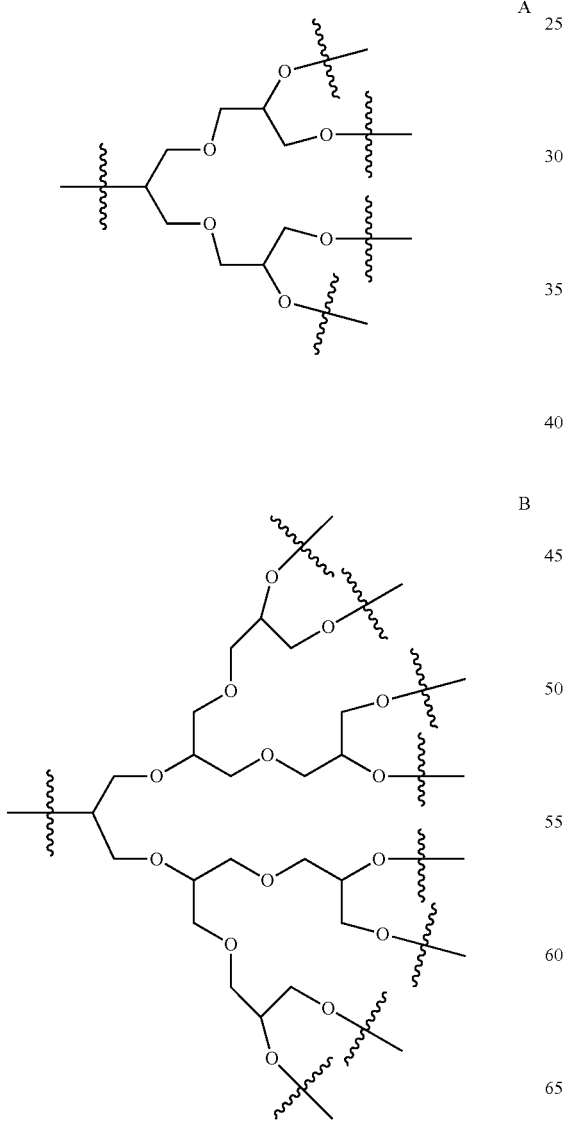

B

-continued

C

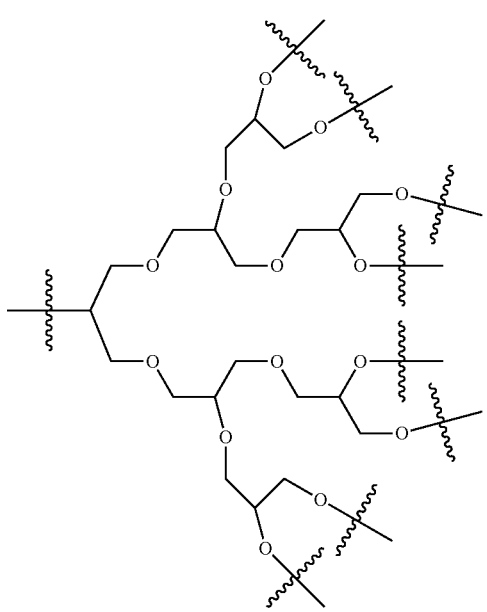

D

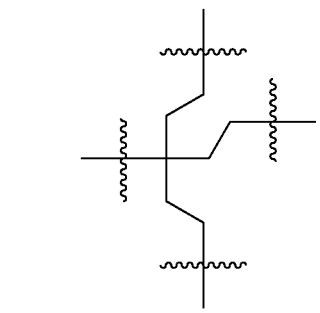

E

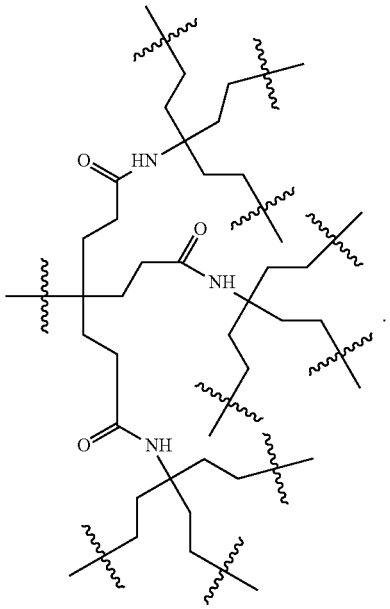

7. The compound according to claim 1, wherein $R^1$ represents H, $C_{1-6}$ alkyl, $C_{1-6}$ acyl, benzyl or benzoyl or a delivery agent fragment of formula II to X.

8. A compound selected from the group consisting of:
(SEQ ID NO: 10)
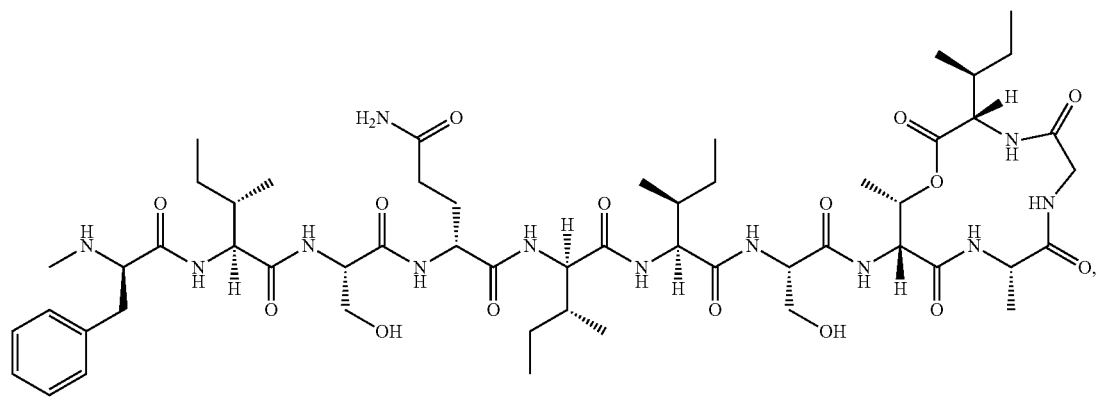
(SEQ ID NO: 10)
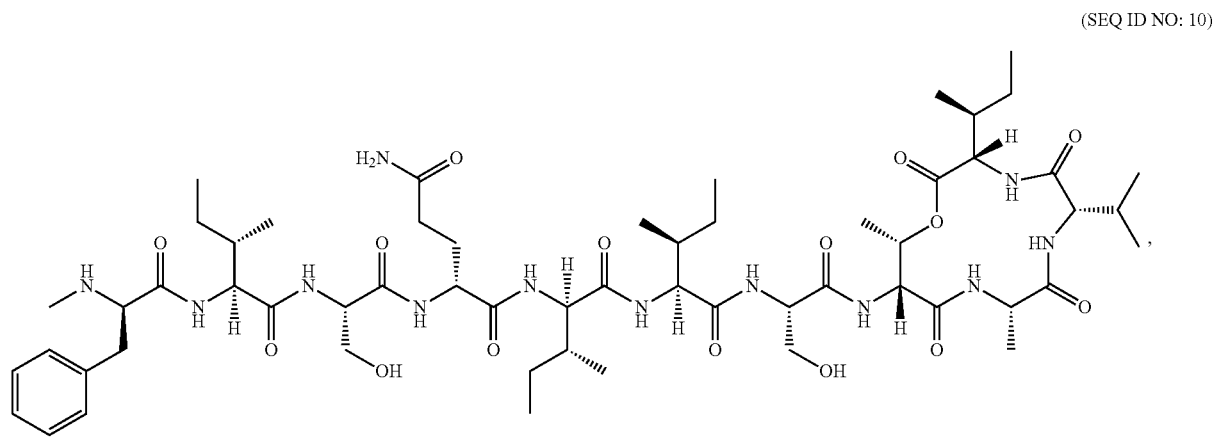
(SEQ ID NO: 10)
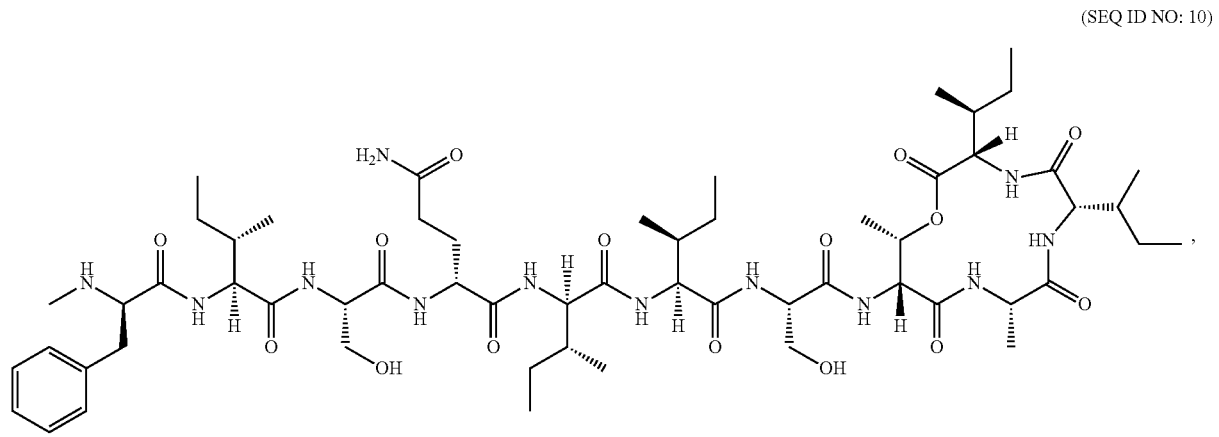

(SEQ ID NO: 10)
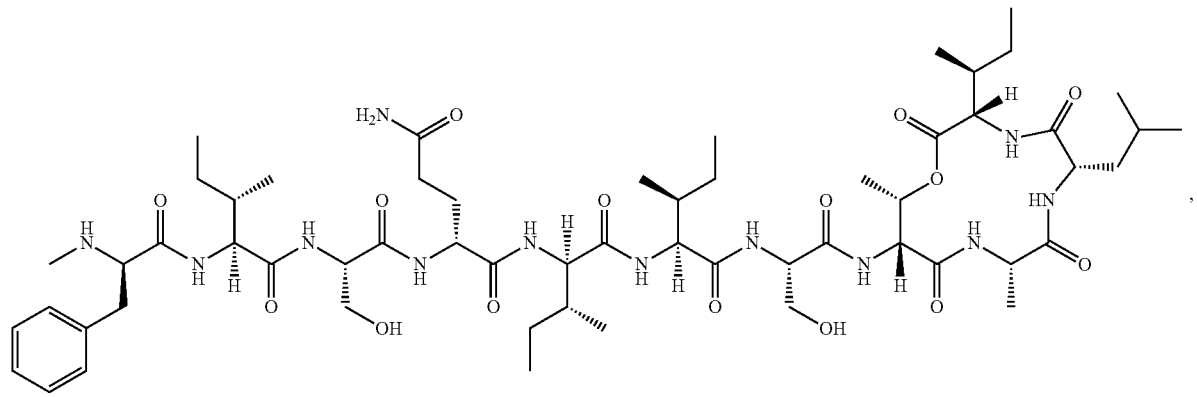
(SEQ ID NO: 18)
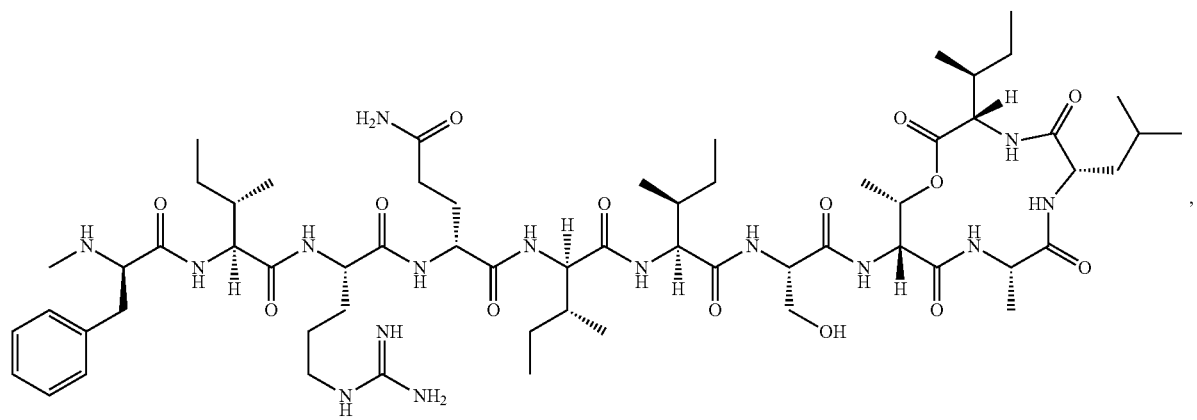
(SEQ ID NO: 19)
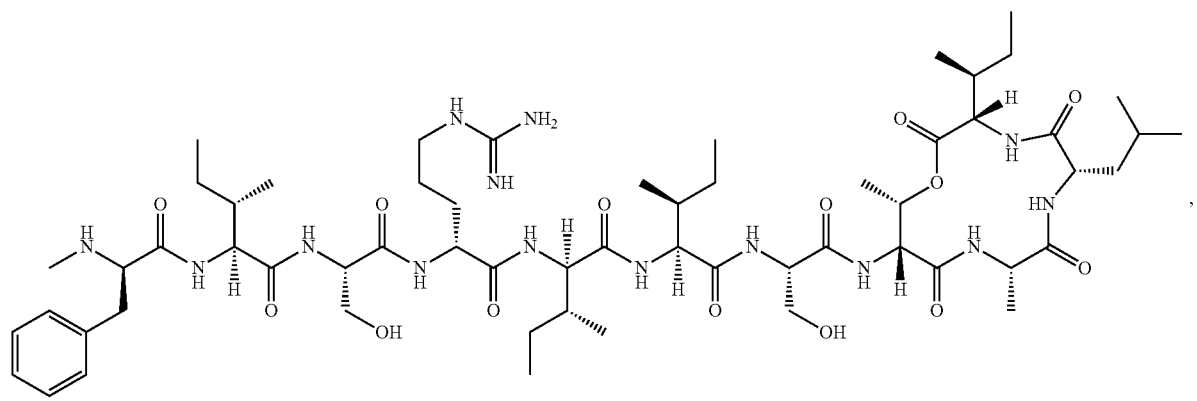

(SEQ ID NO: 10)
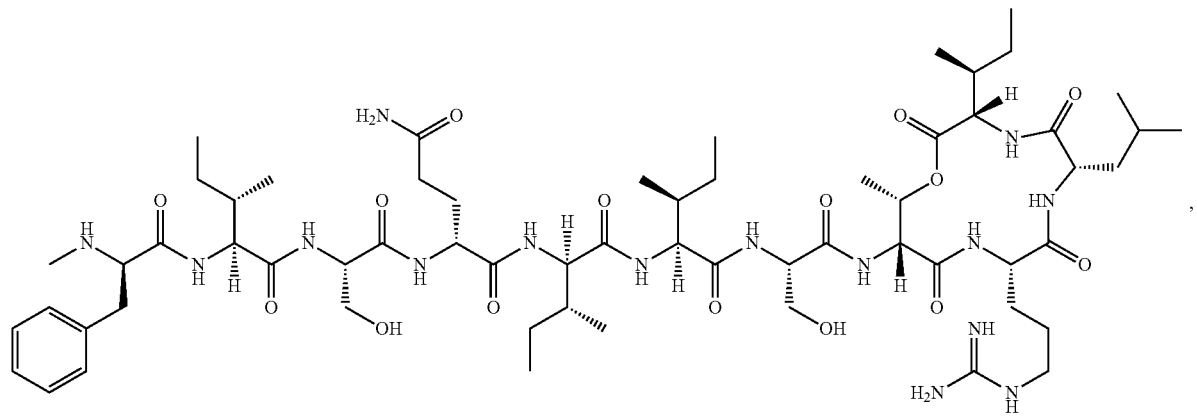
(SEQ ID NO: 20)
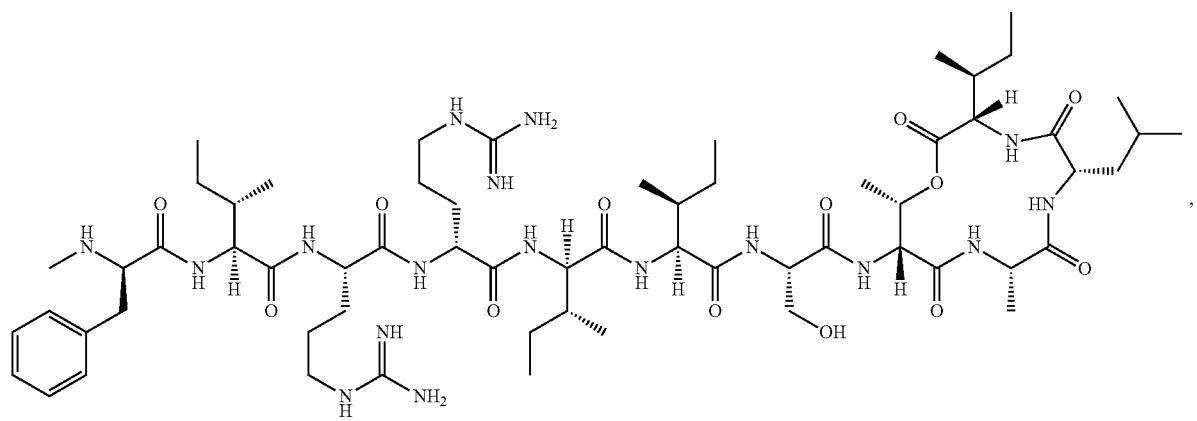
(SEQ ID NO: 21)
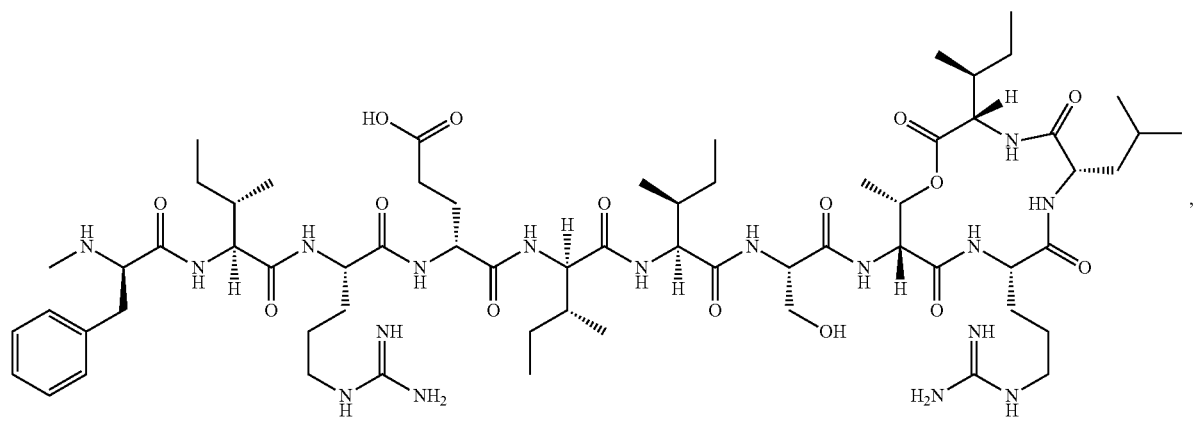

(SEQ ID NO: 19)
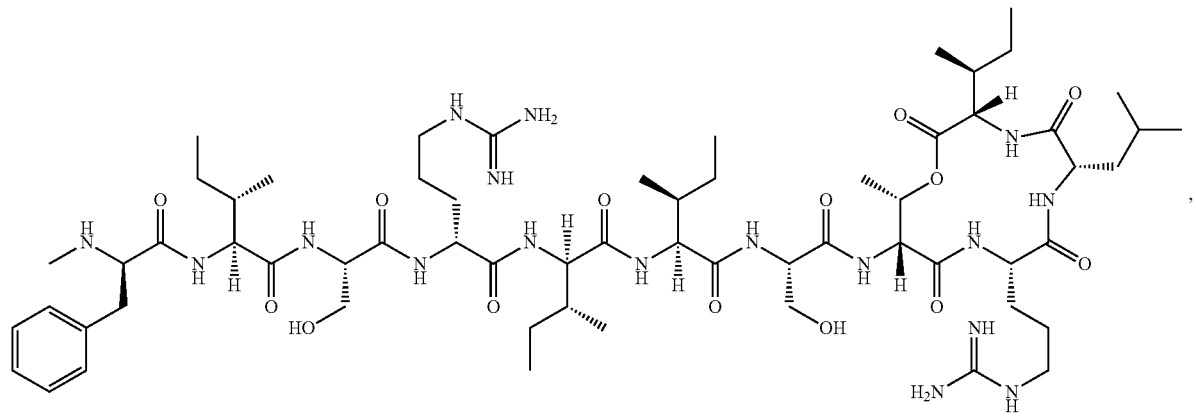
(SEQ ID NO: 20)
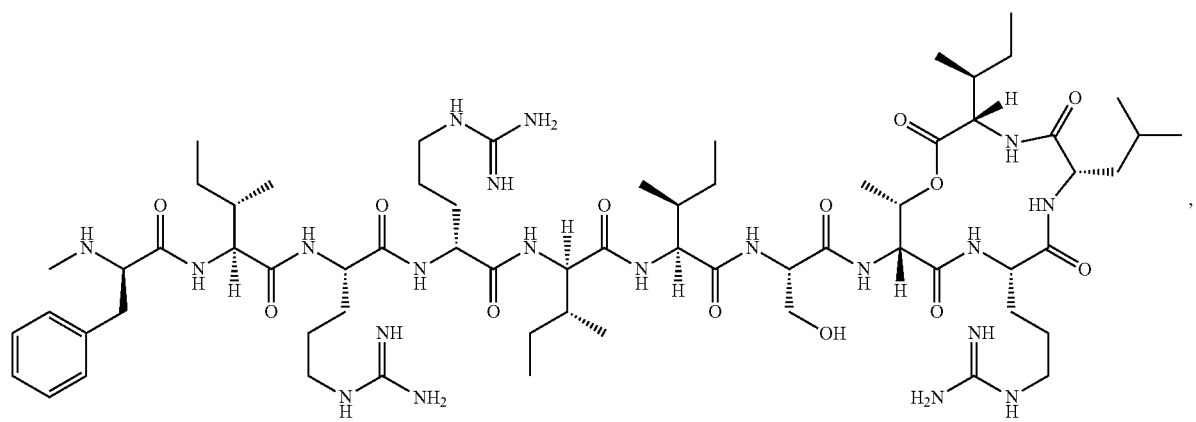
(SEQ ID NO: 18)
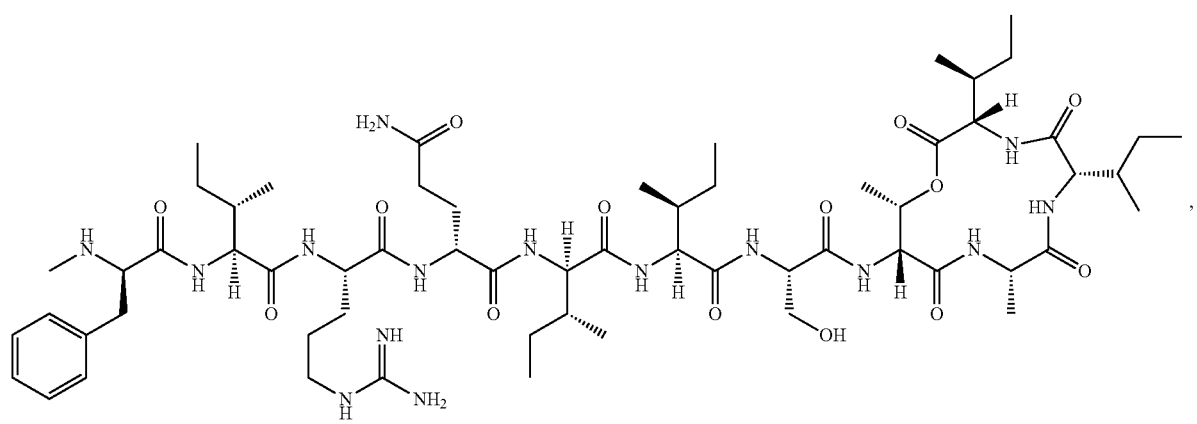

-continued
(SEQ ID NO: 19)
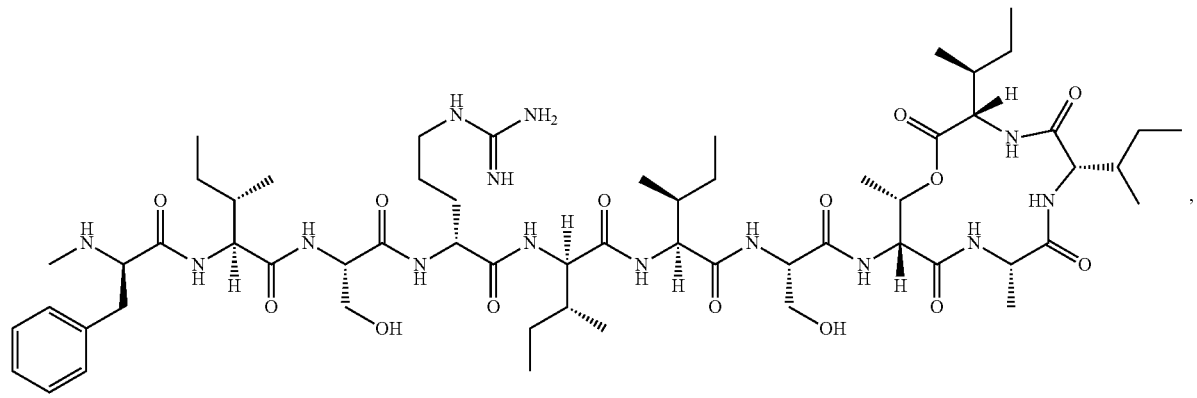
(SEQ ID NO: 10)
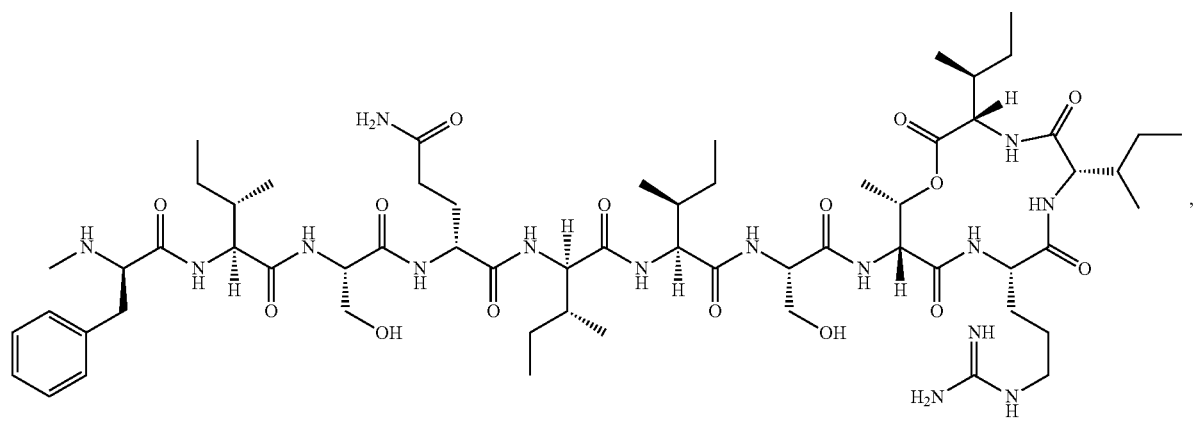
(SEQ ID NO: 20)
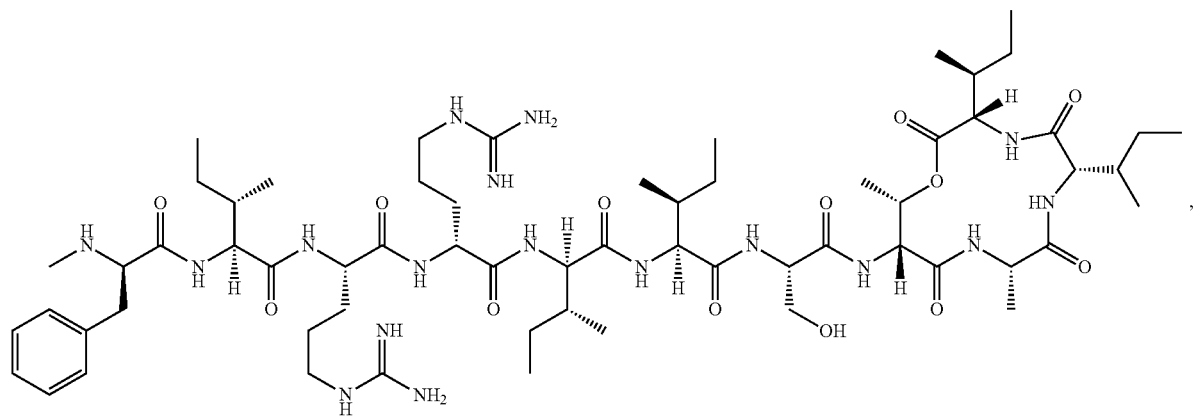

(SEQ ID NO: 10)
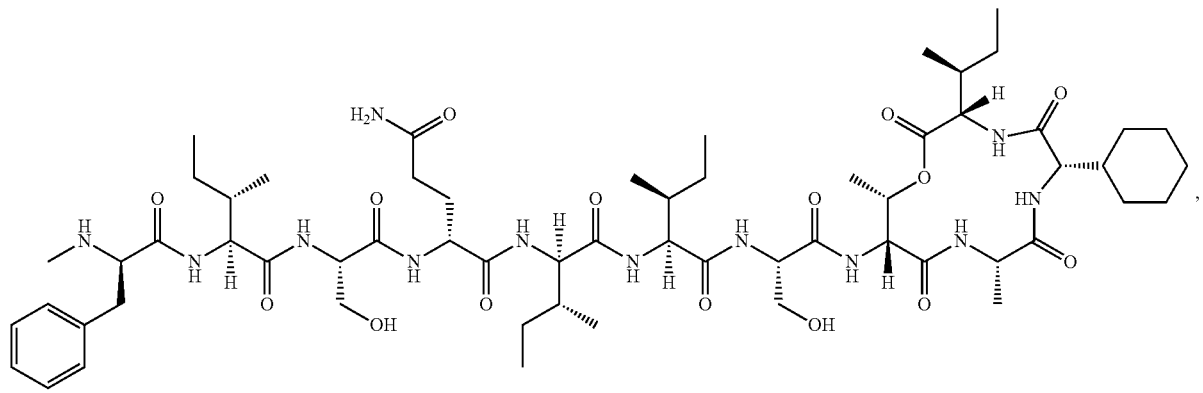
(SEQ ID NO: 18)
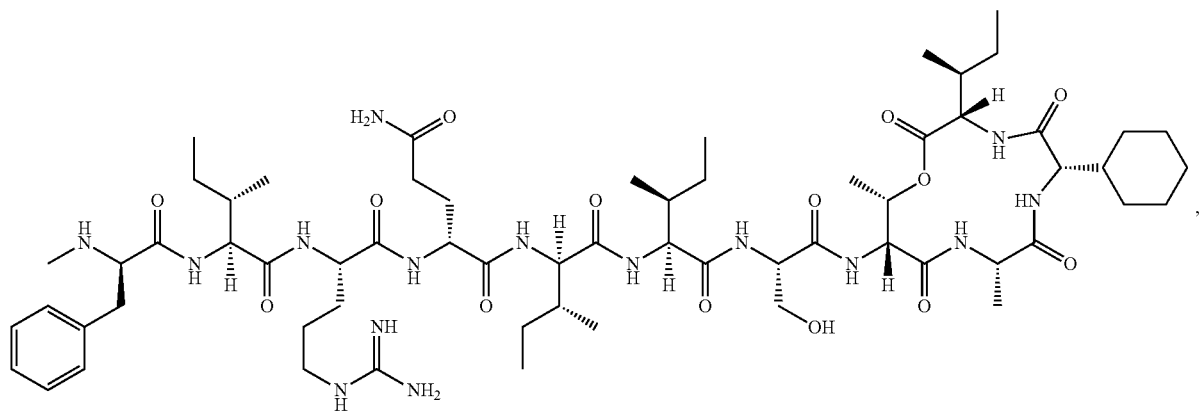
(SEQ ID NO: 19)
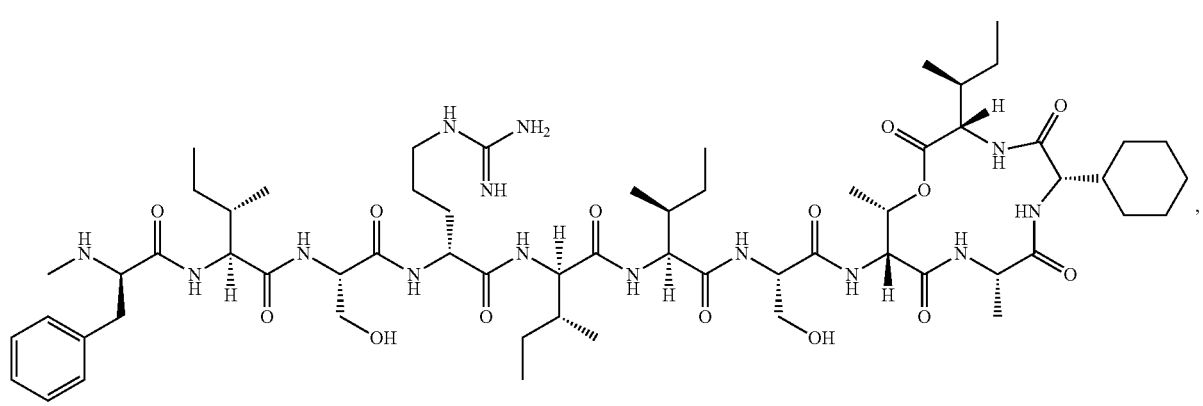

(SEQ ID NO: 10)
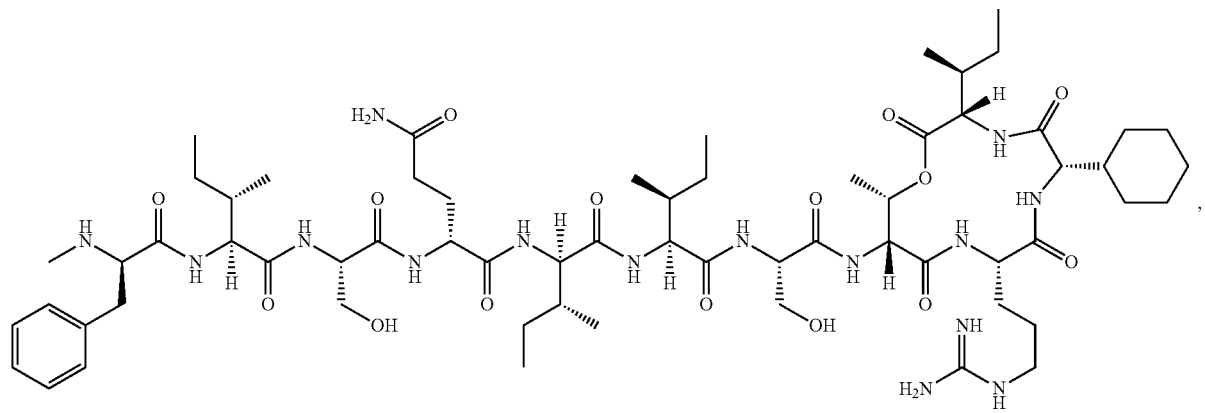
(SEQ ID NO: 20)
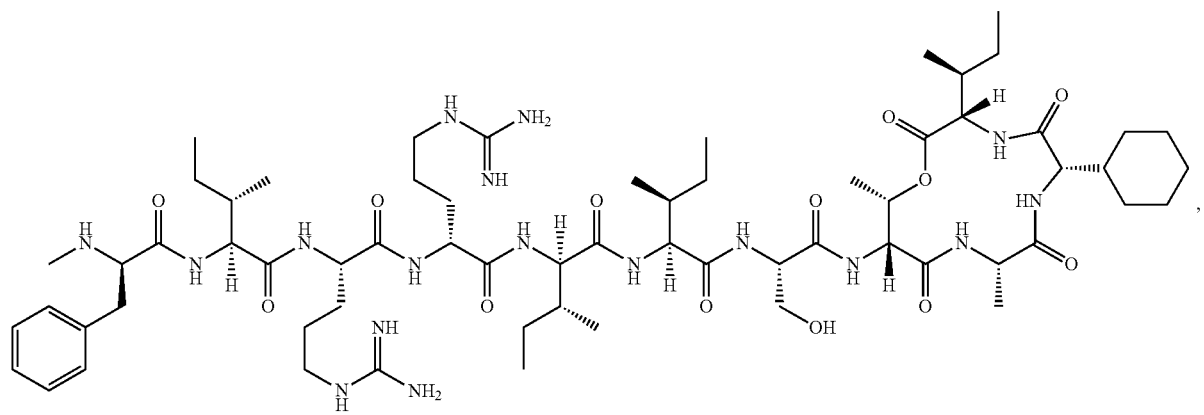
(SEQ ID NO: 21)
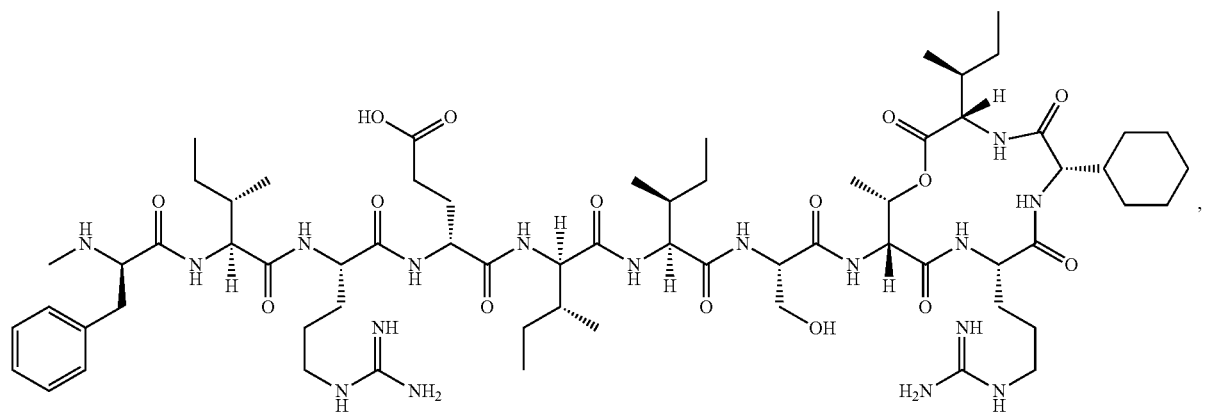

(SEQ ID NO: 19)
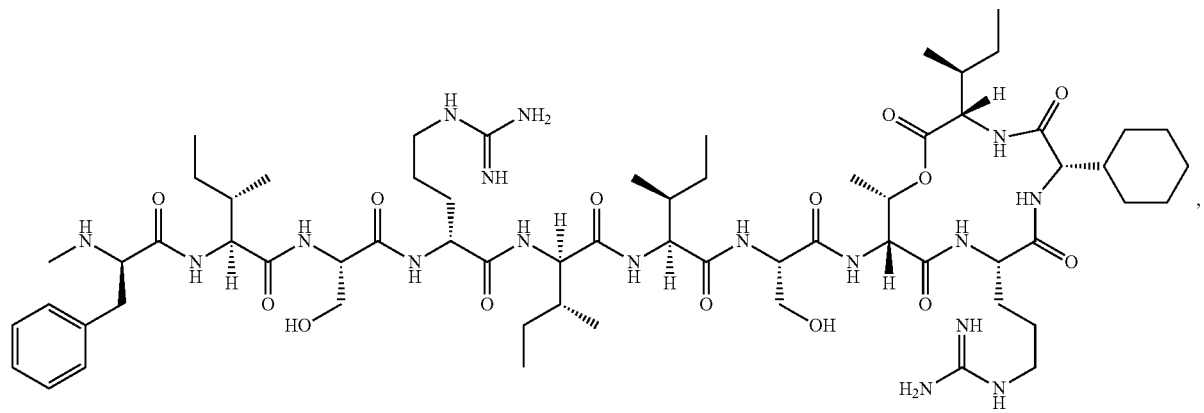
(SEQ ID NO: 20)
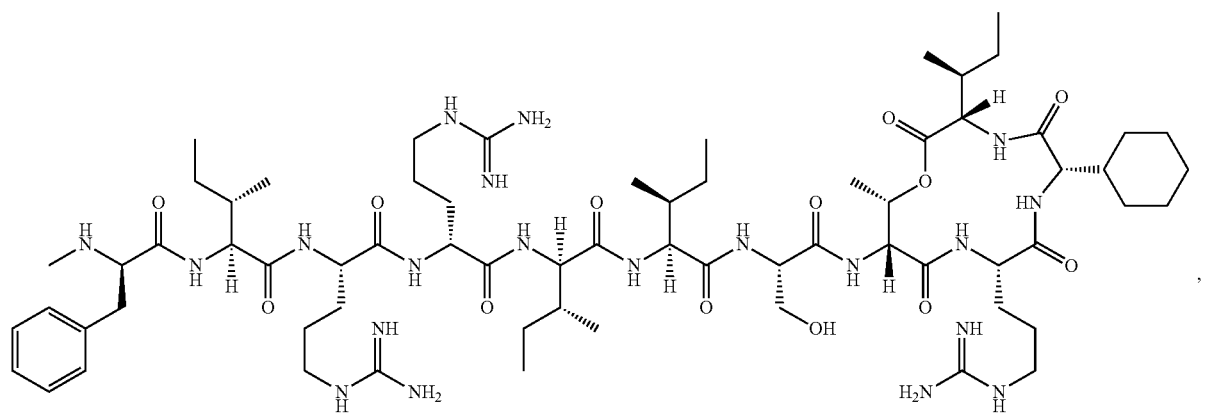
(SEQ ID NO: 10)
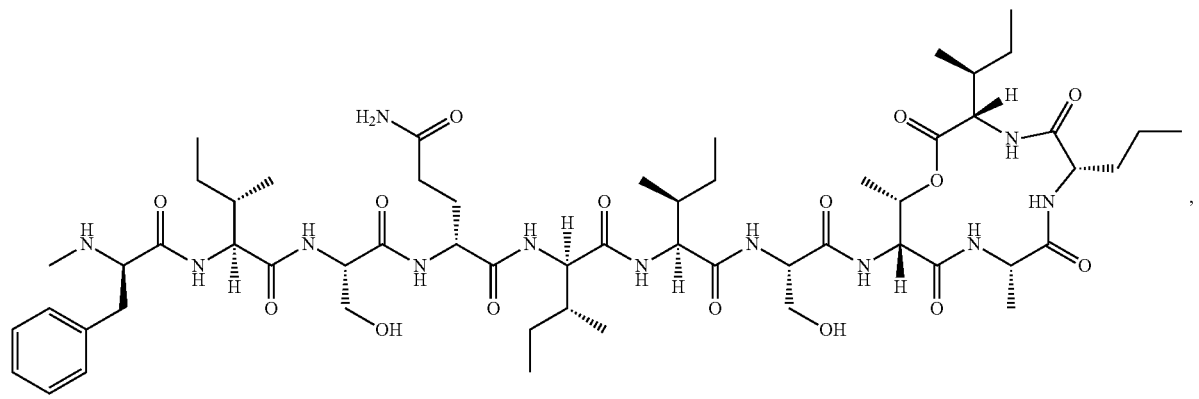

(SEQ ID NO: 18)
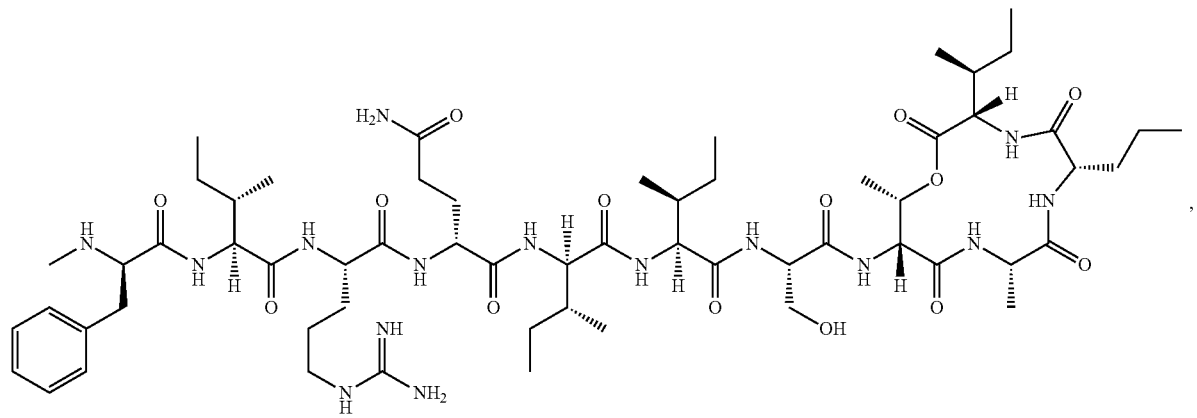
(SEQ ID NO: 19)
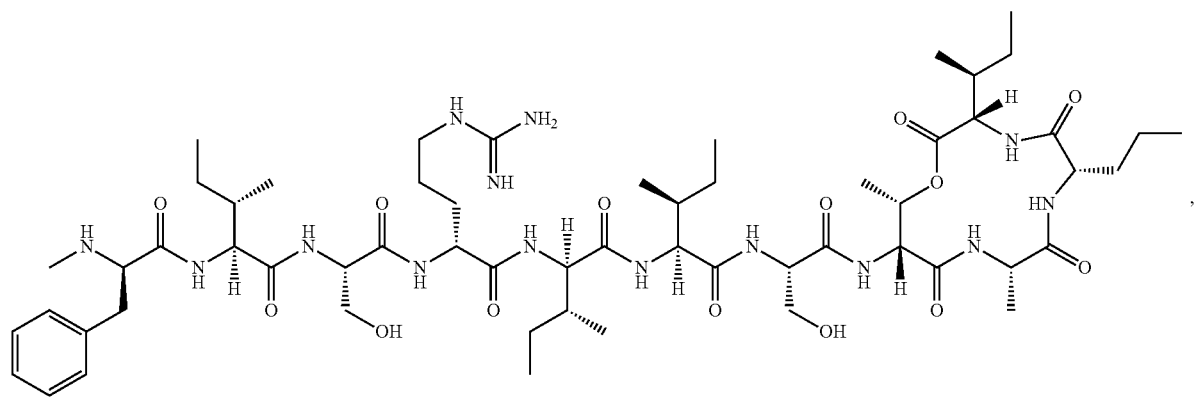
(SEQ ID NO: 10)
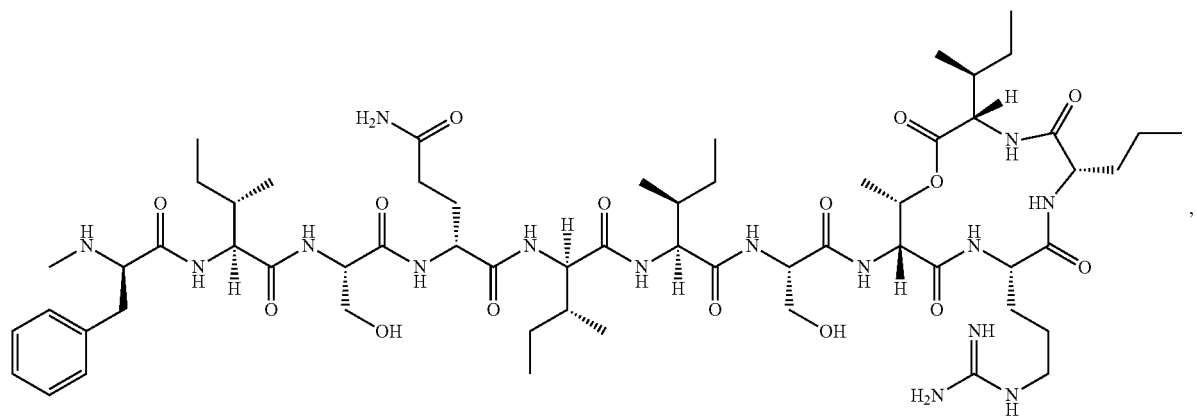

(SEQ ID NO: 20)
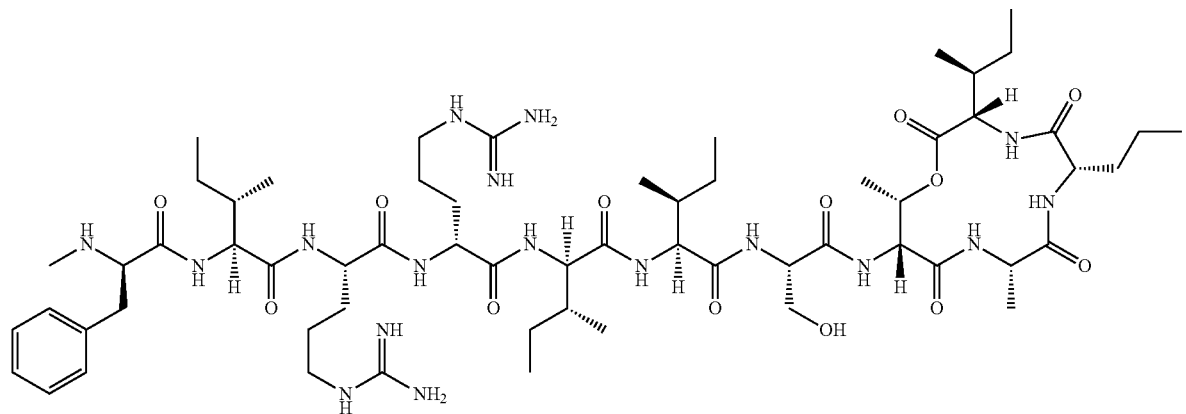
(SEQ ID NO: 21)
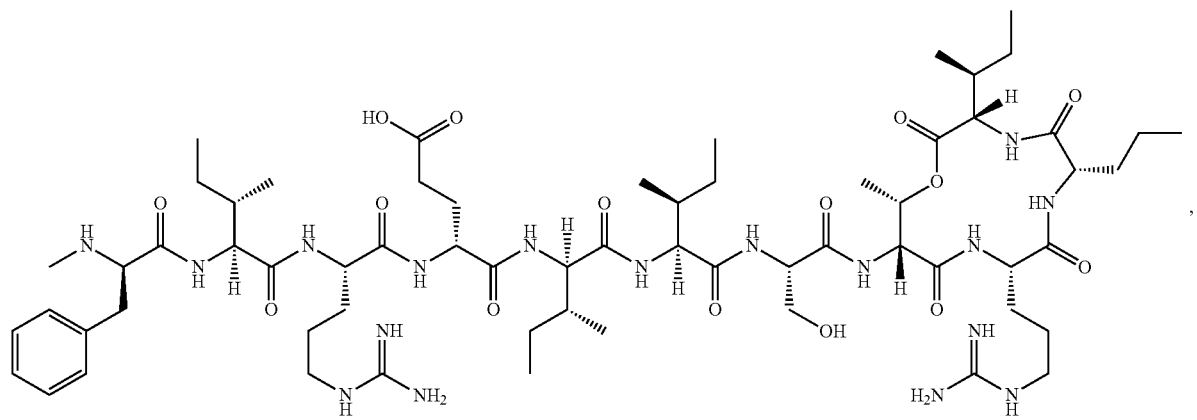
(SEQ ID NO: 19)
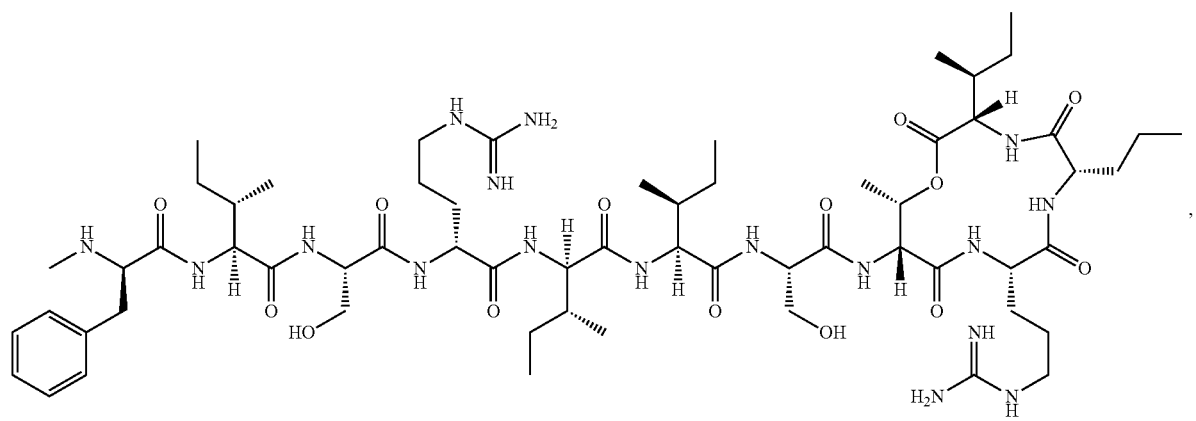

(SEQ ID NO: 20)
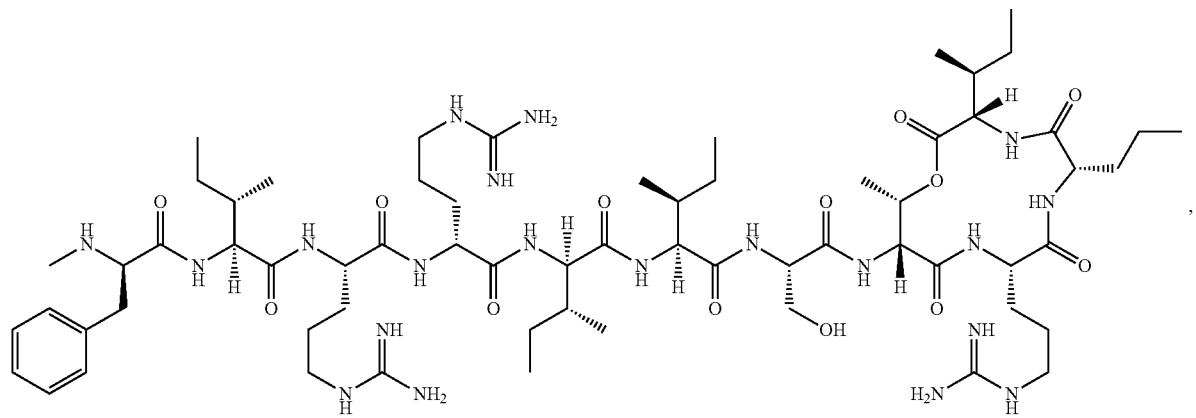
(SEQ ID NO: 19)
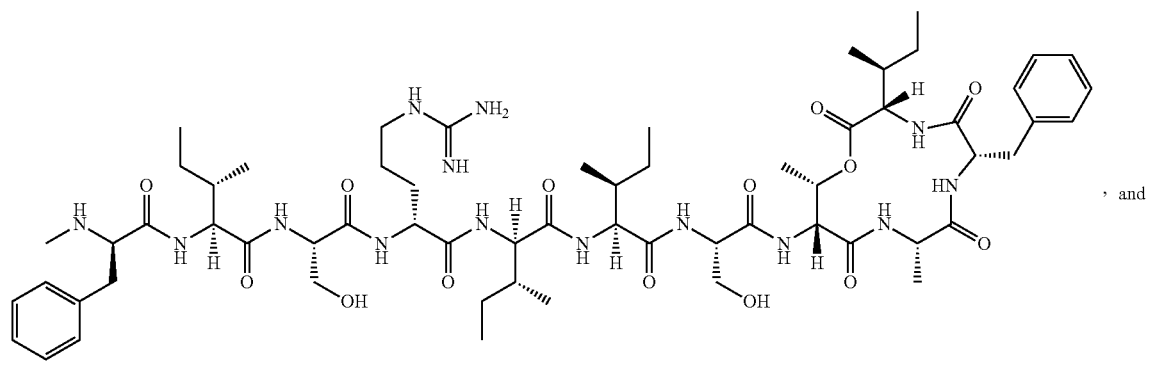
, and

-continued (SEQ ID NO: 22)

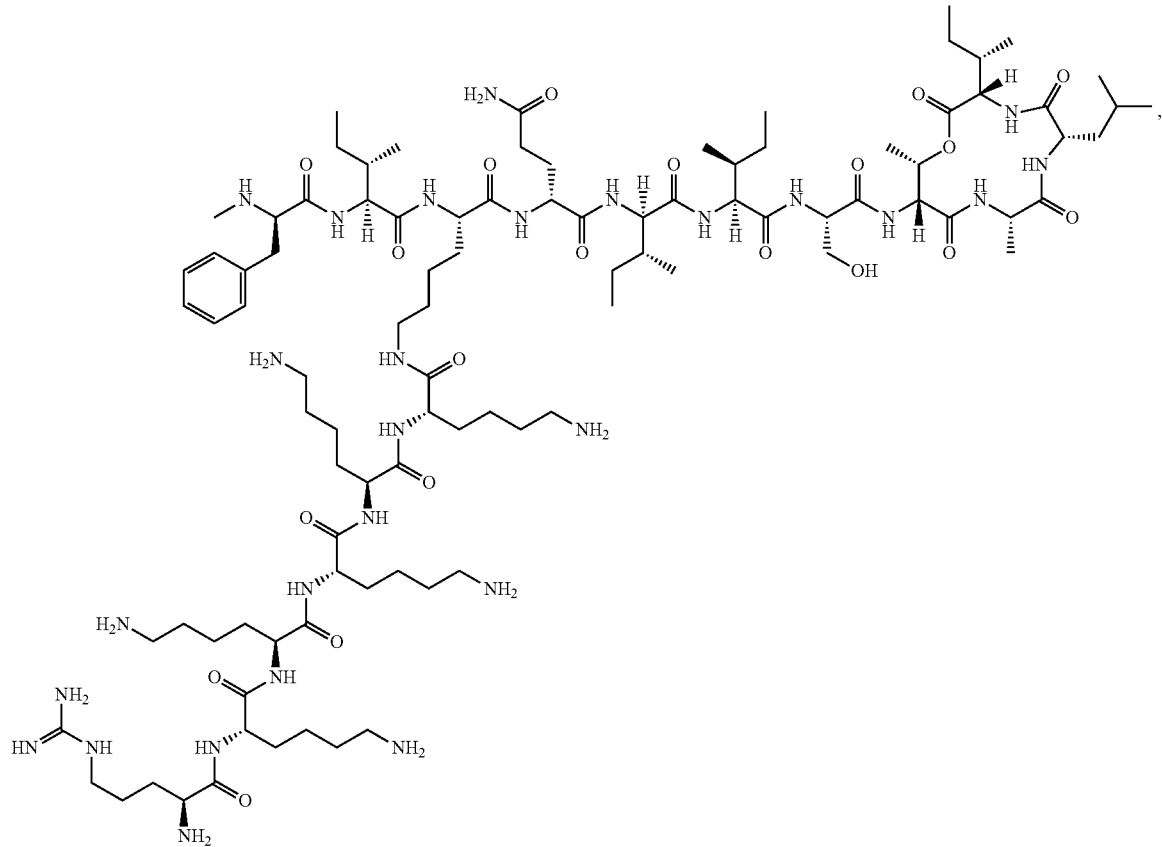

9. A pharmaceutical formulation comprising a compound as defined in claim 1 in combination with a pharmaceutically-acceptable adjuvant, diluent or carrier.

10. A method of treating or preventing a bacterial infection, which method comprises administration of a therapeutically effective amount of a compound as defined in claim 1 to a subject in need thereof.

11. A process for the preparation of a compound of formula IA as defined in claim 1, which process comprises:
 (i) deprotection of a compound of formula IA in which one or more hydroxyl groups are protected with an ether protecting group; in the presence of an acid;
 (ii) deprotection of a compound of formula IA in which one or more primary amide groups are protected with a trityl group; in the presence of an acid;
 (iii) reaction of a compound of formula XIIIA, (SEQ ID NO: 2)

(XIIIA)

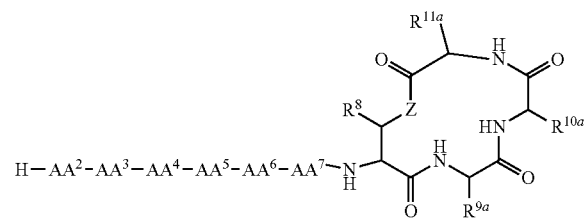

wherein $AA^2$ to $AA^7$ and are as defined in claim 1 and are optionally protected; and Z, $R^8$, $R^{9a}$, $R^{10a}$, and $R^{11a}$ are as defined in claim 1, in a process comprising the steps of:

a) reacting the compound of formula XIIIA with a compound of formula XIV

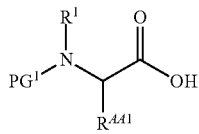
(XIV)

SEQ ID NO: 1

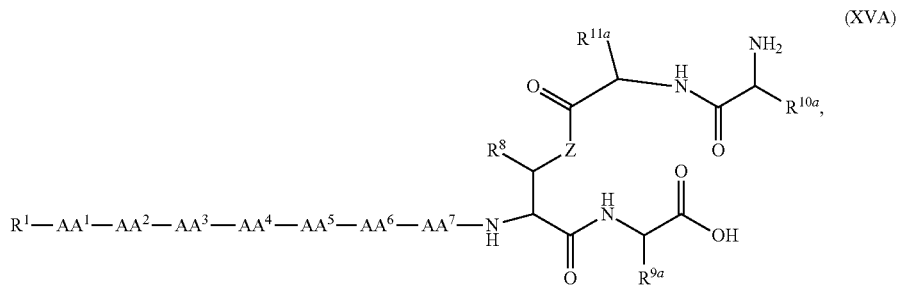

wherein $R^1$ is H, $C_{1-6}$ alkyl, $C_{1-6}$ acyl, benzyl or benzoyl or a delivery agent fragment of formula II to X, $R^{AA1}$ is the side chain of the desired $AA^1$ amino acid (optionally in protected form), and $PG^1$ represents an optional suitable protecting group, and a suitable peptide coupling reagent; followed by b) removal of the protecting group $PG^1$ if present; or (iv) reaction of a compound of formula XVA, wherein $AA^1$ to $AA^7$ are as defined in claim 1 and are optionally protected, Z, $R^8$, $R^{9a}$, $R^{10a}$, and $R^{11a}$ are as defined in claim 1, and $R^1$ is H, $C_{1-6}$ alkyl, $C_{1-6}$ acyl, benzyl or benzoyl or a delivery agent fragment of formula II to X with a suitable peptide coupling agent.

12. A compound according to claim 1, wherein $R^{10a}$ represents a side chain of an amino acid selected from the group consisting of valine, isoleucine, leucine, methionine, phenylalanine, tyrosine and tryptophan, a hydrophobic non-proteinogenic amino acid side chain, or hydrogen.

13. A compound according to claim 1, wherein $R^{10a}$ represents a side chain of an amino acid selected from the group consisting of valine, isoleucine, leucine, methionine, phenylalanine, tyrosine and tryptophan, a hydrophobic non-proteinogenic amino acid side chain selected from the group consisting of $C_{2-12}$ alkyl, $C_{1-12}$ alkylthiomethyl, phenyl, naphthyl, biphenyl, toluyl, and toluylmethyl, hydrogen, or $R^{10a}$ is linked to the adjacent nitrogen atom to form a proline ring.

14. The compound according to claim 1, wherein $R^8$ represents hydrogen or a methyl group.

15. The compound according to claim 1, wherein $R^{9a}$ represents —$CH_2$—$NH_2$, —$(CH_2)_2$—$NH_2$, —$(CH_2)_3$—$NH_2$, a hydroxy group, an amide functional group (which latter two groups are bound to the remainder of the molecule via a linear, branched, cyclic or part cyclic $C_{1-8}$ alkylene group), or the side chain of histidine, lysine, arginine, alanine, valine, isoleucine, leucine, methionine, phenylalanine, tyrosine, tryptophan, norvaline, cyclohexylglycine, cyclohexylalanine, phenylglycine, biphenylglycine, biphenylalanine, naphthylglycine naphthylalanine, serine, threonine, asparagine, or glutamine.

16. The compound according to claim 1, wherein $R^{11a}$ represents the side chain of alanine, valine, isoleucine, leucine, methionine, phenylalanine, tyrosine, tryptophan, norvaline, cyclohexylglycine, cyclohexylalanine, phenylglycine, biphenylglycine, biphenylalanine, naphthylglycine or naphthylalanine.

* * * * *